(12) United States Patent
Corte

(10) Patent No.: US 8,163,749 B2
(45) Date of Patent: Apr. 24, 2012

(54) SIX-MEMBERED HETEROCYCLES USEFUL AS SERINE PROTEASE INHIBITORS

(75) Inventor: James R. Corte, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 757 days.

(21) Appl. No.: 12/097,080

(22) PCT Filed: Dec. 13, 2006

(86) PCT No.: PCT/US2006/061973
§ 371 (c)(1),
(2), (4) Date: Jun. 12, 2008

(87) PCT Pub. No.: WO2007/070818
PCT Pub. Date: Jun. 21, 2007

(65) Prior Publication Data
US 2009/0181983 A1    Jul. 16, 2009

Related U.S. Application Data

(60) Provisional application No. 60/750,416, filed on Dec. 14, 2005.

(51) Int. Cl.
*A01N 43/58* (2006.01)
*A61K 31/50* (2006.01)
*A61K 31/44* (2006.01)
*A61K 31/13* (2006.01)
*C07D 221/18* (2006.01)
*C07D 421/00* (2006.01)

(52) U.S. Cl. ............... 514/248; 514/252.01; 514/257; 514/279; 514/579; 514/822; 546/26; 546/268.1

(58) Field of Classification Search ............... 514/248, 514/252.01, 257, 279, 579, 822; 546/26, 546/268.1
See application file for complete search history.

(56) References Cited

U.S. PATENT DOCUMENTS

| | | |
|---|---|---|
| 2004/0180855 A1 | 9/2004 | Schumacher et al. |
| 2004/0220206 A1 | 11/2004 | Smallheer et al. |
| 2004/0235847 A1 | 11/2004 | Quan et al. |
| 2005/0228000 A1 | 10/2005 | Smallheer et al. |
| 2005/0282805 A1 | 12/2005 | Hangeland et al. |
| 2006/0009455 A1 | 1/2006 | Corte et al. |
| 2006/0154915 A1 | 7/2006 | Corte et al. |
| 2008/0161373 A1 | 7/2008 | Pinto et al. |

FOREIGN PATENT DOCUMENTS

| | | |
|---|---|---|
| WO | WO 01/27079 | 4/2001 |
| WO | WO 02/42273 | 5/2002 |
| WO | WO 2004/014844 | 2/2004 |
| WO | WO2004/019868 | 3/2004 |
| WO | WO 2005/123680 A1 | 12/2005 |

OTHER PUBLICATIONS

Vippagunta SR et al. "Crystalline solids". Advanced Drug Delivery Reviews 48 (2001) 3-26.*

U.S. Appl. No. 12/097,068, filed Dec. 13, 2006, Wei Han.
Hirsch, J. et al., "New Anticoagulants", *Blood*, 2005, vol. 105, pp. 453-363.
Walsh, Peter N., "Platelets and Factor XI Bypass the Contact System of Blood Coagulation", *Thrombosis and Haemostasis*, 1999, 82, 234-242.
Hoffman, M., "A cell-based model of coagulation and the role of factor Vlla", *Blood Reviews*, 2003, 17, S1-S5.
Shariat-Madar et al., "Bradykinin B2 receptor knockout mice are protected from thrombosis by increased nitric oxide and prostacyclin", *Blood*, 2006, 108,192-199.
Coleman, R., "Contact Activation Pathway", *Hemostasis and Thrombosis*, 2001, 103-121.
Schmaier Alvin., "Contact Activation", *Thrombosis and Hemorrhage*, 1998, 105-127.
Renne et al., "Defective thrombus formation in mice lacking coagulation factor XII", *Journal of Experimental Medicine*, 2005, 202, 271-281.
Kleinschnitz et al., "Targeting coagulation factor XII provides protection from pathological thrombosis in cerebral ischemia without interfering with hemostasis", *Journal of Experimental Medicine*, 2006, 203, 513-518.
Gailani et al., "Activation of Factor IX by Factor Xia", *Trends*, 2000. 10, 198-204.
Bouma et al., "Thrombin-Activatable Fibrinolysis Inhibitor (TAFI, Plasma Procarboxypeptidase B, Procarboxypeptidase R, Procarboxypeptidase U)", *Thrombosis Research*, 2001, 101, 329-354.
Rosen, Elliot D., "FXI is Essential for Thrombus Formation Following FeCl$_3$. Induced Injury of the Carotid Artery in the Mouse", *Thromb Haemost*, 2002, 87. 774-776.
Wang X., "Effects of Factor IX or factor XI deficiency on ferric chloride-induced carotid artery occlusion in mice", *J. Thromb. Haemostasis*, 2005, 3, 695-702.
Chan, Joyce et al., The Characterization of Mice with a Targeted Combined Deficiency of Protein C and Factor XI, *Amer. J. Pathology*, 2001, 158, 469-479.
Gruber et al., "Factor XI-dependence of surface- and tissue factor-initiated thrombus propagation in primates", *Blood*, 2003, 102,953-955.

(Continued)

*Primary Examiner* — Sreeni Padmanabhan
*Assistant Examiner* — Renee Claytor
(74) *Attorney, Agent, or Firm* — Hong Liu

(57) ABSTRACT

The present invention provides compounds of Formula (I):

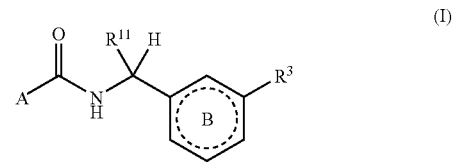

or a stereoisomer, tautomer, pharmaceutically acceptable salt or solvate form thereof, wherein the variables A, B, $R^3$ and $R^{11}$ are as defined herein. The compounds of Formula (I) are useful as selective inhibitors of serine protease enzymes of the coagulation cascade and/or contact activation system; for example thrombin, factor Xa, factor XIa, factor IXa, factor VIIa and/or plasma kallikrein. In particular, it relates to compounds that are selective factor XIa inhibitors or dual inhibitors of fXIa and plasma kallikrein. This invention also relates to pharmaceutical compositions comprising these compounds and methods of treating thromboembolic and/or inflammatory disorders using the same.

10 Claims, No Drawings

OTHER PUBLICATIONS

Gailani, D, "Gene Targeting in Hemostasis, Factor XI", *Frontiers in Bioscience*, 2001, 6. 201-207.

Gailani, D., "A murine model of factor XI deficiency", *Blood Coagulation and Fibrinolysisl*, 1997, 8, 134-144.

Minnema et al., "Activation of Clotting Factors XI and IX in Patients with Acute Myocardial Infarction", *Arterioschler. Thromb. Vasc. Biol.*, 2000, 20, 2489-2493.

Murakami et al., Evaluation of Factor Xia-$\alpha_1$-Antitrypsin in Plasma, a Contact Phase-Activated Coagulation Factor-Inhibitor Complex, in Patients with Coronary Artery Disease, *Arterioscler Thromb Vasc Biol*, 1995, 15, 1107-1113.

Meijers, et al., "High Levels of Coagulation Factor XI as a Risk Factor for Venous Thrombosis", *N. Engl. J. Med*, 2000, 342, 696-701.

Hoekstra et al., Potent, Orally Active GP!!b/IIIa Antagonists Containing a Nipercotic Acid Subunit. Structure-Activity Studies Leading to the Discovery of RWJ-53308, *J. Med. Chem*, 1999, 42, 5254-5265.

U.S. Appl. No. 12/921,177, filed Sep. 7, 2010, Corte, et al.

\* cited by examiner

US 8,163,749 B2

SIX-MEMBERED HETEROCYCLES USEFUL AS SERINE PROTEASE INHIBITORS

CROSS-REFERENCE TO RELATED APPLICATIONS

This application is a 371 application of PCT/US2006/061973 filed Dec. 13, 2006, which claims priority benefit of U.S. provisional application Ser. No. 60/750,416, filed Dec. 14, 2005, which is incorporated by reference herein.

FIELD OF THE INVENTION

The present invention relates generally to novel six-membered heterocyclic compounds, and analogues thereof, which are useful as selective inhibitors of serine protease enzymes of the coagulation cascade and/or contact activation system; for example thrombin, factor XIa, factor Xa, factor IXa, factor VIIa, and/or plasma kallikrein. In particular, it relates to compounds that are selective factor XIa inhibitors or dual inhibitors of fXIa and plasma kallikrein. This invention also relates to pharmaceutical compositions comprising these compounds and methods of using the same.

BACKGROUND OF THE INVENTION

Factor XIa is a plasma serine protease involved in the regulation of blood coagulation. While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thrombotic or thromboembolic disorders and include acute coronary syndrome, unstable angina, myocardial infarction, thrombosis in the cavity of the heart, ischemic stroke, deep vein thrombosis, peripheral occlusive arterial disease, transient ischemic attack, and pulmonary embolism. In addition, thrombosis occurs on artificial surfaces in contact with blood, including catheters and artificial heart valves. Therefore, drugs that inhibit blood coagulation, or anticoagulants, are "pivotal agents for prevention and treatment of thromboembolic disorders" (Hirsh, J. et al. *Blood* 2005, 105, 453-463). Thromboembolic disorders are the largest cause of mortality and disability in the industrialized world.

Blood coagulation is initiated in vivo by the binding of tissue factor (TF) to Factor VII (FVII) to generate Factor VIIa (FVIIa). The resulting TF:FVIIa complex activates Factor IX (FIX) and Factor X (FX) which leads to the production of Factor Xa (FXa). The FXa that is generated catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Walsh, P. N. *Thromb. Haemostasis.* 1999, 82, 234-242.) The resulting burst of thrombin coverts fibrinogen to fibrin, which polymerizes to form the structural framework of a blood clot, and activates platelets, which are a key cellular component of coagulation (Hoffman, M. *Blood Reviews* 2003, 17, S1-S5). Factor XIa plays a key role in propagating this amplification loop and is thus an attractive target for anti-thrombotic therapy.

An alternative way of initiation of coagulation is operative when blood is exposed to artificial surfaces (e.g., during hemodialysis, 'on-pump' cardiovascular surgery, vessel grafts, bacterial sepsis), on cell surfaces, cellular receptors, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al. *Blood* 2006, 108, 192-199). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R. *Contact Activation Pathway*, pages 103-122 in *Hemostasis and Thrombosis*, Lippincott Williams & Wilkins 2001; Schmaier A. H. *Contact Activation*, pages 105-128 in *Thrombosis and Hemorrhage*, 1998). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al. *J. Exp. Medicine* 2005, 202, 271-281; Kleinschmitz et al. *J. Exp.l Medicine*, 2006, 203, 513-518). The fact that factor XI is down-stream from factor XIIa, combined with the identical phenotype of the XII and XI deficient mice suggest that the contact activation system could play a major role in factor XI activation in vivo.

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor IX as its normal macromolecular substrate. (Galiani, D. *Trends Cardiovasc. Med.* 2000, 10, 198-204.)

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al. *Thromb. Res.* 2001, 101, 329-354.) Thus, inhibitors of factor XIa are expected to be anticoagulant and profibrinolytic.

Further evidence for the anti-thromboembolic effects of targeting factor XI is derived from mice deficient in factor XI. It has been demonstrated that complete fXI deficiency protected mice from ferric chloride ($FeCl_3$)-induced carotid artery thrombosis (Rosen et al. *Thromb Haemost* 2002, 87, 774-77; Wang et al., *J Thromb Haemost* 2005, 3, 695-702). Also, factor XI deficiency rescues the perinatal lethal phenotype of complete protein C deficiency (Chan et al., *Amer. J. Pathology* 2001, 158, 469-479). Furthermore, baboon cross-reactive, function blocking antibodies to human factor XI protect against baboon arterial-venous shunt thrombosis (Gruber et al., *Blood* 2003, 102, 953-955). Evidence for an antithrombotic effect of small molecule inhibitors of factor XIa is also disclosed in published U.S. Patent Application US20040180855A1. Taken together, these studies suggest that targeting factor XI will reduce the propensity for thrombotic and thromboembolic diseases.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or posttraumatic, but rarely spontaneous hemorrhage. Postoperative bleeding occurs mostly in tissue with high concentrations of endogenous fibrinolytic activity (e.g. oral cavity, and urogenital system). The majority of the cases are fortuitously identified by preoperative prolongation of APTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The APTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailani, D. *Frontiers in Bioscience* 2001, 6, 201-207; Gailani, D. et al. *Blood Coagulation and Fibrinolysis* 1997, 8, 134-144.) Taken together, these observations suggest that high levels of inhibition of factor XIa should be well tolerated. This is in contrast to gene targeting experiments with other coagulation factors.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al. *Arterioscler. Thromb. Vasc. Biol.* 2000, 20, 2489-2493). A second study establishes a positive correlation between the extent of coronary arteriosclerosis and factor XIa in complex with alpha 1 antitrypsin (Murakami, T. et al. *Arterioscler Thromb Vasc Biol* 1995, 15, 1107-1113.). In another study, Factor XI levels above the 90th percentile in patients were associated with a 2.2-fold increased risk for venous thrombosis (Meijers, J. C. M. et al. *N. Engl. J. Med.* 2000, 342, 696-701.).

Plasma kallikrein is a zymogen of a trypsin-like serine protease and is present in plasma at 35 to 50 µg/mL. The gene structure is similar to that of factor XI. Overall, the amino acid sequence of plasma kallikrein has 58% homology to factor XI. Proteolytic activation by factor XIIa at an internal I 389-R390 bond yields a heavy chain (371 amino acids) and a light chain (248 amino acids). The active site of plasma kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Plasma kallikrein cleaves HMWK to liberate bradykinin. Bradykinin release results in increase of vascular permeability and vasodilation (for review, Coleman, R. *Contact Activation Pathway*, pages 103-122 in *Hemostasis and Thrombosis*, Lippincott Williams & Wilkins 2001; Schmaier A. H. *Contact Activation*, pages 105-128 in *Thrombosis and Hemorrhage*, 1998).

Proteins or peptides that reportedly inhibit Factor XIa are disclosed in WO 01/27079. There are advantages in using small organic compounds, however, in preparing pharmaceuticals, e.g., small compounds generally have better oral bioavailability and compatibility in making formulations to aid in delivery of the drug as compared with large proteins or peptides. Small molecule inhibitors of Factor XIa are disclosed in U.S. Patent Application Publications, e.g., US20040235847A1, US20040220206A1, US20050228000A1, US20060009455A1, and US20050282805A1.

In addition, it is also desirable to find new compounds with improved pharmacological characteristics compared with known serine protease inhibitors. For example, it is preferred to find new compounds with improved factor XIa inhibitory activity and selectivity for factor XIa versus other serine proteases. Also, it is preferred to find new compounds with improved plasma kallikrein inhibitory activity and selectivity for plasma kallikrein versus other serine proteases. It is also desirable and preferable to find compounds with advantageous and improved characteristics in one or more of the following categories, which are given as examples and are not intended to be limiting: (a) pharmacokinetic properties, including oral bioavailability; (b) pharmaceutical properties; (c) dosage requirements; (d) factors which decrease blood concentration peak-to-trough characteristics; (e) factors that increase the concentration of active drug at the receptor; (f) factors that decrease the liability for clinical drug-drug interactions; (g) factors that decrease the potential for adverse side-effects; and (h) factors that improve manufacturing costs or feasibility.

SUMMARY OF THE INVENTION

The present invention provides novel six-membered heterocyclic compounds, and analogues thereof, which are useful as selective inhibitors of serine protease enzymes, especially factor XIa and/or plasma kallikrein, or stereoisomers, tautomers, pharmaceutically acceptable salts, solvates, or prodrugs thereof.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and a therapeutically effective amount of at least one of the compounds of the present invention or stereoisomers, tautomers, pharmaceutically acceptable salts, solvates, or prodrugs thereof.

The present invention also provides a method for modulation of the coagulation cascade and/or the contact activation system comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating thromboembolic disorders comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating inflammatory diseases disorders comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of a thromboembolic disorder.

The present invention also provides the use of the compounds of the present invention or stereoisomers, tautomers, pharmaceutically acceptable salts, solvates, or prodrugs thereof, for the manufacture of a medicament for the treatment of an inflammatory disorder.

These and other features of the invention will be set forth in the expanded form as the disclosure continues.

DETAILED DESCRIPTION OF THE INVENTION

In a first aspect, the present invention provides, inter alia, a compound of Formula (I):

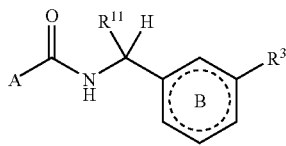

(I)

or stereoisomers, tautomers, pharmaceutically acceptable salts, solvates, or prodrugs thereof, wherein:

A is $C_{3-7}$ cycloalkyl substituted with 0-1 $R^1$ and 0-3 $R^2$, $C_{3-7}$ cycloalkenyl substituted with 0-1 $R^1$ and 0-3 $R^2$, phenyl substituted with 0-1 $R^1$ and 0-3 $R^2$, naphthyl substituted with 0-1 $R^1$ and 0-3 $R^2$, or a 5- to 12-membered heterocycle comprising: carbon atoms and 1-4 heteroatoms selected from N, O, and $S(O)_p$, wherein said heterocycle is substituted 0-1 $R^1$ and 0-3 $R^2$;

provided that A is other than a thienyl substituted with halogen, $C_{1-6}$ alkyl, $C_{2-6}$ alkenyl, or $C_{2-6}$ alkynyl;

the group

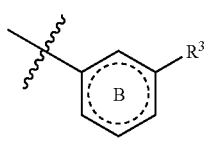

is selected from:

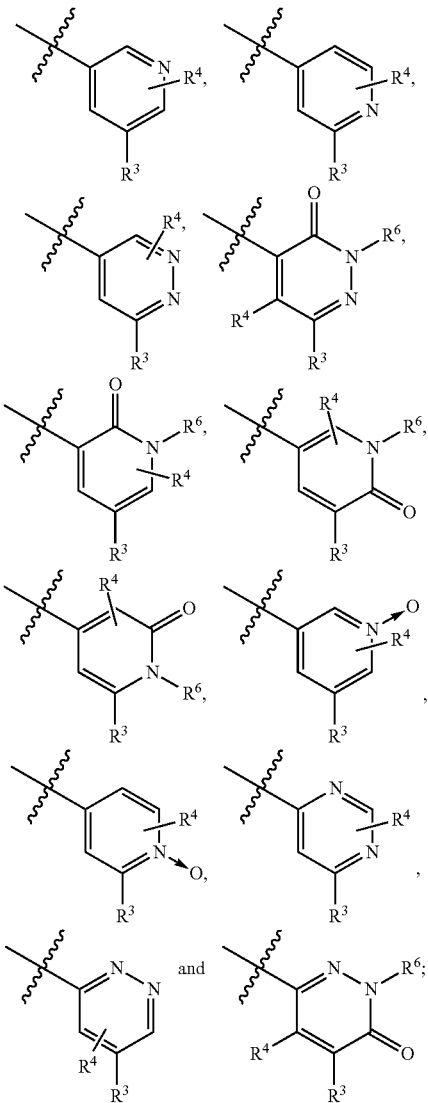

$R^1$ is, independently at each occurrence, —$NH_2$, —$NH$($C_{1-3}$ alkyl), —$N(C_{1-3}$ alkyl$)_2$, —$C(=NH)NH_2$, —$C(O)NH_2$, —$CH_2NH_2$, —$(CH_2)_rNR^7R^8$, —$CH_2NH(C_{1-3}$ alkyl), —$CH_2N(C_{1-3}$ alkyl$)_2$, —$CH_2CH_2NH_2$, —$CH_2CH_2NH(C_{1-3}$ alkyl), —$CH_2CH_2N(C_{1-3}$ alkyl$)_2$, —$CH(C_{1-4}$ alkyl)$NH_2$, —$C(C_{1-4}$ alkyl$)_2NH_2$, —$C(=NR^{8a})NR^7R^8$, —$NR^8CR^8$ ($=NR^{8a}$), —$NHC(=NR^{8a})NR^7R^8$, $=NR^8$, —$C(O)NR^8R^9$, —$S(O)_pNR^8R^9$, —$(CH_2)_rNR^7C(O)OR^a$, F, Cl, Br, I, $OCF_3$, $CF_3$, $OR^a$, $SR^a$, CN, 1-$NH_2$-1-cyclopropyl, or $C_{1-6}$ alkyl substituted with 0-1 $R^{1a}$;

$R^{1a}$ is —$C(=NR^{8a})NR^7R^8$, —$NHC(=NR^{8a})NR^7R^8$, —$NR^8CH(=NR^{8a})$, —$NR^7R^8$, —$C(O)NR^8R^9$, F, $OCF_3$, $CF_3$, $OR^a$, $SR^a$, CN, —$NR^8SO_2NR^8R^9$, —$NR^8SO_2R^c$, —$S(O)_p$—$C_{1-4}$ alkyl, —$S(O)_p$-phenyl, or —$(CF_2)_rCF_3$;

$R^2$ is, independently at each occurrence, $=O$, F, Cl, Br, I, $OCF_3$, $CF_3$, $CHF_2$, CN, $NO_2$, —$(CH_2)_rOR^a$, —$(CH_2)_rSR^a$, —$(CH_2)_rC(O)R^a$, —$(CH_2)_rC(O)OR^a$, —$(CH_2)_rOC(O)R^a$, —$(CH_2)_rNR^7R^8$, —$(CH_2)_rC(O)NR^8R^9$, —$(CH_2)_rNR^8C(O)R^c$, —$(CH_2)_rNR^8C(O)OR^c$, —$NR^8C(O)NR^8R^c$, —$S(O)_pNR^8R^9$, —$NR^8S(O)_2R^c$, —$S(O)R^c$, —$S(O)_2R^c$, $C_{1-6}$ alkyl substituted with 0-2 $R^{2a}$, $C_{2-6}$ alkenyl substituted with 0-2

$R^{2a}$, $C_{2-6}$ alkynyl substituted with 0-2 $R^{2a}$, —$(CH_2)_r$—$C_{3-10}$ carbocycle substituted with 0-3 $R^{2b}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{2b}$;

$R^{2a}$ is, independently at each occurrence, H, F, Cl, Br, I, =O, =$NR^8$, CN, $OCF_3$, $CF_3$, $OR^a$, $SR^a$, —$NR^7R^8$, —C(O)$NR^8R^9$, —$NR^8C(O)R^c$, —$NR^8C(O)OR^c$, —$NR^8C(O)NR^8R^c$, —$S(O)_pNR^8R^9$, —$NR^8SO_2R^c$, —$S(O)R^c$, or —$S(O)_2R^c$;

$R^{2b}$ is, independently at each occurrence, H, F, Cl, Br, I, =O, =$NR^8$, —$(CH_2)_rCN$, —$(CH_2)_rNO_2$, —$(CH_2)_rOR^a$, —$(CH_2)_rSR^a$, —$(CH_2)_rC(O)R^a$, —$(CH_2)_rC(O)OR^a$, —$(CH_2)_rOC(O)R^a$, —$(CH_2)_rNR^7R^8$, —$(CH_2)_rC(O)NR^8R^9$, —$(CH_2)_rNR^8C(O)R^c$, —$(CH_2)_rS(O)_pNR^8R^9$, —$(CH_2)_rSO_2R^c$, —$(CH_2)_rNR^8SO_2NR^8R^9$, —$(CH_2)_rNR^8SO_2R^c$, —$(CF_2)_rCF_3$, $C_{1-6}$ alkyl, $C_{2-6}$ alkenyl, $C_{2-6}$ alkynyl, $C_{3-6}$ cycloalkyl, $C_{1-4}$ haloalkyl, or $C_{1-4}$ haloalkyloxy;

alternately, when $R^1$ and $R^2$ are substituted on adjacent ring atoms, they can be taken together with the ring atoms to which they are attached to form a 5- to 7-membered carbocycle or heterocycle comprising: carbon atoms and 0-4 heteroatoms selected from N, O, and $S(O)_p$, wherein said carbocycle or heterocycle is substituted with 0-2 $R^g$;

$R^3$ is, independently at each occurrence, phenyl substituted with 0-3 $R^{3a}$ and 0-1 $R^{3d}$, naphthyl substituted with 0-3 $R^{3a}$ and 0-1 $R^{3d}$, or —$(CH_2)_r$-5- to 12-membered heterocycle comprising: carbon atoms and 1-4 heteroatoms selected from N, O, and $S(O)_p$, wherein said heterocycle is substituted with 0-3 $R^{3a}$ and 0-1 $R^{3d}$;

$R^{3a}$ is, independently at each occurrence, =O, F, Cl, Br, I, $OCF_3$, $CF_3$, —$(CH_2)_rCN$, $NO_2$, —$(CH_2)_rOR^{3b}$, —$(CH_2)_rSR^{3b}$, —$(CH_2)_rNR^7R^8$, —C(=$NR^{8a}$)$NR^8R^9$, —NHC(=$NR^{8a}$)$NR^7R^8$, —$NR^8CR^8$(=$NR^{8a}$), —$(CH_2)_rNR^8C(O)R^{3b}$, =$NR^8$, —$(CH_2)_rNR^8C(O)R^{3b}$, —$(CH_2)_rNR^8C(O)_2R^{3b}$, —$(CH_2)_rS(O)_pNR^8R^9$, —$(CH_2)_rNR^8S(O)_pR^{3c}$, —$S(O)R^{3c}$, —$S(O)_2R^{3c}$, —C(O)—$C_{1-4}$ alkyl, —$(CH_2)_rCO_2R^{3b}$, —$(CH_2)_rOC(O)R^{3b}$, —$(CH_2)_rC(O)NR^8R^9$, —$(CH_2)_rOC(O)NR^8R^9$, —$NHCOCF_3$, —$NHSO_2CF_3$, —$SO_2NHR^{3b}$, —$SO_2NHCOR^{3c}$, —$SO_2NHCO_2R^{3c}$, —$CONHSO_2R^{3c}$, —$NHSO_2R^{3c}$, —$CONHOR^{3b}$, $C_{1-4}$ haloalkyl, $C_{1-4}$ haloalkyloxy, $C_{1-6}$ alkyl substituted by $R^{3d}$, $C_{2-6}$ alkenyl substituted by $R^{3d}$, $C_{1-6}$ alkynyl substituted by $R^{3d}$, $C_{3-6}$ cycloalkyl substituted by 0-1 $R^{3d}$, —$(CH_2)_r$—$C_{3-10}$ carbocycle substituted with 0-3 $R^{3d}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

alternately, when two $R^{3a}$ groups are substituted on adjacent atoms, they can be taken together with the atoms to which they are attached to form a $C_{3-10}$ carbocycle substituted with 0-2 $R^{3d}$, or a 5- to 10-membered heterocycle comprising: carbon atoms and 1-4 heteroatoms selected from N, O, and $S(O)_p$, wherein said heterocycle is substituted with 0-2 $R^{3d}$;

$R^{3b}$ is, independently at each occurrence, H, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, —$(CH_2)_r$—$C_{3-10}$ carbocycle substituted with 0-3 $R^{3d}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3c}$ is, independently at each occurrence, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, —$(CH_2)_r$—$C_{3-10}$ carbocycle substituted with 0-3 $R^{3d}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3d}$ is, independently at each occurrence, H, =O, —$(CH_2)_rOR^a$, F, Cl, Br, CN, $NO_2$, —$(CH_2)_rNR^7R^8$, —C(O)$R^a$, —C(O)$OR^a$, —OC(O)$R^a$, —$NR^8C(O)R^c$, —C(O)$NR^8R^9$, —$S(O)_2NR^8R^9$, —$NR^8S(O)_2NR^8R^9$, —$NR^8S(O)_2R^c$, —$S(O)_pR^c$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, —$(CH_2)_r$—$C_{3-10}$ carbocycle substituted with 0-3 $R^d$, or —$(CH_2)_r$-5- to 10-membered heterocycle comprising: carbon atoms and 1-4 heteroatoms selected from N, O, and $S(O)_p$, wherein said heterocycle is substituted with 0-3 $R^d$;

$R^4$ is, independently at each occurrence, H, =O, F, Cl, Br, I, $OCF_3$, $CF_3$, CN, $NO_2$, —$(CH_2)_rOR^a$, —$(CH_2)_rSR^a$, —$(CH_2)_rC(O)R^a$, —$(CH_2)_rC(O)OR^a$, —OC(O)$R^a$, —$(CH_2)_rNR^7R^8$, —$NR^8(CH_2)_rC(O)OR^a$, —$(CH_2)_rC(O)NR^8R^9$, —$(CH_2)_rNR^8C(O)R^c$, —$(CH_2)_rNR^8C(O)_2R^b$, —$(CH_2)_rNR^8C(O)NR^8R^9$, —$S(O)_pNR^8R^9$, —$NR^8S(O)_pR^c$, —$S(O)_2R^c$, $C_{1-6}$ alkyl substituted with 0-2 $R^{4a}$, $C_{2-6}$ alkenyl substituted with 0-2 $R^{4a}$, $C_{2-6}$ alkynyl substituted with 0-2 $R^{4a}$, —$(CH_2)_r$—$C_{3-10}$ carbocycle substituted with 0-3 $R^{4b}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{4b}$;

$R^{4a}$ is, independently at each occurrence, H, F, =O, $C_{1-4}$ alkyl, $OR^a$, $SR^a$, $CF_3$, CN, $NO_2$, —C(O)$R^a$, —C(O)$OR^a$, —$NR^7R^8$, —C(O)$NR^8R^9$, —$NR^7C(O)R^c$, —$S(O)_pNR^8R^9$, —$NR^8S(O)_pR^c$, —$S(O)R^c$, or —$S(O)_2R^c$;

$R^{4b}$ is, independently at each occurrence, H, =O, =$NR^8$, F, Cl, Br, I, $OR^a$, $SR^a$, CN, $NO_2$, —$NR^7R^8$, —C(O)$R^a$, —C(O)$OR^a$, —$NR^7C(O)R^b$, —$NR^7C(O)OR^c$, —C(O)$NR^8R^9$, —$SO_2NR^8R^9$, —$S(O)_2R^c$, $C_{1-6}$ alkyl, $C_{2-6}$ alkenyl, $C_{2-6}$ alkynyl, $C_{3-6}$ cycloalkyl, $C_{1-4}$ haloalkyl, or $C_{1-4}$ haloalkyloxy;

alternately, $R^3$ and $R^4$ groups when located on adjacent atoms, can be taken together to form a $C_{3-10}$ carbocycle substituted with 0-2 $R^{3d}$ or a 5- to 10-membered heterocycle comprising: carbon atoms and 1-4 heteroatoms selected from N, O, and $S(O)_p$, wherein said heterocycle is substituted with 0-2 $R^{3d}$;

$R^6$ is, independently at each occurrence, H, $C_{1-6}$ alkyl substituted with 0-3 $R^d$, —$(CH_2)_r$-phenyl substituted with 0-3 $R^d$;

$R^7$ is, independently at each occurrence, H, $C_{1-6}$ alkyl, —$(CH_2)_n$—$C_{3-10}$ carbocycle, —$(CH_2)_n$-(5- to 10-membered heteroaryl), —C(O)$R^c$, —CHO, —C(O)$_2R^c$, —$S(O)_2R^c$, —CON$R^8R^c$, —OCONH$R^c$, —C(O)O—$(C_{1-4}$ alkyl)OC(O)—$(C_{1-4}$ alkyl), or —C(O)O—$(C_{1-4}$ alkyl)OC(O)—$(C_{6-10}$ aryl); wherein said alkyl, carbocycle, heteroaryl, and aryl are substituted with 0-2 $R^f$; wherein said heteroaryl comprises: carbon atoms and 1-4 heteroatoms selected from N, O, and $S(O)_p$;

$R^8$ is, independently at each occurrence, H, $C_{1-6}$ alkyl, —$(CH_2)_n$-phenyl, or —$(CH_2)_n$-5- to 10-membered heterocycle comprising: carbon atoms and 1-4 heteroatoms selected from N, O, and $S(O)_p$; wherein said alkyl, phenyl and heterocycle are optionally substituted with 0-2 $R^f$;

alternatively, $R^7$ and $R^8$, when attached to the same nitrogen, combine to form a 5- to 10-membered heterocycle comprising: carbon atoms and 0-3 additional heteroatoms selected from N, O, and $S(O)_p$, wherein said heterocycle is substituted with 0-2 $R^f$;

$R^{8a}$ is, independently at each occurrence, $R^7$, OH, $C_{1-6}$ alkyl, $C_{1-4}$ alkoxy, ($C_{6-10}$ aryl)-$C_{1-4}$ alkoxy, —$(CH_2)_n$-phenyl, —(CH$_2$)$_n$-(5- to 10-membered heteroaryl); wherein said phenyl, aryl and heteroaryl are optionally substituted with 0-2 R$^f$;

R$^9$ is, independently at each occurrence, H, C$_{1-6}$ alkyl, or —(CH$_2$)$_n$-phenyl; wherein said alkyl and phenyl are optionally substituted with 0-2 R$^f$;

alternatively, R$^8$ and R$^9$, when attached to the same nitrogen, combine to form a 5- to 12-membered heterocycle comprising: carbon atoms and 0-2 additional heteroatoms selected from N, O, and S(O)$_p$, wherein said heterocycle is substituted with 0-2 R$^d$;

R$^{11}$ is C$_{1-4}$ haloalkyl, —C(O)NR$^8$R$^9$, —CH$_2$C(O)NR$^8$R$^9$, —CH$_2$CH$_2$C(O)NR$^8$R$^9$, —C(O)R$^a$, —CH$_2$C(O)R$^a$, —CH$_2$CH$_2$C(O)R$^a$, —C(O)OR$^a$, —CH$_2$C(O)OR$^a$, —CH$_2$CH$_2$C(O)OR$^a$, C$_{1-6}$ alkyl substituted with 0-3 R$^{11c}$, C$_{2-6}$ alkenyl substituted with 0-3 R$^{11a}$; C$_{2-6}$ alkynyl substituted with 0-3 R$^{11a}$, —(CH$_2$)$_s$—C$_{3-7}$ cycloalkyl substituted with 0-2 R$^{11b}$, —(CH$_2$)$_s$-phenyl substituted with 0-3 R$^{11b}$, —(CH$_2$)$_s$-naphthyl substituted with 0-3 R$^{11b}$, or —(CH$_2$)$_s$-5- to 10-membered heterocycle comprising: carbon atoms and 1-4 heteroatoms selected from N, O, and S(O)$_p$, wherein said heterocycle is substituted with 0-3 R$^{11b}$;

R$^{11a}$ is, independently at each occurrence, H, =O, C$_{1-4}$ alkyl, OR$^a$, SR$^a$, F, CF$_3$, CN, NO$_2$, —NR$^7$R$^8$, —C(O)R$^a$, —C(O)OR$^a$, —C(O)NR$^8$R$^9$, —NR$^8$C(O)R$^c$, —NR$^8$C(O)OR$^c$, —NR$^8$CHO, —S(O)$_p$NR$^8$R$^9$, —NR$^8$S(O)$_p$R$^c$, —S(O)$_p$R$^c$, C$_{3-6}$ cycloalkyl, C$_{1-4}$ haloalkyl, C$_{1-4}$ haloalkyloxy, —(CH$_2$)$_r$—C$_{3-10}$ carbocycle substituted with 0-3 R$^d$, or —(CH$_2$)$_r$-5- to 10-membered heterocycle comprising carbon atoms and 1-4 heteroatoms selected from N, O, and S(O)$_p$, and substituted with 0-3 R$^d$;

R$^{11b}$ is, independently at each occurrence, H, =O, =NR$^8$, OR$^a$, SR$^a$, F, Cl, Br, CN, NO$_2$, CF$_3$, OCF$_3$, OCHF$_2$, —NR$^7$R$^8$, —C(O)R$^a$, —C(O)OR$^a$, —C(O)NR$^8$R$^9$, —NR$^8$C(O)R$^c$, —NR$^8$C(O)$_2$R$^c$, —S(O)$_p$NR$^8$R$^9$, —NR$^8$S(O)$_p$R$^c$, —S(O)$_p$R$^c$, C$_{1-6}$ alkyl, C$_{2-6}$ alkenyl, C$_{2-6}$ alkynyl, C$_{3-6}$ cycloalkyl, C$_{1-4}$ haloalkyl, C$_{1-4}$ haloalkyloxy, —(CH$_2$)$_r$—C$_{3-10}$ carbocycle substituted with 0-3 R$^d$, or —(CH$_2$)$_r$-5- to 10-membered heterocycle comprising carbon atoms and 1-4 heteroatoms selected from N, O, and S(O)$_p$, and substituted with 0-3 R$^d$;

alternately, when two R$^{11b}$ groups are substituents on adjacent atoms they may be taken together with the atoms to which they are attached to form a 5- to 7-membered heterocycle comprising carbon atoms and 1-4 heteroatoms selected from N, O, and S(O)$_p$ and substituted with 0-2 R$^g$;

R$^{11c}$ is, independently at each occurrence H, =O, OR$^a$, SR$^a$, F, CF$_3$, CN, NO$_2$, —NR$^7$R$^8$, —NR$^8$C(O)R$^c$, —NR$^8$C(O)OR$^c$, —NR$^8$CHO, —S(O)$_p$NR$^8$R$^9$, —NR$^8$S(O)$_p$R$^c$, —S(O)$_p$R$^c$, C$_{1-4}$ alkyl, C$_{3-6}$ cycloalkyl, C$_{1-4}$ haloalkyl, C$_{1-4}$ haloalkyloxy, —(CH$_2$)$_r$—C$_{3-10}$ carbocycle substituted with 0-3 R$^d$, or —(CH$_2$)$_r$-5- to 10-membered heterocycle comprising carbon atoms and 1-4 heteroatoms selected from N, O, and S(O)$_p$, and substituted with 0-3 R$^d$;

R$^a$ is, independently at each occurrence, H, CF$_3$, C$_{1-6}$ alkyl, —(CH$_2$)$_r$—C$_{3-7}$ cycloalkyl, —(CH$_2$)$_r$—C$_{6-10}$ aryl, or —(CH$_2$)$_r$-5- to 10-membered heterocycle comprising: carbon atoms and 1-4 heteroatoms selected from N, O, and S(O)$_p$; wherein said cycloalkyl, aryl and heterocycle groups are optionally substituted with 0-2 R$^f$;

R$^b$ is, independently at each occurrence, CF$_3$, OH, C$_{1-4}$ alkoxy, C$_{1-6}$ alkyl, —(CH$_2$)$_r$—C$_{3-10}$ carbocycle substituted with 0-3 R$^d$, or —(CH$_2$)$_r$-5- to 10-membered heterocycle comprising: carbon atoms and 1-4 heteroatoms selected from N, O, and S(O)$_p$ and substituted with 0-2 R$^d$;

R$^c$ is, independently at each occurrence, CF$_3$, C$_{1-6}$ alkyl substituted with 0-2 R$^f$, C$_{3-6}$ cycloalkyl substituted with 0-2 R$^f$, C$_{6-10}$ aryl, 5- to 10-membered heteroaryl, (C$_{6-10}$ aryl)-C$_{1-4}$ alkyl, or (5- to 10-membered heteroaryl)-C$_{1-4}$ alkyl, wherein said aryl is substituted with 0-3 R$^f$ and said heteroaryl comprises: carbon atoms and 1-4 heteroatoms selected from N, O, and S(O)$_p$ and substituted with 0-3 R$^f$;

R$^d$ is, independently at each occurrence, H, =O, =NR$^8$, OR$^a$, F, Cl, Br, I, CN, NO$_2$, —NR$^7$R$^8$, —C(O)R$^a$, —C(O)OR$^a$, —OC(O)R$^a$, —NR$^8$C(O)R$^c$, —C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl substituted with 0-2 R$^e$, C$_{2-6}$ alkenyl substituted with 0-2 R$^e$, or C$_{2-6}$ alkynyl substituted with 0-2 R$^e$;

R$^e$ is, independently at each occurrence, =O, OR$^a$, F, Cl, Br, I, CN, NO$_2$, —NR$^7$R$^8$, —C(O)R$^a$, —C(O)OR$^a$, —NR$^8$C(O)R$^c$, —C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

R$^f$ is, independently at each occurrence, H, =O, —(CH$_2$)$_r$OR$^g$, F, Cl, Br, I, CN, NO$_2$, —NR$^g$R$^g$, —C(O)R$^g$, —C(O)OR$^g$, —NR$^g$C(O)R$^g$, —C(O)NR$^g$R$^g$, —SO$_2$NR$^g$R$^g$, —NR$^g$SO$_2$NR$^g$R$^g$, —NR$^g$SO$_2$—C$_{1-4}$ alkyl, —NR$^g$SO$_2$CF$_3$, —NR$^g$SO$_2$-phenyl, —S(O)$_2$CF$_3$, —S(O)$_p$—C$_{1-4}$ alkyl, —S(O)$_p$-phenyl, —(CH$_2$)$_n$-phenyl, —(CF$_2$)$_r$CF$_3$, C$_{1-6}$ alkyl, C$_{2-6}$ alkenyl, C$_{2-6}$ alkynyl, —(CH$_2$)$_n$-phenyl, or —(CH$_2$)$_n$-5- to 10-membered heterocycle comprising carbon atoms and 1-4 heteroatoms selected from N, O, and S(O)$_p$;

alternately, when two R$^f$ groups are substituents on adjacent atoms they may be taken together with the atoms to which they are attached to form a 5-7-membered heterocycle comprising carbon atoms and 1-4 heteroatoms selected from N, O, and S(O)$_p$ and substituted with 0-2 R$^g$;

R$^g$ is, independently at each occurrence, H, C$_{1-6}$ alkyl, or —(CH$_2$)$_n$-phenyl;

n, at each occurrence, is selected from 0, 1, 2, 3, and 4;

p, at each occurrence, is selected from 0, 1, and 2; and r, at each occurrence, is selected from 0, 1, 2, 3, and 4; and s, at each occurrence, is selected from 1, 2, 3, and 4;

provided that: when R$^{11}$ is —CH$_2$CO$_2$H, A is other than substituted piperidyl (J. Med. Chem. (1999), 42(25), 5254-5265).

In a second aspect, the present invention includes a compound of Formula (I), or stereoisomers, tautomers, pharmaceutically acceptable salts, solvates, or prodrugs thereof, within the scope of the first aspect wherein:

the group

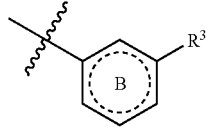

is selected from:

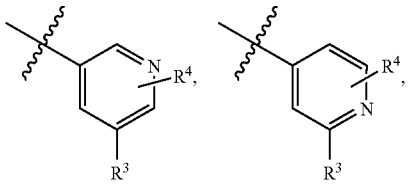

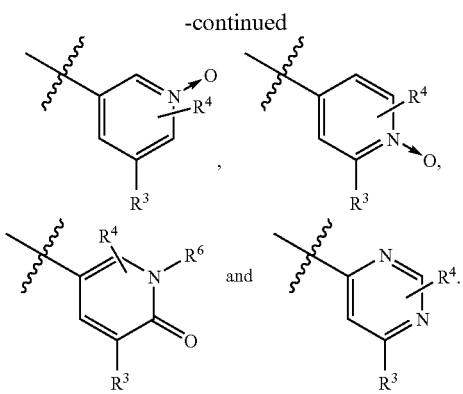

In a third aspect, the present invention includes a compound of Formula (I), or stereoisomers, tautomers, pharmaceutically acceptable salts, solvates, or prodrugs thereof, within the scope of the first or second aspect wherein:

$R^4$ is, independently at each occurrence, H, Me, Et, Pr, F, Cl, Br, I, $OCF_3$, $CF_3$, CN, $NO_2$, $-(CH_2)_rOH$, $-(CH_2)_rC(O)OR^a$, $OR^a$, $SR^a$, $-C(O)R^a$, $-C(O)OR^a$, $-NR^7R^8$, $-(CH_2)_r$ $NH_2$, $-NR^8(CH_2)_rC(O)OR^a$, $-(CH_2)_rC(O)NR^8R^9$, $-NR^8C(O)R^c$, $-NR^8C(O)OR^c$, $-NR^8C(O)NR^8R^9$, $-S(O)_pNR^8R^9$, $-NR^8S(O)_pR^c$, $-S(O)_pR^c$ or phenyl substituted with 0-2 $R^{4b}$;

$R^{4b}$ is, independently at each occurrence, H, F, Cl, Br, I, $OR^a$, $SR^a$, CN, $NO_2$, $-NR^7R^8$, $-C(O)R^a$, $-C(O)OR^a$, $-NR^7C(O)R^b$, $-NR^7C(O)OR^c$, $-C(O)NR^8R^9$, $-SO_2NR^8R^9$, $-S(O)_2R^c$, $C_{1-4}$ alkyl, $C_{3-6}$ cycloalkyl, $C_{1-4}$ haloalkyl, or $C_{1-4}$ haloalkyloxy; and $R^{11}$ is $C_{1-4}$ haloalkyl, $-CH_2C(O)NR^8R^9$, $-CH_2CH_2C(O)NR^8R^9$, $-CH_2C(O)R^a$, $-CH_2CH_2C(O)R^a$, $-CH_2C(O)OR^a$, $-CH_2CH_2C(O)OR^a$, $C_{1-6}$ alkyl substituted with 0-2 $R^{11c}$, $C_{2-6}$ alkenyl substituted with 0-2 $R^{11a}$, $C_{2-6}$ alkynyl substituted with 0-2 $R^{11a}$, $-(CH_2)_r$-$C_{3-10}$ carbocycle substituted with 0-3 $R^{11b}$, or $-(CH_2)_r$-5- to 10-membered heterocycle comprising: carbon atoms and 1-4 heteroatoms selected from N, O, and $S(O)_p$, wherein said heterocycle is substituted with 0-3 $R^{11b}$.

In a fourth aspect, the present invention includes a compound of Formula (I), or stereoisomers, tautomers, pharmaceutically acceptable salts, solvates, or prodrugs thereof, within the scope of the first or second aspect wherein:

$R^1$ is, independently at each occurrence, F, Cl, Br, I, $OCF_3$, $CF_3$, $OCH_3$, $CH_3$, Et, $NH_2$, $-C(=NH)NH_2$, $-C(O)NH_2$, $-CH_2NH_2$, or $-SO_2NH_2$;

$R^2$ is, independently at each occurrence, F, Cl, Br, $CF_3$, $NO_2$, $-(CH_2)_rOR^a$, $-(CH_2)_rSR^a$, $-C(O)OR^a$, $-C(O)NR^8R^9$, $-NR^8C(O)R^c$, $-NR^8C(O)OR^c$, $-NR^8C(O)NR^8R^c$, $-S(O)_pNR^8R^9$, $-NR^8SO_2R^c$, $-NR^7R^8$, $-S(O)R^c$, $-S(O)_2R^c$, $C_{1-6}$ alkyl substituted with 0-1 $R^{2a}$, or a 5-7 membered heterocycle comprising carbon atoms and 1-4 heteroatoms selected from N, O, and $S(O)_p$, wherein said heterocycle is substituted with 0-2 $R^{2b}$;

alternately, when $R^1$ and $R^2$ groups are substituents on adjacent atoms they may be taken together with the atoms to which they are attached to form a 5- to 7-membered carbocycle or heterocycle comprising carbon atoms and 0-4 heteroatoms selected from N, O, and $S(O)_p$ and substituted with 0-2 $R^g$;

$R^3$ is, independently at each occurrence, phenyl substituted with 0-2 $R^{3a}$ and 0-1 $R^{3d}$, naphthyl substituted with 0-2 $R^{3a}$ and 0-1 $R^{3d}$, or a 5- to 12-membered heterocycle substituted with 0-2 $R^{3a}$ and 0-1 $R^{3d}$, wherein said heterocycle is selected from: thiophene, furan, thiazole, tetrazole, pyridine, pyridone, pyrimidine, pyrrole, pyrazole, indole, 2-oxindole, isoindoline, indazole, 7-azaindole, benzofuran, benzothiophene, benzimidazole, benzisoxazole, benzoxazole, quinazoline, quinoline, isoquinoline, quinoxaline, phthalazine, dihydrophthalazine, dihydroisoquinoline, dihydroquinoline, dihydroquinolone, dihydroindole, dihydrobenzimidazole, dihydrobenzoxazine, dihydroquinazoline, dihydroquinoxaline, benzothiazine, benzoxazine, tetrahydrobenzazepine, dihydroazabenzocycloheptene, and tetrahydroquinoline;

$R^{3a}$ is, independently at each occurrence, =O, F, Cl, Br, Me, CN, OH, OMe, $-OC(O)(t-Bu)$, $-CH_2OMe$, $CF_3$, COMe, $CO_2H$, $CO_2Me$, $-CH_2CO_2H$, $-(CH_2)_2CO_2H$, $-CH_2CO_2Me$, $-CH_2CO_2Et$, $-CH_2CH_2CO_2Et$, $-CH_2CN$, $NH_2$, $-CH_2NH_2$, $-CH_2NMe_2$, $-NHCOMe$, $-NHCO_2Me$, $-NHCO_2Et$, $-NHCO_2(i-Pr)$, $-NHCO_2(1-Bu)$, $-NHCO_2(t-Bu)$, $-NHCO_2Bn$, $-NHCH_2CH_2CO_2H$, $-NHCO_2CH_2CH_2OMe$, $-NHCO_2CH_2CH_2CH_2OMe$, $-NHCO_2CH_2CO_2H$, $-NHCO_2CH_2CH_2CO_2H$, $-NHCO_2CH_2CH_2OH$, $-NHCO_2CH_2CH_2NH_2$, $-NHCO_2CH_2$-tetrahydrofuran-2-yl, $-NHCO_2CH_2CH_2$-morpholino, $-CH_2NHCO_2Me$, $-NHC(O)NHMe$, $-NHC(O)N(Me)_2$, 4-[(1-carbamoyl-cyclopropanecarbonyl)-amino]-, $-NHSO_2Me$, $-SO_2NH_2$, $SO_2NHMe$, $-SO_2NHCH_2CH_2OH$, $-CONH_2$, $-CONHMe$, $-CON(Me)_2$, $-C(O)NHCH_2CH_2OMe$, $-CH_2CONH_2$, $-CO(N-morpholino)$, $-NHCH_2CH_2(N-morpholino)$, $-NR^7R^8$, $-NH(1H-imidazol-2-yl)$, 1H-tetrazol-5-yl, tetrazol-1-yl, pyrimidin-5-yl, or N-morpholino;

$R^4$ is, independently at each occurrence, H, F, Cl, Br, OMe, OH, $NH_2$, NHMe, NHEt, NHPr, Me, Et, Pr, 4-(methoxycarbonylamino)phenyl, CN, $CF_3$, $-CH_2OH$, $-(CH_2)_2OH$, $-(CH_2)_3OH$, $-CH_2NH_2$, $-(CH_2)_2NH_2$, $-(CH_2)_3NH_2$, $CO_2H$, $-C(O)NH_2$, $-C(O)NHMe$, $-C(O)N(Me)_2$, $-CH_2CO_2H$, $-CH_2C(O)NH_2$, $-CH_2CH_2CO_2H$, $-NHC(O)Me$, $-NHCO_2Me$, $-NHC(O)NHMe$, $-NHC(O)N(Me)_2$, $-NHCH_2CO_2H$, $-NHSO_2Me$, $-SO_2NH_2$, $-SO_2NHMe$, or $-SO_2N(Me)_2$; and $R^{11}$ is $C_{1-4}$ haloalkyl, $-CH_2C(O)NR^8R^9$, $-CH_2CH_2C(O)NR^8R^9$, $-CH_2C(O)R^a$, $-CH_2CH_2C(O)R^a$, $-CH_2C(O)OR^a$, $-CH_2CH_2C(O)OR^a$, $C_{1-6}$ alkyl substituted with 0-2 $R^{11c}$, $-(CH_2)_r$-$C_{3-7}$ cycloalkyl substituted with 0-2 $R^{11b}$, $-(CH_2)_r$-indanyl substituted with 0-2 $R^{11b}$, $-(CH_2)_r$-indenyl substituted with 0-2 $R^{11b}$, $-(CH_2)_r$-phenyl substituted with 0-2 $R^{11b}$, $-(CH_2)_r$-naphthyl substituted with 0-2 $R^{11b}$, or $-(CH_2)_r$-5- to 10-membered heterocycle comprising carbon atoms and 1-4 heteroatoms selected from N, O, and $S(O)_p$, wherein said heterocycle is substituted with 0-2 $R^{11b}$.

In a fifth aspect, the present invention includes a compound of Formula (I), or stereoisomers, tautomers, pharmaceutically acceptable salts, solvates, or prodrugs thereof, within the scope of the first aspect wherein:

A is substituted with 0-1 $R^1$ and 0-3 $R^2$ and selected from: $C_{3-7}$ cycloalkyl, phenyl, naphthyl, pyridyl, 1,2,3,4-tetrahydronaphthyl, pyrrolidinyl, indazolyl, indolyl, imidazolyl, furanyl, thienyl, benzimidazolyl, benzisoxazolyl, benzothiazolyl, benzothiophenyl, 3,4-methylenedioxy-phenyl, oxazolyl, isoxazolyl, thiazolyl, isothiazolyl, pyrazolyl, quinolinyl, isoquinolinyl, 1H-4-oxo-isoquinazolinyl, 2H-1-oxo-isquinilinyl, 3H-4-oxo-quinazolinyl, 3,4-dihydro-2H-1-oxo-isoquinolinyl, 2,3-dihydro-isoindolinyl, 5,6,7,8-tetrahydroquinolinyl, 1,2,3,4-tetrahydroquinolinyl, 5,6,7,8-tetrahydroisoquinolinyl, 1,2,3,4-tetrahydroisoquinolinyl, quinazolinyl, and phthalazinyl;

provided that A is other than a thienyl substituted with halogen, $C_{1-6}$ alkyl, $C_{2-6}$ alkenyl, or $C_{2-6}$ alkynyl;

the group

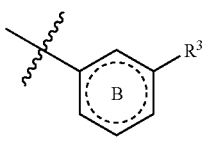

is selected from:

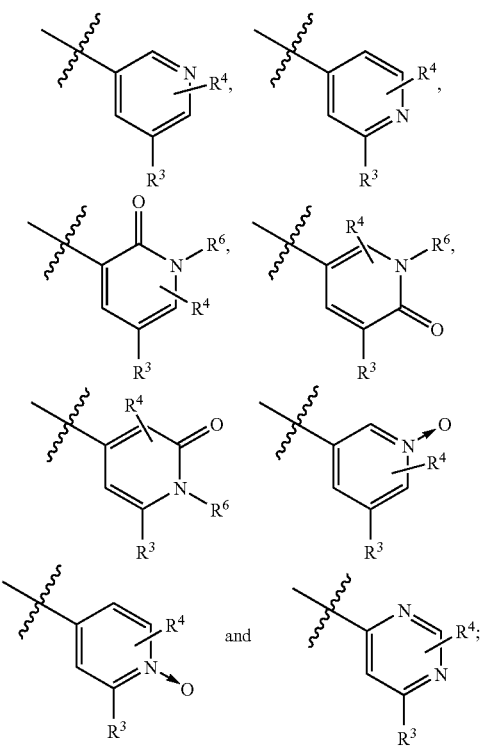

$R^1$ is, independently at each occurrence, F, Cl, Br, $CF_3$, $NH_2$, —$CH_2NH_2$, —C(=NH)$NH_2$, —C(O)$NH_2$, —$SO_2NH_2$, $SR^a$, $OR^a$, or $C_{1-6}$ alkyl substituted with 0-1 $R^{1a}$;

$R^2$ is, independently at each occurrence, =O, F, Cl, Br, $CF_3$, Me, Et, $OR^a$, CN, $NO_2$, $NR^7R^8$, —$CH_2$OMe, —$SR^a$, —$CH_2$SMe, —C(O)$OR^a$, —$CH_2NR^7R^8$, —$SO_2NH_2$, —$SO_2$Me, —$NHSO_2R^c$, —$CH_2NHSO_2R^c$, —C(O)$NR^8R^9$, —NHC(O)$R^c$, —$CH_2$NHC(O)$R^c$, —NHC(O)$OR^c$, —$CH_2$NHC(O)$OR^c$, —NHC(O)$NHR^c$, —$CH_2$NHC(O)$NHR^c$, or a 5-7 membered heterocycle substituted with 0-2 $R^{2b}$ and selected from: pyrrolidinyl, 2-oxo-1-pyrrolidinyl, piperidinyl, pyrazolyl, triazolyl, or tetrazolyl;

alternately, when $R^1$ and $R^2$ groups are substituents on adjacent atoms they may be taken together with the atoms to which they are attached to form a 5- to 6-membered heterocycle comprising carbon atoms and 0-4 heteroatoms selected from N, O, and $S(O)_p$;

$R^3$ is, independently at each occurrence, phenyl substituted with 0-2 $R^{3a}$, naphthyl substituted with 0-2 $R^{3a}$, or a 5- to 12-membered heterocycle comprising: carbon atoms and 1-2 heteroatoms selected from N, O, and $S(O)_p$, wherein said heterocycle is substituted with 0-2 $R^{3a}$;

$R^{3a}$ is, independently at each occurrence, =O, F, Cl, Br, Me, CN, OH, OMe, O(t-Bu), OBn, $CF_3$, —$CH_2$OH, —$CH_2$OMe, $CF_3$, COMe, $CH_2$CN, $CO_2H$, $CO_2$Me, —$CH_2CO_2H$, —$(CH_2)_2CO_2H$, —$CH_2CO_2$Me, —$CH_2CO_2$Et, —$CH_2CH_2CO_2$Et, —OC(O)(t-Bu), —NHCOMe, —$NHCO_2$Me, —$NHCO_2$Et, —$NHCO_2$(i-Pr), —$NHCO_2$(1-Bu), —$NHCO_2$(t-Bu), —$NHCO_2$Bn, —$NHCH_2CH_2CO_2H$, —$NHCO_2CH_2CH_2CO_2H$, —$NHCO_2CH_2CH_2$OH, —$NHCO_2CH_2CH_2NH_2$, —$NHCO_2CH_2CH_2$OMe, —$CHCO_2CH_2CH_2CH_2$OMe, —C(=NH)$NH_2$, —$SO_2$Me, —$SO_2NH_2$, —$NHSO_2$Me, —$CH_2NHCO_2$Me, —C(O)$NHCH_2CH_2$OMe, —$SO_2NHCH_2CH_2$OH, —NHC(O)$NR^8R^9$, —$NR^7R^8$, —$CH_2NR^7R^8$, —$S(O)_pNR^8R^9$, —C(O)$NR^8R^9$, —$CH_2$C(O)$NR^8R^9$, —$NHCH_2CH_2$(N-morpholino), —NH(1H-imidazol-2-yl), —CO(N-morpholino), —$NHCO_2CH_2$-tetrahydrofuran-2-yl, —$NHCO_2CH_2CH_2$-morpholino, 4-[(1-carbamoyl-cyclopropanecarbonyl)-amino]-, 2-oxo-piperidin-1-yl, phenyl substituted with 0-1 $R^{3d}$, or —$(CH_2)_r$-5- to 6-membered heterocycle comprising: carbon atoms and 1-4 heteroatoms selected from N, O, and $S(O)_p$, wherein said heterocycle is substituted with 0-1 $R^{3d}$;

alternatively, when two of $R^{3a}$ groups located on adjacent atoms, they can be taken together with the atoms to which they are attached to form a 5- to 10-membered heterocycle comprising: carbon atoms and 1-4 heteroatoms selected from N, O, and $S(O)_p$, wherein said heterocycle is substituted with 0-2 $R^{3d}$;

$R^4$ is, independently at each occurrence, H, F, Cl, Br, OMe, OH, $NH_2$, NHMe, NHEt, NHPr, Me, Et, Pr, 4-(methoxycarbonylamino)phenyl, CN, $CF_3$, —$CH_2$OH, —$(CH_2)_2$OH, —$(CH_2)_3$OH, —$CH_2NH_2$, —$(CH_2)_2NH_2$, —$(CH_2)_3NH_2$, $CO_2H$, —C(O)$NH_2$, —C(O)NHMe, —C(O)N(Me)$_2$, —$CH_2CO_2H$, —$CH_2$C(O)$NH_2$, —$CH_2CH_2CO_2H$, —NHC(O)Me, —$NHCO_2$Me, —NHC(O)NHMe, —NHC(O)N(Me)$_2$, —$NHCH_2CO_2H$, —$NHSO_2$Me, —$SO_2NH_2$, —$SO_2$NHMe, or —$SO_2$N(Me)$_2$;

$R^6$ is H, or $C_{1-4}$ alkyl;

$R^{11}$ is $C_{1-4}$ haloalkyl, —$CH_2$C(O)$NR^8R^9$, —$CH_2CH_2$C(O)$NR^8R^9$, —$CH_2$C(O)$R^a$, —$CH_2CH_2$C(O)$R^a$, —$CH_2$C(O)$OR^a$, —$CH_2CH_2$C(O)$OR^a$, —$CH_2$OBn, —$CH_2$SBn, $C_{1-6}$ alkyl substituted with 0-2 $R^{11c}$, $C_{2-6}$ alkenyl substituted with 0-2 $R^{11a}$, $C_{2-6}$ alkynyl substituted with 0-2 $R^{11a}$, —$(CH_2)_r$—$C_{3-7}$ cycloalkyl substituted with 0-2 $R^{11b}$, —$(CH_2)_r$-phenyl substituted with 0-2 $R^{11b}$, —$(CH_2)_r$-indanyl substituted with 0-2 $R^{11b}$, —$(CH_2)_r$-indenyl substituted with 0-2 $R^{11b}$, —$(CH_2)_r$-naphthyl substituted with 0-2 $R^{11b}$, or —$(CH_2)_r$-5- to 10-membered heteroaryl substituted with 0-2 $R^{11b}$ and selected from thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, indolinyl, isoindolinyl, benzimidazolyl, benzothiazolyl, benzotriazolyl, quinolinyl, isoquinolinyl, tetrahydroquinolinyl, tetrahydroisoquinolinyl, and 2,2-dioxo-2,3-dihydro-1H-$2\lambda^6$-benzo[c]thiophenyl; and $R^{11b}$ is, independently at each occurrence, H, =O, F, Cl, Br, $CF_3$, OMe, OEt, O(i-Pr), $OCF_3$, $OCHF_2$, CN, OPh, OBn, $NO_2$, $NH_2$, —C(O)$R^a$, —C(O)$OR^a$, —C(O)$NR^7R^8$, —$NR^8$C(O)$R^c$, —$NR^8$C(O)$_2R^c$, —$S(O)_pNR^8R^9$, —$NR^8S(O)_pR^c$, —$S(O)_pR^c$, $C_{1-6}$ alkyl, or —$(CH_2)_r$—$C_{3-10}$ carbocycle substituted with 0-3 $R^d$; and alternatively, when two $R^{11b}$ groups are substituents on adjacent atoms they may be taken together with the atoms to which they are attached to form a 5- to 7-membered heterocycle comprising carbon atoms and 1-4 heteroatoms selected from N, O, and $S(O)_p$ and substituted with 0-2 $R^g$.

In a sixth aspect, the present invention includes compounds of Formula (I) or its stereoisomers, tautomers, pharmaceutically acceptable salts, solvates, or prodrugs thereof, within the scope of any of the first, second and fifth aspects wherein:

A is 4-aminomethyl-cyclohexyl, 4-methylcyclohexyl, 4-methylphenyl, 3-methoxyphenyl, 4-methoxyphenyl, 4-aminomethylphenyl, 3-carbamoylphenyl, 4-carbamoylphenyl, 3-amidinophenyl, 4-amidinophenyl, 2-fluoro-4-methylphenyl, 2,6-difluoro-4-methylphenyl, 2-fluoro-4-methoxyphenyl, 2,6-difluoro-4-methoxyphenyl, 2-fluoro-4-aminomethylphenyl, 2-fluoro-4-carbamoylphenyl, 2-chloro-4-carbamoylphenyl, 2-methoxy-4-carbamoylphenyl, 4-amino-2-fluorophenyl, 4-amino-2,6-difluoromethylphenyl, 4-amino-3-chloro-2,6-difluorophenyl, 4-amino-3-chlorophenyl, 1,2,3,4-tetrahydronaphth-2-yl, 5-chlorothien-2-yl, indol-5-yl, indol-6-yl, indazol-6-yl, 3-amino-indazol-6-yl, 3-amino-indazol-5-yl, 1-methyl-3-amino-indazol-6-yl, 3-amino-benzisoxazol-6-yl, benzimidazol-5-yl, 6-fluoro-benzimidazol-5-yl, 1,2,3,4-tetrahydroisoquinolin-6-yl, 1,2,3,4-tetrahydroisoquinolin-3-yl, 1,2,3,4-tetrahydroisoquinolin-1-on-6-yl, 2H-isoquinolin-1-on-6-yl, isoquinolin-6-yl, 1-amino-isoquinolin-6-yl, 1-amino-3-methyl-isoquinolin-6-yl, 1-amino-5,6,7,8-tetrahydroisoquinolin-6-yl, or 4-amino-quinazolin-7-yl, 3H-quinazolin-4-on-7-yl;

$R^3$ is, independently at each occurrence, phenyl, 3-biphenyl, 4-biphenyl, 3-aminophenyl, 4-aminophenyl, 3-N,N-dimethylaminophenyl, 4-phenoxyphenyl, 4-benzyloxyphenyl, 4-(t-butoxymethyl)-phenyl, 4-methylsulfonylphenyl, 3-cyanophenyl, 4-cyanophenyl, 3-fluorophenyl, 4-fluorophenyl, 3-chlorophenyl, 4-chlorophenyl, 3-bromophenyl, 4-bromophenyl, 3-hydroxyphenyl, 4-hydroxyphenyl, 2-methoxyphenyl, 3-methoxyphenyl, 4-methoxyphenyl, 3-trifluoromethylphenyl, 4-trifluoromethylphenyl, 3-carboxyphenyl, 4-carboxyphenyl, 3-methoxycarbonylphenyl, 4-methoxycarbonylphenyl, 3-carboxymethylphenyl, 4-carboxymethylphenyl, 4-methoxycarbonylmethylphenyl, 3-ethoxycarbonylmethylphenyl, 4-ethoxycarbonylmethylphenyl, 4-ethoxycarbonylethylphenyl, 3-carbamoylphenyl, 4-carbamoylphenyl, 3-aminocarbonylmethylphenyl, 4-aminocarbonylmethylphenyl, 4-methylaminocarbonylphenyl, 4-dimethylaminocarbonylmethylphenyl, 4-amidinophenyl, 3-methylcarbonylaminophenyl, 4-methylcarbonylaminophenyl, 4-methoxycarbonylaminophenyl, 4-aminosulfonylphenyl, 3-methylsulfonylaminophenyl, 4-methylsulfonylamino, 2,4-difluorophenyl, 3-fluoro-4-cyanophenyl, 4-amino-3-carboxyphenyl, 4-amino-3-methoxycarbonylphenyl, 2,4-dichlorophenyl, 3-cyano-5-fluorophenyl, 3-fluoro-4-carbamoylphenyl, 3-carboxy-4-cyanophenyl, 3-phenyl-4-carbamoylphenyl, 4-(2-oxo-1-piperidino)-phenyl, thiazol-2-yl, thien-2-yl, 4-methoxycarbonyl-thiazol-2-yl, 4-carbamoyl-thiazol-2-yl, 1-benzyl-pyazol-4-yl, 5-phenyl-oxazol-2-yl, 5-carbamoyl-thien-2-yl, 5-carboxy-thien-2-yl, pyrid-2-yl, pyrid-3-yl, pyrid-4-yl, 6-amino-pyrid-3-yl, benzimidazol-2-yl, 6-methoxy-pyrid-3-yl, 1-methyl-benzimidazol-2-yl, benzoxazol-2-yl, benzothiazol-2-yl, 3-amino-benzisoxazol-6-yl, 3-amino-benzisoxazol-5-yl, indazol-5-yl, indazol-6-yl, 3-amino-indazol-5-yl, 3-hydroxy-indazol-5-yl, 3-amino-indazol-6-yl, 3-amino-1-methyl-indazol-6-yl, 3-amino-4-fluoro-indazol-6-yl, 3-amino-5-fluoro-indazol-6-yl, 3-amino-7-fluoro-indazol-6-yl, 4-imino-3,4-dihydro-2H-phthalazin-1-on-7-yl, 3-(5-tetrazolyl)-phenyl, 2,3-dihydro-isoindol-1-on-6-yl, quinolin-5-yl, quinolin-6-yl, quinolin-8-yl, isoquinolin-5-yl, 2H-isoquinolin-1-on-6-yl, 2,4-diaminoquinazolin-7-yl, 4-$NH_2$-quinazolin-7-yl,

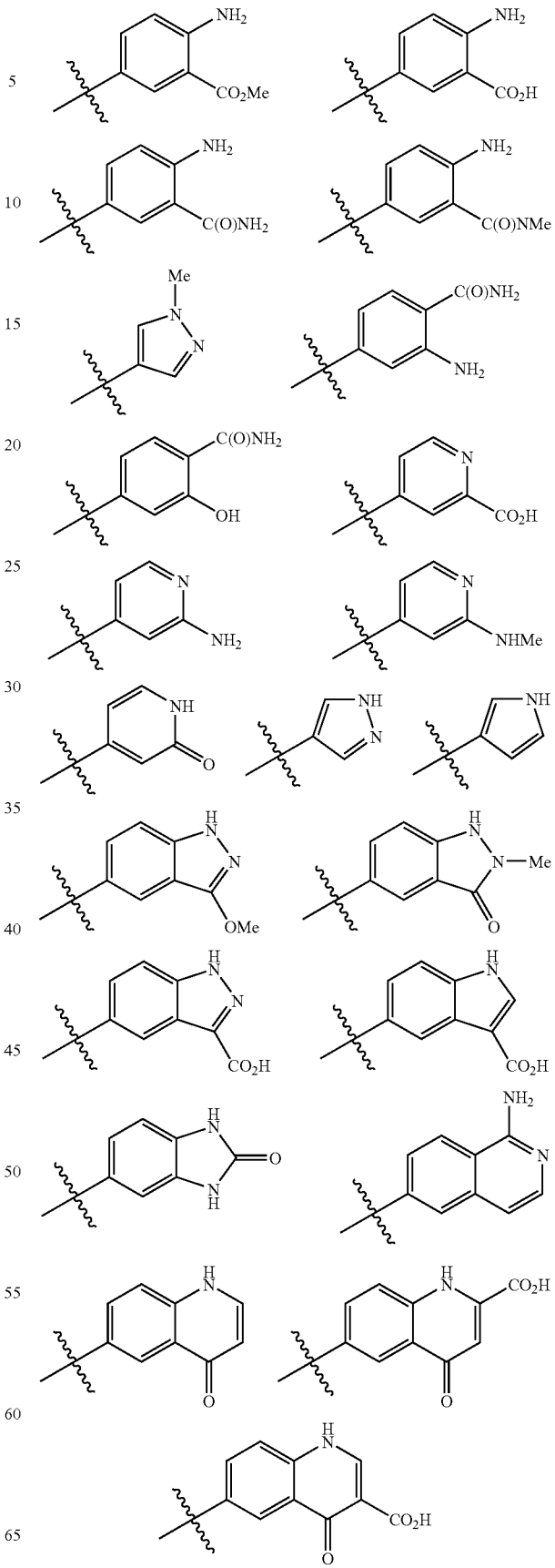

-continued
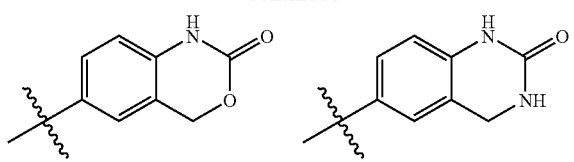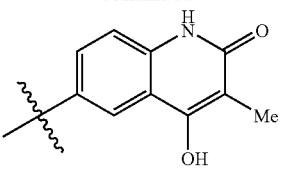
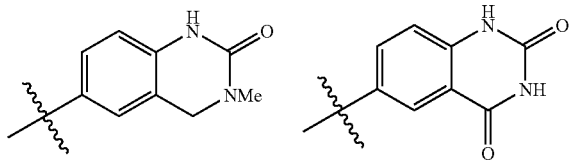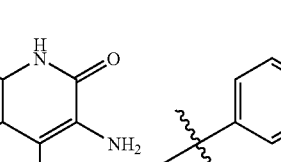
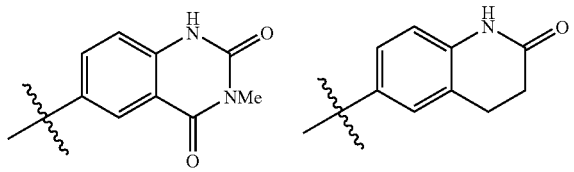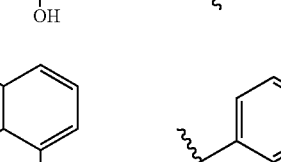
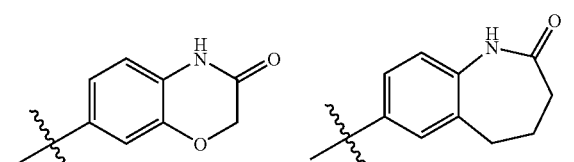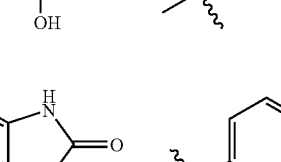
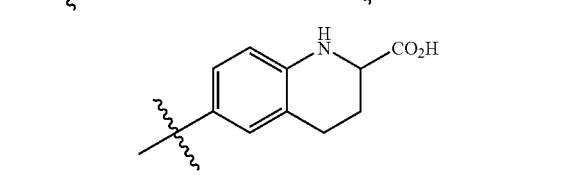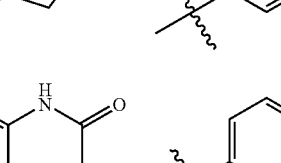
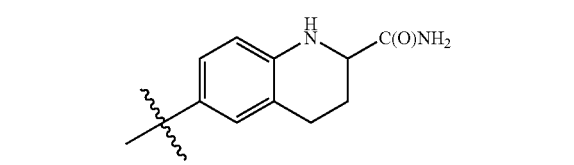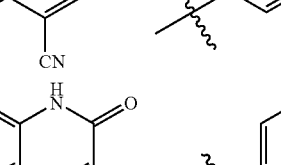
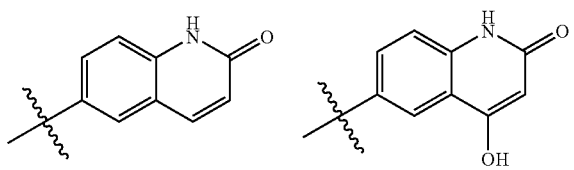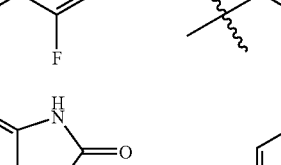
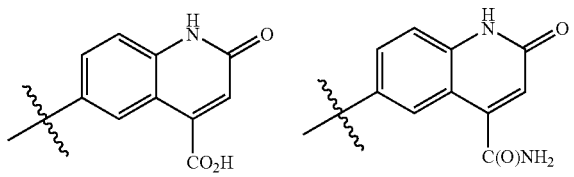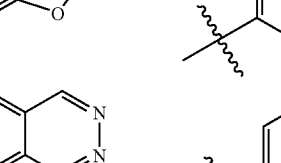
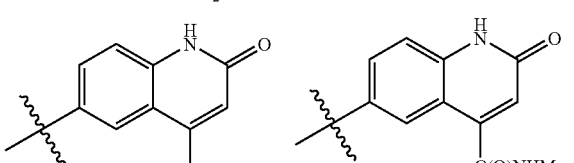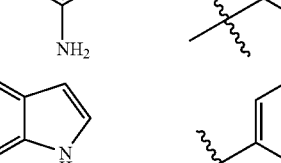
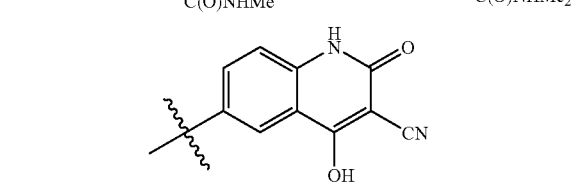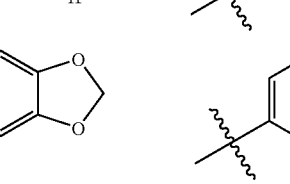

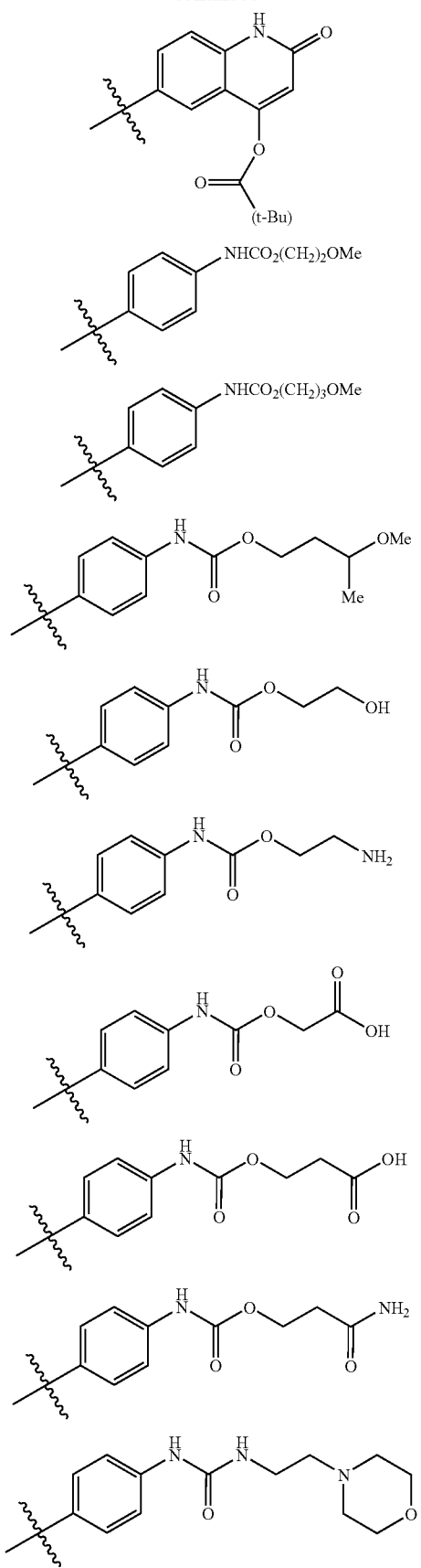
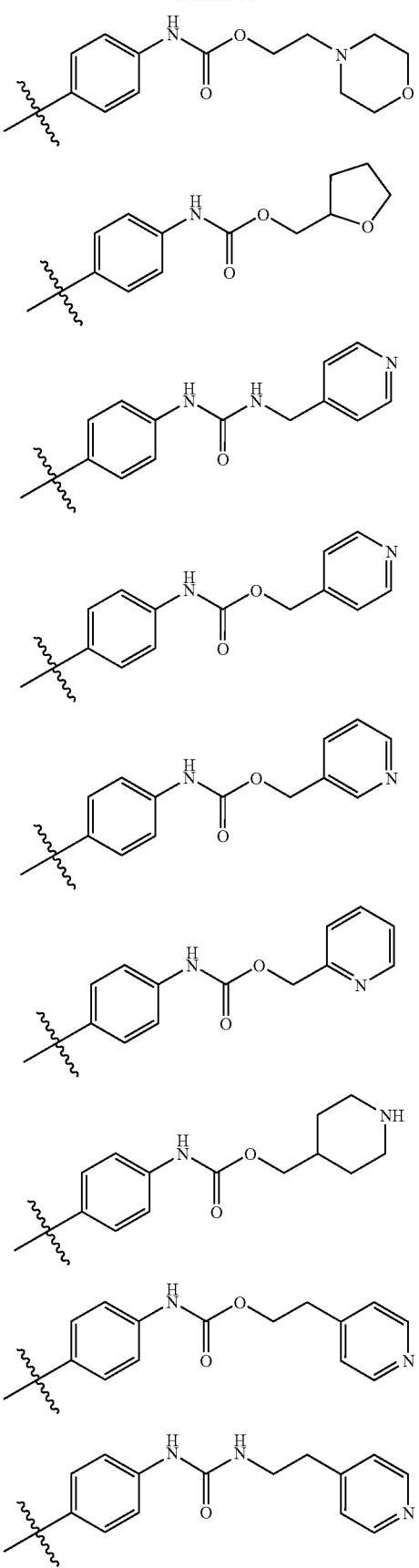

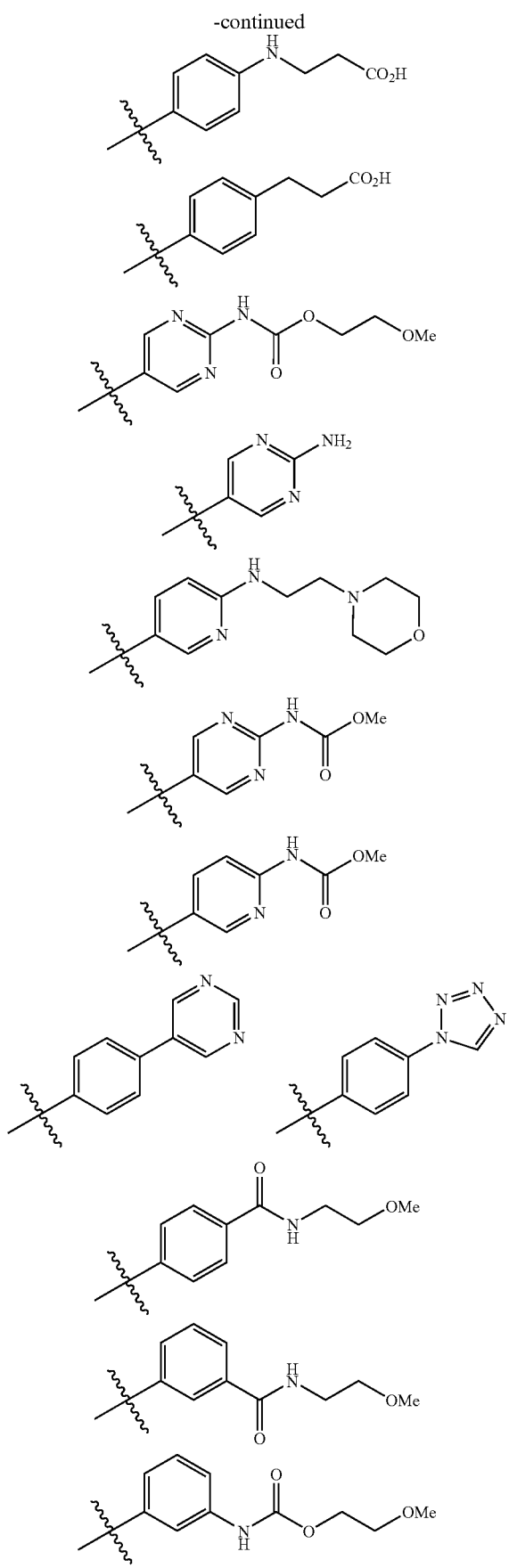
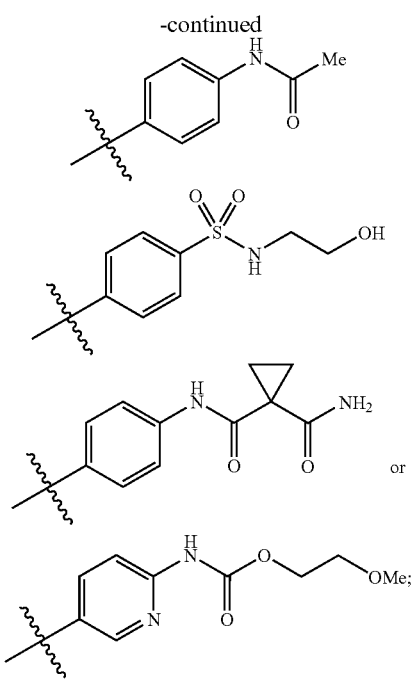

R⁴ is, independently at each occurrence, H, F, Cl, Br, OMe, OH, $NH_2$, Me, Et, Pr, CN, $CF_3$, —$CH_2OH$, —$CH_2NH_2$, —$CO_2H$, —$C(O)NH_2$, —$C(O)NHMe$, —$C(O)N(Me)_2$, —$CH_2CO_2H$, —$CH_2C(O)NH_2$, —$CH_2CH_2CO_2H$, —$NHC(O)Me$, —$NHCO_2Me$, —$NHC(O)NHMe$, —$NHC(O)N(Me)_2$, —$NHCH_2CO_2H$, or —$NHSO_2Me$; and $R^{11}$ is methyl, n-propyl, n-butyl, neopentyl, cyclohexylmethyl, carboxymethyl, benzylaminocarbonylethyl, N-phenethylaminocarbonylethyl, N-benzyl-N-methylaminocarbonylethyl, N-[(pyridine-2-yl)methyl]aminocarbonylethyl, N-[(5-methylpyrazin-2-yl)methyl]aminoethyl, N-(thiazol-2-ylmethyl)aminocarbonylethyl, N-(cyclopropylmethyl)aminocarbonylmethyl, benzyl, phenethyl, 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, 3-carboxybenzyl, 3-carbamoylbenzyl, 3-(N-methylcarbamoyl)-benzyl, 3-(N-ethylcarbamoyl)-benzyl, 3-(N,N-dimethylcarbamoyl)-benzyl, 3-tetrazolyl-benzyl, 2-methylbenzyl, 3-methylbenzyl, 4-methylbenzyl, 3-trifluoromethylbenzyl, 4-trifluoromethylbenzyl, 2-aminobenzyl, 3-aminobenzyl, 2-nitrobenzyl, 3-nitrobenzyl, 4-nitrobenzyl, 3-methoxybenzyl, 4-methoxybenzyl, 3-difluoromethoxybenzyl, 2-trifluoromethoxybenzyl, 3-trifluoromethoxybenzyl, 2-phenoxybenzyl, 3-phenoxybenzyl, 2-benzyloxybenzyl, 3-benzyloxybenzyl, 4-benzyloxybenzyl, 4-phenylcarbonylbenzyl, 3-methoxycarbonylbenzyl, 3-methylcarbonylamino-benzyl, 2-phenylcarbonylamino-benzyl, 2-benzylcarbonylamino-benzyl, 3-benzylcarbonylamino-benzyl, 3-(benzoyl-methyl-amino)-benzyl, 3-(2-phenylethyl)carbonylamino-benzyl, 2-phenylsulfonylamino-benzyl, 3-phenylsulfonylamino-benzyl, 3-[N-methyl-N-phenylaminosulfonyl]-benzyl, 3-[benzenesulfonyl-methyl-amino]-benzyl, 3-isobutylaminocarbonyl-benzyl, 3-t-butylcarbonylamino-benzyl, 3-isopentylaminocarbnoyl-benzyl, 3-(2-methylphenyl)carbamoyl-benzyl, 3-(3-methylphenyl)carbamoyl-benzyl, 3-(4-methylphenyl)carbamoyl-benzyl, 3-(4-fluorophenyl)carbamoyl-benzyl, 3-(1-naphthyl)carbamoyl-benzyl, 3-benzylcarbamoyl-benzyl, 3-(4-chlorophenyl)methylcarbamoyl-benzyl, 3-(4-methoxyphenyl)methylcarbamoyl-benzyl, 3-(2-phenylethyl)carbamoyl-benzyl, 3-[2-(4-methoxyphenyl)ethyl]carbamoyl-benzyl, 3-[2-(2-chlorophenyl)ethyl]carbamoyl-benzyl, 3-[2-(3-chlorophenyl)ethyl]carbamoyl-benzyl, 3-[2-(4-chlorophenyl)ethyl]carbamoyl-benzyl, 3-[methyl-(pyridin-2-ylethyl)]carbamoyl-benzyl 3-(3-phenylpropyl)carbamoyl-benzyl, 3-(ethyl-methyl-carbamoyl)-benzyl, 3-(isopropyl-methyl-carbamoyl)-benzyl, 3-(isobutyl-methyl-carbamoyl)-benzyl, 3-(methyl-phenyl-carbamoyl)-benzyl, 3-[(methyl-(3-methylphenyl)-carbamoyl]-benzyl, 3-[methyl-(4-methylphenyl)-carbamoyl]-benzyl, 3-(benzyl-methyl-carbamoyl)-benzyl, 3-[(3-chlorobenzyl)-methyl-carbamoyl]-benzyl, 3-[(4-chlorobenzyl)-methyl-carbamoyl]-benzyl, 3-[methyl-phenethyl-carbamoyl)]-benzyl, 3-(ethyl-phenyl-carbamoyl)-benzyl, 3-(piperidine-1-carbonyl)-benzyl, 3-(4-phenyl-piperidine-1-carbonyl)-benzyl, 3-(3,4-dihydro-2H-quinoline-1-carbonyl)-benzyl, 3-[(2-methoxyethyl)-methyl-carbamoyl]-benzyl, 3-(4-methoxy-piperidine-1-carbonyl)-benzyl, 3-(morpholine-4-sulfonyl)-benzyl, 3-[(N-(2-methoxyethyl), N-methylamino)sulfonyl]-benzyl, 3-(N,N-dimethylaminosulfonyl)-benzyl, 3-(azetidine-1-carbonyl)-benzyl, 3-(3-methoxy-azetidine-1-carbonyl)-benzyl, 3-(3-hydroxy-pyrrolidine-1-carbonyl)-benzyl, 3-[(4-tetrahydropyranyl)methylcarbonyl]-benzyl, 3-[(2-hydroxyethyl)-methyl-carbamoyl]-benzyl, 3-(3-hydroxy-azetidine-1-carbonyl)-benzyl, 3-(4-hydroxypiperidine-1-carbonyl)-benzyl, 3-[4-(N,N-dimethylamino)-piperidine-1-carbonyl]-benzyl, 3-(4-methyl-piperazine-1-carbonyl)-benzyl, 3-[3-(N,N-dimethylamino)-pyrrolidine-1-carbonyl]-benzyl, 2-phenyl-benzyl, 3-phenyl-benzyl, 4-phenyl-benzyl, 3-phenethyl-benzyl, benzyloxymethyl, benzylthiomethyl, 1-naphthylmethyl, 2-naphthylmethyl, thiazol-4-ylmethyl, pyrid-2-ylmethyl, pyrid-3-ylmethyl, pyrid-4-ylmethyl, 1-benzyl-imidazol-4-ylmethyl, benzothiazol-2-ylmethyl, 3-(1-morpholinocarbonyl)-benzyl, 3-[(2,6-dimethylmorpholine-4-carbonyl)-benzyl, (benzyloxycarbonyl)methyl, (1-methylpyrazol-3-yl)methyl, (1-methylpyrazol-4-yl)methyl, (1-methylpyrazol-5-yl)methyl, (3-methylpyrazol-5-yl)methyl, (1-ethylpyrazol-4-yl)methyl, (1-n-propylpyrazol-4-yl)methyl, (1-isopropylpyrazol-4-yl)methyl, 1-ethylpyrazol-3-ylmethyl, 3-pyrazolylmethyl, (4-chloro-3-methyl-5-pyrazolyl)methyl, (4-chloro-1,5-dimethyl-3-pyrazolyl)methyl, (4-chloro-1,3-dimethyl-5-pyrazolyl)methyl, [1-(4-methoxybenzyl)-pyrazol-3-yl]methyl, (1,5-dimethylpyrazol-3-yl)methyl, (1,3-dimethylpyrazol-5-yl)methyl, [1-(4-methoxybenzyl)-5-methyl-pyrazol-3-yl]methyl, (3-trifluoromethylpyrazol-5-yl)methyl, [1-(4-methoxybenzyl)-3-trifluoromethylpyrazol-5-yl]methyl, [(1-methyl-5-methoxycarbonyl)-pyrazol-3-yl]methyl, [(1-methyl-5-carboxy)-pyrazol-3-yl]methyl, [(1-methyl-5-carbamoyl)-pyrazol-3-yl]methyl, [(5-methoxycarbonyl)-pyrrol-2-yl]methyl, thiazol-2-ylmethyl, thiazol-4-methyl, (2-methoxypyridin-3-yl)methyl, (6-methoxypyridin-3-yl)methyl, (4-(methoxycarbonyl)-oxazol-2-yl)methyl, morpholin-4-ylcarbonylmethyl, N-((5-methylpyrazin-2-yl)methyl)-aminocarbonylmethyl, 2-hydroxy-indan-5-ylmethyl, 4-methylpiperazin-1-ylcarbonylmethyl, 4-methylcarbonylpiperazin-1-ylcarbonylmethyl, pyrrolidin-1-ylcarbonylmethyl, 2-methoxypyrrolidin-1-ylcarbonylmethyl, aziridin-1-ylcarbonylmethyl, 2-hydroxyethylaminocarbonylmethyl, 2-methoxyethylaminocarbonylmethyl, 2-ethoxyethylaminocarbonylmethyl, bis(2-methoxyethyl)aminocarbonylmethyl, 4-dimethylaminopyrrolidin-1-ylcarbonylmethyl, 4-chlorophenylaminocarbonylmethyl, 3-chlorophenylaminocarbonylmethyl, N-methyl-N-benzylaminocarbonylmethyl, cyclopropylaminocarbonylmethyl, cyclopropylmethylaminocarbonylmethyl, cyclopentylaminocarbonylmethyl, (trans-2-phenylcyclopropyl)aminocarbonylmethyl, N,N-dimethylaminoethylaminocarbonylmethyl, N-((pyridin-2-yl)methyl)-aminocarbonylmethyl, N-((pyridin-3-yl)methyl)-aminocarbonylmethyl, N-((pyridin-4-yl)methyl)-aminocarbonylmethyl, N-((pyridin-2-yl)ethyl)-aminocarbonylmethyl, 1-(1,1-dioxo-1$\lambda^6$-thiomorpholin-4-yl)carbonylmethyl, N-(tert-butoxycarbonyl)-1H-indol-3-ylmethyl, 1H-indol-3-ylmethyl, 2,2-dioxo-2,3-dihydro-1H-2$\lambda^6$-benzo[c]thiophen-5-ylmethyl, 4,4,4-trifluorobutyl, cyclopropylmethyl, (4-hydroxy)cyclohexylmethyl, 4-oxo-cyclohexylmethyl,

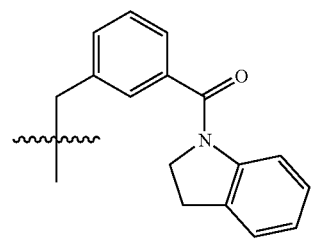

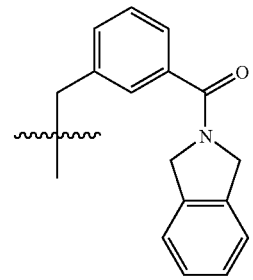

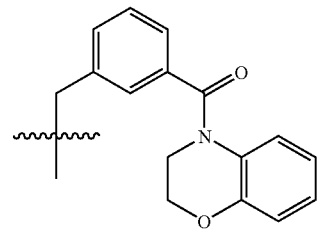

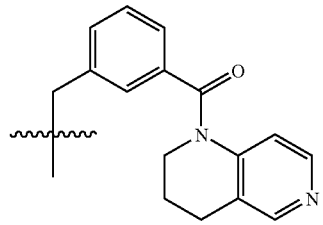

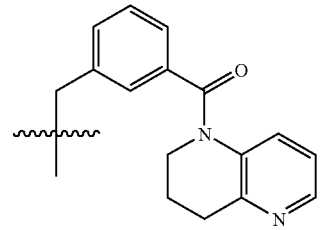

-continued

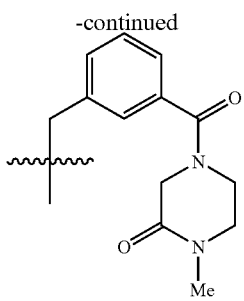

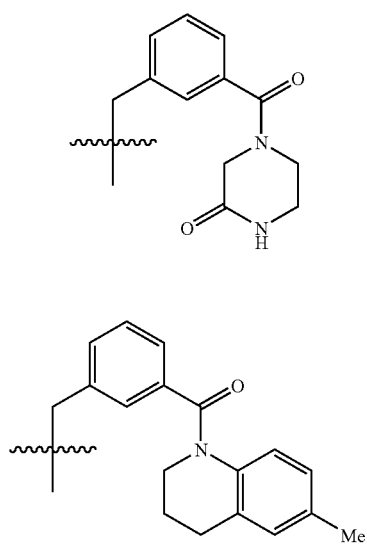

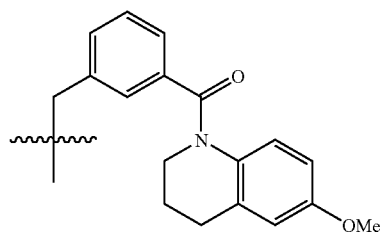

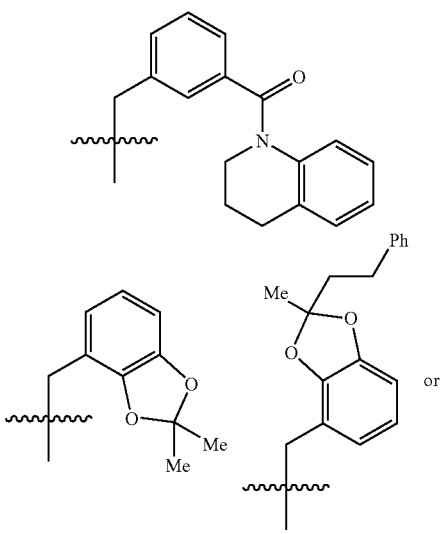

-continued

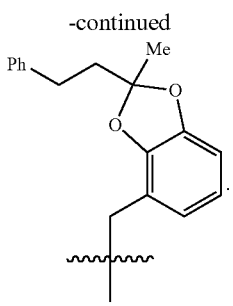

In a seventh aspect, the present invention includes compounds of Formula (I) or its stereoisomers, tautomers, pharmaceutically acceptable salts, solvates, or prodrugs thereof, within the scope of any of the first, second, fifth and sixth aspects wherein:

A is 4-aminomethyl-cyclohexyl, 4-methylcyclohexyl, 4-methoxyphenyl, 4-aminomethylphenyl, 4-carbamoylphenyl, 4-amidinophenyl, 2-fluoro-4-methylphenyl, 2,6-difluoro-4-methylphenyl, 2-fluoro-4-methoxyphenyl, 2,6-difluoro-4-methoxyphenyl, 2-fluoro-4-aminomethylphenyl, 2-fluoro-4-carbamoyl-phenyl, 4-amino-2-fluorophenyl, 4-amino-2,6-difluoromethylphenyl, 4-amino-3-chloro-2,3-difluorophenyl, 4-amino-3-chlorophenyl, 3-chlorothien-2-yl, indol-5-yl, indol-6-yl, indazol-6-yl, 3-amino-indazol-6-yl, 3-amino-indazol-5-yl, 1-methyl-3-amino-indazol-6-yl, 3-amino-benzisoxazol-6-yl, benzimidazol-5-yl, 6-fluoro-benzimidazol-5-yl, 1,2,3,4-tetrahydroisoquinolin-6-yl, 1,2,3,4-tetrahydroisoquinolin-3-yl, 2H-isoquinolin-1-on-6-yl, isoquinolin-6-yl, 1-amino-isoquinolin-6-yl, 1-amino-3-methyl-isoquinolin-6-yl, 1-amino-5,6,7,8-tetrahydroisoquinolin-6-yl, 4-amino-quinazolin-7-yl, or 3H-quinazolin-4-on-7-yl;

$R^3$ is, independently at each occurrence,

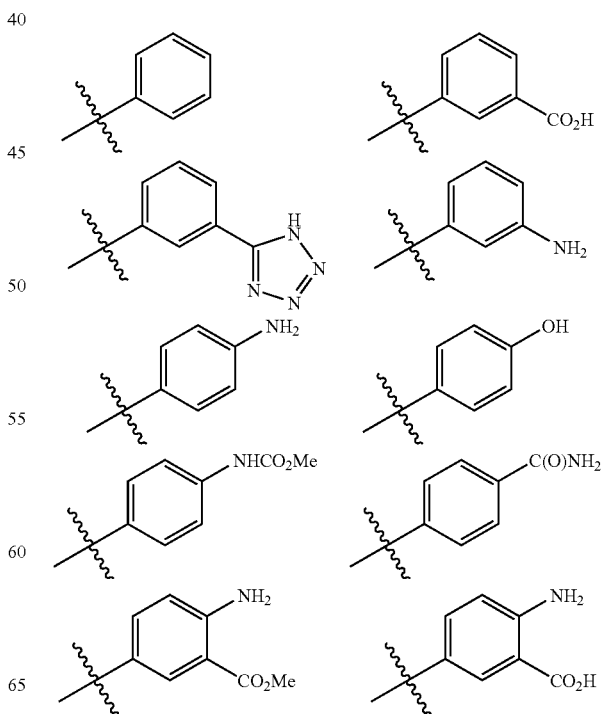

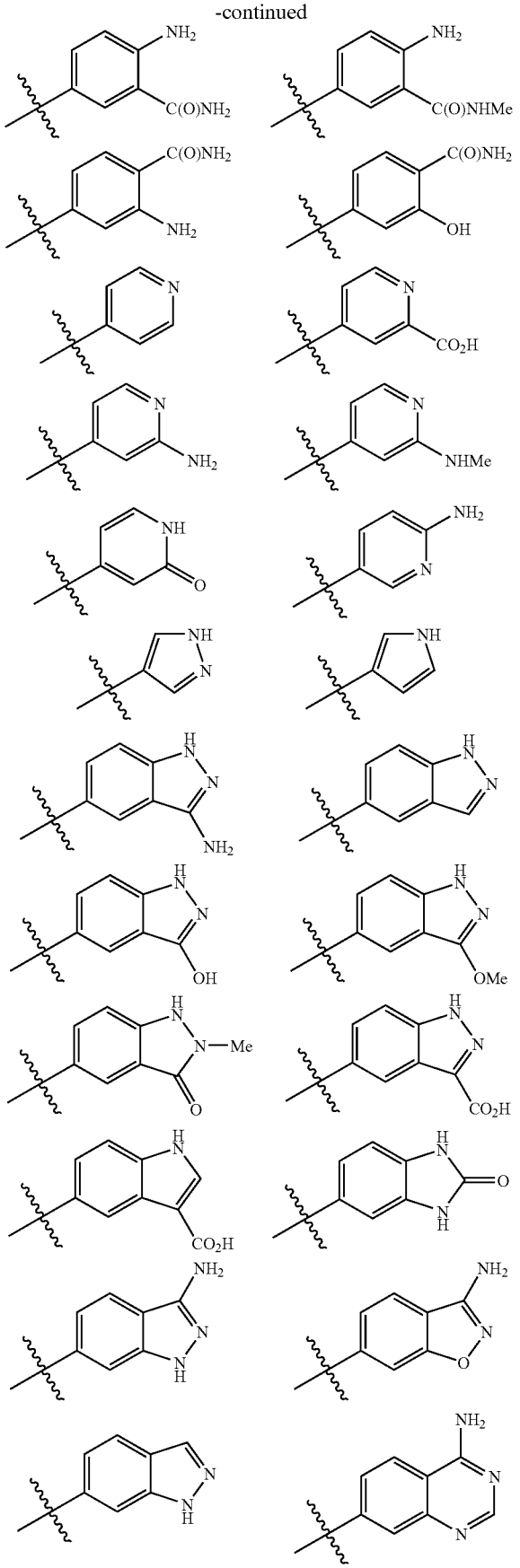
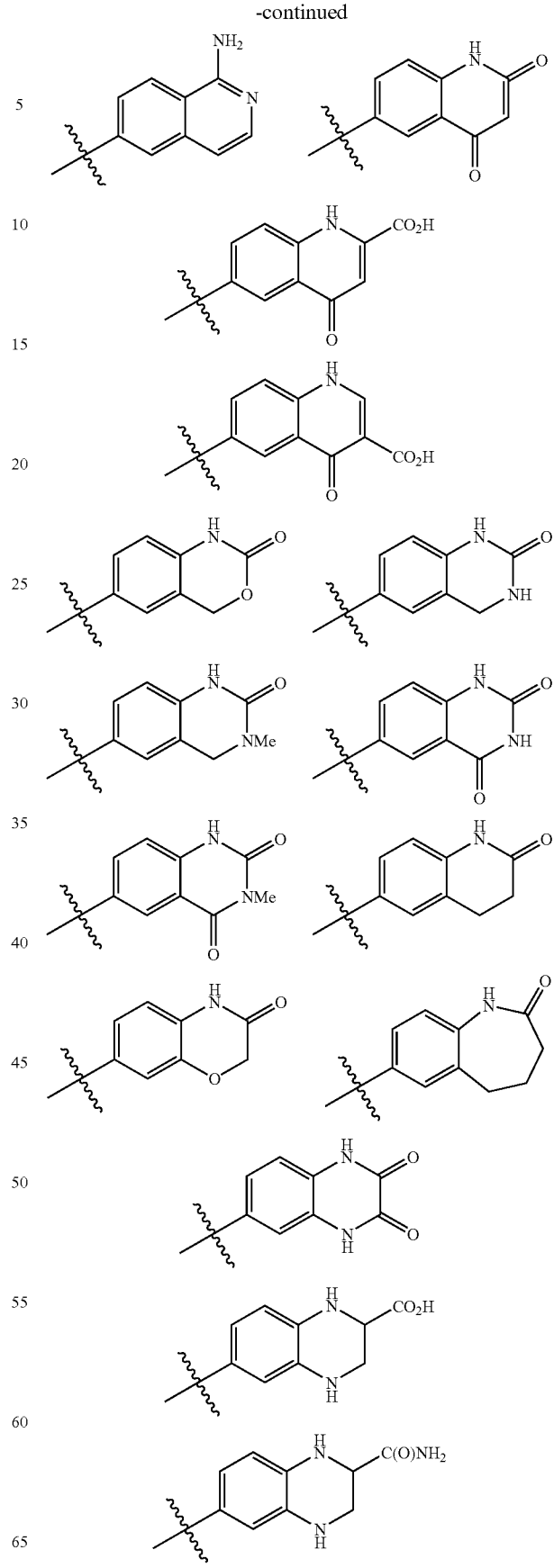

-continued
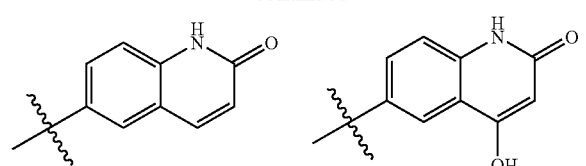
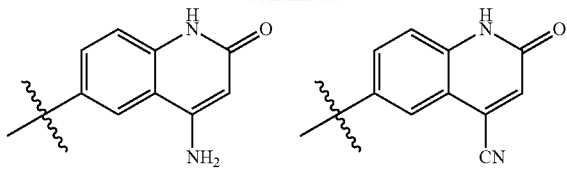
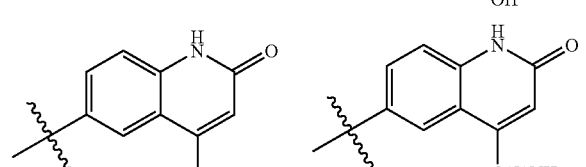
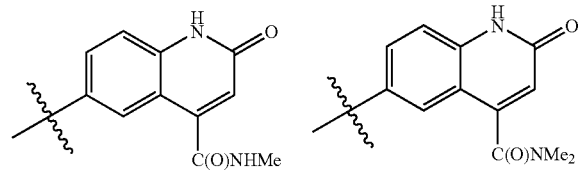
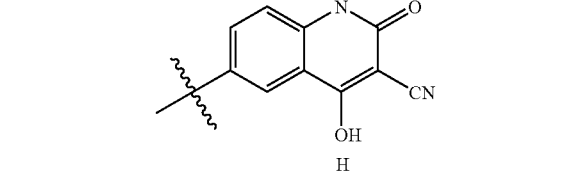
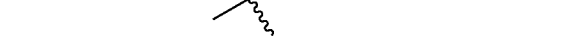
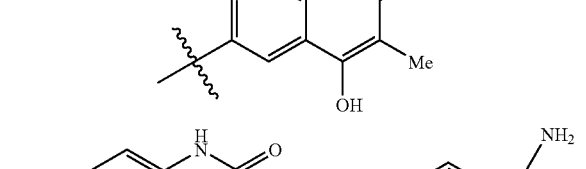
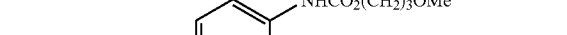
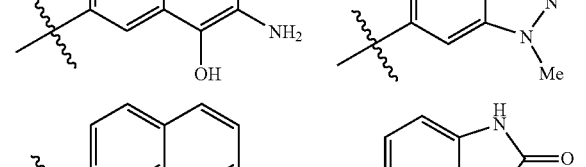
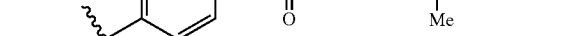
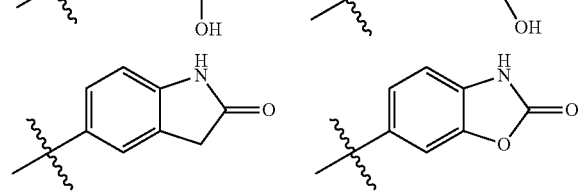
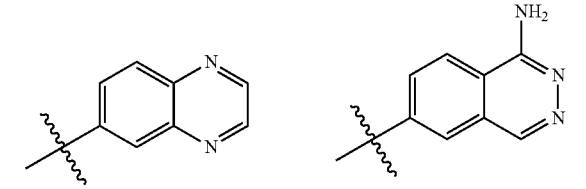
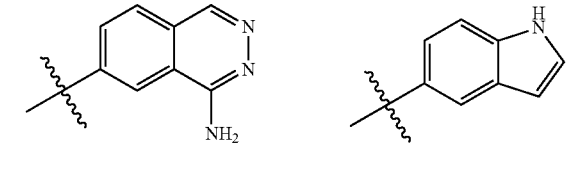

-continued
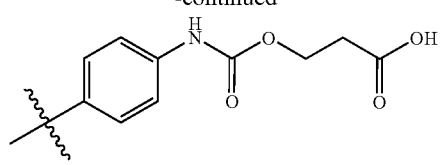
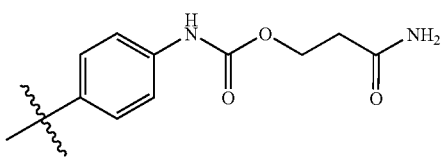
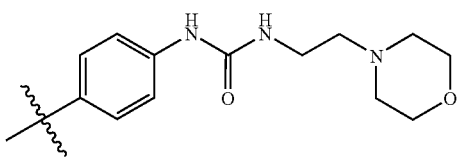
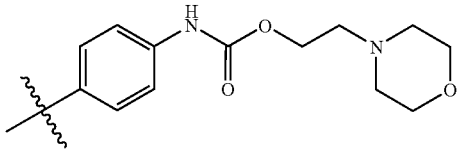
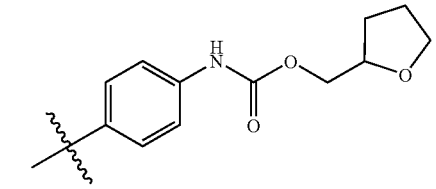
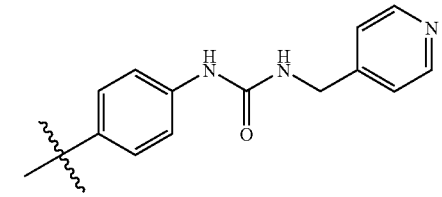
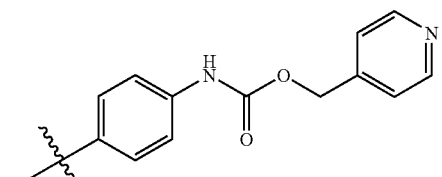
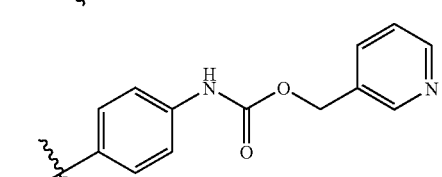
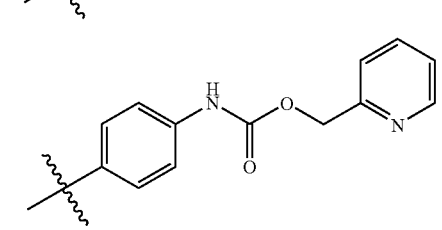
-continued
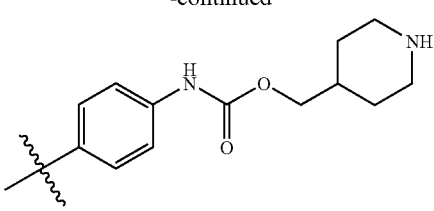
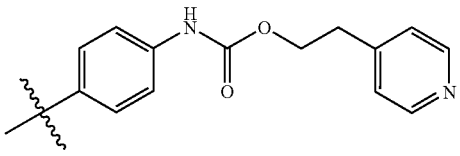
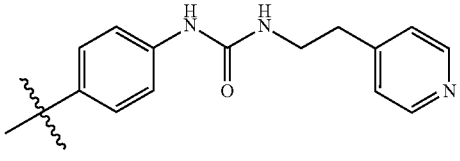
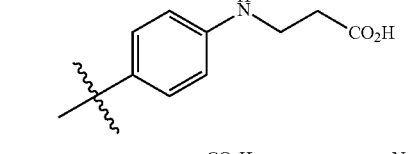
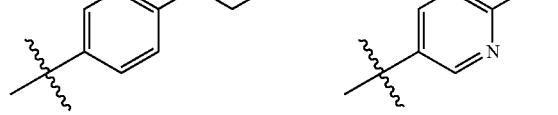
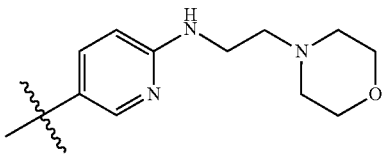
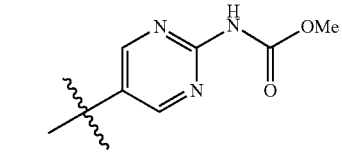
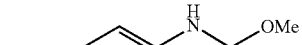
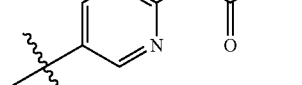
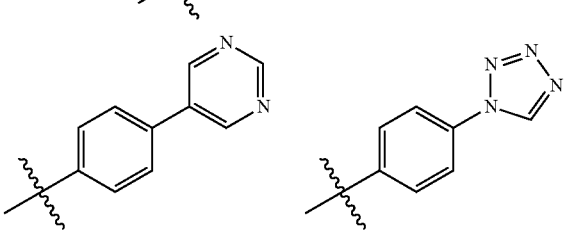
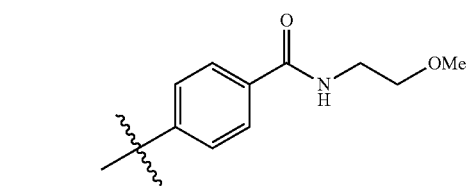

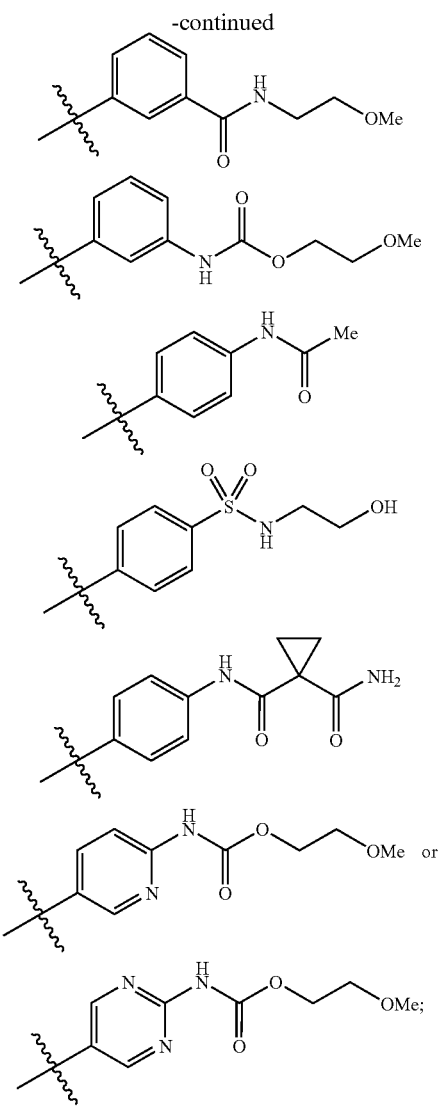

and

R[11] is methyl, n-butyl, cyclohexylmethyl, carboxymethyl, benzyl, phenethyl, 2-fluorobenzyl, 3-fluorobenzyl, 4-fluorobenzyl, 2-chlorobenzyl, 3-chlorobenzyl, 4-chlorobenzyl, 3-carboxybenzyl, 3-carbamoylbenzyl, 3-(N-methylcarbamoyl)-benzyl, 3-(N,N-dimethylcarbamoyl)-benzyl, 3-(N-ethylcarbamoyl)-benzyl, 3-methylbenzyl, 4-methylbenzyl, 3-methoxybenzyl, 3-difluoromethoxybenzyl, 3-trifluoromethoxy-benzyl, 3-methoxycarbonylbenzyl, 3-methylcarbonylamino-benzyl, 3-benzylcarbonylamino-benzyl, 3-(benzoyl-methyl-amino)-benzyl, 3-(2-phenylethyl)carbonylamino-benzyl, 2-phenylsulfonylamino-benzyl, 3-phenylsulfonylamino-benzyl, 3-[N-methyl, N-phenylaminosulfonyl]-benzyl, 3-(benzenesulfonyl-methyl-amino)-benzyl, 3-(2-methylphenyl)carbamoyl-benzyl, 3-(3-methylphenyl)carbamoyl-benzyl, 3-(4-methylphenyl)carbamoyl-benzyl, 3-(4-fluorophenyl)carbamoyl-benzyl, 3-(1-naphthyl)carbamoyl-benzyl, 3-benzylcarbamoyl-benzyl, 3-(4-chlorophenyl)methylcarbamoyl-benzyl, 3-(4-methoxyphenyl)methylcarbamoyl-benzyl, 3-(2-phenylethyl)carbamoyl-benzyl, 3-[2-(4-methoxyphenyl)ethyl]carbamoyl-benzyl, 3-[2-(2-chlorophenyl)ethyl]carbamoyl-benzyl, 3-[2-(3-chlorophenyl)ethyl]carbamoyl-benzyl, 3-[2-(4-chlorophenyl)ethyl]carbamoyl-benzyl, 3-[methyl-(pyridin-2-ylethyl)]carbamoyl-benzyl 3-(3-phenylpropyl)carbamoyl-benzyl, 3-(ethyl-methyl-carbamoyl)-benzyl, 3-(isopropyl-methyl-carbamoyl)-benzyl, 3-(isobutyl-methyl-carbamoyl)-benzyl, 3-(methyl-phenyl-carbamoyl)-benzyl, 3-[(methyl-(3-methylphenyl)-carbamoyl]-benzyl, 3-[methyl-(4-methylphenyl)-carbamoyl]-benzyl, 3-(benzyl-methyl-carbamoyl)-benzyl, 3-[(3-chlorobenzyl)-methyl-carbamoyl]-benzyl, 3-[(4-chlorobenzyl)-methyl-carbamoyl]-benzyl, 3-[methyl-phenethyl-carbamoyl)]-benzyl, 3-(ethyl-phenyl-carbamoyl)-benzyl, 3-(piperidine-1-carbonyl)-benzyl, 3-(3,4-dihydro-2H-quinoline-1-carbonyl)-benzyl, 3-[(2-methoxyethyl)-methyl-carbamoyl]-benzyl, 3-(4-methoxy-piperidine-1-carbonyl)-benzyl, 3-(morpholine-4-sulfonyl)-benzyl, 3-[(N-(2-methoxyethyl), N-methylamino)sulfonyl]-benzyl, 3-(N,N-dimethylaminosulfonyl)-benzyl, 3-(azetidine-1-carbonyl)-benzyl, 3-(3-methoxy-azetidine-1-carbonyl)-benzyl, 3-(3-hydroxy-pyrrolidine-1-carbonyl)-benzyl, 3-[(4-tetrahydropyranyl)methylcarbonyl]-benzyl, 3-[(2-hydroxyethyl)-methyl-carbamoyl]-benzyl, 3-(3-hydroxy-azetidine-1-carbonyl)-benzyl, 3-(4-hydroxypiperidine-1-carbonyl)-benzyl, 3-[4-(N,N-dimethylamino)-piperidine-1-carbonyl]-benzyl, 3-(4-methyl-piperazine-1-carbonyl)-benzyl, 3-[3-(N,N-dimethylamino)-pyrrolidine-1-carbonyl]-benzyl, 1-naphthylmethyl, 2-naphthylmethyl, thiazol-4-ylmethyl, pyrid-2-ylmethyl, pyrid-3-ylmethyl, pyrid-4-ylmethyl, 1-benzyl-imidazol-4-ylmethyl, benzothiazol-2-ylmethyl, 3-(1-morpholinocarbonyl)-benzyl, 3-[(2,6-dimethylmorpholine-1-carbonyl)-benzyl, (benzyloxycarbonyl)methyl, (1-methylpyrazol-3-yl)methyl, (1-methylpyrazol-4-yl)methyl, (1-methylpyrazol-5-yl)methyl, (3-methylpyrazol-5-yl)methyl, (1-ethylpyrazol-4-yl)methyl, (1-n-propylpyrazol-4-yl)methyl, (1-isopropylpyrazol-4-yl)methyl, 1-ethylpyrazol-3-ylmethyl, 3-pyrazolylmethyl, (4-chloro-3-methyl-5-pyrazolyl)methyl, (4-chloro-1,5-dimethyl-3-pyrazolyl)methyl, (4-chloro-1,3-dimethyl-5-pyrazolyl)methyl, [1-(4-methoxybenzyl)-pyrazol-3-yl]methyl, (1,5-dimethylpyrazol-3-yl)methyl, (1,3-dimethylpyrazol-5-yl)methyl, [1-(4-methoxybenzyl)-5-methyl-pyrazol-3-yl]methyl, (3-trifluoromethylpyrazol-5-yl)methyl, [1-(4-methoxybenzyl)-3-trifluoromethylpyrazol-5-yl]methyl, [(1-methyl-5-methoxycarbonyl)-pyrazol-3-yl]methyl, [(1-methyl-5-carboxy)-pyrazol-3-yl]methyl, [(1-methyl-5-carbamoyl)-pyrazol-3-yl]methyl, [(5-methoxycarbonyl)-pyrrol-2-yl]methyl, thiazol-2-ylmethyl, thiazol-4-methyl, (2-methoxypyridin-3-yl)methyl, (6-methoxypyridin-3-yl)methyl, (4-(methoxycarbonyl)-oxazol-2-yl)methyl, morpholin-4-ylcarbonylmethyl, N-((5-methylpyrazin-2-yl)methyl)-aminocarbonylmethyl, 2-hydroxyindan-5-ylmethyl, 4-methylpiperazin-1-ylcarbonylmethyl, 4-methylcarbonylpiperazin-1-ylcarbonylmethyl, pyrrolidin-1-ylcarbonylmethyl, 2-methoxypyrrolidin-1-ylcarbonylmethyl, aziridin-1-ylcarbonylmethyl, 2-hydroxyethylaminocarbonylmethyl, 2-methoxyethylaminocarbonylmethyl, 2-ethoxyethylaminocarbonylmethyl, bis(2-methoxyethyl)aminocarbonylmethyl, 4-dimethylaminopyrrolidin-1-ylcarbonylmethyl, 4-chlorophenylaminocarbonylmethyl, 3-chlorophenylcarbonylmethyl, N-methyl-N-benzylaminocarbonylmethyl, cyclopropylaminocarbonylmethyl, cyclopropylmethylaminocarbonylmethyl, cyclopentylaminocarbonylmethyl, (trans-2-phenylcyclopropyl)aminocarbonylmethyl, N,N-dimethylaminoethylaminocarbonylmethyl, N-((pyridin-2-yl)methyl)-aminocarbonylmethyl, N-((pyridin-3-yl)methyl)-aminocarbonylmethyl, N-((pyridin-4-yl)methyl)-aminocarbonylmethyl, N-((pyridin-2-yl)ethyl)-aminocarbonylmethyl, 1-(1,1-dioxo-1$\lambda^6$-thiomorpholin-4-yl)carbonylmethyl, N-(tert-butoxycarbonyl)-1H-indol-3- ylmethyl, 1H-indol-3-ylmethyl, 2,2-dioxo-2,3-dihydro-1H-2λ⁶-benzo[c]thiophen-5-ylmethyl, 4,4,4-trifluorobutyl, cyclopropylmethyl, (4-hydroxy)cyclohexylmethyl, 4-oxo-cyclohexylmethyl,

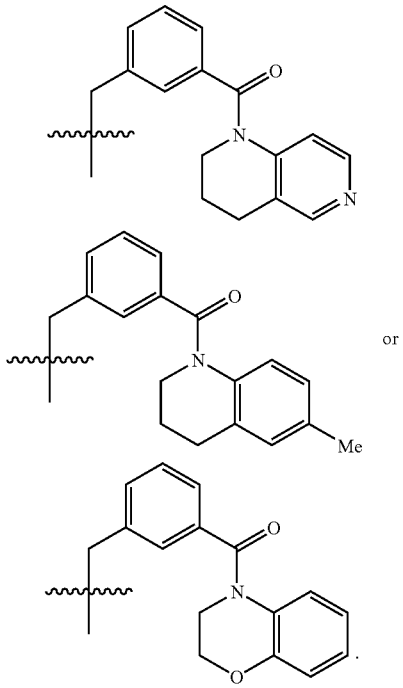

In an eighth aspect, the present invention includes a compound of Formula (I), or its stereoisomers, tautomers, pharmaceutically acceptable salts, solvates, or prodrugs thereof, within the scope of the first aspect wherein:

A is aminomethylcyclohexyl;

the group

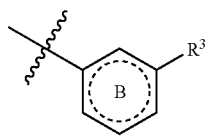

is selected from:

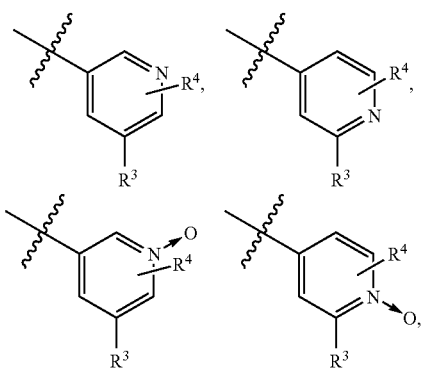

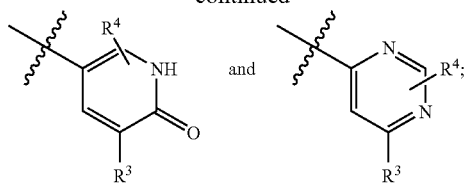

$R^3$ is phenyl, 4-methoxycarbonylaminophenyl, 2-aminopyrid-4-yl, or 4-hydroxy-2-oxo-1,2-dihydro-quinolin-6-yl;

$R^4$ is H; and $R^{11}$ is benzyl.

In a ninth aspect, the present invention provides a compound selected from the exemplified examples or stereoisomers or pharmaceutically acceptable salts, solvates, or prodrugs thereof.

In another aspect, the present invention provides, inter alia, compounds of Formula (II):

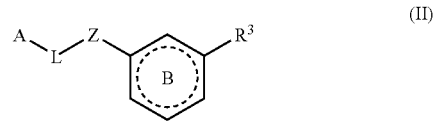

or a stereoisomer, tautomer, pharmaceutically acceptable salt, solvate, or prodrug form thereof, wherein:

A is $C_{3-7}$ cycloalkyl substituted with 0-1 $R^1$ and 0-3 $R^2$, $C_{3-7}$ cycloalkenyl substituted with 0-1 $R^1$ and 0-3 $R^2$, phenyl substituted with 0-1 $R^1$ and 0-3 $R^2$, naphthyl substituted with 0-1 $R^1$ and 0-3 $R^2$, or a 5- to 12-membered heterocycle comprising: carbon atoms and 1-4 heteroatoms selected from N, O, and $S(O)_p$, wherein said heterocycle is substituted 0-1 $R^1$ and 0-3 $R^2$;

provided that A is other than a thienyl substituted with halogen, $C_{1-6}$ alkyl, $C_{2-6}$ alkenyl, or $C_{2-6}$ alkynyl;

the group

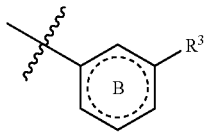

is selected from:

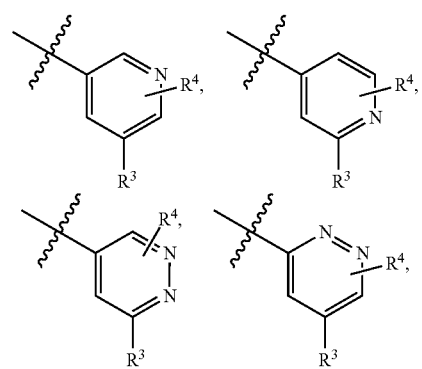

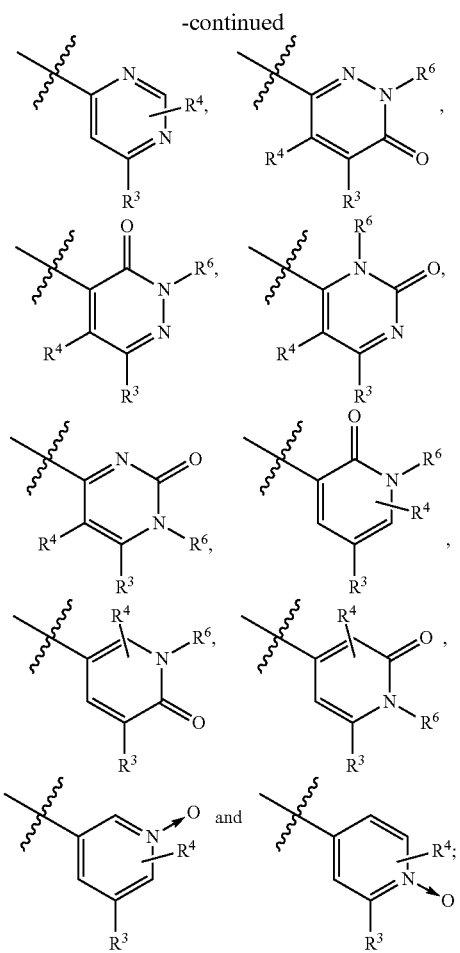

Z is —CH(R$^{11}$)— or NR$^{12}$;

L is —C(O)NR$^{10}$—, —NR$^{10}$C(O)—, —CH$_2$C(O)NR$^{10}$—, —CH$_2$NR$^{10}$C(O)—, —C(O)NR$^{10}$CH$_2$—, or —NR$^{10}$C(O)CH$_2$—;

R$^1$ is, independently at each occurrence, —NH$_2$, —NH(C$_{1-3}$ alkyl), —N(C$_{1-3}$ alkyl)$_2$, —C(=NH)NH$_2$, —C(O)NH$_2$, —CH$_2$NH$_2$, —(CH$_2$)$_r$NR$^7$R$^8$, —CH$_2$NH(C$_{1-3}$ alkyl), —CH$_2$N(C$_{1-3}$ alkyl)$_2$, —CH$_2$CH$_2$NH$_2$, —CH$_2$CH$_2$NH(C$_{1-3}$ alkyl), —CH$_2$CH$_2$N(C$_{1-3}$ alkyl)$_2$, —CH(C$_{1-4}$ alkyl)NH$_2$, —C(C$_{1-4}$ alkyl)$_2$NH$_2$, —C(=NR$^{8a}$)NR$^7$R$^8$, —NR$^8$CR$^8$(=NR$^{8a}$), —NHC(=NR$^{8a}$)NR$^7$R$^8$, =NR$^8$, —C(O)NR$^8$R$^9$, —S(O)$_p$NR$^8$R$^9$, —(CH$_2$)$_r$NR$^7$C(O)OR$^a$, F, Cl, Br, I, OCF$_3$, CF$_3$, OR$^a$, SR$^a$, CN, 1-NH$_2$-1-cyclopropyl, or C$_{1-6}$ alkyl substituted with 0-1 R$^{1a}$;

R$^{1a}$ is —C(=NR$^{8a}$)NR$^7$R$^8$, —NHC(=NR$^{8a}$)NR$^7$R$^8$, —NR$^8$CH(=NR$^{8a}$), —NR$^7$R$^8$, —C(O)NR$^8$R$^9$, F, OCF$_3$, CF$_3$, OR$^a$, SR$^a$, CN, —NR$^8$SO$_2$NR$^8$R$^9$, —NR$^8$SO$_2$R$^c$, —S(O)$_p$—C$_{1-4}$ alkyl, —S(O)$_p$-phenyl, or —(CF$_2$)$_r$CF$_3$;

R$^2$ is, independently at each occurrence, =O, F, Cl, Br, I, OCF$_3$, CF$_3$, CHF$_2$, CN, NO$_2$, —(CH$_2$)$_r$OR$^a$, —(CH$_2$)$_r$SR$^a$, —(CH$_2$)$_r$C(O)R$^a$, —(CH$_2$)$_r$C(O)OR$^a$, —(CH$_2$)$_r$OC(O)R$^a$, —(CH$_2$)$_r$NR$^7$R$^8$, —(CH$_2$)$_r$C(O)NR$^8$R$^9$, —(CH$_2$)$_r$NR$^8$C(O)R$^c$, —(CH$_2$)$_r$NR$^8$C(O)OR$^c$, —NR$^8$C(O)NR$^8$R$^c$, —S(O)$_p$NR$^8$R$^9$, —NR$^8$S(O)$_2$R$^c$, —S(O)R$^c$, —S(O)$_2$R$^c$, C$_{1-6}$ alkyl substituted with 0-2 R$^{2a}$, C$_{2-6}$ alkenyl substituted with 0-2 R$^{2a}$, C$_{2-6}$ alkynyl substituted with 0-2 R$^{2a}$, —(CH$_2$)$_r$—C$_{3-10}$ carbocycle substituted with 0-3 R$^{2b}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{2b}$;

R$^{2a}$ is, independently at each occurrence, H, F, Cl, Br, I, =O, =NR$^8$, CN, OCF$_3$, CF$_3$, OR$^a$, SR$^a$, —NR$^7$R$^8$, —C(O)NR$^8$R$^9$, —NR$^8$C(O)R$^c$, —NR$^8$C(O)OR$^c$, —NR$^8$C(O)NR$^8$R$^c$, —S(O)$_p$NR$^8$R$^9$, —NR$^8$SO$_2$R$^c$, —S(O)R$^c$, or —S(O)$_2$R$^c$;

R$^{2b}$ is, independently at each occurrence, H, F, Cl, Br, I, =O, =NR$^8$, —(CH$_2$)$_r$CN, —(CH$_2$)$_r$NO$_2$, —(CH$_2$)$_r$OR$^a$, —(CH$_2$)$_r$SR$^a$, —(CH$_2$)$_r$C(O)R$^a$, —(CH$_2$)$_r$C(O)OR$^a$, —(CH$_2$)$_r$OC(O)R$^a$, —(CH$_2$)$_r$NR$^7$R$^8$, —(CH$_2$)$_r$C(O)NR$^8$R$^9$, —(CH$_2$)$_r$NR$^8$C(O)R$^c$, —(CH$_2$)$_r$S(O)$_p$NR$^8$R$^9$, —(CH$_2$)$_r$SO$_2$R$^c$, —(CH$_2$)$_r$NR$^8$SO$_2$NR$^8$R$^9$, —(CH$_2$)$_r$NR$^8$SO$_2$R$^c$, —(CF$_2$)$_r$CF$_3$, C$_{1-6}$ alkyl, C$_{2-6}$ alkenyl, C$_{2-6}$ alkynyl, C$_{3-6}$ cycloalkyl, C$_{1-4}$ haloalkyl, or C$_{1-4}$ haloalkyloxy;

alternately, when R$^1$ and R$^2$ are substituted on adjacent ring atoms, they can be taken together with the ring atoms to which they are attached to form a 5- to 7-membered carbocycle or heterocycle comprising: carbon atoms and 0-4 heteroatoms selected from N, O, and S(O)$_p$, wherein said carbocycle or heterocycle is substituted with 0-2 R$^g$;

R$^3$ is, independently at each occurrence, phenyl substituted with 0-3 R$^{3a}$ and 0-1 R$^{3d}$, naphthyl substituted with 0-3 R$^{3a}$ and 0-1 R$^{3d}$, or —(CH$_2$)$_r$-5- to 12-membered heterocycle comprising: carbon atoms and 1-4 heteroatoms selected from N, O, and S(O)$_p$, wherein said heterocycle is substituted with 0-3 R$^{3a}$ and 0-1 R$^{3d}$;

R$^{3a}$ is, independently at each occurrence, =O, F, Cl, Br, I, OCF$_3$, CF$_3$, —(CH$_2$)$_r$CN, NO$_2$, —(CH$_2$)$_r$OR$^{3b}$, —(CH$_2$)$_r$SR$^{3b}$, —(CH$_2$)$_r$NR$^7$R$^8$, —C(=NR$^{8a}$)NR$^8$R$^9$, NHC(=NR$^{8a}$)NR$^7$R$^8$, NR$^8$CR$^8$(=NR$^{8a}$), —(CH$_2$)$_r$NR$^8$C(O)R$^{3b}$, =NR$^8$, —(CH$_2$)$_r$NR$^8$C(O)R$^{3b}$, —(CH$_2$)$_r$NR$^8$C(O)$_2$R$^{3b}$, —(CH$_2$)$_r$S(O)$_p$NR$^8$R$^9$, —(CH$_2$)$_r$NR$^8$S(O)$_p$R$^{3c}$, —S(O)R$^{3c}$, —S(O)$_2$R$^{3c}$, —C(O)—C$_{1-4}$ alkyl, —(CH$_2$)$_r$CO$_2$R$^{3b}$, —(CH$_2$)$_r$OC(O)R$^{3b}$, —(CH$_2$)$_r$C(O)NR$^8$R$^9$, —(CH$_2$)$_r$OC(O)NR$^8$R$^9$, —NHCOCF$_3$, —NHSO$_2$CF$_3$, —SO$_2$NHR$^{3b}$, —SO$_2$NHCOR$^{3c}$, —SO$_2$NHCO$_2$R$^{3c}$, —CONHSO$_2$R$^{3c}$, —NHSO$_2$R$^{3c}$, —CONHOR$^{3b}$, C$_{1-4}$ haloalkyl, C$_{1-4}$ haloalkyloxy, C$_{1-6}$ alkyl substituted by R$^{3d}$, C$_{2-6}$ alkenyl substituted by R$^{3d}$, C$_{1-6}$ alkynyl substituted by R$^{3d}$, C$_{3-6}$ cycloalkyl substituted by 0-1 R$^{3d}$, —(CH$_2$)$_r$—C$_{3-10}$ carbocycle substituted with 0-3 R$^{3d}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{3d}$;

alternately, when two R$^{3a}$ groups are substituted on adjacent atoms, they can be taken together with the atoms to which they are attached to form a C$_{3-10}$ carbocycle substituted with 0-2 R$^{3d}$, or a 5- to 10-membered heterocycle comprising: carbon atoms and 1-4 heteroatoms selected from N, O, and S(O)$_p$, wherein said heterocycle is substituted with 0-2 R$^{3d}$;

R$^{3b}$ is, independently at each occurrence, H, C$_{1-6}$ alkyl substituted with 0-2 R$^{3d}$, C$_{2-6}$ alkenyl substituted with 0-2 R$^{3d}$, C$_{2-6}$ alkynyl substituted with 0-2 R$^{3d}$, —(CH$_2$)$_r$—C$_{3-10}$ carbocycle substituted with 0-3 R$^{3d}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{3d}$;

R$^{3c}$ is, independently at each occurrence, C$_{1-6}$ alkyl substituted with 0-2 R$^{3d}$, C$_{2-6}$ alkenyl substituted with 0-2 R$^{3d}$, C$_{2-6}$ alkynyl substituted with 0-2 R$^{3d}$, —(CH$_2$)$_r$—C$_{3-10}$ carbocycle substituted with 0-3 R$^{3d}$, or —(CH$_2$)$_r$-5- to 10-membered heterocycle comprising: carbon atoms and 1-4 heteroatoms selected from N, O, and S(O)$_p$, wherein said heterocycle is substituted with 0-3 R$^{3d}$;

R$^{3d}$ is, independently at each occurrence, H, =O, —(CH$_2$)$_r$OR$^a$, F, Cl, Br, CN, NO$_2$, —(CH$_2$)$_r$NR$^7$R$^8$, —C(O)R$^a$, —C(O)OR$^a$, —OC(O)R$^a$, —NR$^8$C(O)R$^c$, —C(O)NR$^8$R$^9$, —S(O)$_2$NR$^8$R$^9$, —NR$^8$S(O)$_2$NR$^8$R$^9$, —$NR^8S(O)_2R^c$, —$S(O)_pR^c$, —$(CF_2)_rCF_3$, $C_{1-6}$ alkyl substituted with 0-2 $R^e$, $C_{2-6}$ alkenyl substituted with 0-2 $R^e$, $C_{2-6}$ alkynyl substituted with 0-2 $R^e$, —$(CH_2)_r$—$C_{3-10}$ carbocycle substituted with 0-3 $R^d$, or —$(CH_2)_r$-5- to 10-membered heterocycle comprising: carbon atoms and 1-4 heteroatoms selected from N, O, and $S(O)_p$, wherein said heterocycle is substituted with 0-3 $R^d$;

$R^4$ is, independently at each occurrence, H, =O, F, Cl, Br, I, $OCF_3$, $CF_3$, CN, $NO_2$, —$(CH_2)_rOR^a$, —$(CH_2)_rSR^a$, —$(CH_2)_rC(O)R^a$, —$(CH_2)_rC(O)OR^a$, —$OC(O)R^a$, —$(CH_2)_r$ $NR^7R^8$, —$NR^8(CH_2)_rC(O)OR^a$, —$(CH_2)_rC(O)NR^8R^9$, —$(CH_2)_rNR^8C(O)R^c$, —$(CH_2)_rNR^8C(O)_2R^b$, —$(CH_2)_r$ $NR^8C(O)NR^8R^9$—, —$S(O)_pNR^8R^9$, —$NR^8S(O)_pR^c$, —$S(O)_2R^c$, $C_{1-6}$ alkyl substituted with 0-2 $R^{4a}$, $C_{2-6}$ alkenyl substituted with 0-2 $R^{4a}$, $C_{2-6}$ alkynyl substituted with 0-2 $R^{4a}$, —$(CH_2)_r$—$C_{3-10}$ carbocycle substituted with 0-3 $R^{4b}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{4b}$;

$R^{4a}$ is, independently at each occurrence, H, F, =O, $C_{1-4}$ alkyl, $OR^a$, $SR^a$, $CF_3$, CN, $NO_2$, —$C(O)R^a$, —$C(O)OR^a$, —$NR^7R^8$, —$C(O)NR^8R^9$, —$NR^7C(O)R^c$, —$S(O)_pNR^8R^9$, —$NR^8S(O)_pR^c$, —$S(O)R^c$, or —$S(O)_2R^c$;

$R^{4b}$ is, independently at each occurrence, H, =O, =$NR^8$, F, Cl, Br, I, $OR^a$, $SR^a$, CN, $NO_2$, —$NR^7R^8$, —$C(O)R^a$, —$C(O)OR^a$, —$NR^7C(O)R^b$, —$C(O)NR^8R^9$, —$SO_2NR^8R^9$, —$S(O)_2R^c$, $C_{1-6}$ alkyl, $C_{2-6}$ alkenyl, $C_{2-6}$ alkynyl, $C_{3-6}$ cycloalkyl, $C_{1-4}$ haloalkyl, or $C_{1-4}$ haloalkyloxy;

alternately, $R^3$ and $R^4$ groups when located on adjacent atoms, can be taken together to form a $C_{3-10}$ carbocycle substituted with 0-2 $R^{3d}$ or a 5- to 10-membered heterocycle comprising: carbon atoms and 1-4 heteroatoms selected from N, O, and $S(O)_p$, wherein said heterocycle is substituted with 0-2 $R^{3d}$;

$R^6$ is, independently at each occurrence, H, $C_{1-6}$ alkyl substituted with 0-3 $R^d$, —$(CH_2)_r$-phenyl substituted with 0-3 $R^d$;

$R^7$ is, independently at each occurrence, H, $C_{1-6}$ alkyl, —$(CH_2)_n$—$C_{3-10}$ carbocycle, —$(CH_2)_n$-(5- to 10-membered heteroaryl), —$C(O)R^c$, —CHO, —$C(O)_2R^c$, —$S(O)_2R^c$, —$CONR^8R^c$, —$OCONHR^c$, —-$C(O)O$—$(C_{1-4}$ alkyl)$OC(O)$—$(C_{1-4}$ alkyl), or —$C(O)O$—$(C_{1-4}$ alkyl)$OC(O)$—$(C_{6-10}$ aryl); wherein said alkyl, carbocycle, heteroaryl, and aryl are substituted with 0-2 $R^f$; wherein said heteroaryl comprises: carbon atoms and 1-4 heteroatoms selected from N, O, and $S(O)_p$;

$R^8$ is, independently at each occurrence, H, $C_{1-6}$ alkyl, —$(CH_2)_n$-phenyl, or —$(CH_2)_n$-5- to 10-membered heterocycle comprising: carbon atoms and 1-4 heteroatoms selected from N, O, and $S(O)_p$; wherein said alkyl, phenyl and heterocycle are optionally substituted with 0-2 $R^f$;

alternatively, $R^7$ and $R^8$, when attached to the same nitrogen, combine to form a 5- to 10-membered heterocycle comprising: carbon atoms and 0-3 additional heteroatoms selected from N, O, and $S(O)_p$, wherein said heterocycle is substituted with 0-2 $R^f$;

$R^{8a}$ is, independently at each occurrence, $R^7$, OH, $C_{1-6}$ alkyl, $C_{1-4}$ alkoxy, $(C_{6-10}$ aryl)-$C_{1-4}$ alkoxy, —$(CH_2)_n$-phenyl, —$(CH_2)_n$-(5-10 membered heteroaryl); wherein said phenyl, aryl and heteroaryl are optionally substituted with 0-2 $R^f$;

$R^9$ is, independently at each occurrence, H, $C_{1-6}$ alkyl, or —$(CH_2)_n$-phenyl; wherein said alkyl and phenyl are optionally substituted with 0-2 $R^f$;

alternatively, $R^8$ and $R^9$, when attached to the same nitrogen, combine to form a 5- to 12-membered heterocycle comprising: carbon atoms and 0-2 additional heteroatoms selected from N, O, and $S(O)_p$, wherein said heterocycle is substituted with 0-2 $R^d$;

$R^{10}$ is, independently at each occurrence, H, $C_{1-6}$ alkyl substituted with 0-2 $R^{10a}$, $C_{2-6}$ alkenyl substituted with 0-3 $R^{10a}$, $C_{2-6}$ alkynyl substituted with 0-3 $R^{10a}$, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, wherein said heterocycle is substituted with 0-3 $R^d$;

$R^{10a}$ is, independently at each occurrence, H, =O, $C_{1-4}$ alkyl, $OR^a$, $SR^a$, F, $CF_3$, CN, $NO_2$, —$C(O)R^a$, —$C(O)OR^a$, —$C(O)NR^7R^8$, —$NR^7C(O)R^b$, —$S(O)_pNR^8R^9$, —$NR^8S(O)_pR^c$, —$S(O)R^c$, or —$S(O)_2R^c$;

$R^{11}$ is $C_{1-4}$ haloalkyl, —$C(O)NR^8R^9$, —$CH_2C(O)NR^8R^9$, —$CH_2CH_2C(O)NR^8R^9$, —$C(O)R^a$, —$CH_2C(O)R^a$, —$CH_2CH_2C(O)R^a$, —$C(O)OR^a$, —$CH_2C(O)OR^a$, —$CH_2CH_2C(O)OR^a$, $C_{1-6}$ alkyl substituted with 0-3 $R^{11c}$, $C_{2-6}$ alkenyl substituted with 0-3 $R^{11a}$; $C_{2-6}$ alkynyl substituted with 0-3 $R^{11a}$, —$(CH_2)_s$—$C_{3-7}$ cycloalkyl substituted with 0-2 $R^{11b}$, —$(CH_2)_s$-phenyl substituted with 0-3 $R^{11b}$, —$(CH_2)_s$-naphthyl substituted with 0-3 $R^{11b}$, or —$(CH_2)_s$-5- to 10-membered heterocycle comprising: carbon atoms and 1-4 heteroatoms selected from N, O, and $S(O)_p$, wherein said heterocycle is substituted with 0-3 $R^{11b}$;

$R^{11a}$ is, independently at each occurrence, H, =O, $C_{1-4}$ alkyl, $OR^a$, $SR^2$, F, $CF_3$, CN, $NO_2$, —$NR^7R^8$, —$C(O)R^a$, —$C(O)OR^a$, —$C(O)NR^8R^9$, —$NR^8C(O)R^c$, —$NR^8C(O)OR^c$, —$NR^8CHO$, —$S(O)_pNR^8R^9$, —$NR^8S(O)_pR^c$, —$S(O)_pR^c$, $C_{3-6}$ cycloalkyl, $C_{1-4}$ haloalkyl, $C_{1-4}$ haloalkyloxy, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, and substituted with 0-3 $R^d$;

$R^{11b}$ is, independently at each occurrence, H, =O, =$NR^8$, $OR^a$, $SR^a$, F, Cl, Br, CN, $NO_2$, $CF_3$, $OCF_3$, $OCHF_2$, —$NR^7R^8$, —$C(O)R^a$, —$C(O)OR^a$, —$C(O)NR^8R^9$, —$NR^8C(O)R^c$, —$NR^8C(O)_2R^c$, —$S(O)_pNR^8R^9$, —$NR^8S(O)_pR^c$, —$S(O)_pR^c$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, and substituted with 0-3 $R^d$;

alternately, when two $R^{11b}$ groups are substituents on adjacent atoms they may be taken together with the atoms to which they are attached to form a 5- to 7-membered heterocycle comprising carbon atoms and 1-4 heteroatoms selected from N, O, and $S(O)_p$ and substituted with 0-2 $R^g$;

$R^{11c}$ is, independently at each occurrence H, =O, $OR^a$, $SR^a$, F, $CF_3$, CN, $NO_2$, —$NR^7R^8$, —$NR^8C(O)R^c$, —$NR^8C(O)OR^c$, —$NR^8CHO$, —$S(O)_pNR^8R^9$, —$NR^8S(O)_pR^c$, —$S(O)_pR^c$, $C_{1-4}$ alkyl, $C_{3-6}$ cycloalkyl, $C_{1-4}$ haloalkyl, $C_{1-4}$ haloalkyloxy, —$(CH_2)_r$—$C_{3-10}$ carbocycle substituted with 0-3 $R^d$, or —$(CH_2)_r$-5- to 10-membered heterocycle comprising carbon atoms and 1-4 heteroatoms selected from N, O, and $S(O)_p$, and substituted with 0-3 $R^d$;

$R^{12}$ is $C_{1-6}$ alkyl, —$(CH_2)_s$-cycloalkyl, —$(CH_2)_s$-phenyl, —$(CH_2)_s$-naphthyl, —$(CH_2)_rNR^8C(O)R^a$, —$C(O)R^c$, —$C(O)OR^c$, —$CONR^8R^c$, —$S(O)_2R^c$, —$C(O)O$—$(C_{1-4}$ alkyl)-$OC(O)$—$(C_{1-14}$ alkyl), —$C(O)O$—$(C_{1-4}$ alkyl)-$OC(O)$—$(C_{6-10}$ aryl), or —$(CH_2)_s$-5- to 10-membered heteroaryl comprising: carbon atoms and 1-4 heteroatoms selected from N, O, and $S(O)_p$; wherein said alkyl, phenyl, aryl, and heteroaryl are optionally substituted with 0-3 $R^f$;

$R^a$ is, independently at each occurrence, H, $CF_3$, $C_{1-6}$ alkyl, —$(CH_2)_r$—$C_{3-7}$ cycloalkyl, —$(CH_2)_r$—$C_{6-10}$ aryl, or —(CH$_2$)$_r$-5- to 10-membered heterocycle comprising: carbon atoms and 1-4 heteroatoms selected from N, O, and S(O)$_p$; wherein said cycloalkyl, aryl and heterocycle groups are optionally substituted with 0-2 R$^f$;

R$^b$ is, independently at each occurrence, CF$_3$, OH, C$_{1-4}$ alkoxy, C$_{1-6}$ alkyl, —(CH$_2$)$_r$—C$_{3-10}$ carbocycle substituted with 0-3 R$^d$, or —(CH$_2$)$_r$-5- to 10-membered heterocycle comprising: carbon atoms and 1-4 heteroatoms selected from N, O, and S(O)$_p$ and substituted with 0-2 R$^d$;

R$^c$ is, independently at each occurrence, CF$_3$, C$_{1-6}$ alkyl substituted with 0-2 R$^f$, C$_{3-6}$ cycloalkyl substituted with 0-2 R$^f$, C$_{6-10}$ aryl, 5- to 10-membered heteroaryl, (C$_{6-10}$ aryl)-C$_{1-4}$ alkyl, or (5- to 10-membered heteroaryl)-C$_{1-4}$ alkyl, wherein said aryl is substituted with 0-3 R$^f$ and said heteroaryl comprises: carbon atoms and 1-4 heteroatoms selected from N, O, and S(O)$_p$ and substituted with 0-3 R$^f$;

R$^d$ is, independently at each occurrence, H, =O, =NR$^8$, OR$^a$, F, Cl, Br, I, CN, NO$_2$, —NR$^7$R$^8$, —C(O)R$^a$, —C(O)OR$^a$, —OC(O)R$^a$, —NR$^8$C(O)R$^c$, —C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl substituted with 0-2 R$^e$, C$_{2-6}$ alkenyl substituted with 0-2 R$^e$, or C$_{2-6}$ alkynyl substituted with 0-2 R$^e$;

R$^e$ is, independently at each occurrence, =O, OR$^a$, F, Cl, Br, I, CN, NO$_2$, —NR$^7$R$^8$, —C(O)R$^a$, —C(O)OR$^a$, —NR$^8$C(O)R$^c$, —C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

R$^f$ is, independently at each occurrence, H, =O, —(CH$_2$)$_r$OR$^g$, F, Cl, Br, I, CN, NO$_2$, —NR$^g$R$^g$, —C(O)R$^g$, —C(O)OR$^g$, —NR$^g$C(O)R$^g$, —C(O)NR$^g$R$^g$, —SO$_2$NR$^g$R$^g$, —NR$^g$SO$_2$NR$^g$R$^g$, —NR$^g$SO$_2$—C$_{1-4}$ alkyl, —NR$^g$SO$_2$CF$_3$, —NR$^g$SO$_2$-phenyl, —S(O)$_2$CF$_3$, —S(O)$_p$—C$_{1-4}$ alkyl, —S(O)$_p$-phenyl, —(CH$_2$) α-phenyl, —(CF$_2$)$_r$CF$_3$, C$_{1-6}$ alkyl, C$_{2-6}$ alkenyl, C$_{2-6}$ alkynyl, —(CH$_2$)$_n$-phenyl, or —(CH$_2$)$_n$-5- to 10-membered heterocycle comprising carbon atoms and 1-4 heteroatoms selected from N, O, and S(O)$_p$;

alternately, when two R$^f$ groups are substituents on adjacent atoms they may be taken together with the atoms to which they are attached to form a 5-7-membered heterocycle comprising carbon atoms and 1-4 heteroatoms selected from N, O, and S(O)$_p$ and substituted with 0-2 R$^g$;

R$^g$ is, independently at each occurrence, H, C$_{1-6}$ alkyl, or —(CH$_2$)$_n$-phenyl;

n, at each occurrence, is selected from 0, 1, 2, 3, and 4;
p, at each occurrence, is selected from 0, 1, and 2; and
r, at each occurrence, is selected from 0, 1, 2, 3, and 4; and
s, at each occurrence, is selected from 1, 2, 3, and 4;

provided that: when R$^{11}$ is —CH$_2$CO$_2$H, A is other than substituted piperidyl. (J. Med. Chem. (1999), 42(25), 5254-5265)

In another embodiment, the present invention includes a compound of Formula (II), or stereoisomers, tautomers, pharmaceutically acceptable salts, solvates, or prodrugs thereof, wherein:

the group

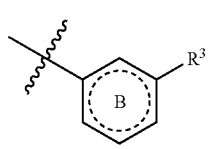

is selected from:

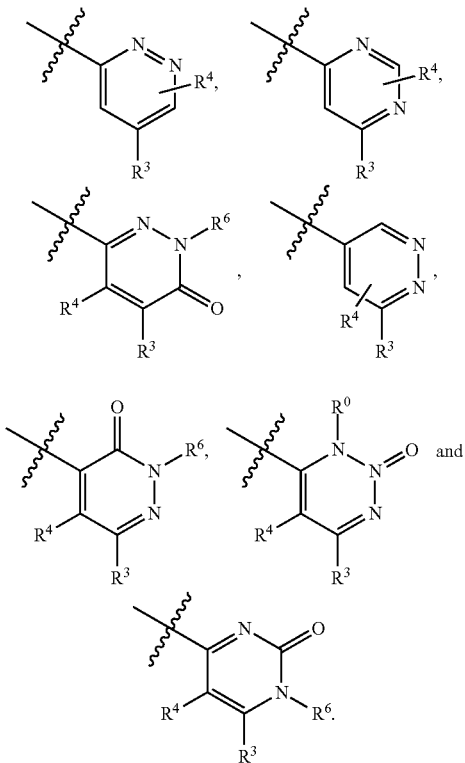

In another embodiment, the group

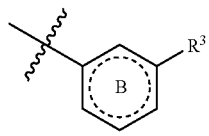

is selected from:

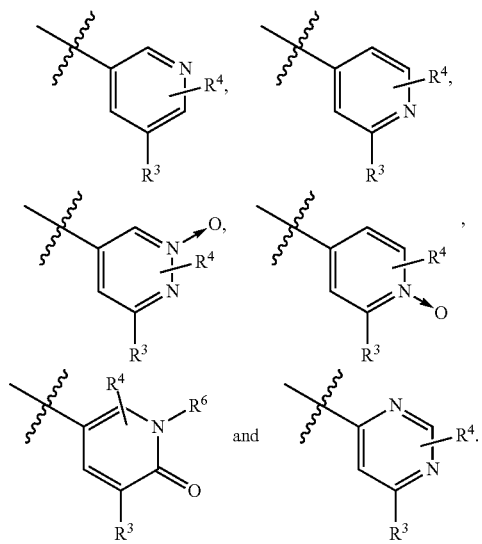

In another embodiment, the group
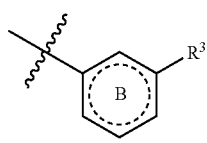
is selected from:
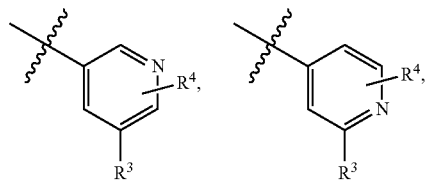
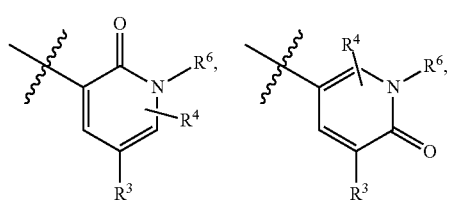
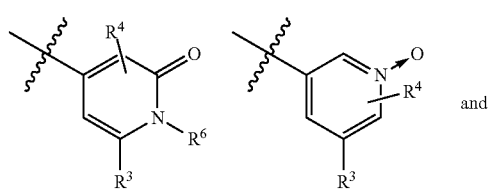
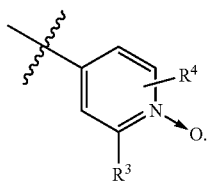
In another embodiment, the group
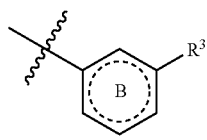
is selected from:
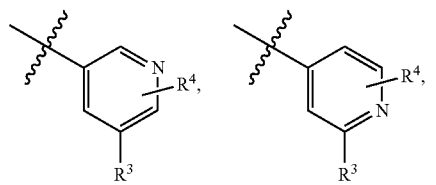
-continued
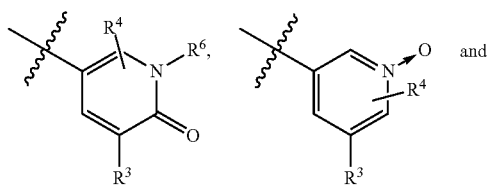 and
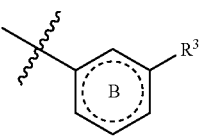
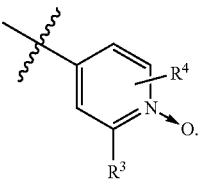
In another embodiment, the group
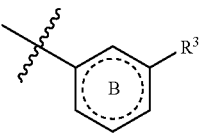
is selected from:
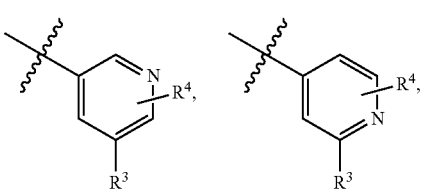
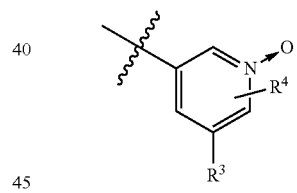 and 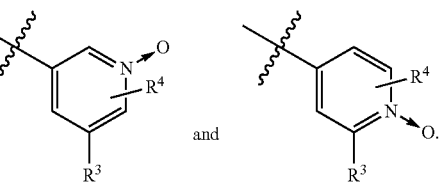
In another embodiment, the group
is selected from:
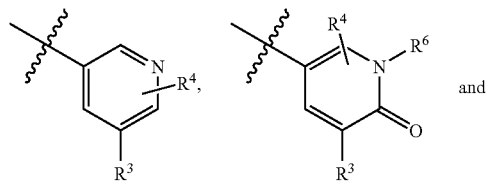 and

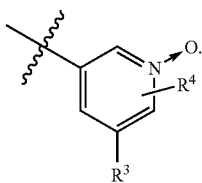

In another embodiment, the group

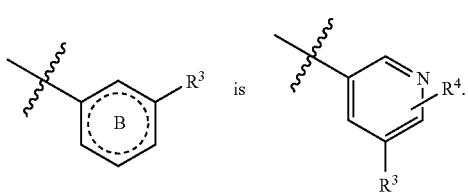

In another embodiment, the group

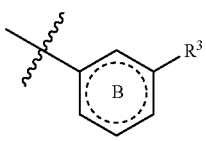

is selected from:

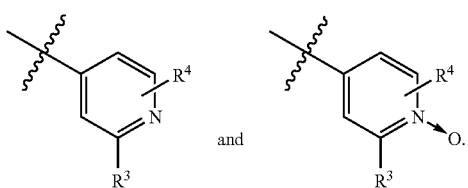

In another embodiment, the group

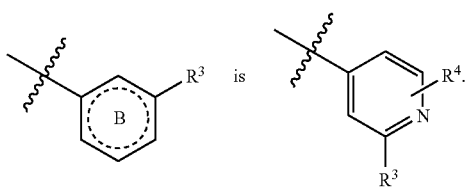

In another embodiment, the group

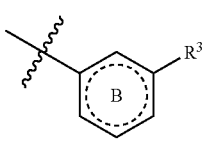

is selected from:

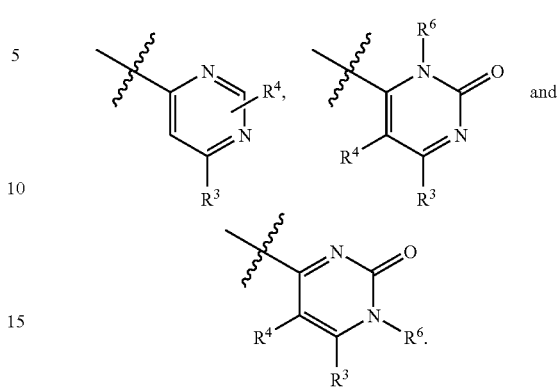

In another embodiment, the group

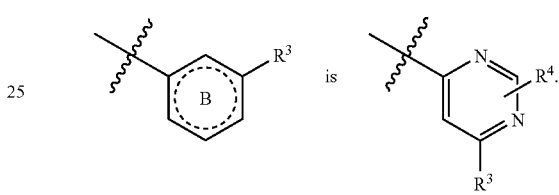

In another embodiment, A is substituted with 0-1 $R^1$ and 0-3 $R^2$ and selected from: $C_{3-7}$ cycloalkyl, phenyl, naphthyl, pyridyl, 1,2,3,4-tetrahydronaphthyl, pyrrolidinyl, indazolyl, indolyl, imidazolyl, furanyl, thienyl, benzimidazolyl, benzisoxazolyl, benzothiazolyl, benzothiophenyl, 3,4-methylenedioxy-phenyl, oxazolyl, isoxazolyl, thiazolyl, isothiazolyl, pyrazolyl, quinolinyl, isoquinolinyl, 1H-4-oxo-isoquinazolinyl, 2H-1-oxo-isquinilinyl, 3H-4-oxo-quinazolinyl, 3,4-dihydro-2H-1-oxo-isoquinolinyl, 2,3-dihydro-isoindolinyl, 5,6,7,8-tetrahydroquinolinyl, 1,2,3,4-tetrahydroquinolinyl, 5,6,7,8-tetrahydroisoquinolinyl, 1,2,3,4-tetrahydroisoquinolinyl, quinazolinyl, and phthalazinyl.

In another embodiment, A is substituted with 0-1 $R^1$ and 0-3 $R^2$ and selected from: $C_{3-7}$ cycloalkyl, phenyl, pyridyl, pyrrolidinyl, indazolyl, indolyl, imidazolyl, furanyl, thienyl, oxazolyl, isoxazolyl, thiazolyl, isothiazolyl, and pyrazolyl.

In another embodiment, A is substituted with 0-1 $R^1$ and 0-3 $R^2$ and selected from: naphthyl, 1,2,3,4-tetrahydronaphthyl, benzimidazolyl, benzisoxazolyl, benzothiazolyl, benzothiophenyl, 3,4-methylenedioxy-phenyl, quinolinyl, isoquinolinyl, 1H-4-oxo-isoquinazolinyl, 2H-1-oxo-isquinilinyl, 3H-4-oxo-quinazolinyl, 3,4-dihydro-2H-1-oxo-isoquinolinyl, 2,3-dihydro-isoindolinyl, 5,6,7,8-tetrahydroquinolinyl, 1,2,3,4-tetrahydroquinolinyl, 5,6,7,8-tetrahydroisoquinolinyl, 1,2,3,4-tetrahydroisoquinolinyl, quinazolinyl, and phthalazinyl.

In another embodiment, A is 4-aminomethyl-cyclohexyl, 4-methylcyclohexyl, 4-methylphenyl, 3-methoxyphenyl, 4-methoxyphenyl, 4-aminomethylphenyl, 3-carbamoylphenyl, 4-carbamoylphenyl, 3-amidinophenyl, 4-amidinophenyl, 2-fluoro-4-methylphenyl, 2,6-difluoro-4-methylphenyl, 2-fluoro-4-methoxyphenyl, 2,6-difluoro-4-methoxyphenyl, 2-fluoro-4-aminomethylphenyl, 2-fluoro-4-carbamoylphenyl, 2-chloro-4-carbamoylphenyl, 2-methoxy-4-carbamoylphenyl, 4-amino-2-fluorophenyl, 4-amino-2,6-difluoromethylphenyl, 4-amino-3-chloro-2,6-difluorophenyl, 4-amino-3-chlorophenyl, 1,2,3,4-tetrahydronaphth-2-yl, 5-chlorothien-2-yl, indol-5-yl, indol-6-yl, indazol-6-yl, 3-amino-indazol-6-yl, 3-amino-indazol-5-yl, 1-methyl-3-amino-indazol-6-yl, 3-amino-benzisoxazol-6-yl, benzimidazol-5-yl, 6-fluoro-benzimidazol-5-yl, 1,2,3,4-tetrahydroisoquinolin-6-yl, 1,2,3,4-tetrahydroisoquinolin-3-yl, 1,2,3,4-tetrahydroisoquinolin-1-on-6-yl, 2H-isoquinolin-1-on-6-yl, isoquinolin-6-yl, 1-amino-isoquinolin-6-yl, 1-amino-3-methyl-isoquinolin-6-yl, 1-amino-5,6,7,8-tetrahydroisoquinolin-6-yl, or 4-amino-quinazolin-7-yl, 3H-quinazolin-4-on-7-yl.

In another embodiment, A is 4-aminomethyl-cyclohexyl, 4-methylcyclohexyl, 4-methoxyphenyl, 4-aminomethylphenyl, 4-carbamoylphenyl, 4-amidinophenyl, 2-fluoro-4-methylphenyl, 2,6-difluoro-4-methylphenyl, 2-fluoro-4-methoxyphenyl, 2,6-difluoro-4-methoxyphenyl, 2-fluoro-4-aminomethylphenyl, 2-fluoro-4-carbamoyl-phenyl, 4-amino-2-fluorophenyl, 4-amino-2,6-difluoromethylphenyl, 4-amino-3-chloro-2,3-difluorophenyl, 4-amino-3-chlorophenyl, or 3-chlorothien-2-yl.

In another embodiment, A is indol-5-yl, indol-6-yl, indazol-6-yl, 3-amino-indazol-6-yl, 3-amino-indazol-5-yl, 1-methyl-3-amino-indazol-6-yl, 3-amino-benzisoxazol-6-yl, benzimidazol-5-yl, 6-fluoro-benzimidazol-5-yl, 1,2,3,4-tetrahydroisoquinolin-6-yl, 1,2,3,4-tetrahydroisoquinolin-3-yl, 2H-isoquinolin-1-on-6-yl, isoquinolin-6-yl, 1-amino-isoquinolin-6-yl, 1-amino-3-methyl-isoquinolin-6-yl, 1-amino-5,6,7,8-tetrahydroisoquinolin-6-yl, 4-amino-quinazolin-7-yl, or 3H-quinazolin-4-on-7-yl.

In another embodiment, $R^1$ is, independently at each occurrence, F, Cl, Br, I, $OCF_3$, $CF_3$, $OCH_3$, $CH_3$, Et, $NH_2$, —C(=NH)$NH_2$, —C(O)$NH_2$, —$CH_2NH_2$ or —$SO_2NH_2$.

In another embodiment, $R^2$ is, independently at each occurrence, F, Cl, Br, $CF_3$, $NO_2$, —$(CH_2)_rOR^a$, —$(CH_2)_rSR^a$, —C(O)$OR^a$, —C(O)$NR^8R^9$, —$NR^8$C(O)$R^c$, —$NR^8$C(O)$OR^c$, —$NR^8$C(O)$NR^8R^c$, —S(O)$_pNR^8R^9$, —$NR^8SO_2R^c$, —$NR^7R^8$, —S(O)$R^c$, —S(O)$_2R^c$, $C_{1-6}$ alkyl substituted with 0-1 $R^{2a}$, or a 5-7 membered heterocycle comprising carbon atoms and 1-4 heteroatoms selected from N, O, and S(O)$_p$, wherein said heterocycle is substituted with 0-2 $R^{2b}$.

In another embodiment, $R^2$ is, independently at each occurrence, =O, F, Cl, Br, $CF_3$, Me, Et, $OR^a$, CN, $NO_2$, $NR^7R^8$, —$CH_2$OMe, —$SR^a$, —$CH_2$SMe, —C(O)$OR^a$, —$CH_2NR^7R^8$, —$SO_2NH_2$, —$SO_2$Me, —$NHSO_2R^c$, —$CH_2NHSO_2R^c$, —C(O)$NR^8R^9$, —NHC(O)$R^c$, —$CH_2$NHC(O)$R^c$, —NHC(O)$OR^c$, —$CH_2$NHC(O)$OR^c$, —NHC(O)$NHR^c$, —$CH_2$NHC(O)$NHR^c$, or a 5-7 membered heterocycle substituted with 0-2 $R^{2b}$ and selected from: pyrrolidinyl, 2-oxo-1-pyrrolidinyl, piperidinyl, pyrazolyl, triazolyl, or tetrazolyl.

In another embodiment, $R^3$ is, independently at each occurrence, phenyl substituted with 0-2 $R^{3a}$ and 0-1 $R^{3d}$, naphthyl substituted with 0-2 $R^{3a}$ and 0-1 $R^{3d}$, or a 5- to 12-membered heterocycle substituted with 0-2 $R^{3a}$ and 0-1 $R^{3d}$, wherein said heterocycle is selected from: thiophene, furan, thiazole, tetrazole, pyridine, pyridone, pyrimidine, pyrrole, pyrazole, indole, 2-oxindole, isoindoline, indazole, 7-azaindole, benzofuran, benzothiophene, benzimidazole, benzisoxazole, benzoxazole, quinazoline, quinoline, isoquinoline, quinoxaline, phthalazine, dihydrophthalazine, dihydroisoquinoline, dihydroquinoline, dihydroquinolone, dihydroindole, dihydrobenzimidazole, dihydrobenzoxazine, dihydroquinazoline, dihydroquinoxaline, benzothiazine, benzoxazine, tetrahydrobenzazepine, dihydroazabenzocycloheptene, and tetrahydroquinoline.

In another embodiment, $R^3$ is, independently at each occurrence, phenyl, 3-biphenyl, 4-biphenyl, 3-aminophenyl, 4-aminophenyl, 3-N,N-dimethylaminophenyl, 4-phenoxyphenyl, 4-benzyloxyphenyl, 4-(t-butoxymethyl)-phenyl, 4-methylsulfonylphenyl, 3-cyanophenyl, 4-cyanophenyl, 3-fluorophenyl, 4-fluorophenyl, 3-chlorophenyl, 4-chlorophenyl, 3-bromophenyl, 4-bromophenyl, 3-hydroxyphenyl, 4-hydroxyphenyl, 2-methoxyphenyl, 3-methoxyphenyl, 4-methoxyphenyl, 3-trifluoromethylphenyl, 4-trifluoromethylphenyl, 3-carboxyphenyl, 4-carboxyphenyl, 3-methoxycarbonylphenyl, 4-methoxycarbonylphenyl, 3-carboxymethylphenyl, 4-carboxymethylphenyl, 4-methoxycarbonylmethylphenyl, 3-ethoxycarbonylmethylphenyl, 4-ethoxycarbonylmethylphenyl, 4-ethoxycarbonylethylphenyl, 3-carbamoylphenyl, 4-carbamoylphenyl, 3-aminocarbonylmethylphenyl, 4-aminocarbonylmethylphenyl, 4-methylaminocarbonylphenyl, 4-dimethylaminocarbonylmethylphenyl, 4-amidinophenyl, 3-methylcarbonylaminophenyl, 4-methylcarbonylaminophenyl, 4-methoxycarbonylaminophenyl, 4-aminosulfonylphenyl, 3-methylsulfonylaminophenyl, 4-methylsulfonylamino, 2,4-difluorophenyl, 3-fluoro-4-cyanophenyl, 4-amino-3-carboxyphenyl, 4-amino-3-methoxycarbonylphenyl, 2,4-dichlorophenyl, 3-cyano-5-fluorophenyl, 3-fluoro-4-carbamoylphenyl, 3-carboxy-4-cyanophenyl, 3-phenyl-4-carbamoylphenyl, 4-(2-oxo-1-piperidino)-phenyl, thiazol-2-yl, thien-2-yl, 4-methoxycarbonyl-thiazol-2-yl, 4-carbamoyl-thiazol-2-yl, 1-benzyl-pyazol-4-yl, 5-phenyl-oxazol-2-yl, 5-carbamoyl-thien-2-yl, 5-carboxy-thien-2-yl, pyrid-2-yl, pyrid-3-yl, pyrid-4-yl, 6-amino-pyrid-3-yl, benzimidazol-2-yl, 6-methoxy-pyrid-3-yl, 1-methyl-benzimidazol-2-yl, benzoxazol-2-yl, benzothiazol-2-yl, 3-amino-benzisoxazol-6-yl, 3-amino-benzisoxazol-5-yl, indazol-5-yl, indazol-6-yl, 3-amino-indazol-5-yl, 3-hydroxy-indazol-5-yl, 3-amino-indazol-6-yl, 3-amino-1-methyl-indazol-6-yl, 3-amino-4-fluoro-indazol-6-yl, 3-amino-5-fluoro-indazol-6-yl, 3-amino-7-fluoro-indazol-6-yl, 4-imino-3,4-dihydro-2H-phthalazin-1-on-7-yl, 3-(5-tetrazolyl)-phenyl, 2,3-dihydro-isoindol-1-on-6-yl, quinolin-5-yl, quinolin-6-yl, quinolin-8-yl, isoquinolin-5-yl, 2H-isoquinolin-1-on-6-yl, 2,4-diaminoquinazolin-7-yl, 4-$NH_2$-quinazolin-7-yl,

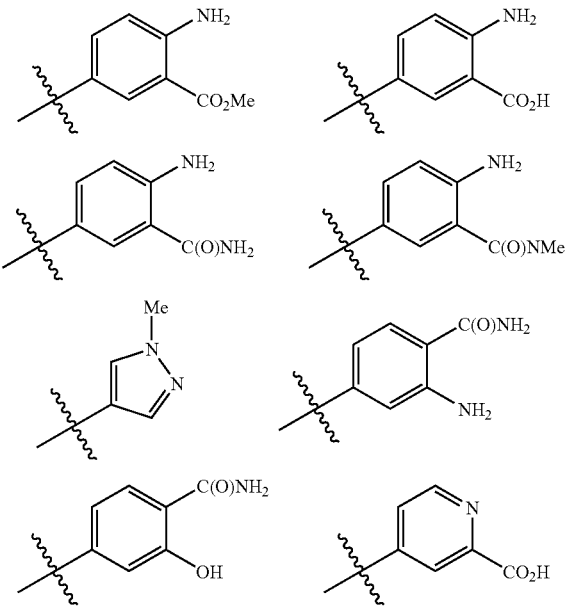

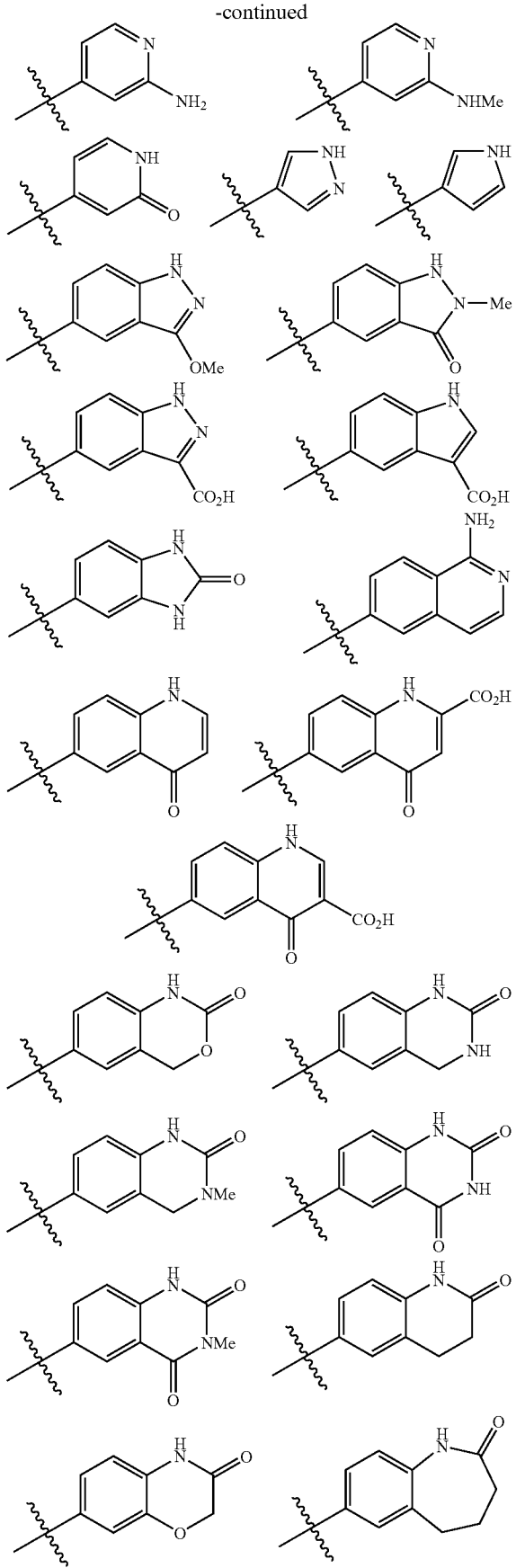
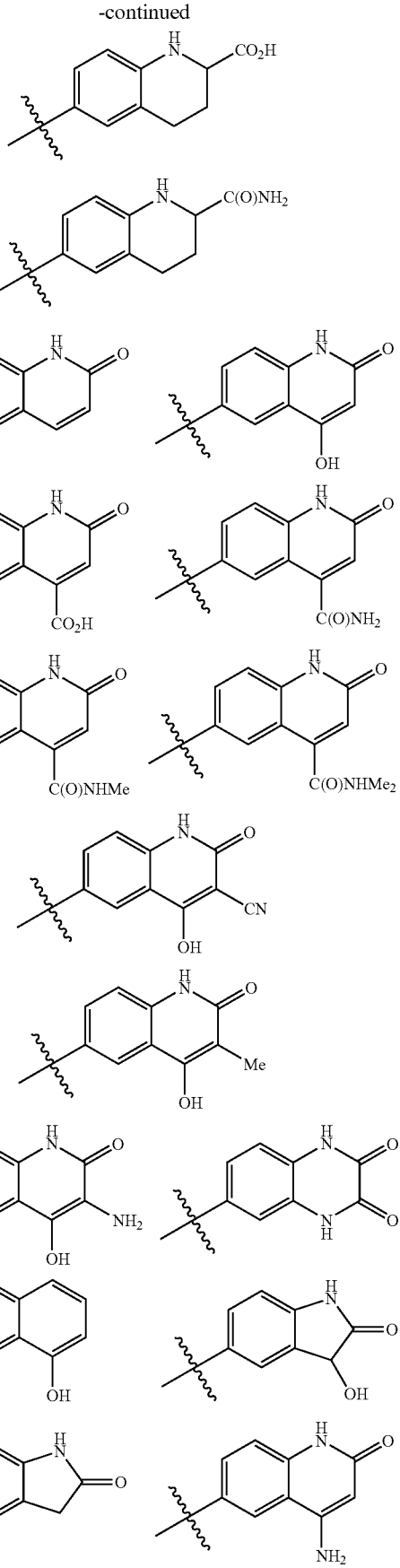

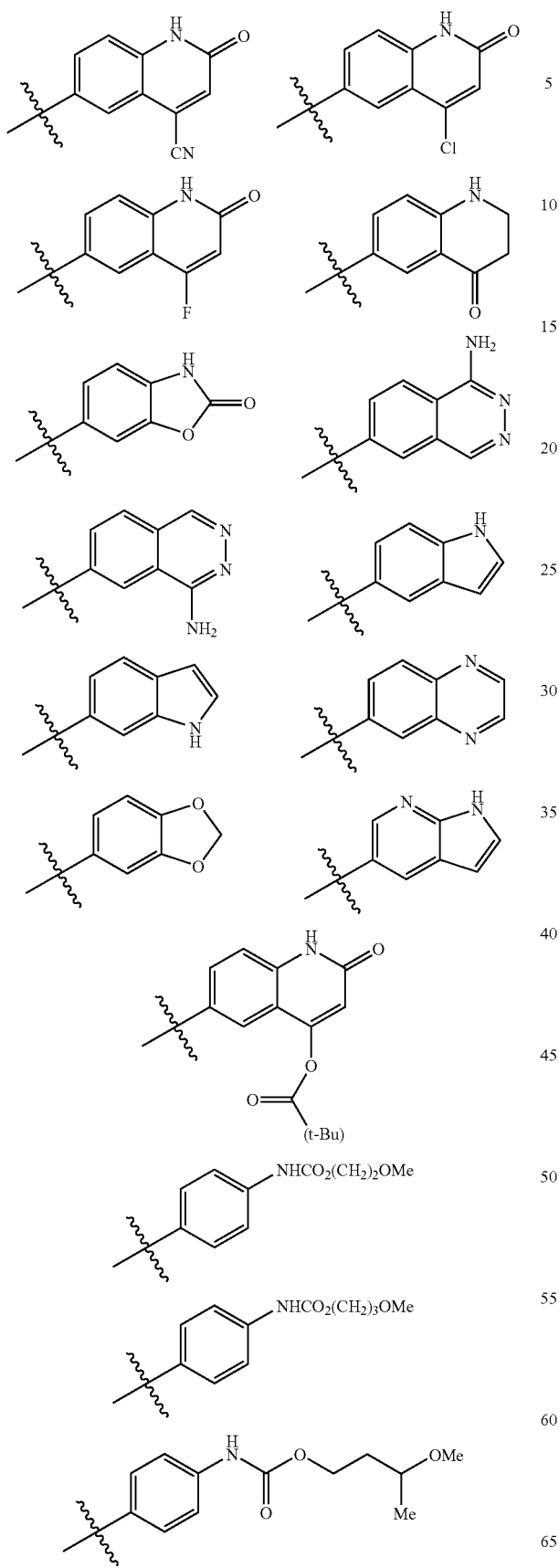
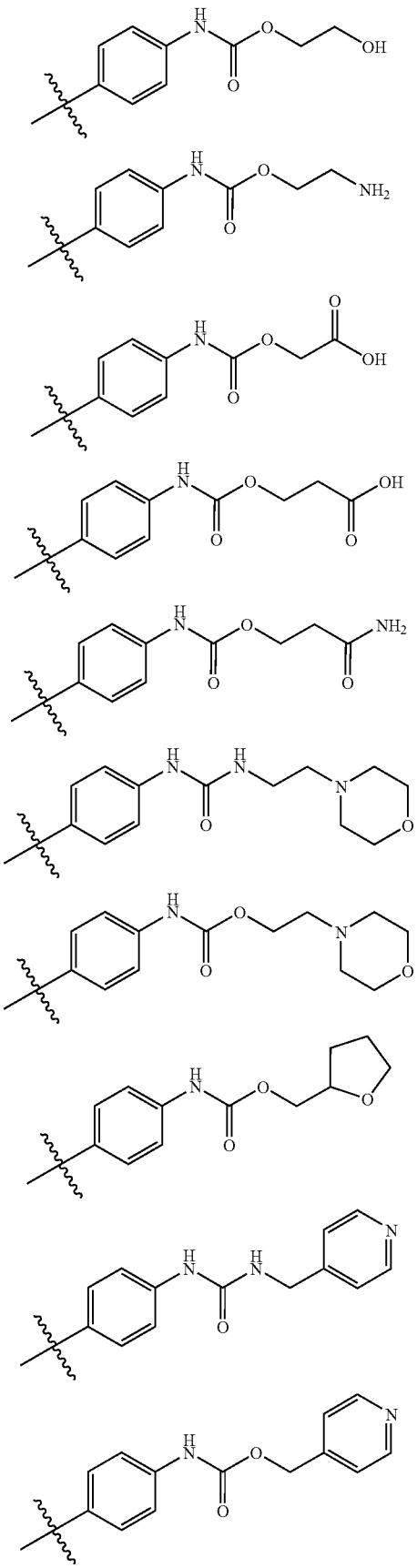

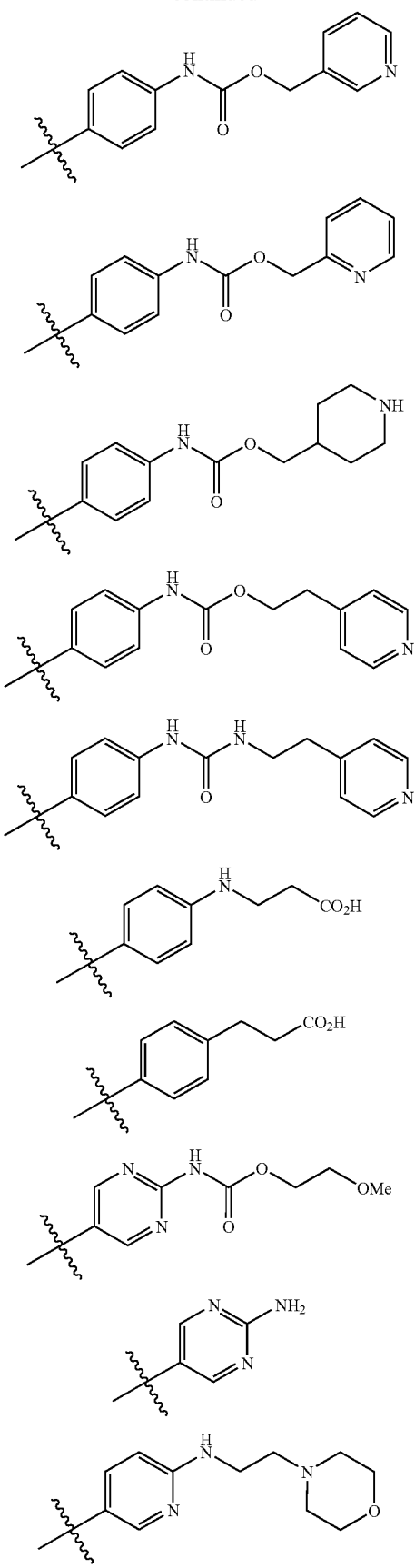
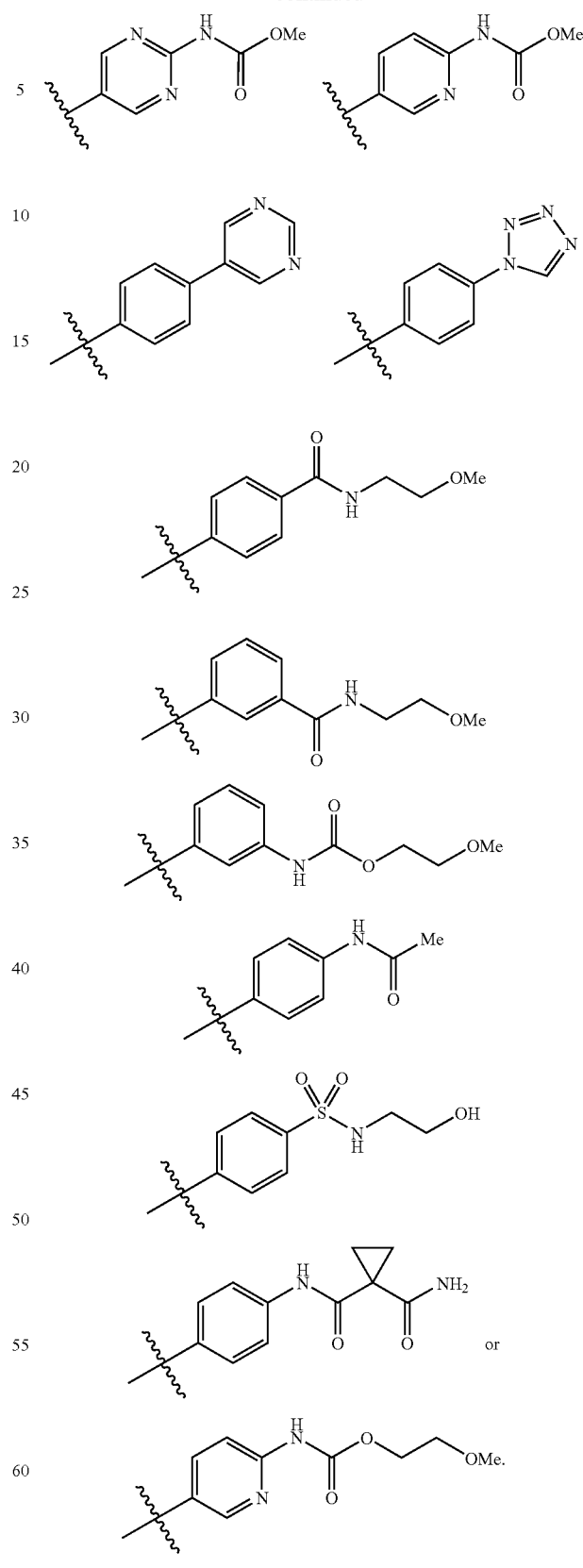
In another embodiment, $R^3$ is, independently at each occurrence,

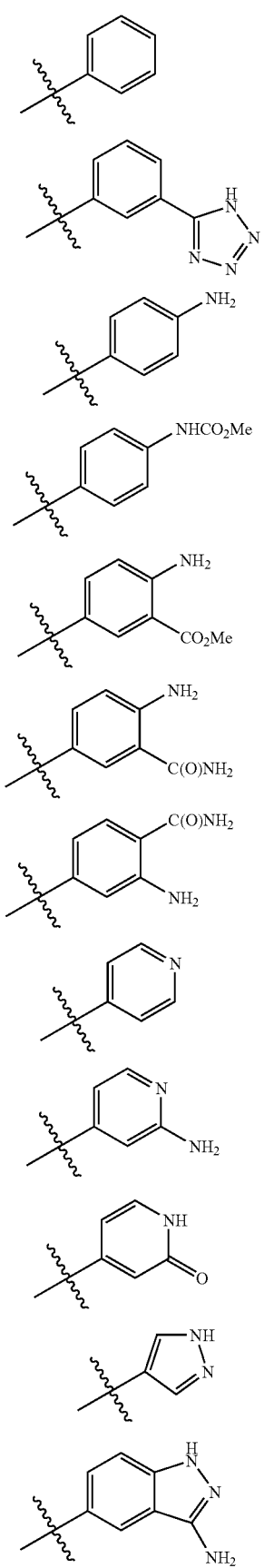
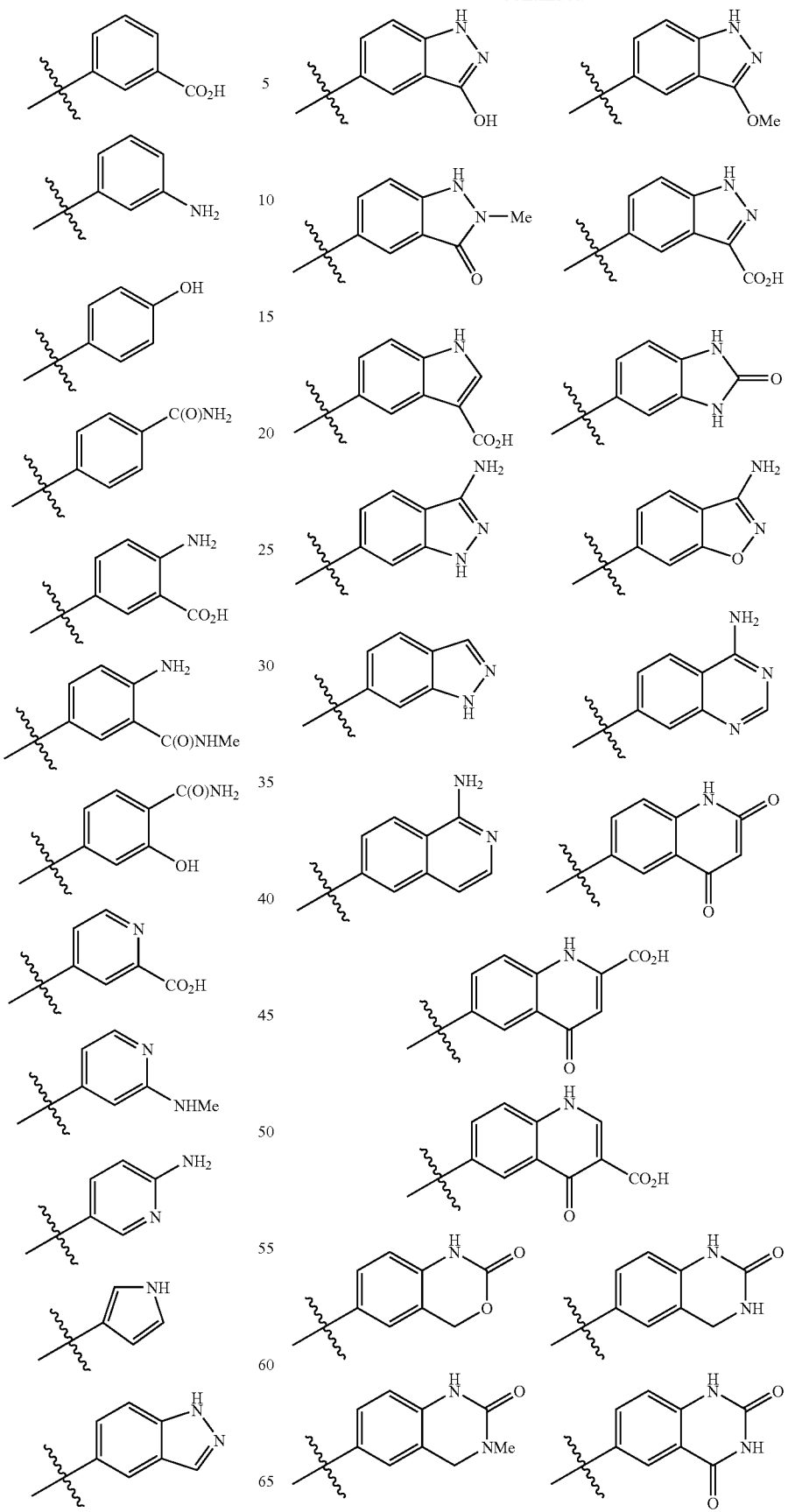

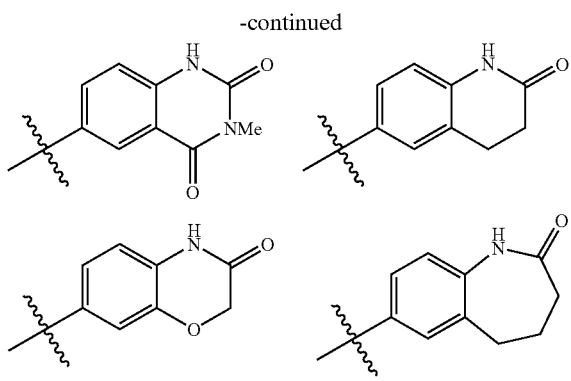
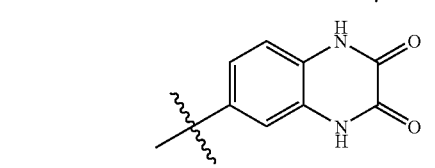
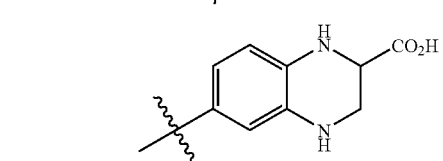
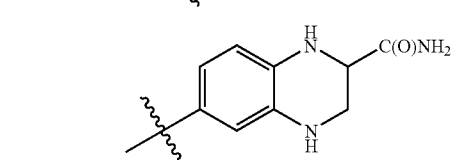
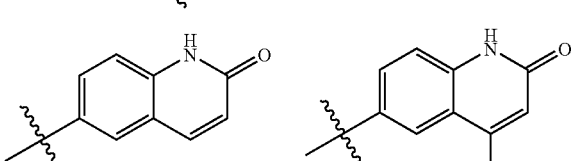
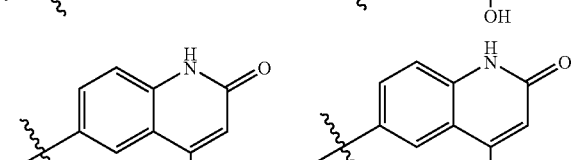
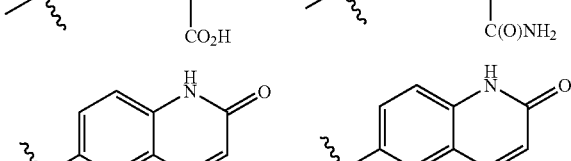
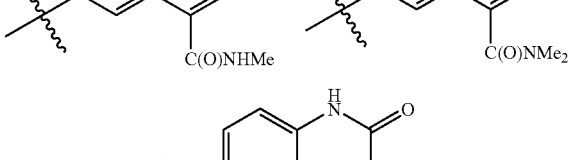
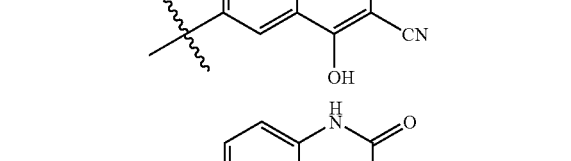
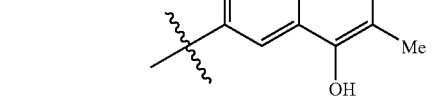
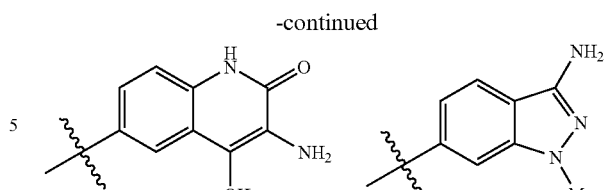
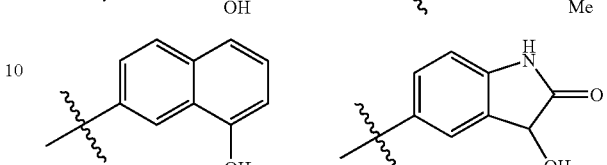
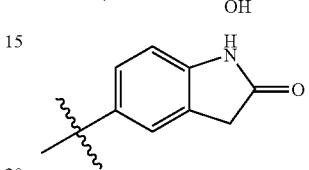
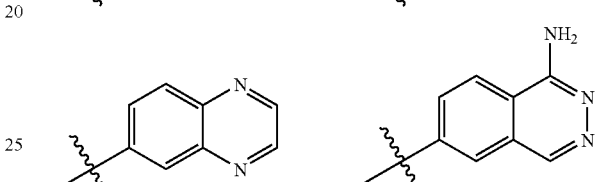
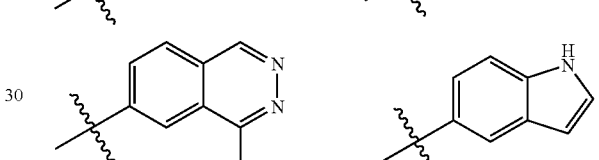
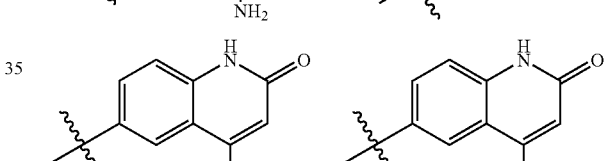
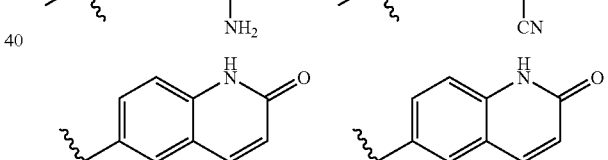
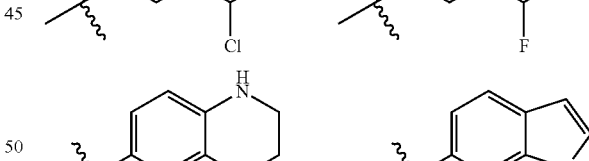
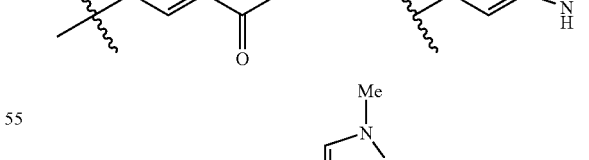
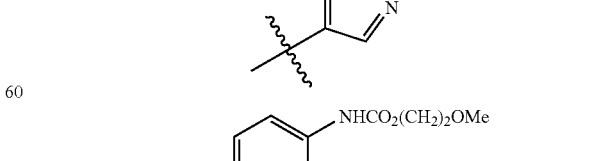
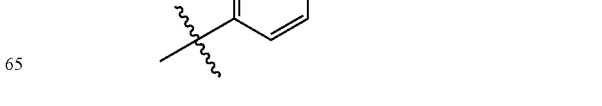

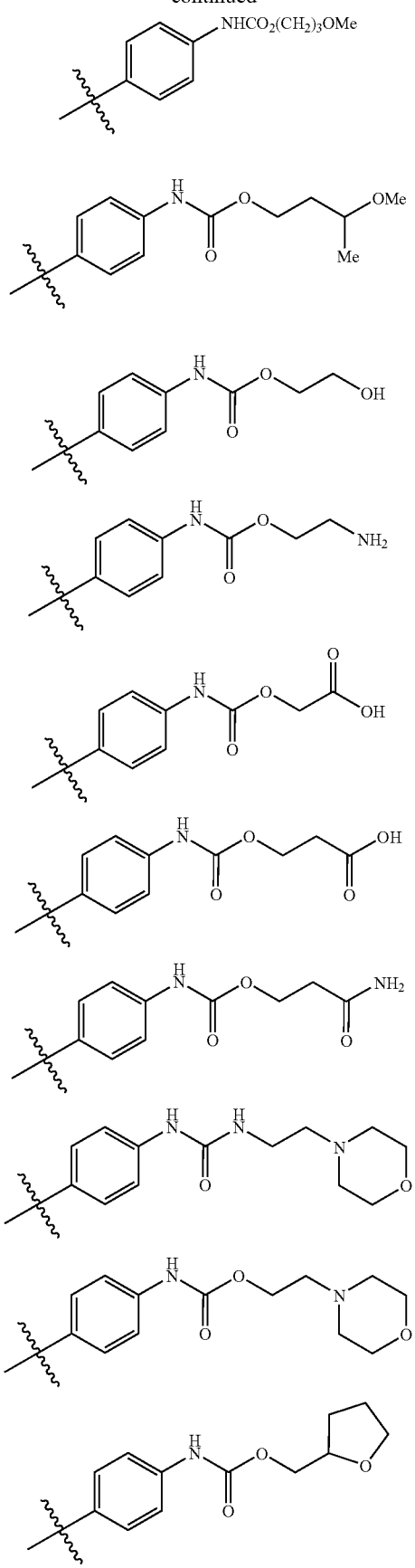
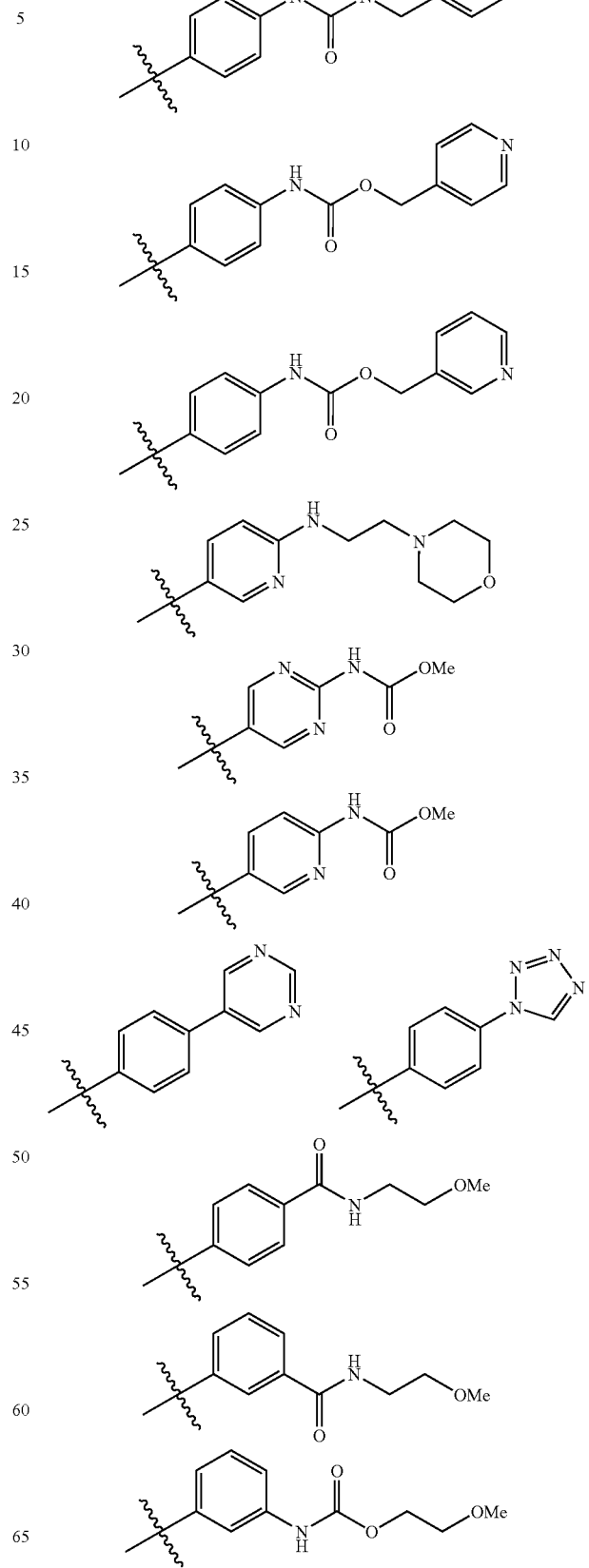

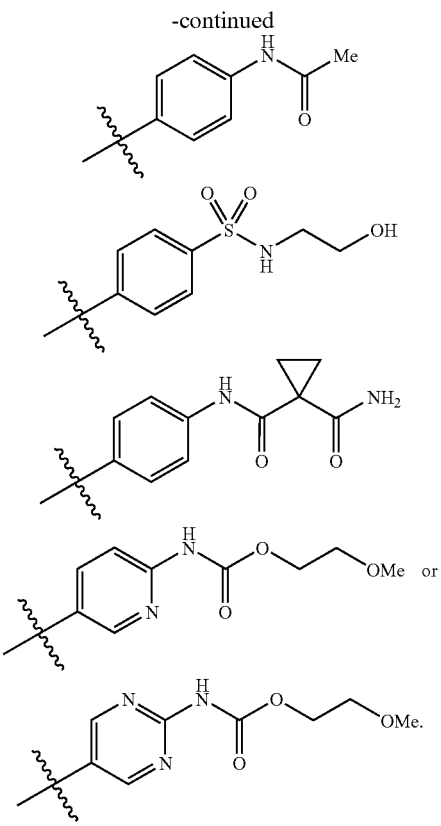

In another embodiment, R⁴ is, independently at each occurrence, H, Me, Et, Pr, F, Cl, Br, I, OCF₃, CF₃, CN, NO₂, —(CH₂)ᵣOH, —(CH₂)ᵣC(O)ORᵃ, ORᵃ, SRᵃ, —C(O)Rᵃ, —C(O)ORᵃ, —NR⁷R⁸, —(CH₂)ᵣNH₂, —NR⁸(CH₂)ᵣC(O)ORᵃ, —(CH₂)ᵣC(O)NR⁸R⁹, —NR⁸C(O)Rᶜ, —NR⁸C(O)ORᶜ, —NR⁸C(O)NR⁸R⁹, —S(O)ₚNR⁸R⁹, —NR⁸S(O)ₚRᶜ, —S(O)ₚRᶜ or phenyl substituted with 0-2 R⁴ᵇ.

In another embodiment, R⁴ is, independently at each occurrence, H, F, Cl, Br, OMe, OH, NH₂, NHMe, NHEt, NHPr, Me, Et, Pr, 4-(methoxycarbonylamino)phenyl, CN, CF₃, —CH₂OH, —(CH₂)₂OH, —(CH₂)₃OH, —CH₂NH₂, —(CH₂)₂NH₂, —(CH₂)₃NH₂, CO₂H, —C(O)NH₂, —C(O)NHMe, —C(O)N(Me)₂, —CH₂CO₂H, —CH₂C(O)NH₂, —CH₂CH₂CO₂H, —NHC(O)Me, —NHCO₂Me, —NHC(O)NHMe, —NHC(O)N(Me)₂, —NHCH₂CO₂H, —NHSO₂Me, —SO₂NH₂, —SO₂NHMe, or —SO₂N(Me)₂.

In another embodiment, R⁴ is, independently at each occurrence, H, F, Cl, Br, OMe, OH, NH₂, Me, Et, Pr, CN, CF₃, —CH₂OH, —CH₂NH₂, —CO₂H, —C(O)NH₂, —C(O)NHMe, —C(O)N(Me)₂, —CH₂CO₂H, —CH₂C(O)NH₂, —CH₂CH₂CO₂H, —NHC(O)Me, —NHCO₂Me, —NHC(O)NHMe, —NHC(O)N(Me)₂, —NHCH₂CO₂H, or —NHSO₂Me.

In another embodiment, R¹¹ is $C_{1-4}$ haloalkyl, —CH₂C(O)NR⁸R⁹, —CH₂CH₂C(O)NR⁸R⁹, —CH₂C(O)Rᵃ, —CH₂CH₂C(O)Rᵃ, —CH₂C(O)ORᵃ, —CH₂CH₂C(O)ORᵃ, $C_{1-6}$ alkyl substituted with 0-2 $R^{11a}$, $C_{2-6}$ alkenyl substituted with 0-2 $R^{11a}$, $C_{2-6}$ alkynyl substituted with 0-2 $R^{11a}$, —(CH₂)ᵣ—$C_{3-10}$ carbocycle substituted with 0-3 $R^{11b}$, or —(CH₂)ᵣ-5- to 10-membered heterocycle comprising: carbon atoms and 1-4 heteroatoms selected from N, O, and S(O)ₚ, wherein said heterocycle is substituted with 0-3 $R^{11b}$.

In another embodiment, R¹¹ is —(CH₂)ᵣ—$C_{3-10}$ carbocycle substituted with 0-3 $R^{11b}$, or —(CH₂)ᵣ-5- to 10-membered heterocycle comprising: carbon atoms and 1-4 heteroatoms selected from N, O, and S(O)ₚ, wherein said heterocycle is substituted with 0-3 $R^{11b}$.

In another embodiment, R¹¹ is $C_{1-4}$ haloalkyl, —CH₂C(O)NR⁸R⁹, —CH₂CH₂C(O)NR⁸R⁹, —CH₂C(O)Rᵃ, —CH₂C(O)ORᵃ, $C_{1-6}$ alkyl substituted with 0-2 $R^{11c}$, —(CH₂)ᵣ—$C_{3-7}$ cycloalkyl substituted with 0-2 $R^{11b}$, —(CH₂)ᵣ-indanyl substituted with 0-2 $R^{11b}$, —(CH₂)ᵣ-indenyl substituted with 0-2 $R^{11b}$, —(CH₂)ᵣ-phenyl substituted with 0-2 $R^{11b}$, —(CH₂)ᵣ-naphthyl substituted with 0-2 $R^{11b}$, or —(CH₂)ᵣ-5- to 10-membered heterocycle comprising carbon atoms and 1-4 heteroatoms selected from N, O, and S(O)ₚ, wherein said heterocycle is substituted with 0-2 $R^{11b}$.

In another embodiment, R¹¹ is —(CH₂)ᵣ—$C_{3-7}$ cycloalkyl substituted with 0-2 $R^{11b}$, —(CH₂)ᵣ-indanyl substituted with 0-2 $R^{11b}$, —(CH₂)ᵣ-indenyl substituted with 0-2 $R^{11b}$, —(CH₂)ᵣ-phenyl substituted with 0-2 $R^{11b}$, —(CH₂)ᵣ-naphthyl substituted with 0-2 $R^{11b}$, or —(CH₂)ᵣ-5- to 10-membered heterocycle comprising carbon atoms and 1-4 heteroatoms selected from N, O, and S(O)ₚ, wherein said heterocycle is substituted with 0-2 $R^{11b}$.

In another embodiment, R¹¹ is $C_{1-4}$ haloalkyl, —CH₂C(O)NR⁸R⁹, —CH₂CH₂C(O)NR⁸R⁹, —CH₂C(O)Rᵃ, —CH₂CH₂C(O)Rᵃ, —CH₂C(O)ORᵃ, —CH₂CH₂C(O)ORᵃ, —CH₂OBn, —CH₂SBn, $C_{1-6}$ alkyl substituted with 0-2 $R^{11c}$, $C_{2-6}$ alkenyl substituted with 0-2 $R^{11a}$, $C_{2-6}$ alkynyl substituted with 0-2 $R^{11a}$, —(CH₂)ᵣ—$C_{3-7}$ cycloalkyl substituted with 0-2 $R^{11b}$, —(CH₂)ᵣ-phenyl substituted with 0-2 $R^{11b}$, —(CH₂)ᵣ-indanyl substituted with 0-2 $R^{11b}$, —(CH₂)ᵣ-indenyl substituted with 0-2 $R^{11b}$, —(CH₂)ᵣ-naphthyl substituted with 0-2 $R^{11b}$, or —(CH₂)ᵣ-5- to 10-membered heteroaryl substituted with 0-2 $R^{11b}$ and selected from thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, indolinyl, isoindolinyl, benzimidazolyl, benzothiazolyl, benzotriazolyl, quinolinyl, isoquinolinyl, tetrahydroquinolinyl, tetrahydroisoquinolinyl, and 2,2-dioxo-2,3-dihydro-1H-2λ⁶-benzo[c]thiophenyl.

In another embodiment, R¹¹ is —CH₂OBn, —CH₂SBn, —(CH₂)ᵣ—$C_{3-7}$ cycloalkyl substituted with 0-2 $R^{11b}$, —(CH₂)ᵣ-phenyl substituted with 0-2 $R^{11b}$, —(CH₂)ᵣ-indanyl substituted with 0-2 $R^{11b}$, —(CH₂)ᵣ-indenyl substituted with 0-2 $R^{11b}$, —(CH₂)ᵣ-naphthyl substituted with 0-2 $R^{11b}$, or —(CH₂)ᵣ-5- to 10-membered heteroaryl substituted with 0-2 $R^{11b}$ and selected from thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, indolinyl, isoindolinyl, benzimidazolyl, benzothiazolyl, benzotriazolyl, quinolinyl, isoquinolinyl, tetrahydroquinolinyl, tetrahydroisoquinolinyl, and 2,2-dioxo-2,3-dihydro-1H-2λ⁶-benzo[c]thiophenyl.

In another embodiment, R¹¹ is methyl, n-butyl, cyclohexylmethyl, carboxymethyl, benzyl, phenethyl, 2-fluorobenzyl, 3-fluorobenzyl, 4-fluorobenzyl, 2-chlorobenzyl, 3-chlorobenzyl, 4-chlorobenzyl, 3-carboxybenzyl, 3-carbamoylbenzyl, 3-(N-methylcarbamoyl)-benzyl, 3-(N,N-dimethylcarbamoyl)-benzyl, 3-(N-ethylcarbamoyl)-benzyl, 3-methylbenzyl, 4-methylbenzyl, 3-methoxybenzyl, 3-difluoromethoxybenzyl, 3-trifluoromethoxy-benzyl, 3-methoxycarbonylbenzyl, 3-methylcarbonylamino-benzyl, 3-benzylcarbonylamino-benzyl, 3-(benzoyl-methyl-amino)-benzyl, 3-(2-phenylethyl)carbonylamino-benzyl, 2-phenylsulfonylamino-benzyl, 3-phenylsulfonylamino-benzyl, 3-[N-methyl, N-phenylaminosulfonyl]-benzyl, 3-benzenesulfonyl-methyl-amino)-benzyl, 3-(2-methylphenyl)carbamoyl-benzyl, 3-(3-methylphenyl)carbamoyl-benzyl, 3-(4-methylphenyl)carbamoyl-benzyl, 3-(4-fluorophenyl)carbamoyl-benzyl, 3-(1-naphthyl)carbamoyl-benzyl, 3-benzylcarbamoyl-benzyl, 3-(4-chlorophenyl)methylcarbamoyl-benzyl, 3-(4-methoxyphenyl)methylcarbamoyl-benzyl, 3-(2-phenylethyl)carbamoyl-benzyl, 3-[2-(4-methoxyphenyl)ethyl]carbamoyl-benzyl, 3-[2-(2-chlorophenyl) ethyl]carbamoyl-benzyl, 3-[2-(3-chlorophenyl)ethyl]carbamoyl-benzyl, 3-[2-(4-chlorophenyl)ethyl]carbamoyl-benzyl, 3-[methyl-(pyridin-2-ylethyl)]carbamoyl-benzyl 3-(3-phenylpropyl)carbamoyl-benzyl, 3-(ethyl-methyl-carbamoyl)-benzyl, 3-(isopropyl-methyl-carbamoyl)-benzyl, 3-(isobutyl-methyl-carbamoyl)-benzyl, 3-(methyl-phenyl-carbamoyl)-benzyl, 3-[(methyl-(3-methylphenyl)-carbamoyl]-benzyl, 3-[(methyl-(4-methylphenyl)-carbamoyl]-benzyl, 3-(benzyl-methyl-carbamoyl)-benzyl, 3-[(3-chlorobenzyl)-methyl-carbamoyl]-benzyl, 3-[(4-chlorobenzyl)-methyl-carbamoyl]-benzyl, 3-[methyl-phenethyl-carbamoyl)]-benzyl, 3-(ethyl-phenyl-carbamoyl)-benzyl, 3-(piperidine-1-carbonyl)-benzyl, 3-(3,4-dihydro-2H-quinoline-1-carbonyl)-benzyl, 3-[(2-methoxyethyl)-methyl-carbamoyl]-benzyl, 3-(4-methoxy-piperidine-1-carbonyl)-benzyl, 3-(morpholine-4-sulfonyl)-benzyl, 3-[(N-(2-methoxyethyl), N-methylamino)sulfonyl]-benzyl, 3-(N,N-dimethylaminosulfonyl)-benzyl, 3-(azetidine-1-carbonyl)-benzyl, 3-(3-methoxy-azetidine-1-carbonyl)-benzyl, 3-(3-hydroxy-pyrrolidine-1-carbonyl)-benzyl, 3-[(4-tetrahydropyranyl)methylcarbonyl]-benzyl, 3-[(2-hydroxyethyl)-methyl-carbamoyl]-benzyl, 3-(3-hydroxy-azetidine-1-carbonyl)-benzyl, 3-(4-hydroxypiperidine-1-carbonyl)-benzyl, 3-[4-(N,N-dimethylamino)-piperidine-1-carbonyl]-benzyl, 3-(4-methyl-piperazine-1-carbonyl)-benzyl, 3-[3-(N,N-dimethylamino)-pyrrolidine-1-carbonyl]-benzyl, 1-naphthylmethyl, 2-naphthylmethyl, thiazol-4-ylmethyl, pyrid-2-ylmethyl, pyrid-3-ylmethyl, pyrid-4-ylmethyl, 1-benzyl-imidazol-4-ylmethyl, benzothiazol-2-ylmethyl, 3-(1-morpholinocarbonyl)-benzyl, 3-[(2,6-dimethylmorpholine-1-carbonyl)-benzyl, (benzyloxycarbonyl)methyl, (1-methylpyrazol-3-yl)methyl, (1-methylpyrazol-4-yl)methyl, (1-methylpyrazol-5-yl)methyl, (3-methylpyrazol-5-yl)methyl, (1-ethylpyrazol-4-yl)methyl, (1-n-propylpyrazol-4-yl)methyl, (1-isopropylpyrazol-4-yl)methyl, 1-ethylpyrazol-3-ylmethyl, 3-pyrazolylmethyl, (4-chloro-3-methyl-5-pyrazolyl)methyl, (4-chloro-1,5-dimethyl-3-pyrazolyl)methyl, (4-chloro-1,3-dimethyl-5-pyrazolyl)methyl, [1-(4-methoxybenzyl)-pyrazol-3-yl]methyl, (1,5-dimethylpyrazol-3-yl)methyl, (1,3-dimethylpyrazol-5-yl)methyl, [1-(4-methoxybenzyl)-5-methyl-pyrazol-3-yl]methyl, (3-trifluoromethylpyrazol-5-yl)methyl, [1-(4-methoxybenzyl)-3-trifluoromethylpyrazol-5-yl]methyl, [(1-methyl-5-methoxycarbonyl)-pyrazol-3-yl] methyl, [(1-methyl-5-carboxy)-pyrazol-3-yl]methyl, [(1-methyl-5-carbamoyl)-pyrazol-3-yl]methyl, [(5-methoxycarbonyl)-pyrrol-2-yl]methyl, thiazol-2-ylmethyl, thiazol-4-methyl, (2-methoxypyridin-3-yl)methyl, (6-methoxypyridin-3-yl)methyl, (4-(methoxycarbonyl)-oxazol-2-yl) methyl, morpholin-4-ylcarbonylmethyl, N-((5-methylpyrazin-2-yl)methyl)-aminocarbonylmethyl, 2-hydroxy-indan-5-ylmethyl, 4-methylpiperazin-1-ylcarbonylmethyl, 4-methylcarbonylpiperazin-1-ylcarbonylmethyl, pyrrolidin-1-ylcarbonylmethyl, 2-methoxypyrrolidin-1-ylcarbonylmethyl, aziridin-1-ylcarbonylmethyl, 2-hydroxyethylaminocarbonylmethyl, 2-methoxyethylaminocarbonylmethyl, 2-ethoxyethylaminocarbonylmethyl, bis(2-methoxyethyl) aminocarbonylmethyl, 4-dimethylaminopyrrolidin-1-ylcarbonylmethyl, 4-chlorophenylaminocarbonylmethyl, 3-chlorophenylaminocarbonylmethyl, N-methyl-N-benzylaminocarbonylmethyl, cyclopropylaminocarbonylmethyl, cyclopropylmethylaminocarbonylmethyl, cyclopentylaminocarbonylmethyl, (trans-2-phenylcyclopropyl)aminocarbonylmethyl, N,N-dimethylaminoethylaminocarbonylmethyl, N-((pyridin-2-yl)methyl)-aminocarbonylmethyl, N-((pyridin-3-yl)methyl)-aminocarbonylmethyl, N-((pyridin-4-yl)methyl)-aminocarbonylmethyl, N-((pyridin-2-yl)ethyl)-aminocarbonylmethyl, 1-(1,1-dioxo-1$\lambda^6$-thiomorpholin-4-yl)carbonylmethyl, N-(tert-butoxycarbonyl)-1H-indol-3-ylmethyl, 1H-indol-3-ylmethyl, 2,2-dioxo-2,3-dihydro-1H-2$\lambda^6$-benzo[c]thiophen-5-ylmethyl, 4,4,4-trifluorobutyl, cyclopropylmethyl, (4-hydroxy)cyclohexylmethyl, 4-oxo-cyclohexylmethyl,

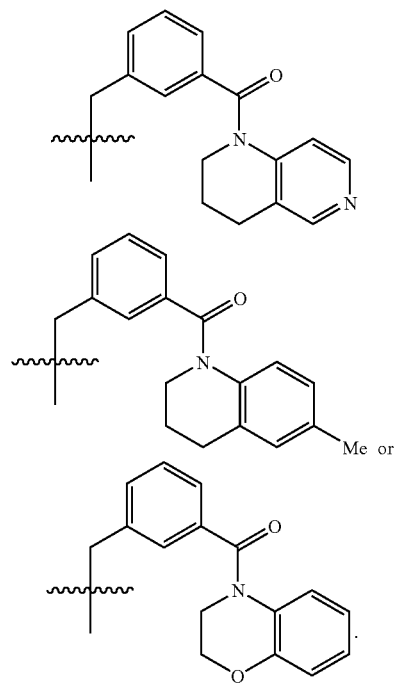

In another embodiment, $R^{11}$ is cyclohexylmethyl, benzyl, phenethyl, 2-fluorobenzyl, 3-fluorobenzyl, 4-fluorobenzyl, 2-chlorobenzyl, 3-chlorobenzyl, 4-chlorobenzyl, 3-carboxybenzyl, 3-carbamoylbenzyl, 3-(N-methylcarbamoyl)-benzyl, 3-(N,N-dimethylcarbamoyl)-benzyl, 3-(N-ethylcarbamoyl)-benzyl, 3-methylbenzyl, 4-methylbenzyl, 3-methoxybenzyl, 3-difluoromethoxybenzyl, 3-trifluoromethoxy-benzyl, 3-methoxycarbonylbenzyl, 3-methylcarbonylamino-benzyl, 3-benzylcarbonylamino-benzyl, 3-(benzoyl-methyl-amino)-benzyl, 3-(2-phenylethyl)carbonylamino-benzyl, 2-phenylsulfonylamino-benzyl, 3-phenylsulfonylamino-benzyl, 3-[N-methyl, N-phenylaminosulfonyl]-benzyl, 3-(benzenesulfonyl-methyl-amino)-benzyl, 3-(2-methylphenyl)carbamoyl-benzyl, 3-(3-methylphenyl)carbamoyl-benzyl, 3-(4-methylphenyl)carbamoyl-benzyl, 3-(4-fluorophenyl) carbamoyl-benzyl, 3-(1-naphthyl)carbamoyl-benzyl, 3-benzylcarbamoyl-benzyl, 3-(4-chlorophenyl)methylcarbamoyl-benzyl, 3-(4-methoxyphenyl)methylcarbamoyl-benzyl, 3-(2-phenylethyl)carbamoyl-benzyl, 3-[2-(4-methoxyphenyl)ethyl]carbamoyl-benzyl, 3-[2-(2-chlorophenyl) ethyl]carbamoyl-benzyl, 3-[2-(3-chlorophenyl)ethyl] carbamoyl-benzyl, 3-[2-(4-chlorophenyl)ethyl]carbamoyl-benzyl, 3-[methyl-(pyridin-2-ylethyl)]carbamoyl-benzyl 3-(3-phenylpropyl)carbamoyl-benzyl, 3-(ethyl-methyl-carbamoyl)-benzyl, 3-(isopropyl-methyl-carbamoyl)-benzyl, 3-(isobutyl-methyl-carbamoyl)-benzyl, 3-(methyl-phenylcarbamoyl)-benzyl, 3-[(methyl-(3-methylphenyl)-carbamoyl]-benzyl, 3-[methyl-(4-methylphenyl)-carbamoyl]-benzyl, 3-(benzyl-methyl-carbamoyl)-benzyl, 3-[(3-chlorobenzyl)-methyl-carbamoyl]-benzyl, 3-[(4-chlorobenzyl)-methyl-carbamoyl]-benzyl, 3-[methyl-phenethyl-carbamoyl)]-benzyl, 3-(ethyl-phenyl-carbamoyl)-benzyl, 3-(piperidine-1-carbonyl)-benzyl, 3-(3,4-dihydro-2H-quinoline-1-carbonyl)-benzyl, 3-[(2-methoxyethyl)-methyl-carbamoyl]-benzyl, 3-(4-methoxy-piperidine-1-carbonyl)-benzyl, 3-(morpholine-4-sulfonyl)-benzyl, 3-[(N-(2-methoxyethyl), N-methylamino)sulfonyl]-benzyl, 3-(N,N-dimethylaminosulfonyl)-benzyl, 3-(azetidine-1-carbonyl)-benzyl, 3-(3-methoxy-azetidine-1-carbonyl)-benzyl, 3-(3-hydroxy-pyrrolidine-1-carbonyl)-benzyl, 3-[(4-tetrahydropyranyl)methylcarbonyl]-benzyl, 3-[(2-hydroxyethyl)-methyl-carbamoyl]-benzyl, 3-(3-hydroxy-azetidine-1-carbonyl)-benzyl, 3-(4-hydroxypiperidine-1-carbonyl)-benzyl, 3-[4-(N,N-dimethylamino)-piperidine-1-carbonyl]-benzyl, 3-(4-methyl-piperazine-1-carbonyl)-benzyl, 3-[3-(N,N-dimethylamino)-pyrrolidine-1-carbonyl]-benzyl, 1-naphthylmethyl, 2-naphthylmethyl, thiazol-4-ylmethyl, pyrid-2-ylmethyl, pyrid-3-ylmethyl, pyrid-4-ylmethyl, 1-benzyl-imidazol-4-ylmethyl, benzothiazol-2-ylmethyl, 3-(1-morpholinocarbonyl)-benzyl, 3-[(2,6-dimethylmorpholine-1-carbonyl)-benzyl, (benzyloxycarbonyl)methyl, (1-methylpyrazol-3-yl)methyl, (1-methylpyrazol-4-yl)methyl, (1-methylpyrazol-5-yl)methyl, (3-methylpyrazol-5-yl)methyl, (1-ethylpyrazol-4-yl)methyl, (1-n-propylpyrazol-4-yl)methyl, (1-isopropylpyrazol-4-yl)methyl, 1-ethylpyrazol-3-ylmethyl, 3-pyrazolylmethyl, (4-chloro-3-methyl-5-pyrazolyl)methyl, (4-chloro-1,5-dimethyl-3-pyrazolyl)methyl, (4-chloro-1,3-dimethyl-5-pyrazolyl)methyl, [1-(4-methoxybenzyl)-pyrazol-3-yl]methyl, (1,5-dimethylpyrazol-3-yl)methyl, (1,3-dimethylpyrazol-5-yl)methyl, [1-(4-methoxybenzyl)-5-methyl-pyrazol-3-yl]methyl, (3-trifluoromethylpyrazol-5-yl)methyl, [1-(4-methoxybenzyl)-3-trifluoromethylpyrazol-5-yl]methyl, [(1-methyl-5-methoxycarbonyl)-pyrazol-3-yl] methyl, [(1-methyl-5-carboxy)-pyrazol-3-yl]methyl, [(1-methyl-5-carbamoyl)-pyrazol-3-yl]methyl, [(5-methoxycarbonyl)-pyrrol-2-yl]methyl, thiazol-2-ylmethyl, thiazol-4-methyl, (2-methoxypyridin-3-yl)methyl, (6-methoxypyridin-3-yl)methyl, (4-(methoxycarbonyl)-oxazol-2-yl) methyl, morpholin-4-ylcarbonylmethyl, N-((5-methylpyrazin-2-yl)methyl)-aminocarbonylmethyl, 2-hydroxy-indan-5-ylmethyl, 4-methylpiperazin-1-ylcarbonylmethyl, 4-methylcarbonylpiperazin-1-ylcarbonylmethyl, pyrrolidin-1-ylcarbonylmethyl, 2-methoxypyrrolidin-1-ylcarbonylmethyl, aziridin-1-ylcarbonylmethyl, 2-hydroxyethylaminocarbonylmethyl, 2-methoxyethylaminocarbonylmethyl, 2-ethoxyethylaminocarbonylmethyl, bis(2-methoxyethyl) aminocarbonylmethyl, 4-dimethylaminopyrrolidin-1-ylcarbonylmethyl, 4-chlorophenylaminocarbonylmethyl, 3-chlorophenylaminocarbonylmethyl, N-methyl-N-benzylaminocarbonylmethyl, cyclopropylaminocarbonylmethyl, cyclopropylmethylaminocarbonylmethyl, cyclopentylaminocarbonylmethyl, (trans-2-phenylcyclopropyl)aminocarbonylmethyl, N,N-dimethylaminoethylaminocarbonylmethyl, N-((pyridin-2-yl)methyl)-aminocarbonylmethyl, N-((pyridin-3-yl)methyl)-aminocarbonylmethyl, N-((pyridin-4-yl)methyl)-aminocarbonylmethyl, N-((pyridin-2-yl)ethyl)-aminocarbonylmethyl, 1-(1,1-dioxo-1$\lambda^6$-thiomorpholin-4-yl)carbonylmethyl, N-(tert-butoxycarbonyl)-1H-indol-3-ylmethyl, 1H-indol-3-ylmethyl, 2,2-dioxo-2,3-dihydro-1H-2$\lambda^6$-benzo[c]thiophen-5-ylmethyl, 4,4,4-trifluorobutyl, cyclopropylmethyl, (4-hydroxy)cyclohexylmethyl, 4-oxo-cyclohexylmethyl,

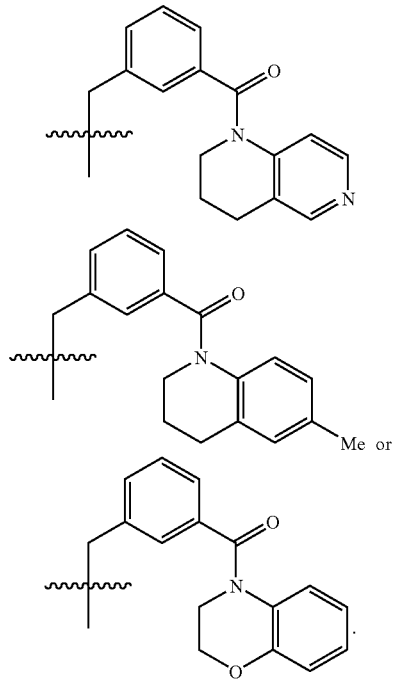

In another embodiment the present invention provides a pharmaceutical composition comprising a pharmaceutically acceptable carrier and at least one of the compounds of the present invention or a stereoisomer, tautomer, pharmaceutically acceptable salt, solvate, or prodrug thereof.

In another embodiment, the present invention provides a novel pharmaceutical composition, comprising: a pharmaceutically acceptable carrier and a therapeutically effective amount of at least one of the compounds of the present invention or a stereoisomer, tautomer, pharmaceutically acceptable salt, solvate or prodrug thereof.

In another embodiment, the present invention provides a novel process for making a compound of the present invention or a stereoisomer, tautomer, pharmaceutically acceptable salt, solvate or prodrug thereof.

In another embodiment, the present invention provides a novel intermediate for making a compound of the present invention or a stereoisomer, tautomer, pharmaceutically acceptable salt, solvate or prodrug thereof.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phosphodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In a preferred embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, and vasopepsidase inhibitors, an antiarrythmic agent selected from IKur inhibitors, an anticoagulant selected from thrombin inhibitors, antithrombin-III activators, heparin co-factor II activators, other factor XIa inhibitors, other kallikrein inhibitors, plasminogen activator inhibitor (PAI-1) antagonists, thrombin activatable fibrinolysis inhibitor (TAFI) inhibitors, factor VIIa inhibitors, factor IXa inhibitors, and factor Xa inhibitors, or an antiplatelet agent selected from GPIIb/IIIa blockers, protease activated receptor (PAR-1) antagonists, phosphodiesterase-III inhibitors, $P2Y_1$ receptor antagonists, $P2Y_{12}$ antagonists, thromboxane receptor antagonists, cyclooxygense-1 inhibitors, and aspirin, or a combination thereof.

In a preferred embodiment, the present invention provides pharmaceutical composition, wherein the additional therapeutic agent(s) are an anti-platelet agent or a combination thereof.

In a preferred embodiment, the present invention provides a pharmaceutical composition, wherein the additional therapeutic agent is the anti-platelet agent clopidogrel.

In another embodiment the present invention provides a method for modulation of the coagulation cascade and/or contact activation system comprising administering to a patient in need of such treatment a therapeutically effective amount of at least one of the compounds of the present invention or a stereoisomer, tautomer, pharmaceutically acceptable salt, solvate or prodrug thereof.

In another embodiment, the present invention provides a novel method for treating thrombotic or thromboembolic disorders comprising: administering to a patient in need of such treatment a therapeutically effective amount of at least one of the compounds of the present invention or a stereoisomer, tautomer, pharmaceutically acceptable salt, solvate or prodrug thereof.

In another embodiment, the present invention provides a novel method, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

In another embodiment, the present invention provides a novel method, wherein the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method for treating inflammatory disorders comprising: administering to a patient in need of such treatment a therapeutically effective amount of at least one of the compounds of the present invention or a stereoisomer, tautomer, pharmaceutically acceptable salt, solvate or prodrug thereof.

In another embodiment, the present invention provides a method, wherein the inflammatory disorder is selected from the group consisting of sepsis, acute respiratory distress syndrome, and systemic inflammatory response syndrome.

In another embodiment, the present invention provides a novel method of treating a patient in need of thromboembolic disorder treatment, comprising: administering a compound of the present invention or a stereoisomer, tautomer, pharmaceutically acceptable salt, solvate, or prodrug form thereof in an amount effective to treat a thrombotic or thromboembolic disorder.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used for the treatment of a thromboembolic and/or inflammatory disorder.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel article of manufacture, comprising: (a) a first container; (b) a pharmaceutical composition located within the first container, wherein the composition, comprises: a first therapeutic agent, comprising: a compound of the present invention; and (c) a package insert stating that the pharmaceutical composition can be used in combination with a second therapeutic agent to treat a thromboembolic and/or inflammatory disorder.

In another preferred embodiment, the present invention provides a novel article of manufacture, further comprising: (d) a second container; wherein components (a) and (b) are located within the second container and component (c) is located within or outside of the second container.

In another embodiment, the present invention provides a novel method, comprising: administering a compound of the present invention or a stereoisomer, tautomer, pharmaceutically acceptable salt, solvate, or prodrug form thereof in an amount effective to treat a thromboembolic and/or inflammatory disorder.

In another embodiment, the present invention provides a compound of the present invention for use in therapy.

In another embodiment, the present invention provides a compound of the present invention for use in therapy for treating a thromboembolic and/or inflammatory disorder.

In another embodiment, the present invention also provides the use of a compound of the present invention for the manufacture of a medicament for the treatment of a thromboembolic and/or inflammatory disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DEFINITIONS

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention. The inventive compounds may be in the free or hydrate form.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g. n-pentyl, isopentyl, neopentyl), and the like.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

The term "alkoxy" or "alkyloxy" refers to an —O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy, and the like. Similarly, "alkylthio" or "thioalkoxy" represents an alkyl group as defined above with the indicated number of carbon atoms attached through a sulphur bridge; for example methyl-S—, ethyl-S—, and the like.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

"Aryl" groups refer to monocyclic or polycyclic aromatic hydrocarbons, including, for example, phenyl, naphthyl, phenanthranyl, and the like. Aryl moieties are well known and described, for example, in *Hawley's Condensed Chemical Dictionary* (13 ed.), R. J. Lewis, ed., J. Wiley & Sons, Inc., New York (1997). Unless otherwise specified, "aryl", "$C_{6-10}$ aryl" or "aromatic residue" may be unsubstituted or substituted with 0 to 3 groups selected from H, OH, $OCH_3$, Cl, F, Br, I, CN, $NO_2$, $NH_2$, $N(CH_3)H$, $N(CH_3)_2$, $CF_3$, $OCF_3$, C(=O)$CH_3$, $SCH_3$, S(=O)$CH_3$, S(=O)$_2CH_3$, $CH_3$, $CH_2CH_3$, $CO_2H$, and $CO_2CH_3$.

As used herein, the term "heterocycle" or "heterocyclic group" is intended to mean a stable 5, 6, or 7-membered monocyclic or bicyclic or 7, 8, 9, 10, 11, 12, 13, or 14-membered bicyclic heterocyclic ring which is saturated, partially unsaturated or fully unsaturated, and which consists of carbon atoms and 1, 2, 3 or 4 heteroatoms independently selected from N, O and S; and including any bicyclic group in which any of the above-defined heterocyclic rings is fused to a benzene ring. The nitrogen and sulfur heteroatoms may optionally be oxidized (i.e., N→O and S(O)$_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, benzodioxane, and the like. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., N→O and S(O)$_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a small, negatively charged species such as chloride, bromide, hydroxide, acetate, sulfate, and the like.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative. In cases wherein there are quarternary carbon atoms on compounds of the present invention, these can be replaced by silicon atoms, provided they do not form Si—N or Si—O bond.

When any variable occurs more than one time in any constituent or formula for a compound, its definition at each occurrence is independent of its definition at every other occurrence. Thus, for example, if a group is shown to be substituted with 0-3 $R^{3a}$, then said group may optionally be substituted with up to three $R^{3a}$ groups and $R^{3a}$ at each occurrence is selected independently from the definition of $R^{3a}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, at pp. 309-396, edited by K. Widder, et. al. (Academic Press, 1985);

b) *A Textbook of Drug Design and Development*, edited by Krosgaard-Larsen and H. Bundgaard, Chapter 5, "Design and Application of Prodrugs," by H. Bundgaard, at pp. 113-191 (1991);

c) H. Bundgaard, *Advanced Drug Delivery Reviews*, Vol. 8, p. 1-38 (1992);

d) H. Bundgaard, et al., *Journal of Pharmaceutical Sciences*, Vol. 77, p. 285 (1988); and e) N. Kakeya, et. al., *Chem Phar Bull.*, Vol. 32, p. 692 (1984).

Compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Preparation of Prodrugs is Well Known in the Art and Described in, for example, *Medicinal Chemistry: Principles and Practice*, ed. F. D. King, The Royal Society of Chemistry, Cambridge, UK, 1994, which is incorporated herein by reference in its entirety.

Isotopically labeled compounds of the present invention, i.e., wherein one or more of the atoms described are replaced by an isotope of that atom (e.g., C replaced by $^{13}$C or by $^{14}$C; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates and the like. Methods of solvation are generally known in the art.

As used herein, the term "patient" encompasses all mammalian species.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor XIa and/or plasma kallikrein or to treat the disorders listed herein. When applied to a combination, the term refers to combined amounts of the active ingredients that result in the therapeutic effect, whether administered in combination, serially or simultaneously. The combination of compounds is preferably a synergistic combination. Synergy, as described, for example, by Chou and Talalay, Adv. Enzyme Regul. 1984, 22:27-55, occurs when the effect (in this case, prevention of thrombosis) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic and/or anti-inflammatory effect, or some other beneficial effect of the combination compared with the individual components.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 18th ed., 1990, which is incorporated herein by reference in its entirety.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LC-MS" for liquid chromatography mass spectrometry, "HPLC" for high pressure liquid chromatography, "RP HPLC" for reverse phase HPLC, "TLC" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "tlc" for thin layer chromatography. "α", "β", "R", "S", "E", and "Z" are stereochemical designations familiar to one skilled in the art.

| | |
|---|---|
| Me | methyl |
| Et | ethyl |
| AcOH | acetic acid |
| MeOH | methanol |
| EtOH | ethanol |
| EtOAc | ethyl acetate |
| $Et_2O$ | diethyl ether |
| i-PrOH or IPA | isopropanol |
| HOAc | acetic acid |
| Ph | phenyl |
| Bn | benzyl |
| t-Bu | tertiary butyl |
| BOP reagent | benzotriazol-1-yloxytris(dimethylamino)phosphonium hexafluorophosphate |
| $BBr_3$ | boron tribromide |
| BINAP | rac-2,2'-Bis(diphenylphosphino)-1,1'-binaphthyl |
| Boc | tert-butyloxycarbonyl |
| 2MeS-ADP | 2 methylthio adenosine diphosphate |
| cDNA | complimentary DNA |
| $CH_2Cl_2$ | dichloromethane |
| $CH_3CN$ | acetonitrile |
| $Cs_2CO_3$ | cesium carbonate |

| | |
|---|---|
| DBAD | Di-tert-butylazodicarboxylate |
| DCE | 1,2-dichloroethane |
| DCM | dichloromethane |
| DCC | dicyclohexylcarbodiimide |
| DEAD | Diethylazodicarboxyalte |
| DIBAL-H | diisobutylaluminum hydride |
| DIC or DIPCDI | diisopropylcarbodiimide |
| DIEA or DIPEA | N,N,-diisopropylethylamine |
| DMEM | Dulbecco's modified Eagle media |
| DME | 1,2-dimethoxyethane |
| DMF | dimethyl formamide |
| DMSO | dimethyl sulfoxide |
| EDC (or EDC.HCl) or EDCI (or EDCI.HCl) or EDAC | 3-ethyl-3'-(dimethylamino)propyl-carbodiimide hydrochloride (or 1-(3-dimethylaminopropyl)-3-ethylcarbodiimide hydrochloride) |
| EDTA | ethylenediaminetetraacetic acid |
| FBS | Fetal Bovine Serum |
| HCl | hydrochloric acid |
| HEPES | 4-(2-hydroxyethyl)piperaxine-1-ethanesulfonic acid |
| Hex | hexane |
| HOBt | 1-hydroxybenzotriazole hydrate |
| Hunig's base | N, N-diisopropylethyl amine |
| LDA | Lithium diisopropylamide |
| LiHMDS | Lithium bis(trimethylsilyl amide) |
| mCPBA | meta-chloroperbenzoic acid |
| NBS | N-bromosuccinimide |
| D-PBS | Dulbecco's Phosphate Buffered Saline |
| Pd/C | palladium on carbon |
| $PCy_3$ | tricyclohexyl phosphine |
| SCX | Strong Cation Exchanger |
| TFA | trifluoroacetic acid |
| THF | tetrahydrofuran |
| TRIS | tris (hydroxymethyl) aminomethane |
| KOAc | potassium acetate |
| $K_3PO_4$ | potassium phosphate |
| LiHMDS | lithium hexamethyldisilazide |
| $MgSO_4$ | magnesium sulfate |
| $Na_2SO_3$ | sodium sulfite |
| $Na_2SO_4$ | sodium sulfate |
| $NH_4Cl$ | ammonium chloride |
| $NH_4OH$ | ammonium hydroxide |
| $Pd_2(dba)_3$ | tris(dibenzylideneacetone)dipalladium(0) |
| $Pd(dppf)Cl_2 \cdot CH_2Cl_2$ | [1, 1'-bis(diphenylphosphino)ferrocene]dichloropalladium(II), complex with dichloromethane |
| $Pd(Ph_3P)_4$ | tetrakis(triphenylphosphine)palladium(0) |
| $(Ph_3P)_2PdCl_2$ | bis(triphenylphosphine)palladium dichloride |

SYNTHESIS

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley-Interscience, 3$^{rd}$ Edition, 1999).

All references cited herein are hereby incorporated in their entirety herein by reference. Methods for synthesis of a large variety of substituted pyridine and pyridone compounds useful as starting materials for the preparation of compounds of the present invention are well known in the art and have been extensively reviewed. (For examples of methods useful for the preparation of pyridine and pyridone starting materials see: Krohnke, F. *Synthesis*, 1976, 1; *Pyridine and Its Derivatives*. In *The Chemistry of Heterocyclic Compounds*, Abramovitch, R. A., Ed.; John Wiley and Sons: New York, 1974; Vol 14; Supplemental 1-4; *Comprehensive Heterocyclic Chemistry*, Vol. 2, Boulton, A. J. and McKillop, A, Eds. Pergamon Press, New York, 1984, pp 165-524; *Comprehensive Heterocyclic Chemistry*, Vol. 5, McKillop, A, Ed. Pergamon Press, New York, 1996, pp 1-300). Methods for synthesis of a large variety of substituted pyrimidine and pyrimidone compounds useful as starting materials for the preparation of compounds of the present invention are well known in the art and have been extensively reviewed. (For examples of methods useful for the preparation of pyrimidine and pyrimidone starting materials see: *The Pyrimidines*. In *The Chemistry of Heterocyclic Compounds*, Taylor, E. C., Ed.; John Wiley and Sons: New York, 1993; Vol 52).

Representative pyridine compounds of this invention can be prepared as shown in Scheme 1. Suzuki coupling between an appropriately functionalized pyridine, such as 1a, and an appropriately substituted aryl or heteroaryl boronic acid or ester 1b in the presence of a base such as aqueous sodium carbonate in a solvent such as toluene using a catalyst such as tetrakis(triphenylphosphine)palladium(0) provides the biaryl compound 1c. Using a modification of the procedure described by Hart (Hart, D. J. et al. *J. Org. Chem.*, 1983, 48(3), 289-294), in situ generation of N-trimethylsilylaldimines from 1c and lithium bis(trimethylsilyl)amide, followed by the addition of Grignard or organolithium reagents, gives, after aqueous workup, the primary amine 1d. Alternately, organozinc reagents can be used for the addition to the N-trimethylsilylaldimines. (See: Miginiac, L. et al., *J. Organometallic Chem.*, 1997, 548, 269, Miginiac, L. et al., *J. Organometallic Chem.*, 1991, 420, 155; Katritzky, A. R. et al., *J. Org. Chem.*, 1995, 60, 3405; Umani-Ronchi, A. et al., *J. Org. Chem.*, 1994, 59, 7766; Villieras, J. et al., *Tetrahedron Asymmetry*, 1996, 7(6), 1835; and Staas, D. D. et al., *J. Org. Chem.*, 2002, 67, 8276.) Amide coupling between 1d and an appropriately substituted carboxylic acid (1e), for example Boc-tranexamic acid, employing suitable coupling reagents, such as EDCI, HOBt, and base, generates 1f (for alternative coupling reagents see: Han, S-Y; Kim, Y-A. *Tetrahedron*, 2004, 60, 2447). Further manipulation of functional groups on A using methods known to one skilled in the art of organic synthesis will give additional compounds of the invention.

For instance, when A is a Boc-tranexamic acid moiety, the Boc group can be deprotected with TFA to give the cyclohexyl methyl amine derivative. The pyridine N-oxide derivatives 1g can be prepared by oxidation of 1f with a suitable oxidant such as m-chloroperbenzoic acid in a solvent such as chloroform or dichloromethane. Further manipulation of functional groups on $R^3$ and $R^4$ in compounds of formulas 1f and 1g using methods known to one skilled in the art of organic synthesis will give additional compounds of this invention.

carboxylic acid 1e employing suitable coupling reagents as described above in Scheme 1 gives 2d. Suzuki coupling between 3-bromopyridine 2d and an appropriately substituted aryl or heteroaryl boronic acid or ester 1b in the presence of a base, such as anhydrous potassium phosphate, in a solvent, such as dimethylsulfoxide, using a catalyst, such as Pd(dppf)Cl$_2$.CH$_2$Cl$_2$ complex, provides the biaryl compound 1f. Further manipulation of functional groups on A, $R^3$, and $R^4$ using methods known to one skilled in the art of organic synthesis will give additional compounds of this invention.

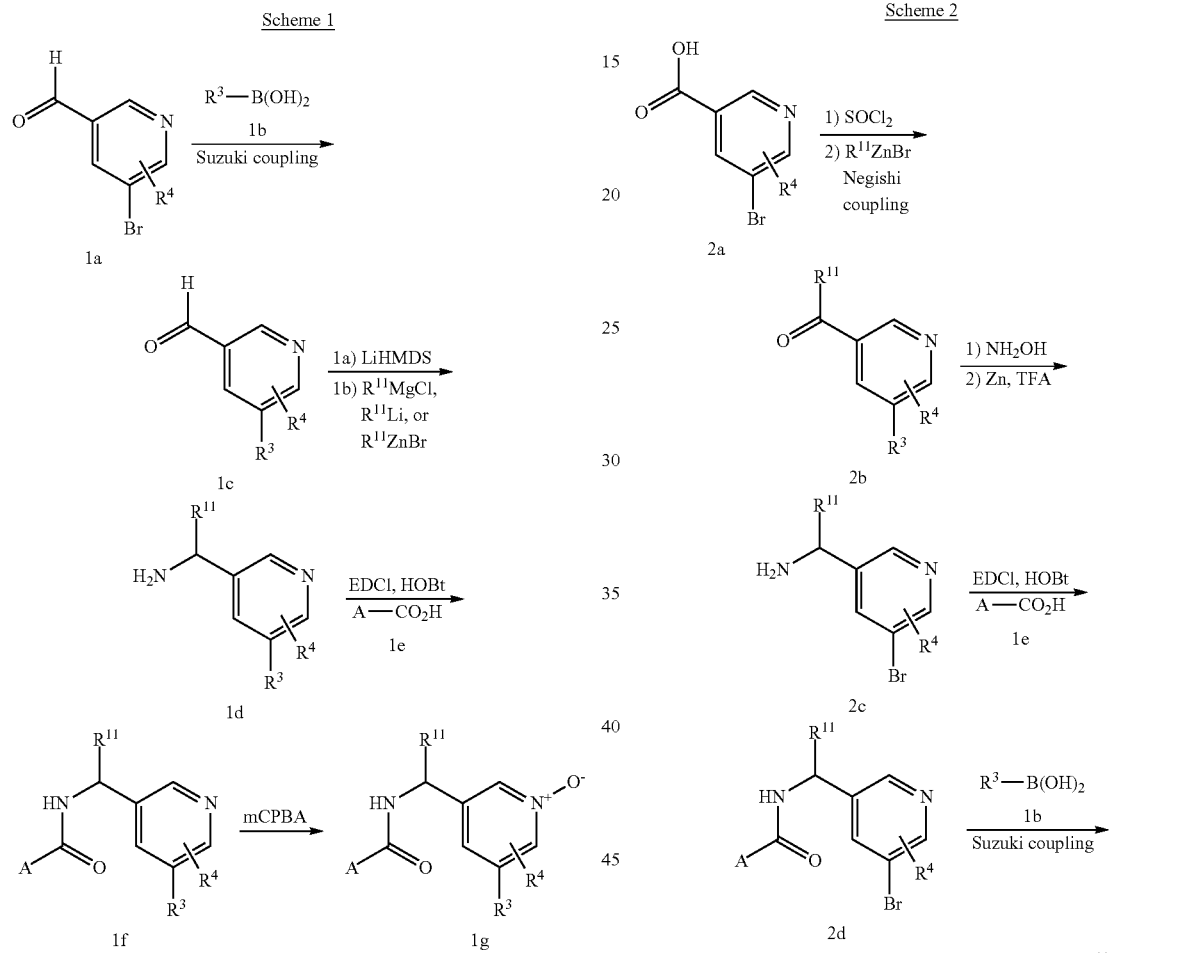

Alternately, the $R^3$ moiety can be introduced via a Suzuki coupling strategy later in the synthesis as shown in Scheme 2. Negishi coupling between an appropriately substituted acid chloride, derived from suitably substituted nicotinic acid derivatives 2a, and an appropriately functionalized organozinc reagent using a catalyst such as tetrakis(triphenylphosphine)palladium(0) in a solvent such as THF provides a ketone of formula 2b. (Tsuji, J. *Transition Metal Reagents and Catalysts: Innovations in Organic Synthesis*, John Wiley & Sons, 2000; Tsuji, J. *Palladium Reagents and Catalysts: Innovations in Organic Synthesis*, John Wiley & Sons, 1996.) Alternately, ketone 2b can be prepared by addition of Grignard or organolithium reagents to an ester or Weinreb amide derived from nicotinic acid derivative 2a. Condensation of 2b with hydroxylamine hydrochloride generates the oxime, which can be reduced to the primary amine 2c with zinc dust and TFA. Amide coupling between 2c and Additional pyridine compounds of this invention can be prepared as shown in Scheme 3. Negishi coupling between an appropriately substituted acid chloride, derived from isonicotinic acid derivatives 3a, and an appropriately substituted organozinc reagent using a catalyst, such as tetrakis(triphenylphosphine)palladium(0), in a solvent, such as THF, provides ketone 3b. Alternately, ketone 3b can be prepared by addition of Grignard or organolithium reagents to the corresponding ester or Weinreb amide derived from isonicotinic acid derivatives 3a. Condensation of 3b with hydroxylamine hydrochloride generates the oxime which can be reduced to the primary amine 3c with zinc dust and TFA. Amide coupling between 3c and carboxylic acid 1e employing suitable coupling reagents as described in Scheme 1 above gives 3d. Suzuki coupling between 2-chloropyridine 3d and an appropriately substituted aryl or heteroaryl boronic acid or ester 1b in the presence of a base, such as anhydrous cesium carbonate, in a solvent, such as dioxane, using a catalyst, such as $Pd_2(dba)_3$/tri-t-butylphosphonium tetrafluoroborate, provides the biaryl compound 3e. The pyridine N-oxide derivatives 3f can be prepared from 3e as described above in Scheme 1. Further manipulation of functional groups on A, $R^3$, and $R^4$ using methods known to one skilled in the art of organic synthesis will give additional compounds of the invention.

-continued

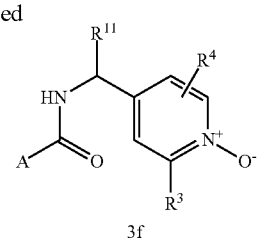

3f

Representative pyridone compounds of this invention can be prepared from protected hydroxypyridines of formulae 4a, 5a, and 6a as shown in Schemes 4-6 by applying the synthetic methods described for Schemes 1-3. The protecting group R, for example Me or Bn, can be removed with either boron tribromide or HCl to reveal the corresponding pyridone compounds of this invention.

Scheme 3

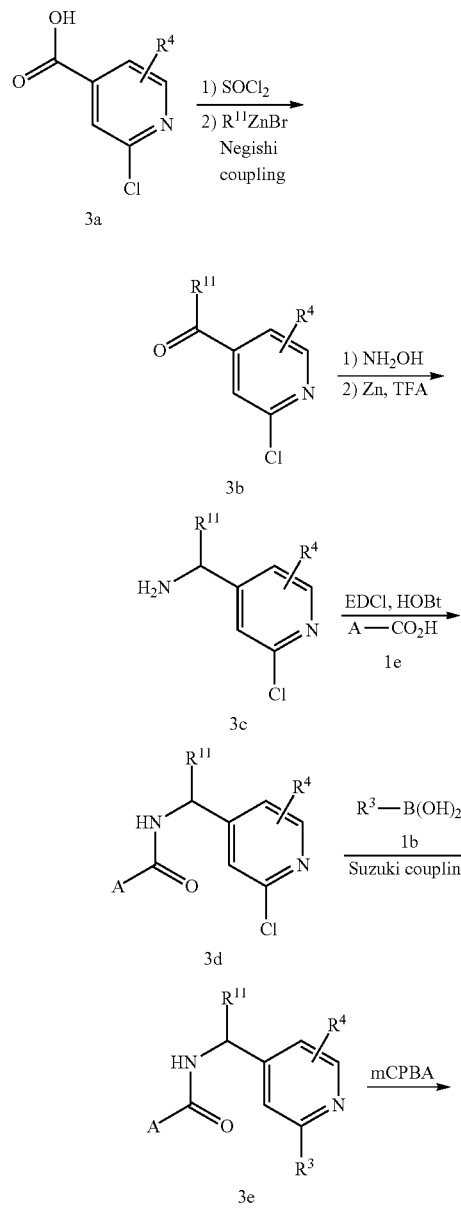

Scheme 4

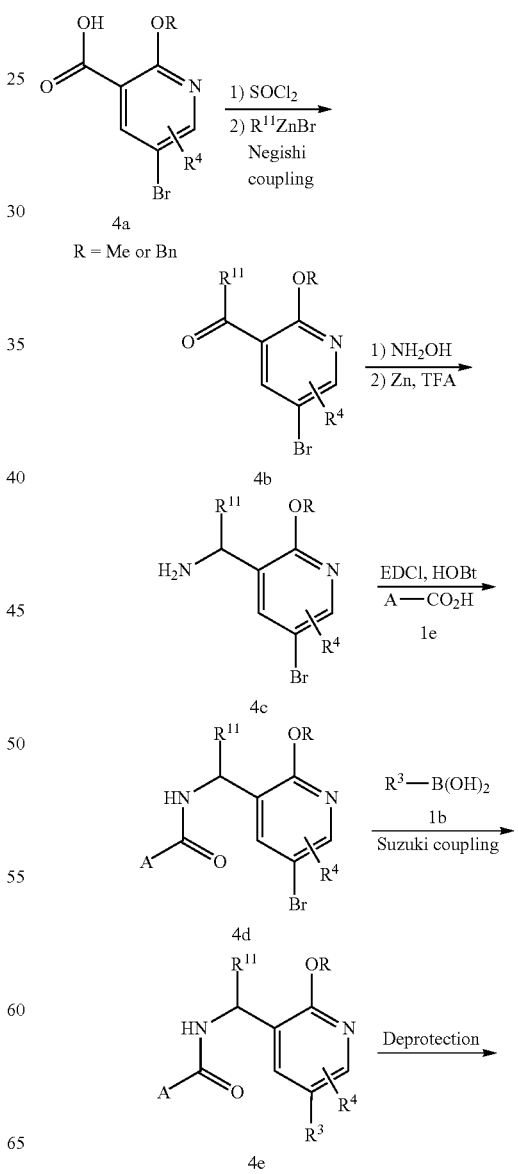

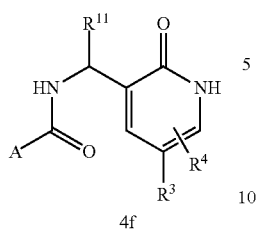
4f
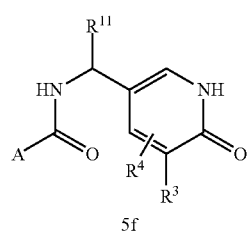
5f
Scheme 5
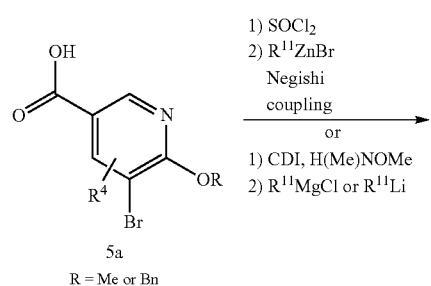
5a
R = Me or Bn
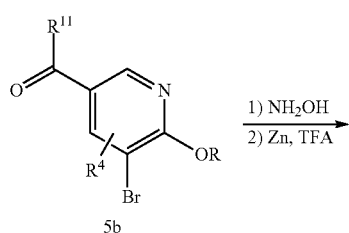
5b
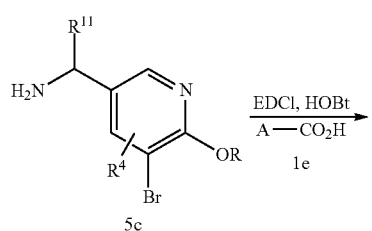
5c
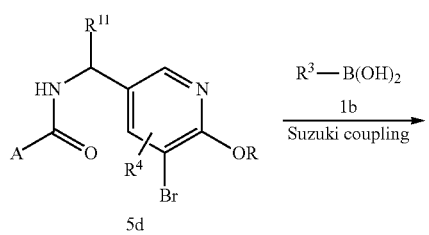
5d
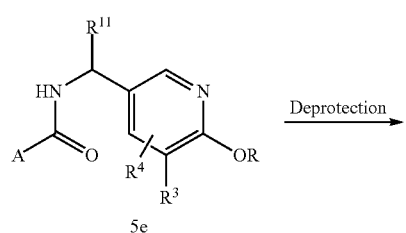
5e
Scheme 6
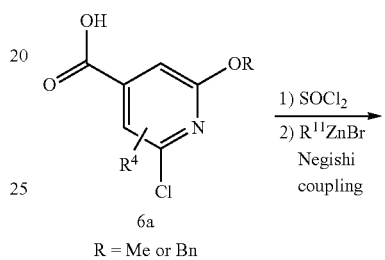
6a
R = Me or Bn
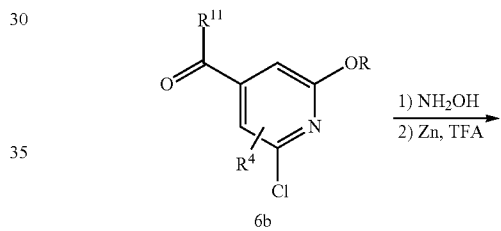
6b
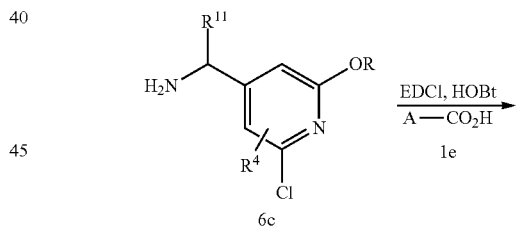
6c
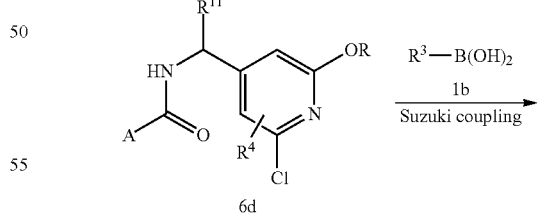
6d
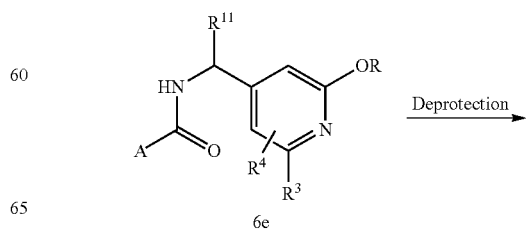
6e

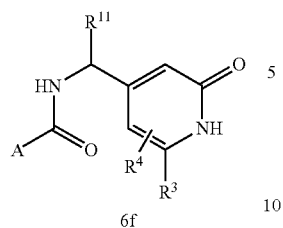

6f

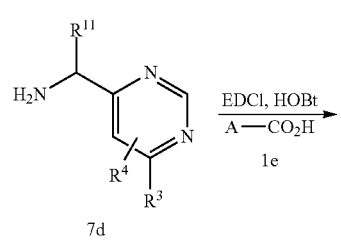

7d

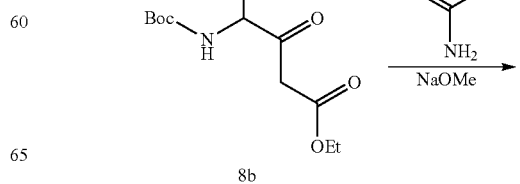

7e

Representative pyrimidine compounds of this invention can be prepared as shown in Scheme 7. Suzuki coupling between an appropriately functionalized pyrimidine 7a and an appropriately substituted aryl or heteroaryl boronic acid or ester 1b, as described for the conversion of 1a to 1c, provides the biaryl compound. Basic hydrolysis affords acid derivatives 7b. Negishi coupling between the acid chloride, derived from acid derivatives 7b, and an appropriately substituted organozinc reagent employing reagents described in Scheme 2 provides ketone 7c. Alternately, ketone 7c can be prepared by addition of Grignard or organolithium reagents to the corresponding ester or Weinreb amide derived from acid derivatives 7b. Condensation of 7c with hydroxylamine hydrochloride generates the oxime, which can be reduced to the primary amine 7d with zinc dust and TFA. Amide coupling between 7d and carboxylic acid 1e employing suitable coupling reagents as described in Scheme 1 gives 7e. Further manipulation of functional groups on A, $R^3$ and $R^4$ using methods known to one skilled in the art of organic synthesis will give additional compounds of the invention.

Alternately, representative pyrimidine compounds of this invention can be prepared as shown in Scheme 8. Condensation of the β-ketoester 8b, prepared according to a modified procedure of Maibaum (*J. Org. Chem.*, 1988, 53, 869.), with an amidine under basic conditions, such as formamidine and sodium methoxide in methanol, yields the pyrimidone 8c. The pyrimidone can be converted to the chloro pyrimidine 8d in two steps with phosphorus oxychloride and then reprotection of the amine with Boc-anhydride. Alternately, the pyrimidone can be converted to the corresponding triflate 8e with sodium hydride and N-phenyltrifluoromethanesulfonimide. Suzuki coupling between an appropriately functionalized pyrimidine 8d/8e and an appropriately substituted aryl or heteroaryl boronic acid or ester 1b, as described for the conversion of 1a to 1c, provides 8f. Following removal of the Boc group with TFA, the resulting amine is coupled with carboxylic acid 1e employing suitable coupling reagents as described in Scheme 1 to give 8g. Further manipulation of functional groups on A, $R^3$, and $R^4$ using methods known to one skilled in the art of organic synthesis will give additional compounds of the invention.

Scheme 7

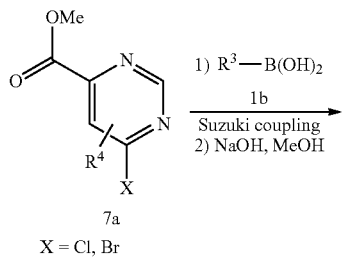

7a
X = Cl, Br

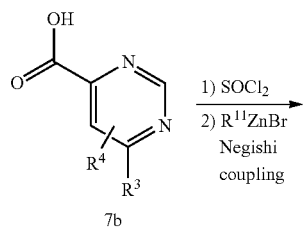

7b

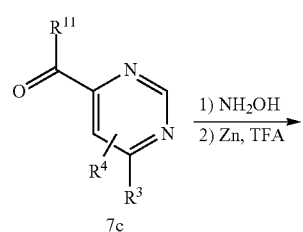

7c

Scheme 8

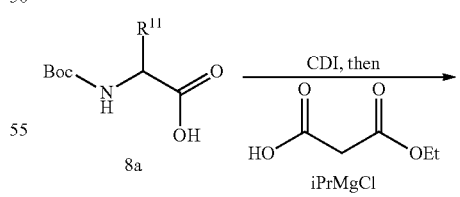

8a

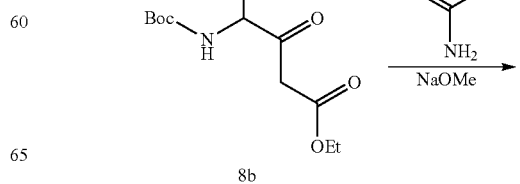

8b

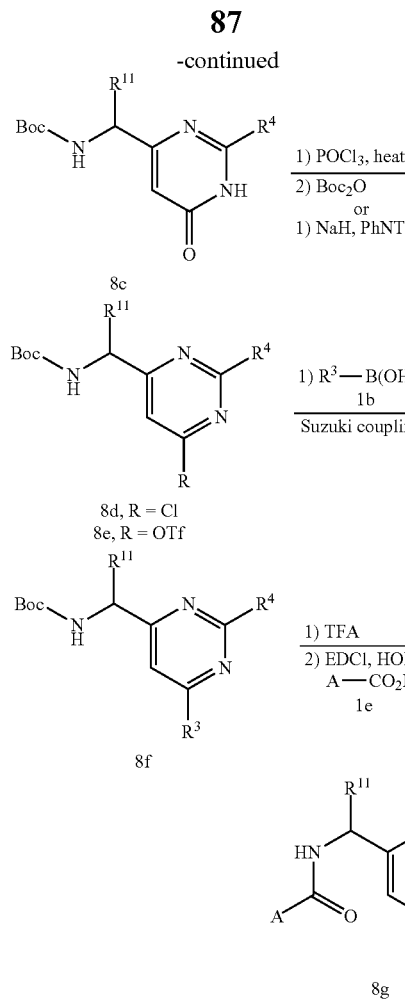

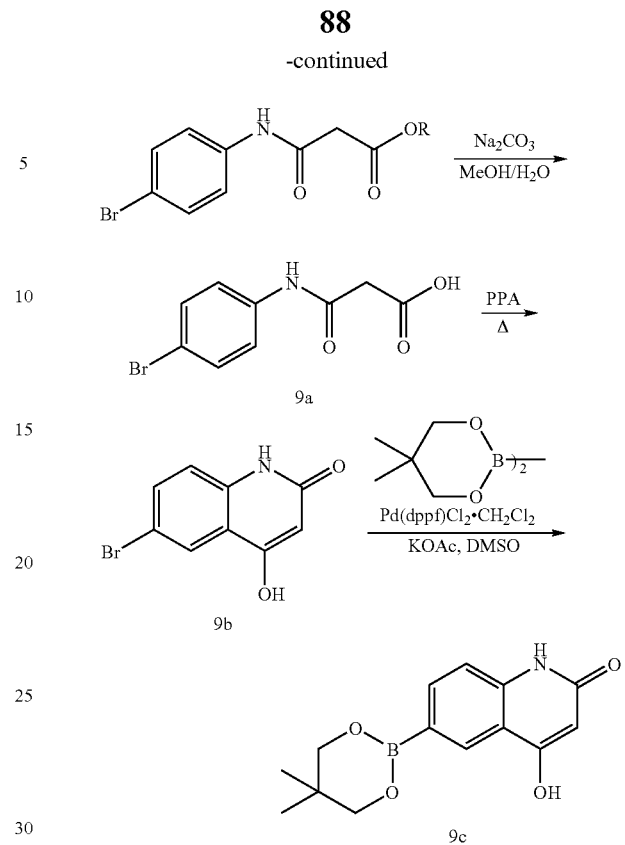

Methods for the synthesis of suitably substituted aryl or heteroaryl boronic acid or esters 1b, suitably substituted carboxylic acids (A-CO$_2$H) 1e, suitably substituted pyridyl aldehydes, and examples of manipulation of functional groups on R$^3$ are described in Published U.S. Patent Applications US20060009455A1 and US20060154915A 1, which are incorporated in their entirety herein by reference.

For example, Scheme 9 describes the synthesis of a specific example of R$^3$—B(OH)$_2$ (1b) when R$^3$ is a 4-hydroxy quinolinone moiety. Intramolecular Friedel-Craft acylation of 9a in the presence of an acid, such as polyphosphoric acid (PPA), at elevated temperature provides the 4-hydroxy quinolinone derivative 9b. Aryl bromide 9b is then subjected to a palladium mediated coupling with a diboron species such as bis(neopentyl glycolato)diboron to provide the corresponding boronate 9c using the method of Ishiyama, T. et al. (*J. Org. Chem.* 1995, 60(23), 7508-7510). The boronate can be used in place of boronic acids for coupling to the aryl/heteroaryl halides or triflates or the boronate can be converted to the boronic acid.

It is also realized that the scope of intermediate synthesis can be further extended outside the use of Suzuki methodology since the precursor aryl halides described above are also precursors for Stille, Negishi, Hiyama, and Kumada-type cross coupling methodologies (Tsuji, J. *Transition Metal Reagents and Catalysts: Innovations in Organic Synthesis*, John Wiley & Sons, 2000; Tsuji, J. *Palladium Reagents and Catalysts: Innovations in Organic Synthesis*, John Wiley & Sons, 1996.)

When required, separation of the racemic material obtained in Schemes 1-8 above can be achieved by HPLC using a chiral column or by a resolution of an appropriate intermediate using a resolving agent, for example as described in Wilen, S. H. *Tables of Resolving Agents and Optical Resolutions* 1972, 308, or using enantiomerically pure acids and bases. Alternatively, the addition of R$^{11}$MgCl to N-tert-butanesulfinyl aldimines, derived from 1c, can provide single stereoisomers as described by Ellman (Ellman, J. A. et al. *Acc. Chem. Res.* 2002, 35, 984). Alternatively, single stereoisomers can be obtained by oxazaborolidine-catalyzed enantioselective reduction of oxime ethers, derived from 2b, 3b, 4b, 5b, 6b, and 7c, as described by Demir (Demir, A. S. et al. *Helv. Chim. Acta.*, 2003, 86, 91).

The compound of the instant invention herein described may have asymmetric center(s). For example, the chiral carbon atom in Formula (I) as indicated below, exists in either as S or R configuration.

Scheme 9

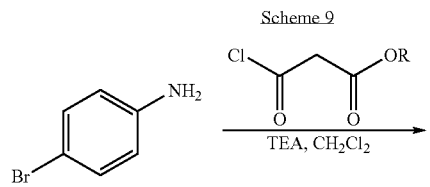

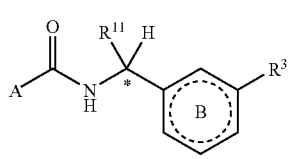

(I)

For example, but not limited to therein, in compounds of Formula (I), the following two stereoisomeric configurations are possible:

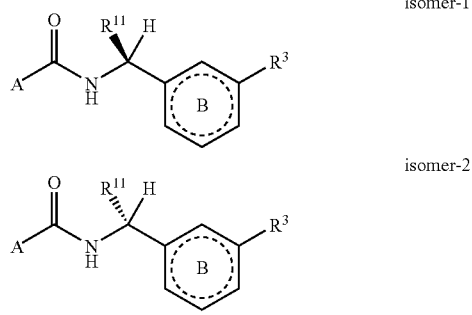

They are collectively, as well as individually, considered part of the invention. In a preferred stereoisomeric embodiment the present invention provides for a stereoisomeric configuration of isomer-1 for Formula (I) or tautomer, pharmaceutically acceptable salt, solvate, or prodrug form thereof.

Other features of the invention will become apparent in the course of the following descriptions of exemplary embodiments that are given for illustration of the invention and are not intended to be limiting thereof.

In the following experimental procedures, solution ratios express a volume relationship, unless stated otherwise. NMR chemical shifts (δ) are reported in parts per million (ppm).

Products were analyzed by reverse phase analytical HPLC carried out on a Shimadzu Analytical HPLC system running Discovery VP software using Method A: Phenomenex Luna C18 column (4.6×50 mm or 4.6×75 mm) eluted at 4 mL/min with a 2, 4 or 8 min gradient from 100% A to 100% B (A: 10% methanol, 89.9% water, 0.1% TFA; B: 10% water, 89.9% methanol, 0.1% TFA, UV 220 nm), or Method B: Phenomenex Luna C18 column (4.6×50 mm) eluted at 4 mL/min with a 4 min gradient from 100% A to 100% B (A: 10% acetonitrile, 89.9% water, 0.1% TFA; B: 10% water, 89.9% acetonitrile, 0.1% TFA, UV 220 nm). Purification of intermediates and final products was carried out via either normal or reverse phase chromatography. Normal phase chromatography was carried out on an ISCO CombiFlash™ System using pre-packed $SiO_2$ cartridges eluted with gradients of hexanes and ethyl acetate or methylene chloride and methanol. Reverse phase preparative HPLC was carried out using a Shimadzu Preparative HPLC system running DiscoveryVP software using Method A: YMC Sunfire 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm), Method B: Phenomenex AXIA Luna 5 μm C18 30×75 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), Method C: Phenomenex Luna 5 μm C18 30×100 mm column with a 10 min gradient at 40 mL/min from 100% A to 100% B (A: 10% acetonitrile, 89.9% water, 0.1% TFA; B: 10% water, 89.9% acetonitrile, 0.1% TFA, UV 220 nm), or Method D: Phenomenex Luna 5 μm C18 30×100 mm column with a 10 min gradient at 40 mL/min from 100% A to 100% B (A: 10% methanol, 89.9% water, 0.1% TFA; B: 10% water, 89.9% methanol, 0.1% TFA, UV 220 nm). Alternatively, reverse phase preparative HPLC was carried out using a Varian ProStar Preparative HPLC System running Star 6.2 Chromatography Workstation software using Method E: Dynamax 10 μm C18 41.4×250 mm column with a 30 min gradient at 30 mL/min from 10% B to 100% B (A 98% water, 2% acetonitrile, 0.05% TFA; B: 98% acetonitrile, 2% water, 0.05% TFA, UV 254 nm). LCMS chromatograms were obtained on a Shimadzu HPLC system running DiscoveryVP software, coupled with a Waters ZQ mass spectrometer running MassLynx version 3.5 software using the same columns and conditions as utilized for analytical described above.

The following Examples have been prepared, isolated and characterized using the methods disclosed herein. The following Examples demonstrate a partial scope of the invention and are not meant to be limiting of the scope of the invention.

EXAMPLES

Example 1 trans-4-Aminomethyl-cyclohexanecarboxylic acid[2-phenyl-1-(5-phenyl-pyridin-3-yl)-ethyl]-amide, bis-trifluoroacetic acid salt 1A. 5-Phenyl-pyridine-3-carbaldehyde: A biphasic mixture of 5-bromo-3-formyl pyridine (0.500 g, 2.69 mmol), $Pd(Ph_3P)_4$ (0.155 g, 0.134 mmol), and phenyl boronic acid (0.492 g, 4.03 mmol) in degassed 2.0 M aqueous $Na_2CO_3$ (6.0 mL) and toluene (6.7 mL) was heated at reflux for 2.5 h. The reaction was cooled to rt, diluted with water and EtOAc. The layers were separated and the aqueous layer was extracted with EtOAc (1×). The combined organic layers were washed with brine, dried over $Na_2SO_4$, filtered, and concentrated to give an orange-brown oil weighing 0.848 g. Column chromatography on silica gel gave 0.447 g (91%) of the biaryl compound as a pale yellow solid. $^1H$ NMR (500 MHz, $CDCl_3$) δ: 10.19 (s, 1H), 9.07 (s, 1H), 9.04 (s, 1H), 8.34 (s, 1H), 7.62 (d, J=7.7 Hz, 2H), 7.52 (t, J=7.7 Hz, 2H), 7.47-7.44 (m, 1H). MS 184.2 $(M+H)^+$; 216.2 $(M+CH_3OH+H)^+$.

1B. 2-Phenyl-1-(5-phenyl-pyridin-3-yl)-ethylamine, bis-trifluoroacetic acid salt: To a cooled (0° C.), yellow solution of 1A (0.437 g, 2.38 mmol) in THF (6.0 mL) was added dropwise 1.0 N lithium bis(trimethylsilyl)amide in THF (2.50 mL, 2.50 mmol). The resulting dark yellow solution was stirred at 0° C. for 20 min. Subsequently, a 2.0 M benzylmagnesium chloride solution in THF (1.25 mL, 2.50 mmol) was added dropwise to give a dark orange solution. The reaction was stirred at 0° C. for 15 min and then quenched with sat. $NH_4Cl$, diluted with water and EtOAc. The layers were separated and the aqueous layer was extracted with EtOAc (1×). The combined organic layers were washed with sat. $NaHCO_3$, brine, dried over $Na_2SO_4$, filtered, and concentrated to give an orange foam weighing 0.526 g. Prep. HPLC afforded 0.152 g (13%, yellow residue) of the amine as the bis-TFA salt. $^1H$ NMR (500 MHz, $CD_3OD$) δ: 8.89 (s, 1H), 8.51 (s, 1H), 8.24 (s, 1H), 7.66 (d, J=7.2 Hz, 2H), 7.53 (t, J=7.2 Hz, 2H), 7.49-7.46 (m, 1H), 7.30-7.23 (m, 3H), 7.17 (d, J=7.2 Hz, 2H), 4.82 (t, J=7.7 Hz, 1H), 3.46 (dd, J=13.4, 6.4 Hz, 1H), 3.31-3.27 (m, 1H). MS 275.2 $(M+H)^+$.

1C. {trans-4-[2-Phenyl-1-(5-phenyl-pyridin-3-yl)-ethylcarbamoyl]-cyclohexylmethyl}-carbamic acid tert-butyl ester: To a cooled (0° C.) solution of 1B (0.152 g, 0.302 mmol) in DMF (1.0 mL) was added Hunig's base (0.16 mL, 0.91 mmol). To the resulting yellow solution were added sequentially Boc-tranexamic acid (0.086 g, 0.33 mmol), HOBt (0.0612 g, 0.453 mmol), and EDCI (0.087 g, 0.453 mmol). After 15 min at 0° C., the solution was warmed to rt. After 6.0 h, the solution was diluted with water to give a suspension. The reaction was extracted with EtOAc. The combined organic layers were washed with 0.5 M HCl and a solid formed. The mixture was basified with 1.0 M NaOH. The layers were separated and the aqueous layer was extracted with EtOAc. The combined organic layers were washed with brine, dried over $Na_2SO_4$, filtered and concentrated to give the amine as a pale yellow solid (0.142 g, 92%) which was used in the next step without further purification. MS 514.5 $(M+H)^+$.

1D: Example 1. A solution of 1C (0.080 g) in 30% TFA in $CH_2Cl_2$ (5.0 mL) was stirred for 30 min and then concentrated. Prep. HPLC afforded, after lyophilization from water, 0.058 g (58%, white, fluffy solid) of Example 1 as the bis-TFA salt. $^1$H NMR (500 MHz, $CD_3OD$) δ: 8.91 (s, 1H), 8.67 (d, J=7.7 Hz, 1H), 8.61 (s, 1H), 8.45 (s, 1H), 7.69 (d, J=7.1 Hz, 2H), 7.57-7.50 (m, 3H), 7.29-7.27 (m, 2H), 7.24-7.20 (m, 3H), 5.36-5.32 (m, 1H), 3.20 (d, J=7.7 Hz, 2H), 2.76 (d, J=7.2 Hz, 2H), 2.25-2.20 (m, 1H), 1.85-1.78 (m, 3H), 1.71-1.68 (m, 1H), 1.60-1.50 (m, 1H), 1.41-1.30 (m, 2H), 1.08-1.00 (m, 2H). MS 414.3 $(M+H)^+$.

Example 2 trans-4-Aminomethyl-cyclohexanecarboxylic acid[1-(1-oxy-5-phenyl-pyridin-3-yl)-2-phenyl-ethyl]-amide, bis-trifluoroacetic acid salt To a suspension of 1C (0.062 g, 0.121 mmol) in dichloromethane (1.2 mL) was added m-chloroperbenzoic acid (0.042 g, 0.181 mmol). The resulting solution was stirred at rt for 2 h. The reaction was diluted with $CH_2Cl_2$ and washed with sat. sodium sulfite, sat. $NaHCO_3$, brine, dried over $MgSO_4$, filtered and concentrated to give a yellow solid (0.062 g). This solid was dissolved in 30% TFA in $CH_2Cl_2$ (5 mL). After 30 min, the reaction was concentrated. Prep. HPLC yielded, after lyophilization from $CH_3CN/H_2O$, 0.0371 g (56%, white solid) of Example 2 as the TFA salt. $^1$H NMR (500 MHz, $CD_3OD$) δ: 8.50 (s, 1H), 8.26 (s, 1H), 7.75 (s, 1H), 7.61 (d, J=7.2 Hz, 2H), 7.53-7.47 (m, 3H), 7.30-7.27 (m, 2H), 7.24-7.20 (m, 3H), 5.26-5.23 (m, 1H), 3.19-3.10 (m, 2H), 2.76 (d, J=7.2 Hz, 2H), 2.23-2.18 (m, 1H), 1.86-1.79 (m, 3H), 1.69-1.67 (m, 1H), 1.60-1.53 (m, 1H), 1.44-1.31 (m, 2H), 1.08-1.00 (m, 2H). MS 430.4 $(M+H)^+$.

Example 3

[trans-4-(5-{1-[(4-Aminomethyl-cyclohexanecarbonyl)-amino]-2-phenyl-ethyl}-pyridin-3-yl)-phenyl]-carbamic acid methyl ester, bis-trifluoroacetic acid salt 3A. 5-bromonicotinoylchloride: A suspension of 5-bromonicotinic acid (5.0 g, 24.8 mmol), thionyl chloride (5.4 mL, 74.2 mmol), and DMF (a few drops) in DCE (83 mL) was warmed to reflux. After 3 h, the reaction was cooled to rt and concentrated to give an off-white solid. The solid was dissolved in $CH_2Cl_2$ and concentrated. The process was repeated twice to give the acid chloride as an off-white solid.

3B. Benzylzinc chloride: To a cooled (0° C.), 0.5 M solution of $ZnCl_2$ in THF (23.8 mL, 11.9 mmol) was added dropwise 2.0 M benzylmagnesium chloride (5.7 mL, 11.3 mmol) to give a milky-white suspension. After 30 min, the reaction was warmed to rt for 10-15 min and then used in the next step.

3C. 1-(5-Bromo-pyridin-3-yl)-2-phenyl-ethanone: To a cooled (−30° C.), solution of 3A (2.5 g, 11.3 mmol) in degassed THF (22.7 mL) was added sequentially $Pd(Ph_3P)_4$ (0.326 g, 0.283 mmol) and then the BnZnCl mixture to give a dull, yellow suspension. The reaction was placed in an ice-bath to maintain the temperature at 0° C. After 1 h, the reaction was quenched with 0.5 M HCl (50 mL) and diluted with EtOAc. The layers were separated. The organic layer was washed with sat. $NaHCO_3$, brine, dried over $Na_2SO_4$, filtered and concentrated to give a yellow oil weighing 2.96 g. Column chromatography on silica gel gave 1.42 g (45%) of the ketone as a yellow solid. $^1$H NMR (500 MHz, $CDCl_3$) δ: 9.11 (d, J=1.9 Hz, 1H), 8.82 (d, J=1.9 Hz, 1H), 8.39 (t, J=1.9 Hz, 1H), 7.36-7.34 (m, 2H), 7.32-7.24 (m, 3H), 4.28 (s, 2H). MS 276.3 $(M+H)^+$; 278.3 $(M+2+H)^+$.

3D. 1-(5-Bromo-pyridin-3-yl)-2-phenyl-ethylamine, bis-trifluoroacetic acid salt: A suspension of 3C (1.31 g, 4.74 mmol) and hydroxylamine hydrochloride (0.989 g, 14.2 mmol) in methanol (19 mL) was stirred at rt for 24 h. The reaction was concentrated, then partitioned between ethyl acetate and sat. $NaHCO_3$. The layers were separated and the aqueous layer was extracted with ethyl acetate. The combined organic layers were washed with brine, dried over $Na_2SO_4$, filtered, and concentrated to yield 1.36 g of the oxime as a yellow solid. To a cooled (15° C.), solution of this oxime in TFA (11 mL) was added zinc dust (2.4 g, 36.7 mmol) in portions so as to keep the temperature below 25° C. After 1.5 h, the reaction was added slowly to a vigorously stirred, cold (0° C.) solution of 1.0 N NaOH (400 mL) and then extracted with $CH_2Cl_2$ (3×). The combined organic layers were washed with brine, dried over $Na_2SO_4$, filtered and concentrated to give a yellow-orange oil weighing 1.26 g. Prep. HPLC yielded 0.850 g (35%, yellow foam) of the amine as the bis-TFA salt. $^1$H NMR (500 MHz, $CD_3OD$) δ: 8.67 (s, 1H), 8.42 (d, J=1.6 Hz, 1H), 8.08 (d, J=1.6 Hz, 1H), 7.29-7.22 (m, 3H), 7.13 (d, J=7.2 Hz, 2H), 4.68 (dd, J=8.8, 6.6 Hz, 1H), 3.37 (dd, J=13.8, 6.3 Hz, 1H), 3.20 (dd, J=13.8, 9.4 Hz, 1H). MS 277.0 $(M+H)^+$ and 279.0 $(M+2+H)^+$. Following neutralization, separation of enantiomers by chiral prep HPLC (Chiralcel OJ; MeOH, EtOH, heptane) gave enantiomer A [>99% ee; $[α]_D^{27.1}$=−88.02 (c=1.37, MeOH)] and enantiomer B [>98% ee; $[α]_D^{25.2}$=+84.47 (c=1.22; MeOH)].

3E. {trans-4-[1-(5-Bromo-pyridin-3-yl)-2-phenyl-ethylcarbamoyl]-cyclohexylmethyl}-carbamic acid tert-butyl ester: To solution of 3D (0.250 g, 0.495 mmol) in DMF (1.6 mL) was added sequentially Boc-tranexamic acid (0.140 g, 0.544 mmol), HOBt (0.100 g, 0.742 mmol), Hunig's base (0.34 mL, 1.98 mmol) and EDC (0.142 g, 0.742 mmol). After 3.5 h, the reaction was poured into vigorously stirred cold water to obtain a white suspension that was extracted with EtOAc. The combined organic layers were washed with 0.5 M HCl, sat. $NaHCO_3$, brine, dried over $Na_2SO_4$, filtered and concentrated to give a white solid (0.267 g). Following trituration from MeOH (3 mL), the solid was collected by filtration, rinsed with MeOH (1 mL), air-dried, and dried under vacuum to give 0.103 g (40%, white solid) of the amide. $^1$H NMR (500 MHz, $CD_3OD$) δ: 8.51 (d, J=2.2 Hz, 1H), 8.39 (d, J=1.1 Hz, 1H), 7.94 (s, 1H), 7.27-7.24 (m, 2H), 7.20-7.16 (m, 3H), 5.15 (t, J=8.0 Hz, 1H), 3.07 (d, J=8.2 Hz, 2H), 2.85 (d, J=6.6 Hz, 2H), 2.14-2.08 (m, 1H), 1.78-1.69 (m, 3H), 1.64-1.60 (m, 1H), 1.42 (s, 9H), 1.38-1.25 (m, 3H), 0.99-0.89 (m, 2H). MS 516.0 $(M+H)^+$.

3F. {trans-4-[5-(1-{[4-(tert-Butoxycarbonylamino-methyl)-cyclohexanecarbonyl]-amino}-2-phenyl-ethyl)-pyridin-3-yl]-phenyl}-carbamic acid methyl ester: To a flame-dried 1 dram vial (with a teflon cap) was added 3E (0.050 g, 0.0968 mmol), 4-(methoxycarbonylamino)phenyl boronic acid (0.0378 g, 0.194 mmol), $Pd(dppf)Cl_2 \cdot CH_2Cl_2$ (0.0079 g, 0.0097 mmol), and potassium phosphate (0.0411 g, 0.194 mmol). The vial was purged with argon for several minutes and degassed DMSO (0.64 mL) was added. The vial was capped with a Teflon-coated cap under a blanket of argon. The vial was placed in a preheated (90° C.) shaker or oil bath. After 12 h, the reaction was cooled to rt, diluted with MeOH (2.3 mL), and filtered through a 0.45 μm nylon filter. The filtrate was purified by Prep. HPLC [21.2×100 mm; 8 min. gradient; 30-100% B; 20 mL/min.] to afford 0.054 g (white solid) of the biaryl compound as the TFA salt. MS 587.2 $(M+H)^+$.

3G. Example 3: Compound 3F was dissolved in 30% TFA in $CH_2Cl_2$ (5 mL). After 30 min, the reaction was concentrated. Prep. HPLC gave, after lyophilization from $CH_3CN/H_2O$, 0.0406 g (57%, white fluffy solid) of Example 3 as the bis-TFA salt. $^1H$ NMR (500 MHz, $CD_3OD$) δ: 8.83 (s, 1H), 8.51 (s, 1H), 8.29 (s, 1H), 7.62 (s, 4H), 7.29-7.26 (m, 2H), 7.23-7.19 (m, 3H), 5.33-5.30 (m, 1H), 3.76 (s, 3H), 3.18 (d, J=8.2 Hz, 2H), 2.76 (d, J=7.2 Hz, 2H), 2.24-2.19 (m, 1H), 1.85-1.78 (m, 3H), 1.71-1.68 (m, 1H), 1.60-1.53 (m, 1H), 1.45-1.34 (m, 2H), 1.08-1.00 (m, 2H). MS 487.4 $(M+H)^+$.

Example 4 trans-4-Aminomethyl-cyclohexanecarboxylic acid[2-phenyl-1-(2-phenyl-pyridin-4-yl)-ethyl]-amide, bis-trifluoroacetic acid salt 4A. {trans-4-[1-(2-Chloro-pyridin-4-yl)-2-phenyl-ethylcarbamoyl]-cyclohexylmethyl}-carbamic acid tert-butyl ester. This compound was prepared from 2-chloro isonicotinic acid following the procedures described in 3A-3E. $^1H$ NMR (500 MHz, $CDCl_3$) δ: 8.29 (d, J=5.0 Hz, 1H), 7.30-7.24 (m, 3H), 7.16 (s, 1H), 7.05-7.03 (m, 3H), 5.85 (d, J=7.2 Hz, 1H), 5.23-5.19 (m, 1H), 4.59 (bs, 1H), 3.11 (dd, J=14.2, 6.6 Hz, 1H), 3.00-2.94 (m, 3H), 2.02-1.97 (m, 1H), 1.83-1.70 (m, 4H), 1.44 (s, 9H), 1.42-1.28 (m, 3H), 0.94-0.87 (m, 2H). MS 416.4 $(M-C_4H_8+H)^+$; 418.4 $(M+2-C_4H_8+H)^+$.

4B: {trans-4-[2-Phenyl-1-(2-phenyl-pyridin-4-yl)-ethylcarbamoyl]-cyclohexylmethyl}-carbamic acid tert-butyl ester. To a flame-dried 1 dram vial (with a teflon cap) was added 4A (0.050 g, 0.106 mmol), phenylboronic acid (0.0258 g, 0.212 mmol), tris(dibenzylideneacetone)dipalladium(0) (0.0048 g, 0.0053 mmol), tri-t-butylphosphonium tetrafluoroborate (0.0037 g, 0.0127 mmol), and cesium carbonate (0.069 g, 0.212 mmol). The vial was purged with argon for several minutes and degassed dioxane (0.53 mL) was added. The vial was capped with a Teflon-coated cap under a blanket of argon. The purple suspension was stirred at rt for 1 h and then placed in a preheated (90° C.) shaker or oil bath. After 13 h, the reaction was cooled to rt, diluted with $CH_2Cl_2$, and filtered through a 0.45 μm nylon filter. The filtrate was concentrated to yield an orange solid (0.069 g). Ethyl acetate (1.5 mL) was added. The mixture was sonicated, and the solid was collected by filtration, rinsed with EtOAc (1 mL), air-dried, then dried under vacuum to give the biaryl compound as a white solid (0.0418 g, 77%). MS 514.5 $(M+H)^+$.

4C. Example 4. This compound was prepared from compound 4B following the procedure described for 1D. $^1H$ NMR (500 MHz, $CD_3OD$) δ: 8.68 (d, J=6.0 Hz, 1H), 8.00 (s, 1H), 7.84 (d, J=8.2 Hz, 2H), 7.73 (d, J=6.0 Hz, 1H), 7.62-7.59 (m, 3H), 7.30-7.22 (m, 5H), 5.37-5.31 (m, 1H), 3.22-3.12 (m, 2H), 2.77 (d, J=6.6 Hz, 2H), 2.29-2.21 (m, 1H), 1.89-1.79 (m, 3H), 1.72-1.68 (m, 1H), 1.60-1.50 (m, 1H), 1.43-1.30 (m, 2H), 1.10-1.00 (m, 2H). MS 414.4 $(M+H)^+$.

Example 5 trans-4-Aminomethyl-cyclohexanecarboxylic acid[1-(1-oxy-2-phenyl-pyridin-4-yl)-2-phenyl-ethyl]-amide, trifluoroacetic acid salt Example 5 was prepared as the TFA salt starting from compound 4B following the procedure described in Example 2. $^1H$ NMR (500 MHz, $CD_3OD$) δ: 8.54 (d, J=7.7 Hz, 1H), 8.36 (d, J=6.6 Hz, 1H), 7.70-7.67 (m, 2H), 7.52-7.50 (m, 3H), 7.46-7.44 (m, 2H), 7.30-7.26 (m, 2H), 7.22-7.19 (m, 3H), 5.23-5.18 (m, 1H), 3.16-3.07 (m, 2H), 2.76 (d, J=7.2 Hz, 2H), 2.22-2.18 (m, 1H), 1.85-1.79 (m, 3H), 1.70-1.66 (m, 1H), 1.60-1.50 (m, 1H), 1.44-1.30 (m, 2H), 1.08-1.00 (m, 2H). MS 430.4 $(M+H)^+$.

Example 6

[4-(4-{1-[(trans-4-aminomethyl-cyclohexanecarbonyl)-amino]-2-phenyl-ethyl}-pyridin-2-yl)-phenyl]-carbamic acid methyl ester, bis-trifluoroacetic acid salt Example 6 was prepared as the bis-TFA salt starting from compound 4A following the procedures described for 4B and 4C, replacing phenylboronic acid with 4-(methoxycarbonylamino)phenylboronic acid. $^1H$ NMR (500 MHz, $CD_3OD$) δ: 9.71 (s, 1H), 8.67 (d, J=7.2 Hz, 1H), 8.62 (d, J=6.0 Hz, 1H), 8.00 (s, 1H), 7.80 (d, J=8.8 Hz, 2H), 7.74-7.69 (m, 3H), 7.30-7.21 (m, 5H), 5.37-5.30 (m, 1H), 3.78 (s, 3H), 3.24-3.13 (m, 2H), 2.77 (d, J=7.2 Hz, 2H), 2.30-2.20 (m, 1H), 1.90-1.80 (m, 3H), 1.72-1.68 (m, 1H), 1.60-1.50 (m, 1H), 1.44-1.30 (m, 2H), 1.11-0.99 (m, 2H). MS 487.5 $(M+H)^+$.

Example 7 trans-4-Aminomethyl-cyclohexanecarboxylic acid {1-[5-(4-hydroxy-2-oxo-1,2-dihydro-quinolin-6-yl)-pyridin-3-yl]-2-phenyl-ethyl}-amide, bis-trifluoroacetic acid salt 7A. N-(4-Bromo-phenyl)-malonamic acid ethyl ester: To a solution of 4-bromo aniline (1.78 g, 10.3 mmol) in dichloromethane (20 mL) and TEA (2.0 mL, 15.5 mmol) was added dropwise ethyl 3-chloro-3-oxo-propionate (1.6 mL, 12.4 mmol) at 0° C. After 2 h, the mixture was diluted with dichloromethane (20 mL), washed with 1.0 N HCl (1×), brine (2×), dried over sodium sulfate, filtered and concentrated. Column chromatography on silica gel (0-30% EtOAc/Hex) gave 2.80 g (95%) of 7A as a light yellow solid. MS 287.9 $(M+2+H)^+$. $^1H$ NMR (400 MHz, $CDCl_3$) δ: 1.33 (t, J=7.25 Hz, 3H) 3.46 (s, 2H) 4.26 (q, J=7.32 Hz, 2H) 7.41-7.49 (m, 4H) 9.34 (s, 1H).

7B. 6-Bromo-4-hydroxy-1H-quinolin-2-one: To 7A (2.8 g, 9.8 mmol) in methanol/water (30 mL/10 mL) was added sodium carbonate (1.55 g, 14.6 mmol) and the mixture was stirred at rt for 3 days. The reaction mixture was added slowly to a stirred solution of aq. 1.0 N HCl (150 mL). The resulting white precipitate was collected by filtration. The solid cake was washed thoroughly with water and then dried under vacuum to give 2.57 g (100%) of the acid. MS 259.9 $(M+2+H)^+$.

A mixture of the acid (0.70 g, 2.7 mmol) and PPA (ca. 10 g) was stirred at 120° C. under argon. After ca. 1 h, the reaction was cooled to rt and carefully poured onto ice. The resulting white precipitate was collected and washed thoroughly with water to give 0.65 g (100%) of 7B. MS 241.91 $(M+2+H)^+$. $^1H$ NMR (400 MHz, $DMSO-d_6$) δ: 5.75 (s, 1H) 7.21 (d, J=8.79 Hz, 1H) 7.65 (dd, J=8.79, 2.20 Hz, 1H) 7.85 (d, J=2.20 Hz, 1H).

7C. 6-(5,5-dimethyl-1,3,2-dioxaborinan-2-yl)-4-hydroxyquinolin-2(1H)-one and 4-hydroxy-2-oxo-1,2-dihydroquinolin-6-ylboronic acid: To 7B (815 mg, 3.37 mmol) in DMSO (25 mL) was added 5,5,5',5'-tetramethyl-2,2'-bi(1,3,2-dioxaborinane) (837 mg, 3.70 mmol), potassium acetate (500 mg, 5.06 mmol) and Pd(dppf)Cl$_2$·CH$_2$Cl$_2$ (74 mg, 0.10 mmol). The reaction was degassed and heated under argon at 80° C. for about 3 h. The reaction was cooled to rt and a precipitate formed. The solid was collected by filtration and purification by reverse phase HPLC (acetonitritrile/water/ 0.1% TFA) to give 0.655 g of 7C as a white solid. This was a ~2:1 mixture of boronate and boronic acid. For boronic acid: MS 206.0 (M+H)$^+$. $^1$H NMR (400 MHz, DMSO-d$_6$) for boronic acid: δ: 5.74 (s, 1H) 7.20 (d, J=7.92 Hz, 1H) 7.88 (dd, J=8.35, 1.82 Hz, 1H) 8.31 (s, 1H). For boronate: δ: 0.96 (s, 6H)) 3.76 (s, 4H) 5.73 (s, 1H) 7.22 (d, J=7.91 Hz, 1H) 7.76 (dd, J=8.35, 1.82 Hz, 1H) 8.19 (s, 2H).

7D. Example 7 was prepared as the bis-TFA salt starting from compound 3D (enantiomer B) following the procedures described for 3E-G, by replacing 4-(methoxycarbonylamino) phenylboronic acid with 7C. MS 497.2 (M+H)$^+$. $^1$H NMR (400 MHz, CD$_3$OD) δ: 8.91-8.89 (m, 1H), 8.56-8.55 (m, 1H), 8.34-8.30 (m, 1H), 8.24 (d, J=1.8 Hz, 1H), 7.89 (dd, J=8.8, 1.8 Hz, 1H), 7.49 (d, J=8.8 Hz, 1H), 7.31-7.20 (m, 5H), 5.96 (s, 1H), 5.36-5.30 (m, 1H), 3.19 (d, J=7.9 Hz, 2H), 2.76 (d, J=7.0 Hz, 2H), 2.28-2.20 (m, 1H), 1.86-1.78 (m, 3H), 1.74-1.68 (m, 1H), 1.62-1.50 (m, 1H), 1.46-1.30 (m, 2H), 1.12-1.00 (m, 2H).

Example 8

[4-(5-{1-[(trans-4-Aminomethyl-cyclohexanecarbonyl)-amino]-2-phenyl-ethyl}-2-oxo-1,2-dihydropyridin-3-yl)-phenyl]-carbamic acid methyl ester, trifluoroacetic acid salt 8A. 5-bromo-6-hydroxynicotinic acid: To 6-hydroxynicotinic acid (8 g, 57.6 mmol) suspended in water (30 mL) cooled in an ice bath was added bromine (4.2 mL, 81.4 mmol). After the addition was complete the reaction was stirred at rt for 24 h. The solid was collected by filtration, washed with water and dried at 40° C. in a vacuum oven for 24 h. A total of 12.1 g (97%) of 8A as a tan solid was collected. $^1$H NMR (400 MHz, DMSO-d$_6$) δ: 8.04 (d, J=2.53 Hz, 1H) 8.16 (d, J=2.27 Hz, 1H), 12.59 (brd s, 1H), 12.90 (brd s, 1H).

8B. 5-Bromo-6-chloro-nicotinic acid: To 8A (10 g, 45 mmol) was added tetra-methylammonium chloride (5.4 g, 49 mmol) and phosphorous oxychloride (20 mL) and the reaction was heated at reflux for 3 h. The reaction was poured onto ice and stirred 2 h. The solid was filtered off, dissolved in EtOAc (300 mL) and dried (Na$_2$SO$_4$). After filtration and concentration, 10.5 g (97%) of 8B as a pink solid was collected. $^1$H NMR (400 MHz, DMSO-d$_6$) δ: 8.53 (d, J=2.02 Hz, 1H) 8.85 (d, J=2.02 Hz, 1H) 13.57 (s, 1H).

8C. 6-Benzyloxy-5-bromo-nicotinic acid: To 8B (3.3 g, 14 mmol) in DMF (25 mL) and benzyl alcohol (6 mL) at 0° C. was added 60% sodium hydride (1.6 g, 42 mmol). After 1 h at rt, the reaction was heated at 85° C. for 24 h, quenched with ice water and acidified with 1N HCl to pH 6; the product precipitated. The aqueous layer was extracted with EtOAc (3×50 mL), washed with water and brine and dried (Na$_2$SO$_4$), filtered and concentrated to a crude solid. The solid was suspended in DCM/hexanes and then filtered to give 3.6 g (84%) of 8C as a white solid. MS 307 (M+H)$^+$; 309.9 (M+2+H)$^+$. $^1$H NMR (400 MHz, CDCl$_3$) δ: 5.55 (s, 2H) 7.29-7.42 (m, 3H) 7.49 (d, J=7.33 Hz, 2H) 8.45 (d, J=2.02 Hz, 1H) 8.81 (d, J=2.02 Hz, 1H). MS 307 (M+H)$^+$ and 309.9 (M+2+H)$^+$.

8D. 6-Benzyloxy-5-bromo-N-methoxy-N-methyl-nicotinamide: To 8C (3.29 g, 10.6 mmol) in DCM (20 mL) was added carbonyl diimidazole (1.9 g, 11.7 mmol) and TEA (2.98 mL, 21 mmol) and the reaction was stirred 1.5 h. N,O-Dimethylhydroxylamine (3.2 g, 32 mmol) was added and the reaction was stirred 24 h. The reaction was quenched with water and extracted with DCM (3×50 mL), washed with brine and dried (Na$_2$SO$_4$). Purification by column chromatography on silica gel (0-100% EtOAc/Hex) afforded 3.51 g (94%) of 8D as a clear oil. MS 350.8 (M+H)$^+$; 352.8 (M+2+H)$^+$. $^1$H NMR (400 MHz, CDCl$_3$) δ: 3.37 (s, 3H) 3.59 (s, 3H) 5.51 (s, 2H) 7.27-7.42 (m, 3H) 7.49 (d, J=7.33 Hz, 2H) 8.27 (d, J=2.02 Hz, 1H) 8.58 (d, J=2.02 Hz, 1H).

8E. 1-(6-Benzyloxy-5-bromo-pyridin-3-yl)-2-phenyl-ethanone: To a −78° C. solution of 8D (0.96 g, 2.70 mmol) in THF (10 mL) was added benzyl magnesium chloride (2M, 3 mL, 5.90 mmol) and the reaction was allowed to warm to rt and stirred for 72 h. The reaction was re-cooled to 0° C. and an additional 3 mL of 2M benzyl magnesium chloride solution was added. The reaction was complete after 3 h. The reaction was quenched with sat'd NH$_4$Cl and extracted with EtOAc (3×50 mL). The combined organic layers were washed with brine and dried (MgSO$_4$). Purification by column chromatography on silica gel (0-100% EtOAc/Hex) afforded 0.65 g (65%) of 8E as a yellow solid. MS 381.8 (M+H)$^+$ and 383.8 (M+2+H)$^+$. $^1$H NMR (400 MHz, CDCl$_3$) δ: 4.20 (s, 2H) 5.52 (s, 1H) 7.23-7.29 (m, 3H) 7.29-7.40 (m, 6H) 7.47 (d, J=6.57 Hz, 2H) 8.41 (d, J=2.27 Hz, 1H) 8.74 (d, J=2.27 Hz, 1H).

8F. Example 8 was prepared as the TFA salt starting from compound 8E and following the procedures described for 3D-G. In procedure 3F, Pd(dppf)Cl$_2$·CH$_2$Cl$_2$, potassium phosphate, DMSO, and 90° C. were replaced with bis(tri-t-butylphosphine) palladium(0), potassium carbonate, 4:1 DME/water and 70° C. MS 503.4 (M+H)$^+$. $^1$H NMR (400 MHz, CD$_3$OD) δ: 0.85-1.03 (m, 2H) 1.15-1.38 (m, 3H) 1.41-1.51 (m, 1H) 1.54-1.64 (m, 1H) 1.65-1.86 (m, 3H) 2.02-2.11 (m, 1H) 2.66 (d, J=7.07 Hz, 2H) 2.97 (d, J=7.83 Hz, 2H) 3.65 (s, 3H) 4.91 (q, J=7.83 Hz, 1H) 7.06-7.19 (m, 5H) 7.38 (d, J=8.84 Hz, 2H) 7.45-7.51 (d, J=8.59 Hz, 2H) 7.58 (d, J=2.53 Hz, 1H) 8.21 (d, J=8.34 Hz, 1H).

Example 9 trans-4-aminomethyl-cyclohexanecarboxylic acid[2-phenyl-1-(6-phenyl-pyrimidin-4-yl)-ethyl]-amide, trifluoroacetic acid salt Example 9 was prepared as the TFA salt following the procedures described for 3A, 3C-E, and 3G, by replacing 5-bromonicotinic acid with 6-phenyl-pyrimidine-4-carboxylic acid. MS 415.3 (M+H)$^+$. $^1$H NMR (500 MHz, CD$_3$OD) δ: 9.15 (s, 1H), 8.04 (d, J=8.3 Hz, 2H), 7.73 (s, 1H), 7.55-7.48 (m, 3H), 7.27-7.16 (m, 5H), 5.28-5.26 (m, 1H), 3.27 (dd, J=13.7, 6.0 Hz, 1H), 3.09 (dd, J=13.7, 9.3 Hz, 1H), 2.77 (d, J=7.2 Hz, 2H), 2.29-2.24 (m, 1H), 1.85-1.80 (m, 3H), 1.74-1.68 (m, 1H), 1.62-1.52 (m, 1H), 1.47-1.32 (m 2H), 1.09-1.01 (m, 2H).

Example 10

[4-(6-{1-[(trans-4-aminomethyl-cyclohexanecarbonyl)-amino]-2-phenyl-ethyl}-pyrimidin-4-yl)-phenyl]-carbamic acid methyl ester, trifluoroacetic acid salt 10A. [1-(6-Oxo-1,6-dihydro-pyrimidin-4-yl)-2-phenyl-ethyl]-carbamic acid tert-butyl ester: To a solution of 0.5 M sodium methoxide in methanol (58.4 mL, 29.2 mmol) was added formamidine acetate (1.521 g, 14.61 mmol) to give a clear, colorless solution. Next a solution of 4-tert-butoxycarbonylamino-3-oxo-5-phenyl-pentanoic acid ethyl ester (3.5 g, 10.44 mmol, Maibaum, J. et al., *J. Org. Chem.*, 1988, 53, 869.) in methanol (20.9 mL) was added. The resulting clear colorless solution was stirred at rt. After 8 h, the clear, yellow solution was quenched with acetic acid (1.67 mL, 29.2 mmol) and the reaction was concentrated to give a solid. The solid was partitioned between water and $CHCl_3$ (750 mL). The layers were separated and the aqueous layer was extracted with $CHCl_3$ (250 mL). The combined organic layers were washed with sat. $NaHCO_3$, brine, dried over $MgSO_4$, filtered, and concentrated to give an off-white solid weighing 3.45 g. Recrystallization from EtOAc gave a white solid weighing 1.49 g. The filtrate was concentrated and purified by column chromatography on silica gel (gradient elution 0-8% $CHCl_3$/MeOH) gave 0.410 g of an off-white solid. Combination of 1.49 g and 0.41 g gave 1.90 g (58%) of 10A. MS 316.2 $(M+H)^+$. $^1H$ NMR (400 MHz, DMSO-$d_6$) δ: (rotamers) 12.46 (s, 1H), 8.17 (s, 1H), 7.36 (d, J=8.8 Hz, 1H), 7.26-7.16 (m, 5H), 6.16 (s, 1H), 4.47-4.41 (m, 1H), 3.07 (d, J=13.6, 4.4 Hz, 1H), 2.71 (dd, J=13.6, 10.5 Hz, 1H), 1.28 (s, 9H).

10B. [1-(6-Chloro-pyrimidin-4-yl)-2-phenyl-ethyl]-carbamic acid tert-butyl ester: A white suspension of 10A (1.39 g, 4.41 mmol) in phosphorus oxychloride (20.54 mL, 220 mmol) was warmed to 50° C. to give a clear, pale yellow solution. After 3 h, the orange-brown solution was cooled to rt and concentrated in vacuo to give an orange-brown residue. The residue was dissolved in $CH_2Cl_2$ and concentrated (2×). The residue was dissolved in $CH_2Cl_2$ and sat. $NaHCO_3$ was added. The mixture was stirred vigorously for 10-15 min. The layers were separated and the aqueous layer was extracted with $CH_2Cl_2$ (1×). The combined organic layers were washed with brine, dried over $MgSO_4$, filtered and concentrated to give 0.990 g of 1-(6-chloropyrimidin-4-yl)-2-phenylethanamine as a thick, viscous orange-brown residue. MS 234.0 $(M+H)^+$; 236 $(M+2+H)^+$.

To a suspension 1-(6-chloropyrimidin-4-yl)-2-phenylethanamine (0.990 g, 4.24 mmol) in acetonitrile (14.1 mL) was added Boc-anhydride (1.082 mL, 4.66 mmol) and triethylamine (0.590 mL, 4.24 mmol). The resulting clear, orange-brown solution was stirred at rt overnight. The reaction was partitioned between $CH_2Cl_2$/sat. $NaHCO_3$. The layers were separated. The aqueous layer was extracted with $CH_2Cl_2$ (1×). The combined organic layers were washed with brine, dried over $Na_2SO_4$, filtered, and concentrated to give an orange-brown solid weighing 1.54 g. Purification by column chromatography on silica gel (gradient elution 0-12% $CH_2Cl_2$:EtOAc) provided 0.716 g (51%, pale, yellow solid) of 10B. MS 334.2 $(M+H)^+$. $^1H$ NMR (400 MHz, $CDCl_3$) δ: 8.95 (s, 1H), 7.30-7.18 (m, 3H), 7.05-6.96 (m, 3H), 5.41-5.37 (m, 1H), 4.99-4.92 (m, 1H), 3.17 (dd, J=13.6, 6.6 Hz, 1H), 3.08 (dd, J=13.6, 7.3 Hz, 1H), 1.41 (bs, 9H). Separation of the enantiomers by chiral prep HPLC (Chiralpak AD; IPA/heptane) gave: enantiomer A [>99% ee; $[α]_D^{25}$=−26.74 (c=0.93, MeOH)] and enantiomer B [>99% ee; $[α]_D^{25}$=+25.49 (c=0.88, MeOH].

10C. Example 10 was prepared as the TFA salt following the procedures described for 3F-G and 1C-D, by replacing 3E with 10B. MS 488.3 $(M+H)^+$. $^1H$ NMR (400 MHz, $CD_3OD$) δ: 9.56 (s, 1H), 9.09 (s, 1H), 8.01 (d, J=8.8 Hz, 2H), 7.69 (s, 1H), 7.60 (d, J=8.8 Hz, 2H), 7.28-7.18 (m, 5H), 5.25 (dd, J=9.2, 6.2 Hz, 1H), 3.76 (s, 3H), 3.26 (dd, J=14.0, 6.2 Hz, 1H), 3.07 (dd, J=14.0, 9.2 Hz, 1H), 2.77 (d, J=7.0 Hz, 2H), 2.29-2.23 (m, 1H), 1.87-1.81 (m, 3H), 1.72-1.65 (m, 1H), 1.62-1.50 (m, 1H), 1.45-1.30 (m, 2H), 1.12-1.00 (m, 2H).

Example 11

[4-(6-{1-[(trans-4-Aminomethyl-cyclohexanecarbonyl)-amino]-2-phenyl-ethyl}-pyrimidin-4-yl)-phenyl]-carbamic acid methyl ester, trifluoroacetic acid salt Example 11 was prepared as the TFA salt following the procedures described for 3F-G and 1C-D, by replacing 3E with 10B (enantiomer A). The enantiomeric excess was determined to be 73% ee by chiral analytical HPLC (Chiralcel OJ; MeOH/EtOH/Heptane). Racemization occurred somewhere during 3F-G or 1C-D.

Example 12 trans-4-Aminomethyl-cyclohexanecarboxylic acid {1-[6-(4-hydroxy-2-oxo-1,2-dihydro-quinolin-6-yl)-pyrimidin-4-yl]-2-phenyl-ethyl}-amide, trifluoroacetic acid salt Example 12 was prepared as the TFA salt following the procedures described for 3F-G and 1C-D, by replacing 3E with 10B (enantiomer A) and by replacing 4-(methoxycarbonylamino)phenylboronic acid with 7C. MS 498.3 $(M+H)^+$. $^1H$ NMR (500 MHz, $CD_3OD$) δ: 9.15 (s, 1H), 8.65 (s, 1H), 8.47 (d, J=8.2 Hz, 1H), 8.28 (dd, J=8.8, 1.6 Hz, 1H), 7.77 (s, 1H), 7.44 (d, J=8.8 Hz, 1H), 7.28-7.18 (m, 5H), 5.93 (s, 1H), 5.30-5.26 (m, 1H), 3.26 (dd, J=13.8, 6.0 Hz, 1H), 3.10 (d, J=13.8, 8.8 Hz, 1H), 2.77 (d, J=7.2 Hz, 2H), 2.31-2.25 (m, 1H), 1.89-1.83 (m, 3H), 1.74-1.70 (m, 1H), 1.62-1.52 (m, 1H), 1.47-1.36 (m, 2H), 1.12-1.03 (m, 2H).

Example 13 trans-4-Aminomethyl-cyclohexanecarboxylic acid[1-(2'-amino-[2,4']bipyridinyl-4-yl)-2-phenyl-ethyl]-amide, tris-trifluoroacetic acid salt 13A. trans-4-Aminomethyl-cyclohexanecarboxylic acid [1-(2'-fluoro-[2,4']bipyridinyl-4-yl)-2-phenyl-ethyl]-amide, tris-trifluoroacetic acid salt: 13A was prepared as the tris-TFA salt starting from compound 4A following the procedures described for 4B and 4C, replacing phenylboronic acid with 2-fluoro-pyridine-4-boronic acid. MS 433.3 $(M+H)^+$.

13B. Example 13. A suspension of 13A (0.029 g, 0.037 mmol) in sat. $NH_4OH$ (1.0 mL) was heated in a microwave vial at 150° C. for 2 h. The resulting clear, colorless solution was concentrated to give an off-white solid. Prep. HPLC yielded, after lyophilization from $CH_3CN/H_2O$, 0.0050 g (17%, white solid) of Example 13 as the tris-TFA salt. MS 430.3 $(M+H)^+$. $^1H$ NMR (400 MHz, $CD_3OD$) δ: 8.69 (d, J=4.8 Hz, 1H), 7.93 (d, J=6.6 Hz, 1H), 7.88 (bs, 1H), 7.64 (d, J=1.0 Hz, 1H), 7.49 (dd, J=5.3, 1.3 Hz, 1H), 7.44 (dd, J=7.0, 1.8 Hz, 1H), 7.28-7.19 (m, 5H), 5.24 (dd, J=9.2, 6.6 Hz, 1H), 3.16 (dd, J=14.0, 6.6 Hz, 1H), 3.08 (dd, J=13.6, 9.2 Hz, 1H), 2.76 (d, J=7.0 Hz, 2H), 2.22 (tt, J=12.3, 3.5 Hz, 1H), 1.85-1.75 (m, 3H), 1.69-1.63 (m, 1H), 1.60-1.50 (m, 1H), 1.44-1.28 (m, 2H), 1.08-0.99 (m, 2H).

Table 1 below summarizes representative examples, the synthesis of which is described above, of the compounds in the present invention.

TABLE 1
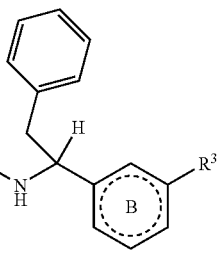
| Ex # | B | R³ | MS (M + H)⁺ |
|---|---|---|---|
| 1 | 3,5-pyridyl | phenyl | 414.3 |
| 2 | 3,5-pyridyl N-oxide | phenyl | 430.4 |
| 3 | 3,5-pyridyl | 4-(NHCO₂Me)phenyl | 487.4 |
| 4 | 2,4-pyridyl | phenyl | 414.4 |
| 5 | 2,4-pyridyl N-oxide | phenyl | 430.4 |
| 6 | 2,4-pyridyl | 4-(NHCO₂Me)phenyl | 487.5 |
| 7 | 3,5-pyridyl | 4-hydroxy-2-oxo-1,2-dihydroquinolin-6-yl | 497.2 |

TABLE 1-continued

[Structure: H₂N-cyclohexyl-C(=O)-NH-CH(CH₂Ph)-[ring B]-R³]

| Ex # | B | R³ | MS (M + H)⁺ |
|---|---|---|---|
| 8 | 5,3-pyridinone (2-oxo-1H-pyridine) | 4-(NHCO₂Me)-phenyl | 503.4 |
| 9 | 4,6-pyrimidine | phenyl | 415.3 |
| 10 | 4,6-pyrimidine | 4-(NHCO₂Me)-phenyl | 488.3 |
| 11 | 4,6-pyrimidine | 4-(NHCO₂Me)-phenyl | 488.3 |
| 12 | 4,6-pyrimidine | 4-hydroxy-2-oxo-quinolin-6-yl | 498.3 |
| 13 | 2,4-pyridine | 2-amino-pyridin-4-yl | 430.3 |

Utility

The compounds of this invention are inhibitors of factor XIa and are useful as anticoagulants for the treatment or prevention of thromboembolic disorders in mammals (i.e., factor XIa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of serine proteases involved in the coagulation cascade and/or contact activation system, more specifically, inhibition of the coagulation factors: factor XIa, factor VIIa, factor IXa, factor Xa, plasma kallikrein or thrombin.

The term "thrombosis", as used herein, refers to formation or presence of a thrombus (pl. thrombi); clotting within a blood vessel which may cause ischemia or infarction of tissues supplied by the vessel. The term "embolism", as used herein, refers to sudden blocking of an artery by a clot or foreign material which has been brought to its site of lodgment by the blood current. The term "thromboembolism", as used herein, refers to obstruction of a blood vessel with thrombotic material carried by the blood stream from the site of origin to plug another vessel. The term "stroke", as used herein, refers to embolic stroke or atherothrombotic stroke arising from occlusive thrombosis in the carotid communis, carotid interna, or intracerebral arteries.

The compounds of this invention also are inhibitors of plasma kallikrein and are useful as anti-inflammatory agents for the treatment or prevention of diseases associated with an activation of the contact activation system (i.e., plasma kallikrein associated disorders). In general, a contact activation system disorder is a disease caused by activation of blood on artificial surfaces, including prosthetic valves or other implants, indwelling catheters, stents, cardiopulmonary bypass, hemodialysis, microorganism (e.g., bacteria, virus), or other procedures in which blood is exposed to an artificial surface that promotes contact activation, blood clots (i.e., diseases involving fibrin formation, platelet activation, and/or platelet aggregation). Contact activation can also occur on cell surfaces, cellular receptors or extracellular matrices, Diseases of the contact activation system also include systemic inflammatory response syndrome, sepsis, acute respiratory distress syndrome, hereditary angioedema or other inherited or aquired deficiencies of contact activation components or their inhibitors (plasma kallikrein, factor XIIa, high molecular weight kininogen, C1-esterase inhibitor). It may also include acute and chronic inflammations of joints, vessels, or other mammalian organs.

The effectiveness of compounds of the present invention as inhibitors of the coagulation factors XIa, VIIa, IXa, Xa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 pM (Haematologic Technologies) and the synthetic substrate S-2366 (pyroGlu-Pro-Arg-pNA; Chromogenix) at a concentration of 0.0002-0.00025 M. In general, preferred compounds of the present invention, such as the particular compounds disclosed in the above examples, have been identified to be active and exhibit $K_i$'s of equal to or less than 15 μM in the Factor XIa assay, thereby demonstrating the utility of the compounds of the present invention as especially effective inhibitors of coagulation Factor XIa. More preferred compounds have $K_i$'s of equal to or less than 5 μM, preferably equal to or less than 1 μM, more preferably equal to or less than 0.5 μM.

Factor VIIa determinations were made in 0.005 M calcium chloride, 0.15 M sodium chloride, 0.05 M HEPES buffer containing 0.5% PEG 8000 at a pH of 7.4. Determinations were made using purified human Factor VIIa (Haematologic Technologies) or recombinant human Factor VIIa (Novo Nordisk) at a final assay concentration of 2-5 nM, recombinant soluble tissue factor at a concentration of 18-35 nM and the synthetic substrate H-D-Ile-Pro-Arg-pNA (S-2288; Chromogenix or BMPM-2; AnaSpec) at a concentration of 0.001 M. In general, compounds tested in the Factor VIIa assay are considered to be active if they exhibit a $K_i$ of equal to or less than 15 μM.

Factor IXa determinations were made in 0.005 M calcium chloride, 0.1 M sodium chloride, 0.05 M TRIS base and 0.5% PEG 8000 at a pH of 7.4. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M. In general, compounds tested in the Factor IXa assay are considered to be active if they exhibit a $K_i$ of equal to or less than 15 μM.

Factor Xa determinations were made in 0.1 M sodium phosphate buffer at a pH of 7.4 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; Chromogenix) at a concentration of 0.0002-0.0003 M. In general, compounds tested in the Factor Xa assay are considered to be active if they exhibit a $K_i$ of equal to or less than 15 μM.

Plasma kallikrein determinations were made in 0.1 M sodium phosphate buffer at a pH of 7.4 containing 0.2 M sodium chloride and 0.5% PEG 8000. Determinations were made using purified human kallikrein (Enzyme Research Laboratories) at a final assay concentration of 200 μM and the synthetic substrate S-2302 (H-(D)-Pro-Phe-Arg-pNA; Chromogenix) at a concentration of 0.00008-0.0004 M. The Km value used for calculation of Ki was 0.00005 to 0.00007 M. In general, Compounds tested in the plasma kallikrein assay are considered to be active if they exhibit a $K_i$ of equal to or less than 15 μM.

Thrombin determinations were made in 0.1 M sodium phosphate buffer at a pH of 7.4 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; Chromogenix) at a concentration of 0.0002 M. In general, compounds tested in the thrombin assay are considered to be active if they exhibit a $K_i$ of equal to or less than 15 μM.

In general, preferred compounds of the present invention have demonstrated $K_i$ values of equal to or less than 15 μM in at least one of the above assays, thereby confirming the utility of the compounds of the present invention as effective inhibitors of the coagulation cascade and/or contact activation system, and useful as anticoagulants for the prevention or treatment of thromboembolic disorders in mammals and/or as anti-inflammatory agents for the prevention or treatment of inflammatory disorders in mammals.

The Michaelis constant, $K_m$, for substrate hydrolysis by each protease was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_i$ values:

$(v_o-v_s)/v_s=I/(K_i(1+S/K_m))$ for a competitive inhibitor with one binding site; or $v_s/v_o=A+((B-A)/1+((IC_{50}/(I)^n)))$ and $K_i=IC_{50}/(1+S/K_m)$ for a competitive inhibitor where:

$v_o$ is the velocity of the control in the absence of inhibitor;
$v_s$ is the velocity in the presence of inhibitor;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme: inhibitor complex;
S is the concentration of substrate; and
$K_m$ is the Michaelis constant for the substrate.

The effectiveness of compounds of the present invention as antithrombotic agents can be determined using relevant in vivo thrombosis models, including In Vivo Electrically-induced Carotid Artery Thrombosis Models and In Vivo Rabbit Arterio-venous Shunt Thrombosis Models.

In Vivo Electrically-Induced Carotid Artery Thrombosis (ECAT) Model:

The rabbit ECAT model, described by Wong et al. (*J Pharmacol Exp Ther* 2000, 295, 212-218), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to the initiation of thrombosis. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

In Vivo Rabbit Arterio-venous (AV) Shunt Thrombosis Model

The rabbit AV shunt model, described by Wong et al. (Wong, P. C. et al. *J Pharmacol Exp Ther* 2000, 292, 351-357), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by a nonlinear least square regression program using the Hill sigmoid $E_{max}$ equation (DeltaGraph; SPSS Inc., Chicago, Ill.).

The anti-inflammatory effect of these compounds can be demonstrated in an Evans Blue dye extravasation assay using C1-esterase inhibitor deficient mice. In this model, mice are dosed with a compound of the present invention, Evans Blue is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The utility of the compounds of the current invention to reduce or prevent the morbidity and/or mortality of sepsis can be assessed by injecting a mammalian host with bacteria or viruses or extracts there of and compounds of the present invention. Typical read-outs of the efficacy include changes in the LD50 and blood pressure preservation.

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

The compounds of the present invention can be administered alone or in combination with one or more additional therapeutic agents. These include other anti-coagulant or coagulation inhibitory agents, anti-platelet or platelet inhibitory agents, anti-inflammatory agents, thrombin inhibitors, or thrombolytic or fibrinolytic agents.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Compounds which can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX™), synthetic pentasaccharide, direct acting thrombin inhibitors including hirudin and argatroban, as well as other factor VIIa inhibitors, factor IXa inhibitors, factor Xa inhibitors (e.g., Arixtra™, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDS) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDS, aspirin (acetylsalicylic acid or ASA), and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR1) antagonists (e.g., SCH-530348, SCH-203099, SCH-529153 and SCH-205831), and pharmaceutically acceptable salts or prodrugs thereof.

Other examples of suitable anti-platelet agents for use in combination with the compounds of the present invention, with or without aspirin, ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include clopidogrel, ticlopidine, prasugrel, and AZD-6140, and pharmaceutically acceptable salts or prodrugs thereof. Ticlopidine and clopidogrel are also preferred compounds since they are known to be more gentle than aspirin on the gastro-intestinal tract in use. Clopidogrel is an even more preferred agent.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable anti-arrhythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); $K^+$ channel openers such as $I_{Ach}$ inhibitors, and $I_{Kur}$ inhibitors (e.g., compounds such as those disclosed in WO01/40231).

Examples of suitable antihypertensive agents for use in combination with the compounds of the present invention include alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; angiotensin-converting enzyme (ACE) inhibitors (e.g., captopril, lisinopril, fosinopril, enalapril, ceranopril, cilazopril, delapril, pentopril, quinapril, ramipril, lisinopril), angiotensin AT-1 receptor antagonists (e.g., irbesartan, losartan, valsartan); ET-A receptor antagonists (e.g., sitaxsentan, atrsentan and compounds disclosed in U.S. Pat. Nos. 5,612,359 and 6,043,265); Dual ET-A/AT-1 antagonist (e.g., compounds disclosed in WO 00/01389); neutral endopeptidase (NEP) inhibitors; vasopepsidase inhibitors (dual ACE/NEP inhibitors, e.g., omapatrilat gemopatrilat, nitrates) and β-blockers (for example propanolol, nadolo, or carvedilol).

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain.

Examples of suitable diruetics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone.

Examples of suitable mineralocorticoid receptor antagonists for use in combination with the compounds of the present invention include sprionolactone and eplirinone.

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DPP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-obesity agents for use in combination with the compounds of the present invention include orlistat, aP2 inhibitors (such as those disclosed in WO00/59506), and cannabinoid receptor CB1 antagonists (e.g., rimonabant, AVE-1625, SR-147778, and CP-945598).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable holesterol/lipid lowering agents and lipid profile therapies for use in combination with the compounds of the present invention include HMG-CoA reductase inhibitors (e.g., pravastatin, lovastatin, simvastatin, fluvastatin, atorvsatatin, rosuvastatin, and other statins), sequestrants (e.g., cholestyramine and colestipol), nicotonic acid, fenofibric acid derivatives (e.g., gemfibrozil, clofibrat, fenofibrate and benzafibrate), probucol, cholesterol absorption inhibitors, and cholesterol ester transfer protein inhibitors (e.g., CP-529414).

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each. A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 µM against the target protease and greater than or equal to 0.1 µM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent and selective Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof, and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 0.1 to 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of the present invention and about 0.1 to 7.5 milligrams of the second anti-coagulant, per kilogram of patient body weight. For a tablet dosage form, the compounds of this invention generally may be present in an amount of about 5 to 100 milligrams per dosage unit, and the second anti-coagulant in an amount of about 1 to 50 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolyic agent when administered alone may be reduced by about 50-80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

What is claimed is:

1. A compound of Formula (I):

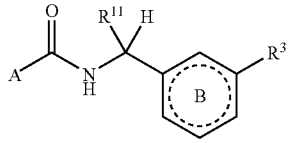 (I)

or a stereoisomer, tautomer, pharmaceutically acceptable salt thereof, wherein:

A is $C_{3-7}$ cycloalkyl substituted with 0-1 $R^1$ and 0-3 $R^2$, $C_{3-7}$ cycloalkenyl substituted with 0-1 $R^1$ and 0-3 $R^2$, phenyl substituted with 0-1 $R^1$ and 0-3 $R^2$, naphthyl substituted with 0-1 $R^1$ and 0-3 $R^2$, or a 5- to 12-membered heterocycle comprising: carbon atoms and 1-4 heteroatoms selected from N, O, and $S(O)_p$, wherein said heterocycle is substituted 0-1 $R^1$ and 0-3 $R^2$;

provided that A is other than a thienyl substituted with halogen, $C_{1-6}$ alkyl, $C_{2-6}$ alkenyl, or $C_{2-6}$ alkynyl;

the group

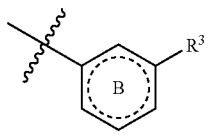

is selected from:

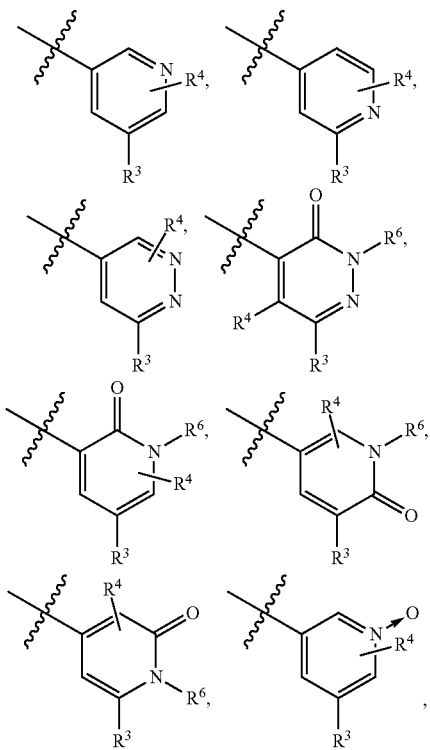

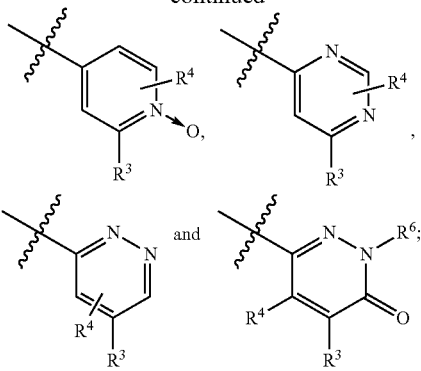

$R^1$ is, independently at each occurrence, F, Cl, Br, I, $OCF_3$, $CF_3$, $OCH_3$, $CH_3$, Et, $NH_2$, —C(=NH)$NH_2$, —C(O)$NH_2$, —$CH_2NH_2$, or —$SO_2NH_2$;

$R^2$ is, independently at each occurrence, F, Cl, Br, $CF_3$, $NO_2$, —$(CH_2)_rOR^a$, —$(CH_2)_rSR^a$, —C(O)$OR^a$, —C(O)$NR^8R^9$, —$NR^8C(O)R^c$, —$NR^8C(O)OR^c$, —$NR^8C(O)NR^8R^c$, —$S(O)_pNR^8R^9$, —$NR^8SO_2R^c$, —$NR^7R^8$, —$S(O)R^c$, —$S(O)_2R^c$, $C_{1-6}$ alkyl substituted with 0-1 $R^{2a}$, or a 5-7 membered heterocycle comprising carbon atoms and 1-4 heteroatoms selected from N, O, and $S(O)_p$, wherein said heterocycle is substituted with 0-2 $R^{2b}$;

$R^{2a}$ is, independently at each occurrence, H, F, Cl, Br, I, =O, =$NR^8$, CN, $OCF_3$, $CF_3$, $OR^a$, $SR^a$, —$NR^7R^8$, —C(O)$NR^8R^9$, —$NR^8C(O)R^c$, —$NR^8C(O)OR^c$, —$NR^8C(O)NR^8R^c$, —$S(O)_pNR^8R^9$, —$NR^8SO_2R^c$, —$S(O)R^c$, or —$S(O)_2R^c$;

$R^{2b}$ is, independently at each occurrence, H, F, Cl, Br, I, =O, =$NR^8$, —$(CH_2)_rCN$, —$(CH_2)_rNO_2$, —$(CH_2)_rOR^a$, —$(CH_2)_rSR^a$, —$(CH_2)_rC(O)R^a$, —$(CH_2)_rC(O)OR^a$, —$(CH_2)_rOC(O)R^a$, —$(CH_2)_rNR^7R^8$, —$(CH_2)_rC(O)NR^8R^9$, —$(CH_2)_rNR^8C(O)R^c$, —$(CH_2)_rS(O)_pNR^8R^9$, —$(CH_2)_rSO_2R^c$, —$(CH_2)_rNR^8SO_2NR^8R^9$, —$(CH_2)_rNR^8SO_2R^c$, —$(CF_2)_rCF_3$, $C_{1-6}$ alkyl, $C_{2-6}$ alkenyl, $C_{2-6}$ alkynyl, $C_{3-6}$ cycloalkyl, $C_{1-4}$ haloalkyl, or $C_{1-4}$haloalkyloxy;

alternately, when $R^1$ and $R^2$ are substituted on adjacent ring atoms, they can be taken together with the ring atoms to which they are attached to form a 5- to 7-membered carbocycle or heterocycle comprising: carbon atoms and 0-4 heteroatoms selected from N, O, and $S(O)_p$, wherein said carbocycle or heterocycle is substituted with 0-2 $R^g$;

$R^3$ is, independently at each occurrence, phenyl substituted with 0-3 $R^{3a}$ and 0-1 $R^{3d}$, naphthyl substituted with 0-3 $R^{3a}$ and 0-1 $R^{3d}$, or —$(CH_2)_r$-5- to 12-membered heterocycle comprising: carbon atoms and 1-4 heteroatoms selected from N, O, and $S(O)_p$, wherein said heterocycle is substituted with 0-3 $R^{3a}$ and 0-1 $R^{3d}$;

$R^{3a}$ is, independently at each occurrence, =O, F, Cl, Br, I, $OCF_3$, $CF_3$, —$(CH_2)_rCN$, $NO_2$, —$(CH_2)_rOR^{3b}$, —$(CH_2)_rSR^{3b}$, —$(CH_2)_rNR^7R^8$, —C(=$NR^{8a}$)$NR^8R^9$, —NHC(=$NR^{8a}$)$NR^7R^8$, —$NR^8CR^8$(=$NR^{8a}$), —$(CH_2)_rNR^8C(O)R^{3b}$, =$NR^8$, —$(CH_2)_rNR^8C(O)R^{3b}$, —$(CH_2)_rNR^8C(O)_2R^{3b}$, —$(CH_2)_rS(O)_pNR^8R^9$, —$(CH_2)_rNR^8S(O)_pR^{3c}$, —$S(O)R^{3c}$, —$S(O)_2R^{3c}$, —C(O)—$C_{1-4}$ alkyl, —$(CH_2)_rCO_2R^{3b}$, —$(CH_2)_rOC(O)R^{3b}$, —$(CH_2)_rC(O)NR^8R^9$, —$(CH_2)_rOC(O)NR^8R^9$, —$NHCOCF_3$, —$NHSO_2CF_3$, —$SO_2NHR^{3b}$, —$SO_2NHCOR^{3c}$, —$SO_2NHCO_2R^{3c}$, —$CONHSO_2R^{3c}$, —$NHSO_2R^{3c}$, —$CONHOR^{3b}$, $C_{1-4}$ haloalkyl, $C_{1-4}$ haloalkyloxy, $C_{1-6}$ alkyl substituted by $R^{3d}$, $C_{2-6}$ alkenyl substituted by $R^{3d}$, $C_{1-6}$ alkynyl substituted by $R^{3d}$, $C_{3-6}$ cycloalkyl substituted by 0-1 $R^{3d}$, —$(CH_2)_r C_{3-10}$ carbocycle substituted with 0-3 $R^{3d}$, or —$(CH_2)_r$5- to 10-membered heterocycle comprising: carbon atoms and 1-4 heteroatoms selected from N, O, and $S(O)_p$, wherein said heterocycle is substituted with 0-3 $R^{3d}$;

alternately, when two $R^{3a}$ groups are substituted on adjacent atoms, they can be taken together with the atoms to which they are attached to form a $C_{3-10}$ carbocycle substituted with 0-2 $R^{3d}$, or a 5- to 10-membered heterocycle comprising: carbon atoms and 1-4 heteroatoms selected from N, O, and $S(O)_p$, wherein said heterocycle is substituted with 0-2 $R^{3d}$;

$R^{3b}$ is, independently at each occurrence, H, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, —$(CH_2)_r$—$C_{3-10}$ carbocycle substituted with 0-3 $R^{3d}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3c}$ is, independently at each occurrence, $C_{1-6}$ alkyl substituted with 0-2 $R^{3d}$, $C_{2-6}$ alkenyl substituted with 0-2 $R^{3d}$, $C_{2-6}$ alkynyl substituted with 0-2 $R^{3d}$, —$(CH_2)_r$—$C_{3-10}$ carbocycle substituted with 0-3 $R^{3d}$, or —$(CH_2)_r$-5- to 10-membered heterocycle comprising: carbon atoms and 1-4 heteroatoms selected from N, O, and $S(O)_p$, wherein said heterocycle is substituted with 0-3 $R^{3d}$;

$R^{3d}$ is, independently at each occurrence, H, =O, —$(CH_2)_r$ $OR^a$, F, Cl, Br, CN, $NO_2$, —$(CH_2)_r NR^7R^8$, —$C(O)R^a$, —$C(O)OR^a$, —$OC(O)R^a$, —$NR^8C(O)R^c$, —$C(O)NR^8R^9$, —$S(O)_2NR^8R^9$, —$NR^8S(O)_2NR^8R^9$, —$NR^8S(O)_2R^c$, —$S(O)_pR^c$, —$(CF_2)_rCF_3$, $C_{2-6}$ alkyl substituted with 0-2 $R^e$, $C_{2-6}$ alkenyl substituted with 0-2 $R^e$, $C_{2-6}$ alkynyl substituted with 0-2 $R^e$, —$(CH_2)_r$—$C_{3-10}$ carbocycle substituted with 0-3 $R^d$, or —$(CH_2)_r$5- to 10-membered heterocycle comprising: carbon atoms and 1-4 heteroatoms selected from N, O, and $S(O)_p$, wherein said heterocycle is substituted with 0-3 $R^d$;

$R^4$ is, independently at each occurrence, H, F, Cl, Br, OMe, OH, $NH_2$, NHMe, NHEt, NHPr, Me, Et, Pr, CN, $CF_3$, —$CH_2OH$, —$(CH_2)_2OH$, —$(CH_2)_3OH$, —$CH_2NH_2$, —$(CH_2)_2NH_2$, —$(CH_2)_3NH_2$, $CO_2H$, —$C(O)NH_2$, —$C(O)NHMe$, —$C(O)N(Me)_2$, —$CH_2CO_2H$, —$CH_2C(O)NH_2$, —$CH_2CH_2CO_2H$, —$NHC(O)Me$, —$NHCO_2Me$, —$NHC(O)NHMe$, —$NHC(O)N(Me)_2$, —$NHCH_2CO_2H$, —$NHSO_2Me$, —$SO_2NH_2$, —$SO_2NHMe$, or —$SO_2N(Me)_2$;

$R^6$ is, independently at each occurrence, H, $C_{1-6}$ alkyl substituted with 0-3 $R^d$, —$(CH_2)_r$-phenyl substituted with 0-3 $R^d$;

$R^7$ is, independently at each occurrence, H, $C_{1-6}$ alkyl, —$(CH_2)_n$—$C_{3-10}$ carbocycle, —$(CH_2)_n$—(5- to 10-membered heteroaryl), —$C(O)R^c$, —CHO, —$C(O)_2R^c$, —$S(O)_2R^c$, —$CONR^8R^c$, —$OCONHR^c$, —$C(O)O$—$(C_{1-4}$ alkyl)$OC(O)$—$(C_{1-4}$ alkyl), or —$C(O)O$—$(C_{1-4}$ alkyl)$OC(O)$—$(C_{6-10}$ aryl); wherein said alkyl, carbocycle, heteroaryl, and aryl are substituted with 0-2 $R^f$; wherein said heteroaryl comprises: carbon atoms and 1-4 heteroatoms selected from N, O, and $S(O)_p$;

$R^8$ is, independently at each occurrence, H, $C_{1-6}$ alkyl, —$(CH_2)_n$-phenyl, or —$(CH_2)_n$-5- to 10-membered heterocycle comprising: carbon atoms and 1-4 heteroatoms selected from N, O, and $S(O)_p$; wherein said alkyl, phenyl and heterocycle are optionally substituted with 0-2 $R^f$;

alternatively, $R^7$ and $R^8$, when attached to the same nitrogen, combine to form a 5- to 10-membered heterocycle comprising: carbon atoms and 0-3 additional heteroatoms selected from N, O, and $S(O)_p$, wherein said heterocycle is substituted with 0-2 $R^f$;

$R^{8a}$ is, independently at each occurrence, $R^7$, OH, $C_{1-6}$ alkyl, $C_{1-4}$ alkoxy, $(C_{6-10}$ aryl)-$C_{1-4}$ alkoxy, —$(CH_2)_n$-phenyl, —$(CH_2)_n$-(5- to 10-membered heteroaryl); wherein said phenyl, aryl and heteroaryl are optionally substituted with 0-2 $R^f$;

$R^9$ is, independently at each occurrence, H, $C_{1-6}$ alkyl, or —$(CH_2)_n$-phenyl; wherein said alkyl and phenyl are optionally substituted with 0-2 $R^f$;

alternatively, $R^8$ and $R^9$, when attached to the same nitrogen, combine to form a 5- to 12-membered heterocycle comprising: carbon atoms and 0-2 additional heteroatoms selected from N, O, and $S(O)_p$, wherein said heterocycle is substituted with 0-2 $R^d$;

$R^{11}$ is $C_{1-4}$ haloalkyl, —$C(O)NR^8R^9$, —$CH_2C(O)NR^8R^9$, —$CH_2CH_2C(O)NR^8R^9$, —$C(O)R^a$, —$CH_2C(O)R^a$, —$CH_2CH_2C(O)R^a$, —$C(O)OR^a$, —$CH_2C(O)OR^a$, —$CH_2CH_2C(O)OR^a$, —$C_{1-6}$ alkyl substituted with 0-3 $R^{11c}$, $C_{2-6}$ alkenyl substituted with 0-3 $R^{11a}$, $C_{2-6}$ alkynyl substituted with 0-3 $R^{11a}$, —$(CH_2)_s$—$C_{3-7}$ cycloalkyl substituted with 0-2 $R^{11b}$, —$(CH_2)_s$-phenyl substituted with 0-3 $R^{11b}$, —$(CH_2)_s$-naphthyl substituted with 0-3 $R^{11b}$, or —$(CH_2)_s$-5- to 10-membered heterocycle comprising: carbon atoms and 1-4 heteroatoms selected from N, O, and $S(O)_p$, wherein said heterocycle is substituted with 0-3 $R^{11n}$;

$R^{11a}$ is, independently at each occurrence, H, =O, $C_{1-4}$ alkyl, $OR^a$, $SR^a$, F, $CF_3$, CN, $NO_2$, —$NR^7R^8$, —$C(O)R^a$, —$C(O)OR^a$, —$C(O)NR^8R^9$, —$NR^8C(O)R^c$, —$NR^8C(O)OR^c$, —$NR^8CHO$, —$S(O)_pNR^8R^9$, —$NR^8S(O)_pR^c$, —$S(O)_pR^c$, $C_{3-6}$ cycloalkyl, $C_{1-4}$ haloalkyl, $C_{1-4}$ haloalkyloxy, —$(CH_2)_r$—$C_{3-10}$ carbocycle substituted with 0-3 $R^d$, or —$(CH_2)_r$5- to 10-membered heterocycle comprising carbon atoms and 1-4 heteroatoms selected from N, O, and $S(O)_p$, and substituted with 0-3 $R^d$;

$R^{11b}$ is, independently at each occurrence, H, =O, =$NR^8$, $OR^a$, $SR^a$, F, Cl, Br, CN, $NO_2$, $CF_3$, $OCF_3$, $OCHF_2$, —$NR^7R^8$, —$C(O)R^a$, —$C(O)OR^a$, —$C(O)NR^8R^9$, —$NR^8C(O)R^c$, —$NR^8C(O)_2R^c$, —$S(O)_pNR^8R^9$, —$NR^8S(O)_pR^c$, —$S(O)_pR^c$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy, —$(CH_2)_r$—$C_{3-10}$ carbocycle substituted with 0-3 $R^d$, or —$(CH_2)_r$5- to 10-membered heterocycle comprising carbon atoms and 1-4 heteroatoms selected from N, O, and $S(O)_p$, and substituted with 0-3 $R^d$;

alternately, when two $R^{11b}$ groups are substituents on adjacent atoms they may be taken together with the atoms to which they are attached to form a 5- to 7-membered heterocycle comprising carbon atoms and 1-4 heteroatoms selected from N, O, and $S(O)_p$ and substituted with 0-2 $R^g$;

$R^{11c}$ is, independently at each occurrence H, =O, $OR^a$, $SR^a$, F, $CF_3$, CN, $NO_2$, —$NR^7R^8$, —$NR^8C(O)R^c$, —$NR^8C(O)OR^c$, —$NR^8CHO$, —$S(O)_pNR^8R^9$, —$NR^8S(O)_pR^c$, —$S(O)_pR^c$, $C_{1-4}$ alkyl, $C_{3-6}$ cycloalkyl, $C_{1-4}$ haloalkyl, $C_{1-4}$ haloalkyloxy, —$(CH_2)_r$—$C_{3-10}$ carbocycle substituted with 0-3 $R^d$, or —$(CH_2)_r$5- to 10-membered heterocycle comprising carbon atoms and 1-4 heteroatoms selected from N, O, and $S(O)_p$, and substituted with 0-3 $R^d$;

$R^a$ is, independently at each occurrence, H, $CF_3$, $C_{1-6}$ alkyl, —$(CH_2)_r$—$C_{3-7}$ cycloalkyl, —$(CH_2)_r$—$C_{6-10}$ aryl, or —$(CH_2)_r$-5- to 10-membered heterocycle comprising: carbon atoms and 1-4 heteroatoms selected from N, O, and $S(O)_p$; wherein said cycloalkyl, aryl and heterocycle groups are optionally substituted with 0-2 $R^f$;

$R^b$ is, independently at each occurrence, $CF_3$, OH, $C_{1-4}$ alkoxy, $C_{1-6}$ alkyl, —$(CH_2)_r$—$C_{3-10}$ carbocycle substituted with 0-3 $R^d$, or —$(CH_2)_r$-5- to 10-membered heterocycle comprising: carbon atoms and 1-4 heteroatoms selected from N, O, and $S(O)_p$ and substituted with 0-2 $R^d$;

$R^c$ is, independently at each occurrence, $CF_3$, $C_{1-6}$ alkyl substituted with 0-2 $R^f$, $C_{3-6}$ cycloalkyl substituted with 0-2 $R^f$, $C_{6-10}$ aryl, 5- to 10-membered heteroaryl, ($C_{6-10}$ aryl)-$C_{1-4}$ alkyl, or (5- to 10 membered heteroaryl)-$C_{1-4}$ alkyl, wherein said aryl is substituted with 0-3 $R^f$ and said heteroaryl comprises: carbon atoms and 1-4 heteroatoms selected from N, O, and $S(O)_p$ and substituted with 0-3 $R^f$;

$R^d$ is, independently at each occurrence, H, =O, =$NR^8$, $OR^a$, F, Cl, Br, I, CN, $NO_2$, —$NR^7R^8$, —$C(O)R^a$, —$C(O)OR^a$, —$OC(O)R^a$, —$NR^8C(O)R^c$, —$C(O)NR^8R^9$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$;

$R^e$ is, independently at each occurrence, =O, $OR^a$, F, Cl, Br, I, CN, $NO_2$, —$NR^7R^8$, —$C(O)R^a$, —$C(O)OR^a$, —$NR^8C(O)R^c$, —$C(O)NR^8R^9$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, or —$(CF_2)_rCF_3$;

$R^f$ is, independently at each occurrence, H, =O, —$(CH_2)_r$ $OR^g$, F, Cl, Br, I, CN, $NO_2$, —$NR^gR^g$, —$C(O)R^g$, —$C(O)OR^g$, —$NR^gC(O)R^g$, —$C(O)NR^gR^g$, —$SO_2NR^gR^g$, —$NR^gSO_2NR^gR^g$, —$NR^gSO_2$—$C_{1-4}$ alkyl, —$NR^gSO_2CF_3$, —$NR^gSO_2$-phenyl, —$S(O)_2CF_3$, —$S(O)_p$—$C_{1-4}$ alkyl, —$S(O)_p$-phenyl, —$(CH_2)_n$-phenyl, —$(CF_2)_rCF_3$, $C_{1-6}$ alkyl, $C_{2-6}$ alkenyl, $C_{2-6}$ alkynyl, —$(CH_2)_n$-phenyl, or —$(CH_2)_n$-5- to 10-membered heterocycle comprising carbon atoms and 1-4 heteroatoms selected from N, O, and $S(O)_p$;

alternately, when two $R^f$ groups are substituents on adjacent atoms they may be taken together with the atoms to which they are attached to form a 5-7-membered heterocycle comprising carbon atoms and 1-4 heteroatoms selected from N, O, and $S(O)_p$ and substituted with 0-2 $R^g$;

$R^g$ is, independently at each occurrence, H, $C_{1-6}$ alkyl, or —$(CH_2)_n$-phenyl;

n, at each occurrence, is selected from 0, 1, 2, 3, and 4;
p, at each occurrence, is selected from 0, 1, and 2; and
r, at each occurrence, is selected from 0, 1, 2, 3, and 4; and
s, at each occurrence, is selected from 1, 2, 3, and 4;
provided that: when $R^{11}$ is —$CH_2CO_2H$, A is other than substituted piperidyl.

2. A compound according to claim 1, wherein the compound is of Formula (I), or a stereoisomer, tautomer, pharmaceutically acceptable salt thereof, wherein:

the group

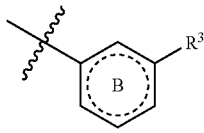

is selected from:

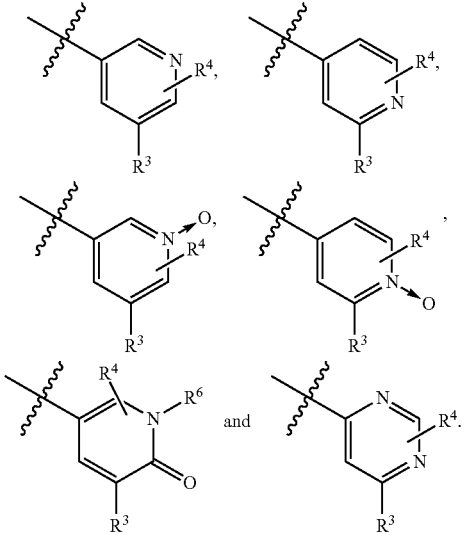

3. A compound according to claim 2, wherein the compound is of Formula (I), or a stereoisomer, tautomer, pharmaceutically acceptable salt thereof, wherein:

$R^1$ is, independently at each occurrence, F, Cl, Br, I, $OCF_3$, $CF_3$, $OCH_3$, $CH_3$, Et, $NH_2$, —C(=NH)$NH_2$, —C(O)$NH_2$, —$CH_2NH_2$, or —$SO_2NH_2$;

$R^2$ is, independently at each occurrence, F, Cl, Br, $CF_3$, $NO_2$, —$(CH_2)_rOR^a$, —$(CH_2)_rSR^a$, —$C(O)OR^a$, —$C(O)NR^8R^9$, —$NR^8C(O)R^c$, —$NR^8C(O)OR^c$, —$NR^8C(O)NR^8R^c$, —$S(O)_pNR^8R^9$, —$NR^8SO_2R^c$, —$NR^7R^8$, —$S(O)R^c$, —$S(O)_2R^c$, $C_{1-6}$ alkyl substituted with 0-1 $R^{2a}$, or a 5-7 membered heterocycle comprising carbon atoms and 1-4 heteroatoms selected from N, O, and $S(O)_p$, wherein said heterocycle is substituted with 0-2 $R^{2b}$;

alternately, when $R^1$ and $R^2$ groups are substituents on adjacent atoms they may be taken together with the atoms to which they are attached to form a 5- to 7-membered carbocycle or heterocycle comprising carbon atoms and 0-4 heteroatoms selected from N, O, and $S(O)_p$ and substituted with 0-2 $R^g$;

$R^3$ is, independently at each occurrence, phenyl substituted with 0-2 $R^{3a}$ and 0-1 $R^{3d}$, naphthyl substituted with 0-2 $R^{3a}$ and 0-1 $R^{3d}$, or a 5- to 12-membered heterocycle substituted with 0-2 $R^{3a}$ and 0-1 $R^{3d}$, wherein said heterocycle is selected from: thiophene, furan, thiazole, tetrazole, pyridine, pyridone, pyrimidine, pyrrole, pyrazole, indole, 2-oxindole, isoindoline, indazole, 7-azaindole, benzofuran, benzothiophene, benzimidazole, benzisoxazole, benzoxazole, quinazoline, quinoline, isoquinoline, quinoxaline, phthalazine, dihydrophthalazine, dihydroisoquinoline, dihydroquinoline, dihydroquinolone, dihydroindole, dihydrobenzimidazole, dihydrobenzoxazine, dihydroquinazoline, dihydroquinoxaline, benzothiazine, benzoxazine, tetrahydrobenzazepine, dihydroazabenzocycloheptene, and tetrahydroquinoline;

$R^{3a}$ is, independently at each occurrence, =O, F, Cl, Br, Me, CN, OH, OMe, —OC(O)(t-Bu), —CH$_2$OMe, CF$_3$, COMe, CO$_2$H, CO$_2$Me, —CH$_2$CO$_2$H, —(CH$_2$)$_2$CO$_2$H, —CH$_2$CO$_2$Me, —CH$_2$CO$_2$Et, —CH$_2$CH$_2$CO$_2$Et, —CH$_2$CN, NH$_2$, —CH$_2$NH$_2$, —CH$_2$NMe$_2$, —NHCOMe, —NHCO$_2$Me, —NHCO$_2$Et, —NHCO$_2$(i-Pr), —NHCO$_2$(i-Bu), —NHCO$_2$(t-Bu), —NHCO$_2$Bn, —NHCH$_2$CH$_2$CO$_2$H, —NHCO$_2$CH$_2$CH$_2$OMe, —NHCO$_2$CH$_2$CH$_2$CH$_2$OMe, —NHCO$_2$CH$_2$CO$_2$H, —NHCO$_2$CH$_2$CH$_2$CO$_2$H, —NHCO$_2$CH$_2$CH$_2$OH, —NHCO$_2$CH$_2$CH$_2$NH$_2$, —NHCO$_2$CH$_2$-tetrahydrofuran-2-yl, —NHCO$_2$CH$_2$CH$_2$-morpholino, —CH$_2$NHCO$_2$Me, —NHC(O)NHMe, —NHC(O)N(Me)$_2$, 4-[(1-carbamoyl-cyclopropanecarbonyl)-amino]-, —NHSO$_2$Me, —SO$_2$NH$_2$, SO$_2$NHMe, —SO$_2$NHCH$_2$CH$_2$OH, —CONH$_2$, —CONHMe, —CON(Me)$_2$, —C(O)NHCH$_2$CH$_2$OMe, —CH$_2$CONH$_2$, —CO(N-morpholino), —NHCH$_2$CH$_2$(N-morpholino), —NR$^7$R$^8$, —NH(1H-imidazol-2-yl), 1H-tetrazol-5-yl, tetrazol-1-yl, pyrimidin-5-yl, or N-morpholino;

$R^4$ is, independently at each occurrence, H, F, Cl, Br, OMe, OH, NH$_2$, NHMe, NHEt, NHPr, Me, Et, Pr, CN, CF$_3$, —CH$_2$OH, —(CH$_2$)$_2$OH, —(CH$_2$)$_3$OH, —CH$_2$NH$_2$, —(CH$_2$)$_2$NH$_2$, —(CH$_2$)$_3$NH$_2$, CO$_2$H, —C(O)NH$_2$, —C(O)NHMe, —C(O)N(Me)$_2$, —CH$_2$CO$_2$H, —CH$_2$C(O)NH$_2$, —CH$_2$CH$_2$CO$_2$H, —NHC(O)Me, —NHCO$_2$Me, —NHC(O)NHMe, —NHC(O)N(Me)$_2$, —NHCH$_2$CO$_2$H, —NHSO$_2$Me, —SO$_2$NH$_2$, —SO$_2$NHMe, or —SO$_2$N(Me)$_2$; and $R^{11}$ is C$_{1-4}$ haloalkyl, —CH$_2$C(O)NR$^8$R$^9$, —CH$_2$CH$_2$C(O)NR$^8$R$^9$, —CH$_2$C(O)R$^a$, —CH$_2$CH$_2$C(O)R$^a$, —CH$_2$C(O)OR$^a$, —CH$_2$CH$_2$C(O)OR$^a$, C$_{1-6}$ alkyl substituted with 0-2 R$^{11c}$, —(CH$_2$)$_s$—C$_{3-7}$ cycloalkyl substituted with 0-2 R$^{11b}$, —(CH$_2$)$_s$-phenyl substituted with 0-2 R$^{11b}$, —(CH$_2$)$_s$-naphtyl substituted with 0-2 R$^{11b}$, or —(CH$_2$)$_s$-5- to 10-membered heterocycle comprising carbon atoms and 1-4 heteroatoms selected from N, O, and S(O)$_p$, wherein said heterocycle is substituted with 0-2 R$^{11b}$.

4. A compound according to claim 1, wherein the compound is of Formula (I), or a stereoisomer, tautomer, pharmaceutically acceptable salt thereof, wherein:

A is substituted with 0-1 R$^1$ and 0-3 R$^2$ and selected from: C$_{3-7}$ cycloalkyl, phenyl, naphthyl, pyridyl, 1,2,3,4-tetrahydronaphthyl, pyrrolidinyl, indazolyl, indolyl, imidazolyl, furanyl, thienyl, benzimidazolyl, benzisoxazolyl, benzothiazolyl, benzothiophenyl, 3,4-methylenedioxy-phenyl, oxazolyl, isoxazolyl, thiazolyl, isothiazolyl, pyrazolyl, quinolinyl, isoquinolinyl, 1H-4-oxo-isoquinazolinyl, 2H-1-oxo-isquinilinyl, 3H-4-oxoquinazolinyl, 3,4-dihydro-2H-1-oxo-isoquinolinyl, 2,3-dihydro-isoindolinyl, 5,6,7,8-tetrahydroquinolinyl, 1,2,3,4-tetrahydroquinolinyl, 5,6,7,8-tetrahydroisoquinolinyl, 1,2,3,4-tetrahydroisoquinolinyl, quinazolinyl, and phthalazinyl;
provided that A is other than a thienyl substituted with halogen, C$_{1-6}$ alkyl, C$_{2-6}$ alkenyl, or C$_{2-6}$ alkynyl;

the group

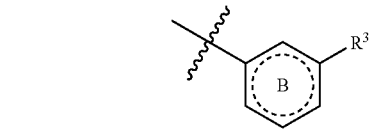

is selected from:

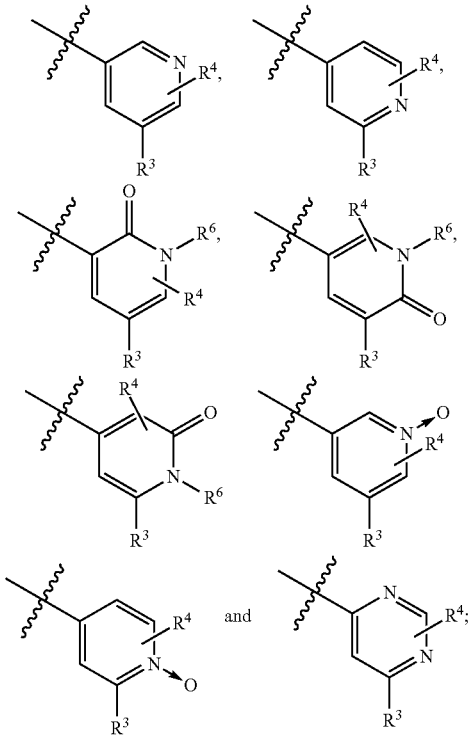

$R^1$ is, independently at each occurrence, F, Cl, Br, CF$_3$, NH$_2$, —CH$_2$NH$_2$, —C(=NH)NH$_2$, —C(O)NH$_2$, —SO$_2$NH$_2$, SR$^a$, OR$^a$, or C$_{1-6}$ alkyl substituted with 0-1 R$^{1a}$;

$R^2$ is, independently at each occurrence, =O, F, Cl, Br, CF$_3$, Me, Et, OR$^a$, CN, NO$_2$, NR$^7$R$^8$, —CH$_2$OMe, —SR$^a$, —CH$_2$SMe, —C(O)OR$^a$, —CH$_2$NR$^7$R$^8$, —SO$_2$NH$_2$, —SO$_2$Me, —NHSO$_2$R$^c$, —CH$_2$NHSO$_2$R$^c$, —C(O)NR$^8$R$^9$, —NHC(O)R$^c$, —CH$_2$NHC(O)R$^c$, —NHC(O)OR$^c$, —CH$_2$NHC(O)OR$^c$, —NHC(O)NHR$^c$, —CH$_2$NHC(O)NHR$^c$, or a 5-7 membered heterocycle substituted with 0-2 R$^{2b}$ and selected from: pyrrolidinyl, 2-oxo-1-pyrrolidinyl, piperidinyl, pyrazolyl, triazolyl, or tetrazolyl;
alternately, when R$^1$ and R$^2$ groups are substituents on adjacent atoms they may be taken together with the atoms to which they are attached to form a 5- to 6-membered heterocycle comprising carbon atoms and 0-4 heteroatoms selected from N, O, and S(O)$_p$;

$R^3$ is, independently at each occurrence, phenyl substituted with 0-2 R$^{1a}$, naphthyl substituted with 0-2 R$^{1a}$, or a 5- to 12-membered heterocycle comprising: carbon atoms and 1-2 heteroatoms selected from N, O, and S(O)$_p$, wherein said heterocycle is substituted with 0-2 R$^{1a}$;

$R^{3a}$ is, independently at each occurrence, =O, F, Cl, Br, Me, CN, OH, OMe, O(t-Bu), OBn, CF$_3$, —CH$_2$OH, —CH₂OMe, CF₃, COMe, CH₂CN, CO₂H, CO₂Me, —CH₂CO₂H, —(CH₂)₂CO₂H, —CH₂CO₂Me, —CH₂CO₂Et, —CH₂CH₂CO₂Et, —OC(O)(t-Bu), —NHCOMe, —NHCO₂Me, —NHCO₂Et, —NHCO₂(i-Pr), —NHCO₂(i-Bu), —NHCO₂(t-Bu), —NHCO₂Bn, —NHCH₂CH₂CO₂H, —NHCO₂CH₂CH₂CO₂H, —NHCO₂CH₂CH₂OH, —NHCO₂CH₂CH₂NH₂, —NHCO₂CH₂CH₂OMe, —CHCO₂CH₂CH₂CH₂OMe, —C(=NH)NH₂, —SO₂Me, —SO₂NH₂, —NHSO₂Me, —CH₂NHCO₂Me, —C(O)NHCH₂CH₂OMe, —SO₂NHCH₂CH₂OH, —NHC(O)NR⁸R⁹, —NR⁷R⁸, —CH₂NR⁷R⁸, —S(O)ₚNR⁸R⁹, —C(O)NR⁸R⁹, —CH₂C(O)NR⁸R⁹, —NHCH₂CH₂(N-morpholino), —NH(1H-imidazol-2-yl), —CO(N-morpholino), —NHCO₂CH₂-tetrahydrofuran-2-yl, —NHCO₂CH₂CH₂-morpholino, 4-[(1-carbamoyl-cyclopropanecarbonyl)-amino]-, 2-oxo-piperidin-1-yl, phenyl substituted with 0-1 R³ᵈ, or —(CH₂)ᵣ-5- to 6-membered heterocycle comprising: carbon atoms and 1-4 heteroatoms selected from N, O, and S(O)ₚ, wherein said heterocycle is substituted with 0-1 R³ᵈ;

alternatively, when two of R¹ᵃ groups located on adjacent atoms, they can be taken together with the atoms to which they are attached to form a 5- to 10-membered heterocycle comprising: carbon atoms and 1-4 heteroatoms selected from N, O, and S(O)ₚ, wherein said heterocycle is substituted with 0-2 R³ᵈ;

R⁴ is, independently at each occurrence, H, F, Cl, Br, OMe, OH, NH₂, NHMe, NHEt, NHPr, Me, Et, Pr, CN, CF₃, —CH₂OH, —(CH₂)₂OH, —(CH₂)₃OH, —CH₂NH₂, —(CH₂)₂NH₂, —(CH₂)₃NH₂, CO₂H, —C(O)NH₂, —C(O)NHMe, —C(O)N(Me)₂, —CH₂CO₂H, —CH₂C(O)NH₂, —CH₂CH₂CO₂H, —NHC(O)Me, —NHCO₂Me, —NHC(O)NHMe, —NHC(O)N(Me)₂, —NHCH₂CO₂H, —NHSO₂Me, —SO₂NH₂, —SO₂NHMe, or —SO₂N(Me)₂;

R⁶ is H, or C₁₋₄ alkyl;

R¹¹ is C₁₋₄ haloalkyl, —CH₂C(O)NR⁸R⁹, —CH₂CH₂C(O)NR⁸R⁹, —CH₂C(O)Rᵃ, —CH₂CH₂C(O)Rᵃ, —CH₂C(O)ORᵃ, —CH₂CH₂C(O)ORᵃ, —CH₂OBn, —CH₂SBn, C₁₋₆ alkyl substituted with 0-2 R¹¹ᶜ, C₂₋₆ alkenyl substituted with 0-2 R¹¹ᵃ, C₂₋₆ alkynyl substituted with 0-2 R¹¹ᵃ, —(CH₂)ₛ—C₃₋₇ cycloalkyl substituted with 0-2 R¹¹ᵇ, —(CH₂)ₛ-phenyl substituted with 0-2 R¹¹ᵇ, —(CH₂)ₛ-naphthyl substituted with 0-2 R¹¹ᵇ, or —(CH₂)ₛ-5- to 10-membered heteroaryl substituted with 0-2 R¹¹b and selected from thiazolyl, oxazolyl, pyrazolyl, triazolyl, tetrazolyl, thiadiazolyl, isoxazolyl, imidazolyl, pyridyl, pyrimidinyl, pyrazinyl, pyridazinyl, indolyl, indazolyl, isoindolyl, indolinyl, isoindolinyl, benzimidazolyl, benzothiazolyl, benzotriazolyl, quinolinyl, isoquinolinyl, tetrahydroquinolinyl, tetrahydroisoquinolinyl, and 2,2-dioxo-2,3-dihydro-1H-2λ⁶-benzo[c]thiophenyl;

R¹¹ᵇ is, independently at each occurrence, H, =O, F, Cl, Br, CF₃, OMe, OEt, O(i-Pr), OCF₃, OCHF₂, CN, OPh, OBn, NO₂, NH₂, —C(O)Rᵃ, —C(O)ORᵃ, —C(O)NR⁷R⁸, —NR⁸C(O)Rᶜ, —NR⁸C(O)₂Rᶜ, —S(O)ₚNR⁸R⁹, —NR⁸S(O)ₚRᶜ, —S(O)ₚRᶜ, C₁₋₆ alkyl, or —(CH₂)ᵣC₃₋₁₀ carbocycle substituted with 0-3 Rᵈ; and alternately, when two R¹¹ᵇ groups are substituents on adjacent atoms they may be taken together with the atoms to which they are attached to form a 5- to 7-membered heterocycle comprising carbon atoms and 1-4 heteroatoms selected from N, O, and S(O)ₚ and substituted with 0-2 Rᵍ.

5. A compound according to claim 4, wherein the compound is of Formula (I) or its stereoisomers, tautomers, pharmaceutically acceptable salts thereof, wherein:

A is 4-aminomethyl-cyclohexyl, 4-methylcyclohexyl, 4-methylphenyl, 3-methoxyphenyl, 4-methoxyphenyl, 4-aminomethylphenyl, 3-carbamoylphenyl, 4-carbamoylphenyl, 3-amidinophenyl, 4-amidinophenyl, 2-fluoro-4-methylphenyl, 2,6-difluoro-4-methylphenyl, 2-fluoro-4-methoxyphenyl, 2,6-difluoro-4-methoxyphenyl, 2-fluoro-4-aminomethylphenyl, 2-fluoro-4-carbamoylphenyl, 2-chloro-4-carbamoylphenyl, 2-methoxy-4-carbamoylphenyl, 4-amino-2-fluorophenyl, 4-amino-2,6-difluoromethylphenyl, 4-amino-3-chloro-2,6-difluorophenyl, 4-amino-3-chlorophenyl, 1,2,3,4-tetrahydronaphth-2-yl, 5-chlorothien-2-yl, indol-5-yl, indol-6-yl, indazol-6-yl, 3-amino-indazol-6-yl, 3-amino-indazol-5-yl, 1-methyl-3-amino-indazol-6-yl, 3-amino-benzisoxazol-6-yl, benzimidazol-5-yl, 6-fluoro-benzimidazol-5-yl, 1,2,3,4-tetrahydroisoquinolin-6-yl, 1,2,3,4-tetrahydroisoquinolin-3-yl, 1,2,3,4-tetrahydroisoquinolin-1-on-6-yl, 2H-isoquinolin-1-on-6-yl, isoquinolin-6-yl, 1-amino-isoquinolin-6-yl, 1-amino-3-methyl-isoquinolin-6-yl, 1-amino-5,6,7,8-tetrahydroisoquinolin-6-yl, or 4-amino-quinazolin-7-yl, 3H-quinazolin-4-on-7-yl;

R³ is, independently at each occurrence, phenyl, 3-biphenyl, 4-biphenyl, 3-aminophenyl, 4-aminophenyl, 3-N,N-dimethylaminophenyl, 4-phenoxyphenyl, 4-benzyloxyphenyl, 4-(t-butoxymethyl)-phenyl, 4-methylsulfonylphenyl, 3-cyanophenyl, 4-cyanophenyl, 3-fluorophenyl, 4-fluorophenyl, 3-chlorophenyl, 4-chlorophenyl, 3-bromophenyl, 4-bromophenyl, 3-hydroxyphenyl, 4-hydroxyphenyl, 2-methoxyphenyl, 3-methoxyphenyl, 4-methoxyphenyl, 3-trifluoromethylphenyl, 4-trifluoromethylphenyl, 3-carboxyphenyl, 4-carboxyphenyl, 3-methoxycarbonylphenyl, 4-methoxycarbonylphenyl, 3-carboxymethylphenyl, 4-carboxymethylphenyl, 4-methoxycarbonylmethylphenyl, 3-ethoxycarbonylmethylphenyl, 4-ethoxycarbonylmethylphenyl, 4-ethoxycarbonylethylphenyl, 3-carbamoylphenyl, 4-carbamoylphenyl, 3-aminocarbonylmethylphenyl, 4-aminocarbonylmethylphenyl, 4-methylaminocarbonylphenyl, 4-dimethylaminocarbonylmethylphenyl, 4-amidinophenyl, 3-methylcarbonylaminophenyl, 4-methylcarbonylaminophenyl, 4-methoxycarbonylaminophenyl, 4-aminosulfonylphenyl, 3-methylsulfonylaminophenyl, 4-methylsulfonylamino, 2,4-difluorophenyl, 3-fluoro-4-cyanophenyl, 4-amino-3-carboxyphenyl, 4-amino-3-methoxycarbonylphenyl, 2,4-dichlorophenyl, 3-cyano-5-fluorophenyl, 3-fluoro-4-carbamoylphenyl, 3-carboxy-4-cyanophenyl, 3-phenyl-4-carbamoylphenyl, 4-(2-oxo-1-piperidino)-phenyl, thiazol-2-yl, thien-2-yl, 4-methoxycarbonyl-thiazol-2-yl, 4-carbamoyl-thiazol-2-yl, 1-benzyl-pyazol-4-yl, 5-phenyl-oxazol-2-yl, 5-carbamoyl-thien-2-yl, 5-carboxy-thien-2-yl, pyrid-2-yl, pyrid-3-yl, pyrid-4-yl, 6-amino-pyrid-3-yl, benzimidazol-2-yl, 6-methoxy-pyrid-3-yl, 1-methyl-benzimidazol-2-yl, benzoxazol-2-yl, benzothiazol-2-yl, 3-amino-benzisoxazol-6-yl, 3-amino-benzisoxazol-5-yl, indazol-5-yl, indazol-6-yl, 3-amino-indazol-5-yl, 3-hydroxy-indazol-5-yl, 3-amino-indazol-6-yl, 3-amino-1-methyl-indazol-6-yl, 3-amino-4-fluoro-indazol-6-yl, 3-amino-5-fluoro-indazol-6-yl, 3-amino-7-fluoro-indazol-6-yl, 4-imino-3,4-dihydro-2H-phthalazin-1-on-7-yl, 3-(5-tetrazolyl)-phenyl, 2,3-dihydro-isoindol-1-on-6-yl, quinolin-5-yl, quinolin-6-yl, quinolin-8-yl, isoquinolin- 5-yl, 2H-isoquinolin-1-on-6-yl, 2,4-diaminoquinazolin-7-yl, 4-NH$_2$-quinazolin-7-yl,
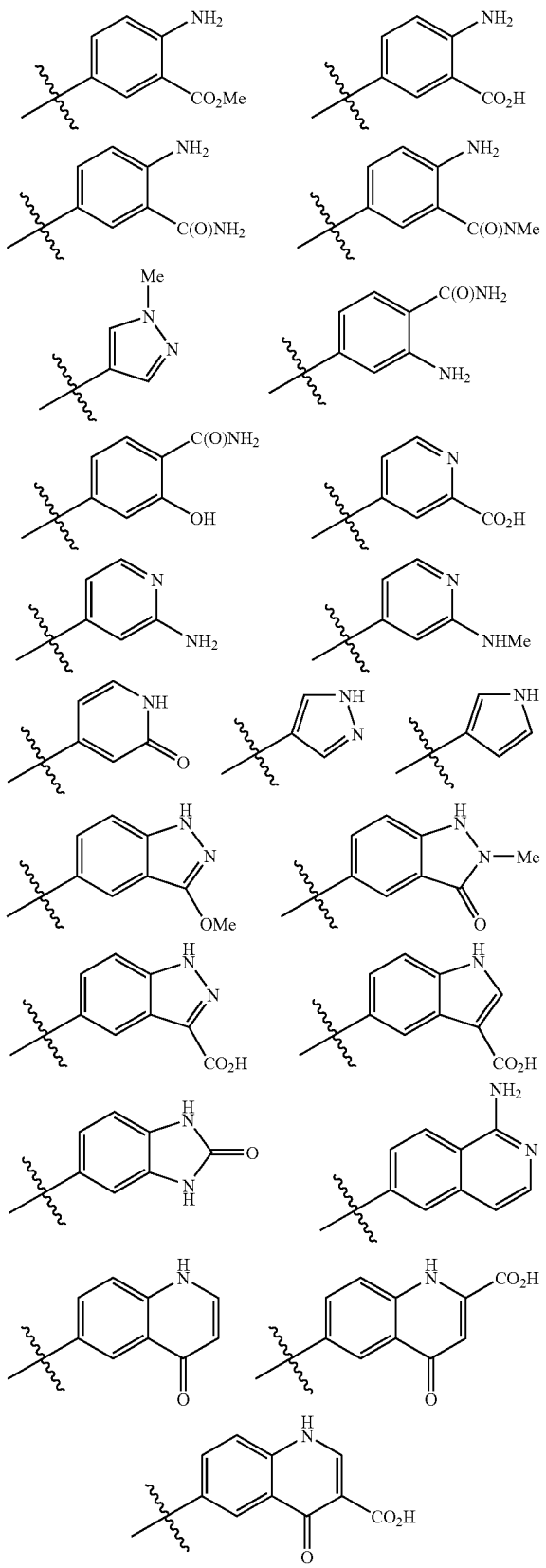
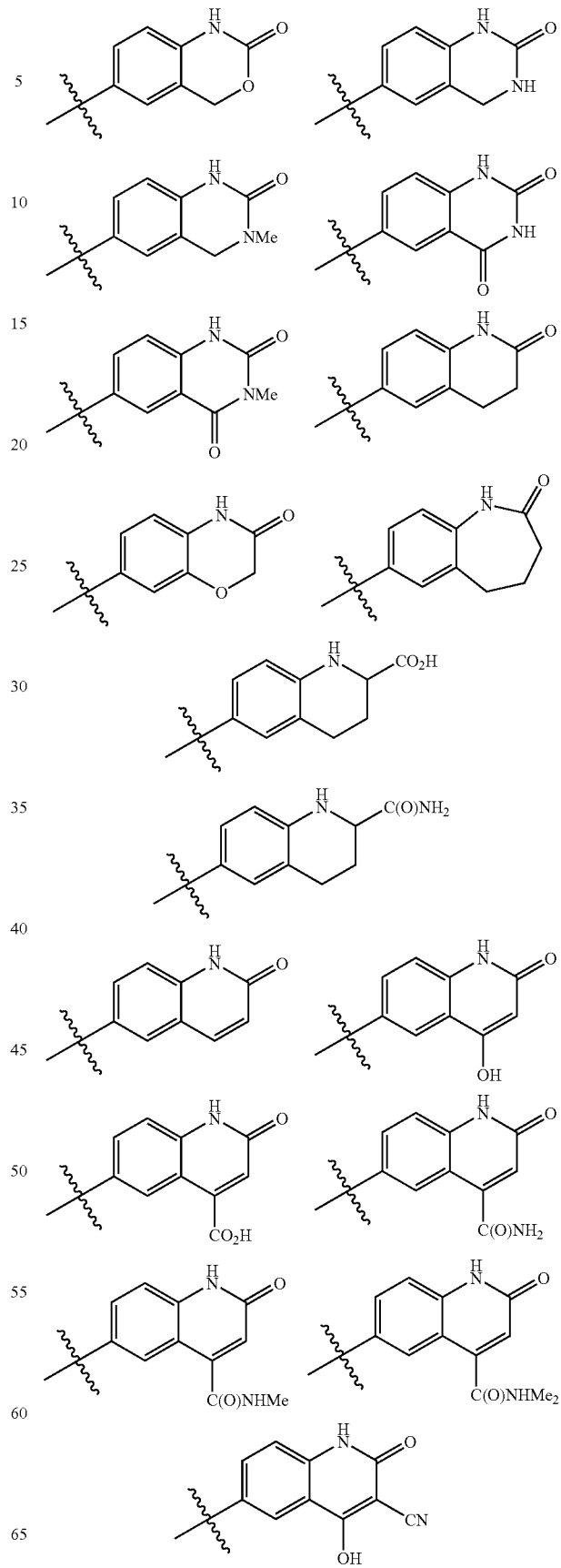

127
-continued
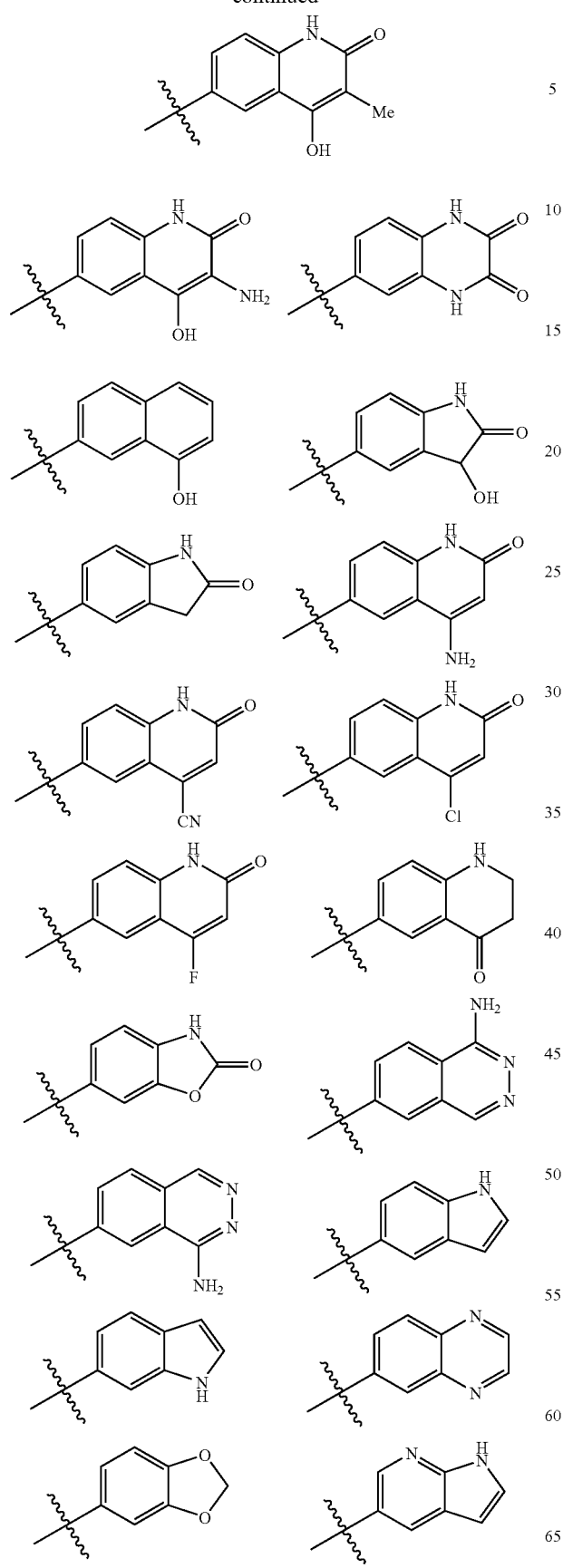
128
-continued
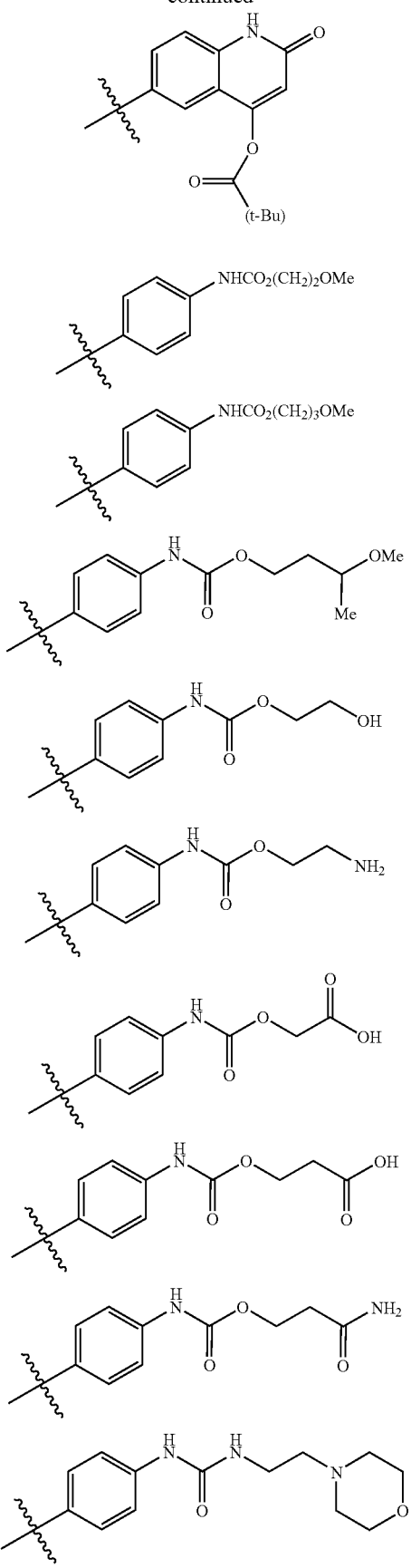

129
-continued
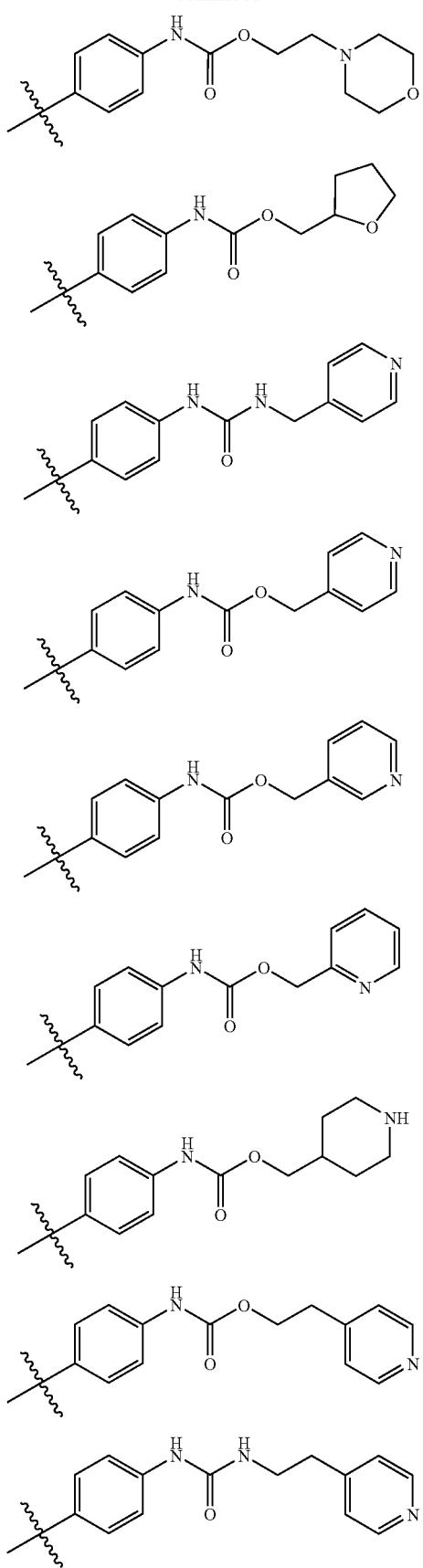
130
-continued
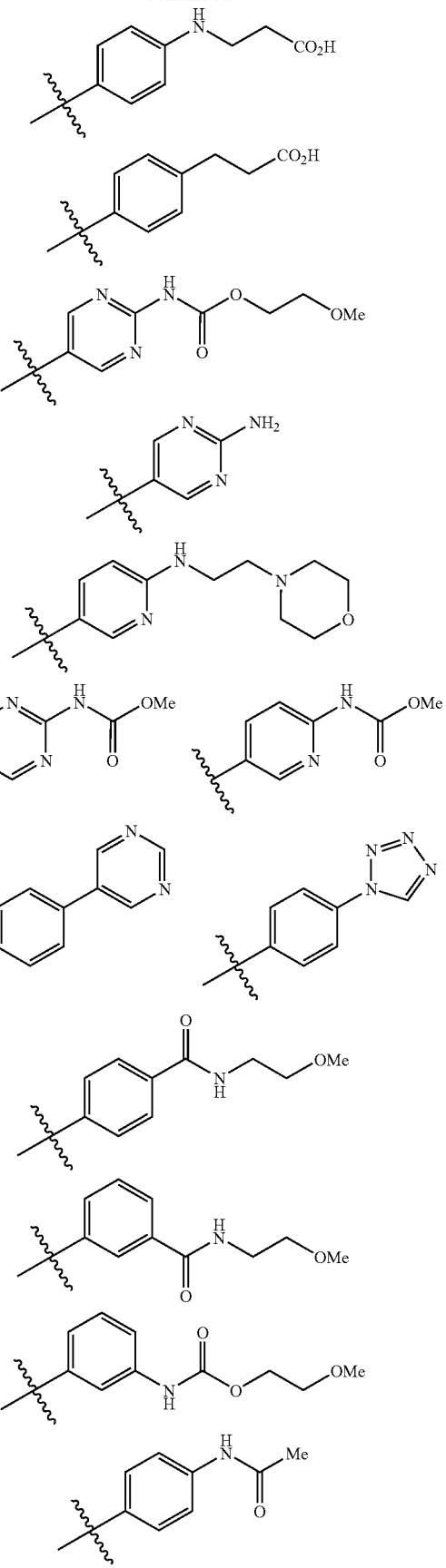

-continued

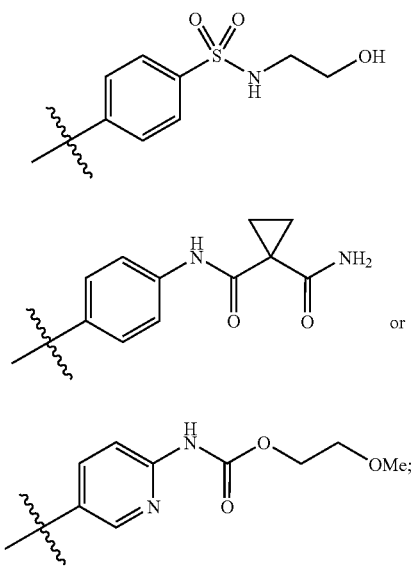

R[4] is, independently at each occurrence, H, F, Cl, Br, OMe, OH, NH$_2$, Me, Et, Pr, CN, CF$_3$, —CH$_2$OH, —CH$_2$NH$_2$, —CO$_2$H, —C(O)NH$_2$, —C(O)NHMe, —C(O)N(Me)$_2$, —CH$_2$CO$_2$H, —CH$_2$C(O)NH$_2$, —CH$_2$CH$_2$CO$_2$H, —NHC(O)Me, —NHCO$_2$Me, —NHC(O)NHMe, —NHC(O)N(Me)$_2$, —NHCH$_2$CO$_2$H, or —NHSO$_2$Me; and R[11] is methyl, n-propyl, n-butyl, neopentyl, cyclohexylmethyl, carboxymethyl, benzylaminocarbonylethyl, N-phenethylaminocarbonylethyl, N-benzyl-N-methylaminocarbonylethyl, N-[(pyridine-2-yl)methyl]aminocarbonylethyl, N-[(5-methylpyrazin-2-yl)methyl]aminoethyl, N-(thiazol-2-ylmethyl)aminocarbonylethyl, N-(cyclopropylmethyl)aminocarbonylmethyl, benzyl, phenethyl, 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, 3-carboxybenzyl, 3-carbamoylbenzyl, 3-(N-methylcarbamoyl)-benzyl, 3-(N-ethylcarbamoyl)-benzyl, 3-(N,N-dimethylcarbamoyl)-benzyl, 3-tetrazolyl-benzyl, 2-methylbenzyl, 3-methylbenzyl, 4-methylbenzyl, 3-trifluoromethylbenzyl, 4-trifluoromethylbenzyl, 2-aminobenzyl, 3-aminobenzyl, 2-nitrobenzyl, 3-nitrobenzyl, 4-nitrobenzyl, 3-methoxybenzyl, 4-methoxybenzyl, 3-difluoromethoxybenzyl, 2-trifluoromethoxybenzyl, 3-trifluoromethoxybenzyl, 2-phenoxybenzyl, 3-phenoxybenzyl, 2-benzyloxybenzyl, 3-benzyloxybenzyl, 4-benzyloxybenzyl, 4-phenylcarbonylbenzyl, 3-methoxycarbonylbenzyl, 3-methylcarbonylamino-benzyl, 2-phenylcarbonylamino-benzyl, 2-benzylcarbonylamino-benzyl, 3-benzylcarbonylamino-benzyl, 3-(benzoyl-methyl-amino)-benzyl, 3-(2-phenylethyl)carbonylamino-benzyl, 2-phenylsulfonylamino-benzyl, 3-phenylsulfonylamino-benzyl, 3-[N-methyl-N-phenylaminosulfonyl]-benzyl, 3-[benzenesulfonyl-methyl-amino]-benzyl, 3-isobutylaminocarbonyl-benzyl, 3-t-butylcarbonylamino-benzyl, 3-isopentylaminocarbnoyl-benzyl, 3-(2-methylphenyl)carbamoyl-benzyl, 3-(3-methylphenyl)carbamoyl-benzyl, 3-(4-methylphenyl)carbamoyl-benzyl, 3-(4-fluorophenyl)carbamoyl-benzyl, 3-(1-naphthyl)carbamoyl-benzyl, 3-benzylcarbamoyl-benzyl, 3-(4-chlorophenyl)methylcarbamoyl-benzyl, 3-(4-methoxyphenyl)methylcarbamoyl-benzyl, 3-(2-phenylethyl)carbamoyl-benzyl, 3-[2-(4-methoxyphenyl)ethyl]carbamoyl-benzyl, 3-[2-(2-chlorophenyl)ethyl]carbamoyl-benzyl, 3-[2-(3-chlorophenyl)ethyl]carbamoyl-benzyl, 3-[2-(4-chlorophenyl)ethyl]carbamoyl-benzyl, 3-[methyl-(pyridin-2-ylethyl)]carbamoyl-benzyl, 3-(3-phenylpropyl)carbamoyl-benzyl, 3-(ethyl-methyl-carbamoyl)-benzyl, 3-(isopropyl-methyl-carbamoyl)-benzyl, 3-(isobutyl-methyl-carbamoyl)-benzyl, 3-(methyl-phenyl-carbamoyl)-benzyl, 3-[(methyl-(3-methylphenyl)-carbamoyl]-benzyl, 3-[methyl-(4-methylphenyl)-carbamoyl]-benzyl, 3-(benzyl-methyl-carbamoyl)-benzyl, 3-[(3-chlorobenzyl)-methyl-carbamoyl]-benzyl, 3-[(4-chlorobenzyl)-methyl-carbamoyl]-benzyl, 3-[methyl-phenethyl-carbamoyl)]-benzyl, 3-(ethyl-phenyl-carbamoyl)-benzyl, 3-(piperidine-1-carbonyl)-benzyl, 3-(4-phenyl-piperidine-1-carbonyl)-benzyl, 3-(3,4-dihydro-2H-quinoline-1-carbonyl)-benzyl, 3-[(2-methoxyethyl)-methyl-carbamoyl]-benzyl, 3-(4-methoxy-piperidine-1-carbonyl)-benzyl, 3-(morpholine-4-sulfonyl)-benzyl, 3-[(N-(2-methoxyethyl), N-methylamino)sulfonyl]-benzyl, 3-(N,N-dimethylaminosulfonyl)-benzyl, 3-(azetidine-1-carbonyl)-benzyl, 3-(3-methoxy-azetidine-1-carbonyl)-benzyl, 3-(3-hydroxy-pyrrolidine-1-carbonyl)-benzyl, 3-[(4-tetrahydropyranyl)methylcarbonyl]-benzyl, 3-[(2-hydroxyethyl)-methyl-carbamoyl]-benzyl, 3-(3-hydroxy-azetidine-1-carbonyl)-benzyl, 3-(4-hydroxypiperidine-1-carbonyl)-benzyl, 3-[4-(N,N-dimethylamino)-piperidine-1-carbonyl]-benzyl, 3-(4-methyl-piperazine-1-carbonyl)-benzyl, 3-[3-(N,N-dimethylamino)-pyrrolidine-1-carbonyl]-benzyl, 2-phenyl-benzyl, 3-phenyl-benzyl, 4-phenyl-benzyl, 3-phenethyl-benzyl, benzyloxymethyl, benzylthiomethyl, 1-naphthylmethyl, 2-naphthylmethyl, thiazol-4-ylmethyl, pyrid-2-ylmethyl, pyrid-3-ylmethyl, pyrid-4-ylmethyl, 1-benzyl-imidazol-4-ylmethyl, benzothiazol-2-ylmethyl, 3-(1-morpholinocarbonyl)-benzyl, 3-[(2,6-dimethylmorpholine-4-carbonyl)-benzyl, (benzyloxycarbonyl)methyl, (1-methylpyrazol-3-yl)methyl, (1-methylpyrazol-4-yl)methyl, (1-methylpyrazol-5-yl)methyl, (3-methylpyrazol-5-yl)methyl, (1-ethylpyrazol-4-yl)methyl, (1-n-propylpyrazol-4-yl)methyl, (1-isopropylpyrazol-4-yl)methyl, 1-ethylpyrazol-3-ylmethyl, 3-pyrazolylmethyl, (4-chloro-3-methyl-5-pyrazolyl)methyl, (4-chloro-1,5-dimethyl-3-pyrazolyl)methyl, (4-chloro-1,3-dimethyl-5-pyrazolyl)methyl, [1-(4-methoxybenzyl)-pyrazol-3-yl]methyl, (1,5-dimethylpyrazol-3-yl)methyl, (1,3-dimethylpyrazol-5-yl)methyl, [1-(4-methoxybenzyl)-5-methyl-pyrazol-3-yl]methyl, (3-trifluoromethylpyrazol-5-yl)methyl, [1-(4-methoxybenzyl)-3-trifluoromethylpyrazol-5-yl]methyl, [(1-methyl-5-methoxycarbonyl)-pyrazol-3-yl]methyl, [(1-methyl-5-carboxy)-pyrazol-3-yl]methyl, [(1-methyl-5-carbamoyl)-pyrazol-3-yl]methyl, [(5-methoxycarbonyl)-pyrrol-2-yl]methyl, thiazol-2-ylmethyl, thiazol-4-methyl, (2-methoxypyridin-3-yl)methyl, (6-methoxypyridin-3-yl)methyl, (4-(methoxycarbonyl)-oxazol-2-yl)methyl, morpholin-4-ylcarbonylmethyl, N-((5-methylpyrazin-2-yl)methyl)-aminocarbonylmethyl, 2-hydroxy-indan-5-ylmethyl, 4-methylpiperazin-1-ylcarbonylmethyl, 4-methylcarbonylpiperazin-1-ylcarbonylmethyl, pyrrolidin-1-ylcarbonylmethyl, 2-methoxypyrrolidin-1-ylcarbonylmethyl, aziridin-1-ylcarbonylmethyl, 2-hydroxyethylaminocarbonylmethyl, 2-methoxyethylaminocarbonylmethyl, 2-ethoxyethylaminocarbonylmethyl, bis(2-methoxyethyl)aminocarbonylmethyl, 4-dimethylaminopyrrolidin-1-ylcarbonylmethyl, 4-chlorophenylaminocarbonylmethyl, 3-chlorophenylcarbonylmethyl, N-methyl-N-benzylaminocarbonylmethyl, cyclopropylaminocarbonylmethyl, cyclopropylmethylaminocarbonylmethyl, cyclopentylaminocarbonylmethyl, (trans-2-phenylcyclopropyl)aminocarbonylmethyl, N,N-dimethylaminoethylaminocarbonylmethyl, N-((pyridin-2-yl)methyl)aminocarbonylmethyl, N-((pyridin-3-yl)methyl)aminocarbonylmethyl, N-((pyridin-4-yl)methyl)aminocarbonylmethyl, N-((pyridin-2-yl)ethyl)aminocarbonylmethyl, 1-(1,1-dioxo-1$\lambda^6$-thiomorpholin-4-yl)carbonylmethyl, N-(tert-butoxycarbonyl)-1H-indol-3-ylmethyl, 1H-indol-3-ylmethyl, 2,2-dioxo-2,3-dihydro-1H-2$\lambda^6$-benzo[c]thiophen-5-ylmethyl, 4,4,4-trifluorobutyl, cyclopropylmethyl, (4-hydroxy)cyclohexylmethyl, 4-oxo-cyclohexylmethyl,

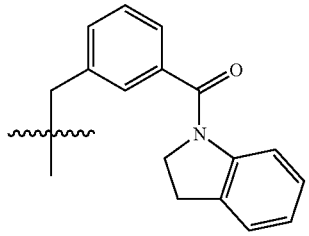

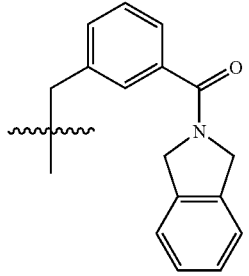

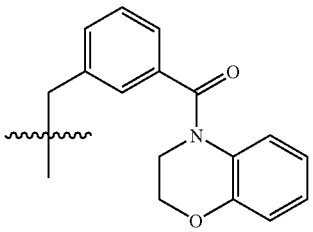

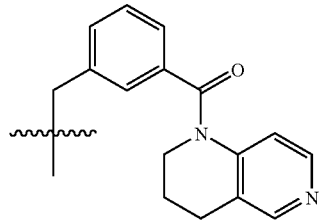

-continued

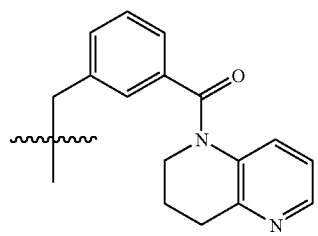

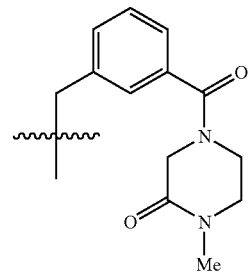

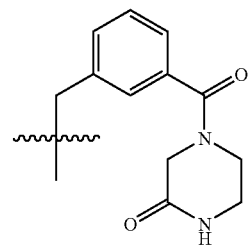

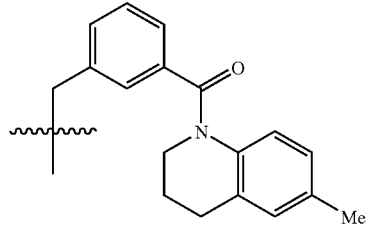

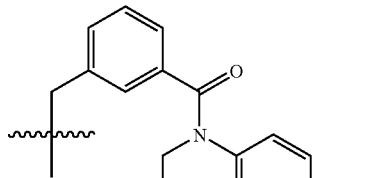

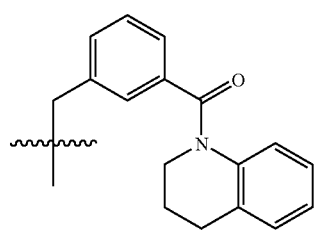

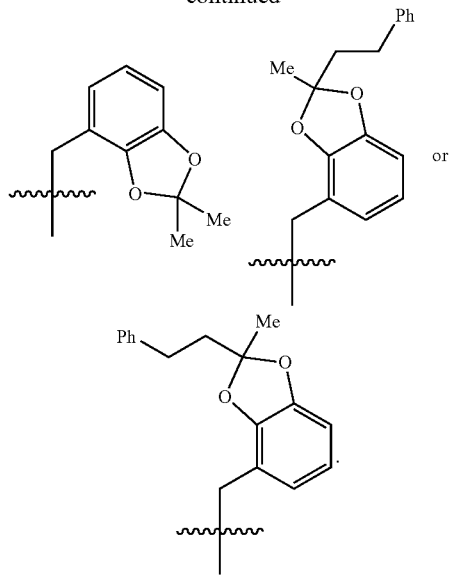

6. A compound according to claim 5, wherein the compound is of Formula (I) or its stereoisomers, tautomers, pharmaceutically acceptable salts thereof, wherein:

A is 4-aminomethyl-cyclohexyl, 4-methylcyclohexyl, 4-methoxyphenyl, 4-aminomethylphenyl, 4-carbamoylphenyl, 4-amidinophenyl, 2-fluoro-4-methylphenyl, 2,6-difluoro-4-methylphenyl, 2-fluoro-4-methoxyphenyl, 2,6-difluoro-4-methoxyphenyl, 2-fluoro-4-aminomethylphenyl, 2-fluoro-4-carbamoyl-phenyl, 4-amino-2-fluorophenyl, 4-amino-2,6-difluoromethylphenyl, 4-amino-3-chloro-2,3-difluorophenyl, 4-amino-3-chlorophenyl, 3-chlorothien-2-yl, indol-5-yl, indol-6-yl, indazol-6-yl, 3-amino-indazol-6-yl, 3-amino-indazol-5-yl, 1-methyl-3-amino-indazol-6-yl, 3-amino-benzisoxazol-6-yl, benzimidazol-5-yl, 6-fluoro-benzimidazol-5-yl, 1,2,3,4-tetrahydroisoquinolin-6-yl, 1,2,3,4-tetrahydroisoquinolin-3-yl, 2H-isoquinolin-1-on-6-yl, isoquinolin-6-yl, 1-aminoisoquinolin-6-yl, 1-amino-3-methyl-isoquinolin-6-yl, 1-amino-5,6,7,8-tetrahydroisoquinolin-6-yl, 4-aminoquinazolin-7-yl, or 3H-quinazolin-4-on-7-yl;

$R^3$ is, independently at each occurrence,

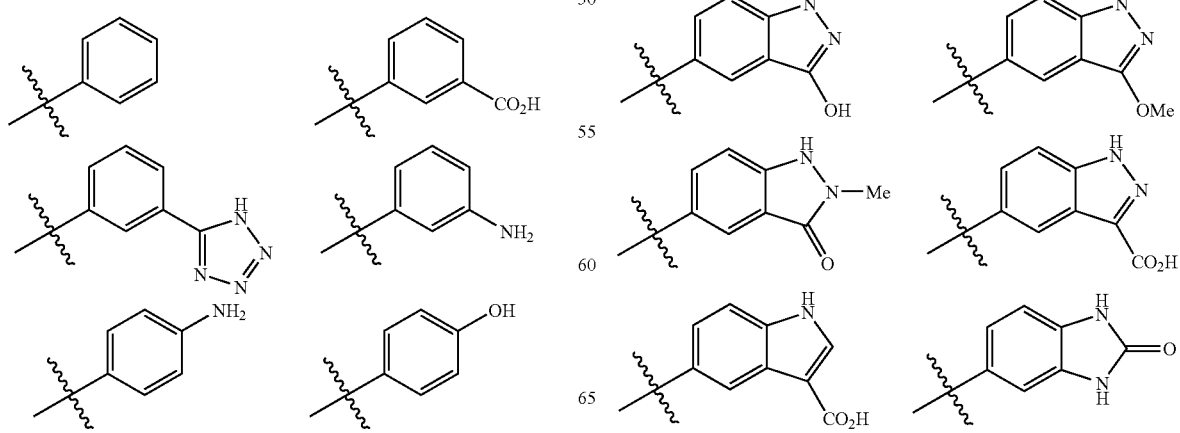

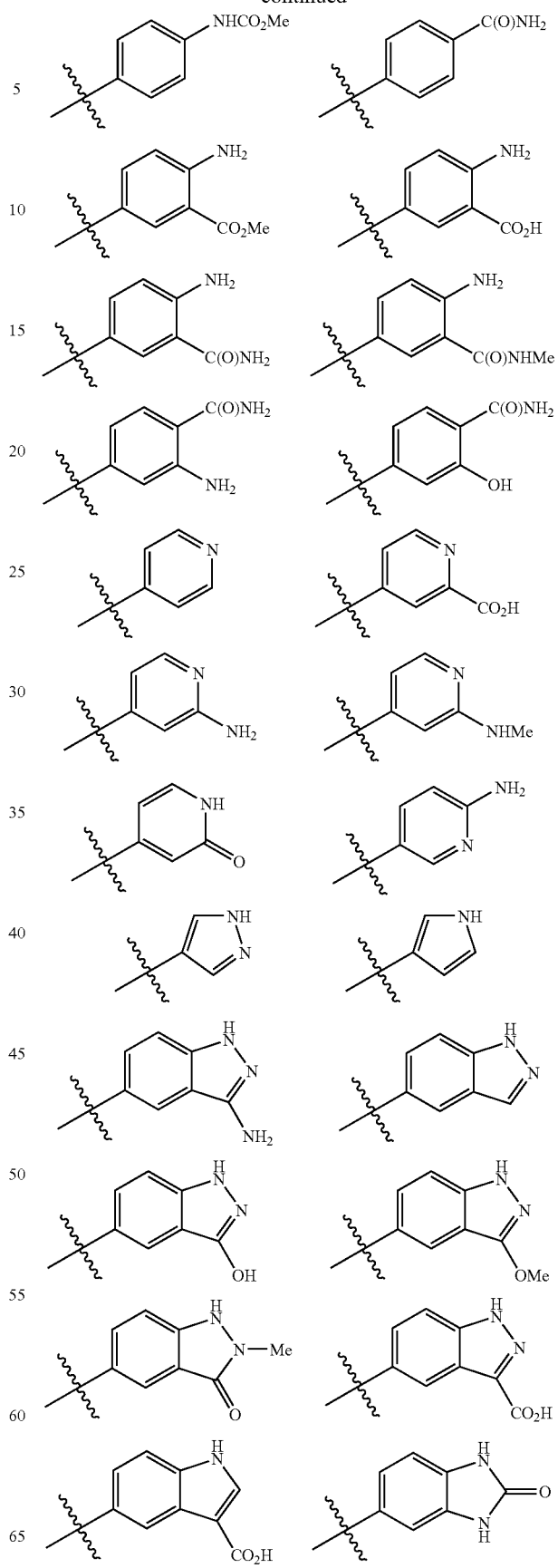

137
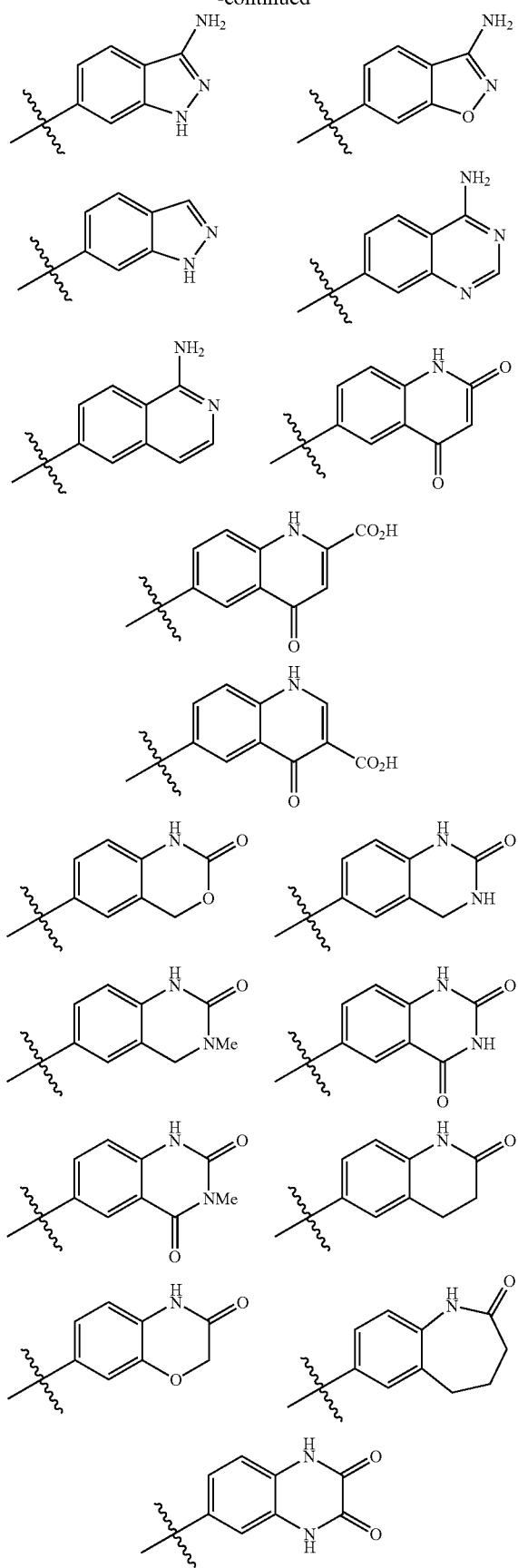
138
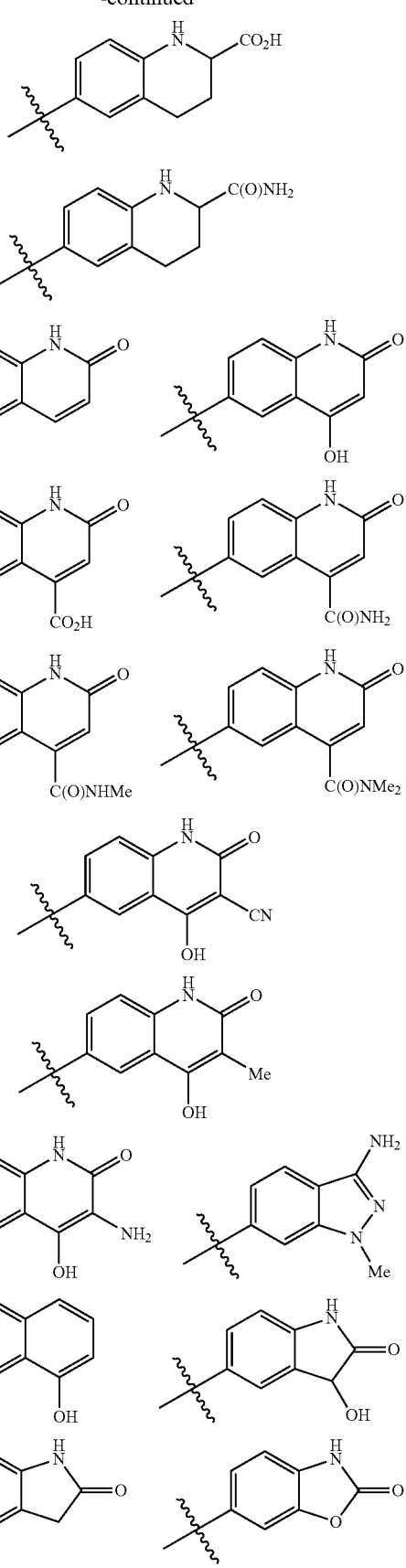

-continued
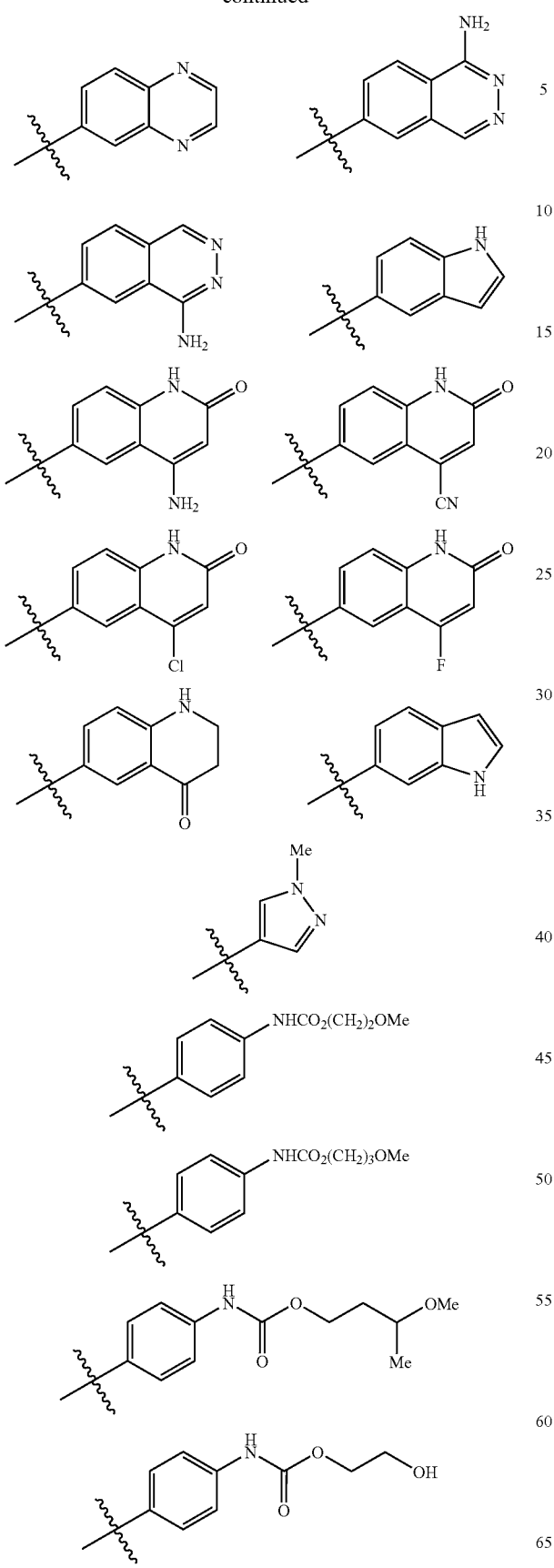
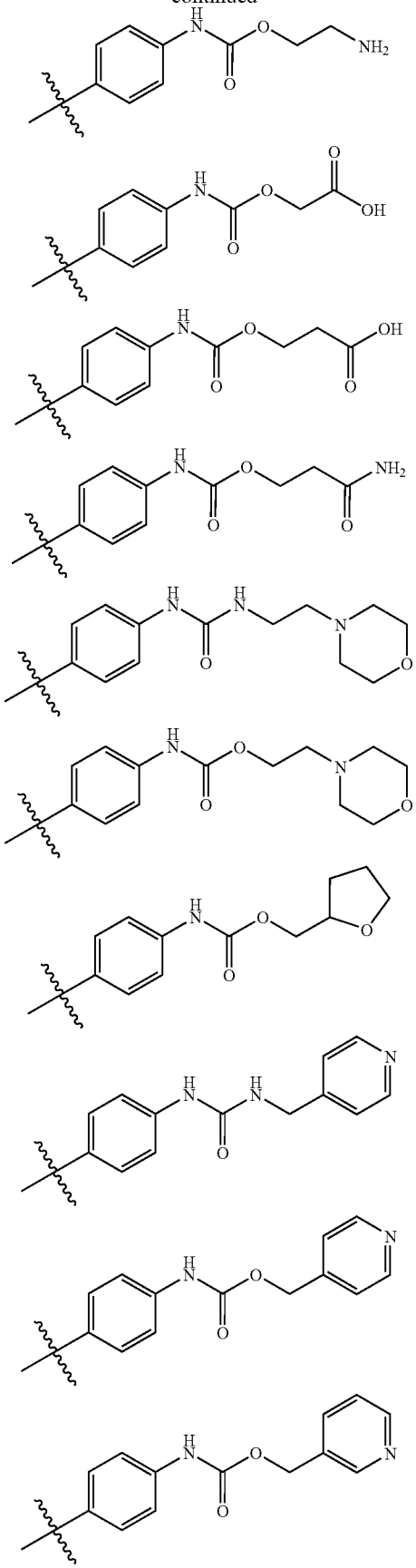

-continued

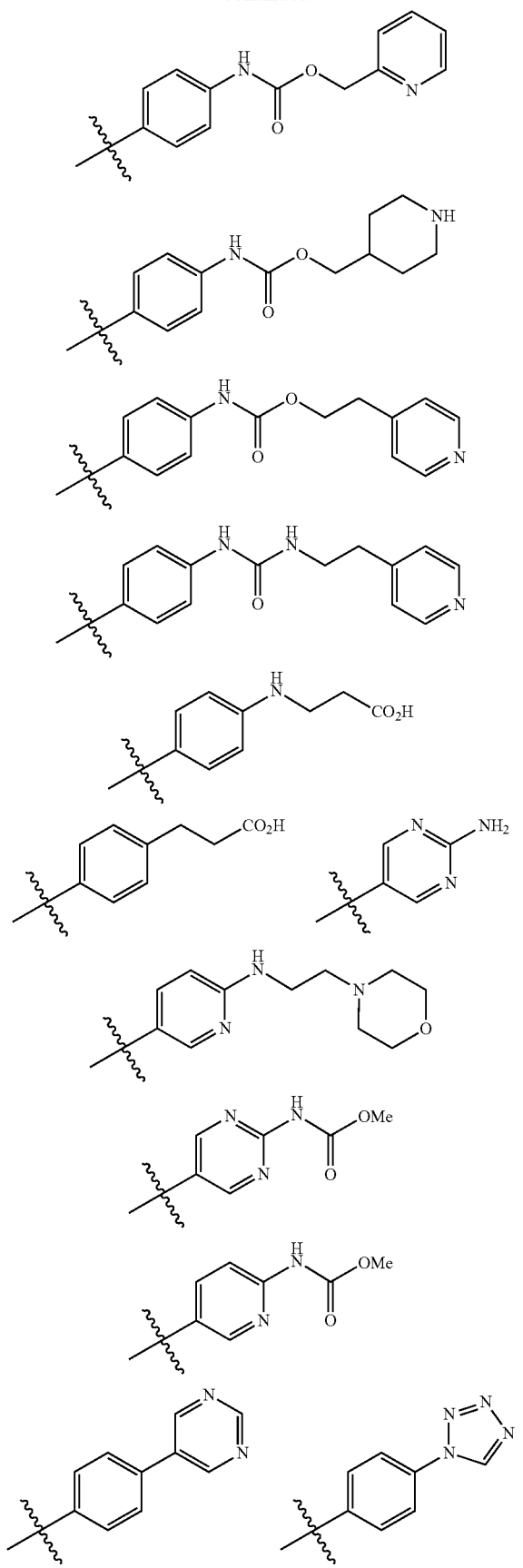

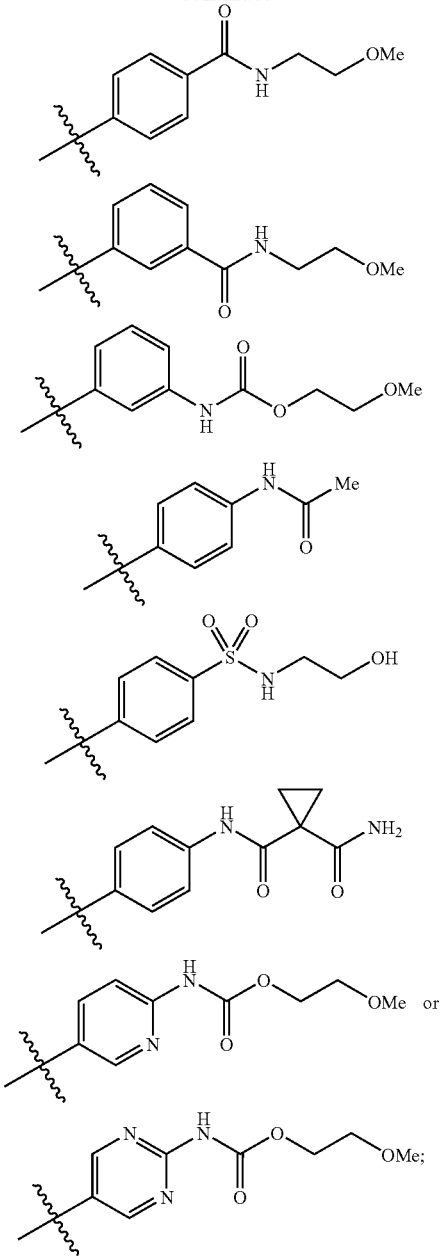

and $R^{11}$ is methyl, n-butyl, cyclohexylmethyl, carboxymethyl, benzyl, phenethyl, 2-fluorobenzyl, 3-fluorobenzyl, 4-fluorobenzyl, 2-chlorobenzyl, 3-chlorobenzyl, 4-chlorobenzyl, 3-carboxybenzyl, 3-carbamoylbenzyl, 3-(N-methylcarbamoyl)-benzyl, 3-(N,N-dimethylcarbamoyl)-benzyl, 3-(N-ethylcarbamoyl)-benzyl, 3-methylbenzyl, 4-methylbenzyl, 3-methoxybenzyl, 3-difluoromethoxybenzyl, 3-trifluoromethoxy-benzyl, 3-methoxycarbonylbenzyl, 3-methylcarbonylamino-benzyl, 3-benzylcarbonylamino-benzyl, 3-(benzoyl-methyl-amino)-benzyl, 3-(2-phenylethyl)carbonylamino-benzyl, 2-phenylsulfonylamino-benzyl, 3-phenylsulfonylamino-benzyl, 3-[N-methyl, N-phenylaminosulfonyl]-benzyl, 3-(benzenesulfonyl-methylamino)-benzyl, 3-(2-methylphenyl)carbamoyl-benzyl, 3-(3-methylphenyl)carbamoyl-benzyl, 3-(4-methylphenyl)carbamoyl-benzyl, 3-(4-fluorophenyl)carbamoyl-benzyl, 3-(1-naphthyl)carbamoyl-benzyl, 3-benzylcarbamoyl-benzyl, 3-(4-chlorophenyl)methylcarbamoyl-benzyl, 3-(4-methoxyphenyl)methylcarbamoyl-benzyl, 3-(2-phenylethyl)carbamoyl-benzyl, 3-[2-(4-methoxyphenyl)ethyl]carbamoyl-benzyl, 3-[2-(2-chlorophenyl)ethyl]carbamoyl-benzyl, 3-[2-(3-chlorophenyl)ethyl]carbamoyl-benzyl, 3-[2-(4-chlorophenyl)ethyl]carbamoyl-benzyl, 3-[methyl-(pyridin-2-ylethyl)]carbamoyl-benzyl 3-(3-phenylpropyl)carbamoyl-benzyl, 3-(ethyl-methyl-carbamoyl)-benzyl, 3-(isopropyl-methyl-carbamoyl)-benzyl, 3-(isobutyl-methyl-carbamoyl)-benzyl, 3-(methyl-phenyl-carbamoyl)-benzyl, 3-[(methyl-(3-methylphenyl)-carbamoyl]-benzyl, 3-[methyl-(4-methylphenyl)-carbamoyl]-benzyl, 3-(benzyl-methyl-carbamoyl)-benzyl, 3-[(3-chlorobenzyl)-methyl-carbamoyl]-benzyl, 3-[(4-chlorobenzyl)-methyl-carbamoyl]-benzyl, 3-[methyl-phenethyl-carbamoyl)]-benzyl, 3-(ethyl-phenyl-carbamoyl)-benzyl, 3-(piperidine-1-carbonyl)-benzyl, 3-(3,4-dihydro-2H-quinoline-1-carbonyl)-benzyl, 3-[(2-methoxyethyl)-methyl-carbamoyl]-benzyl, 3-(4-methoxy-piperidine-1-carbonyl)-benzyl, 3-(morpholine-4-sulfonyl)-benzyl, 3-[(N-(2-methoxyethyl), N-methylamino)sulfonyl]-benzyl, 3-(N,N-dimethylaminosulfonyl)-benzyl, 3-(azetidine-1-carbonyl)-benzyl, 3-(3-methoxy-azetidine-1-carbonyl)-benzyl, 3-(3-hydroxy-pyrrolidine-1-carbonyl)-benzyl, 3-[(4-tetrahydropyranyl)methylcarbonyl]-benzyl, 3-[(2-hydroxyethyl)-methyl-carbamoyl]-benzyl, 3-(3-hydroxy-azetidine-1-carbonyl)-benzyl, 3-(4-hydroxypiperidine-1-carbonyl)-benzyl, 3-[4-(N,N-dimethylamino)-piperidine-1-carbonyl]-benzyl, 3-(4-methyl-piperazine-1-carbonyl)-benzyl, 3-[3-(N,N-dimethylamino)-pyrrolidine-1-carbonyl]-benzyl, 1-naphthylmethyl, 2-naphthylmethyl, thiazol-4-ylmethyl, pyrid-2-ylmethyl, pyrid-3-ylmethyl, pyrid-4-ylmethyl, 1-benzyl-imidazol-4-ylmethyl, benzothiazol-2-ylmethyl, 3-(1-morpholinocarbonyl)-benzyl, 3-[(2,6-dimethylmorpholine-1-carbonyl)-benzyl, (benzyloxycarbonyl)methyl, (1-methylpyrazol-3-yl)methyl, (1-methylpyrazol-4-yl)methyl, (1-methylpyrazol-5-yl)methyl, (3-methylpyrazol-5-yl)methyl, (1-ethylpyrazol-4-yl)methyl, (1-n-propylpyrazol-4-yl)methyl, (1-isopropylpyrazol-4-yl)methyl, 1-ethylpyrazol-3-ylmethyl, 3-pyrazolylmethyl, (4-chloro-3-methyl-5-pyrazolyl)methyl, (4-chloro-1,5-dimethyl-3-pyrazolyl)methyl, (4-chloro-1,3-dimethyl-5-pyrazolyl)methyl, [1-(4-methoxybenzyl)-pyrazol-3-yl]methyl, (1,5-dimethylpyrazol-3-yl)methyl, (1,3-dimethylpyrazol-5-yl)methyl, [1-(4-methoxybenzyl)-5-methyl-pyrazol-3-yl]methyl, (3-trifluoromethylpyrazol-5-yl)methyl, [1-(4-methoxybenzyl)-3-trifluoromethylpyrazol-5-yl]methyl, [(1-methyl-5-methoxycarbonyl)-pyrazol-3-yl]methyl, [(1-methyl-5-carboxy)-pyrazol-3-yl]methyl, [(1-methyl-5-carbamoyl)-pyrazol-3-yl]methyl, [(5-methoxycarbonyl)-pyrrol-2-yl]methyl, thiazol-2-ylmethyl, thiazol-4-methyl, (2-methoxypyridin-3-yl)methyl, (6-methoxypyridin-3-yl)methyl, (4-(methoxycarbonyl)-oxazol-2-yl)methyl, morpholin-4-ylcarbonylmethyl, N-((5-methylpyrazin-2-yl)methyl)-aminocarbonylmethyl, 2-hydroxy-indan-5-ylmethyl, 4-methylpiperazin-1-ylcarbonylmethyl, 4-methylcarbonylpiperazin-1-ylcarbonylmethyl, pyrrolidin-1-yl-carbonylmethyl, 2-methoxypyrrolidin-1-ylcarbonylmethyl, aziridin-1-ylcarbonylmethyl, 2-hydroxyethylaminocarbonylmethyl, 2-methoxyethylaminocarbonylmethyl, 2-ethoxyethylaminocarbonylmethyl, bis(2-methoxyethyl)aminocarbonylmethyl, 4-dimethylaminopyrrolidin-1-ylcarbonylmethyl, 4-chlorophenylaminocarbonylmethyl, 3-chlorophenylcarbonylmethyl, N-methyl-N-benzylaminocarbonylmethyl, cyclopropylaminocarbonylmethyl, cyclopropylmethylaminocarbonylmethyl, cyclopentylaminocarbonylmethyl, (trans-2-phenylcyclopropyl)aminocarbonylmethyl, N,N-dimethylaminoethylaminocarbonylmethyl, N-((pyridin-2-yl)methyl)-aminocarbonylmethyl, N-((pyridin-3-yl)methyl)-aminocarbonylmethyl, N-((pyridin-4-yl)methyl)-aminocarbonylmethyl, N-((pyridin-2-yl)ethyl)-aminocarbonylmethyl, 1-(1,1-dioxo-1$\lambda^6$-thiomorpholin-4-yl)carbonylmethyl, N-(tert-butoxycarbonyl)-1H-indol-3-ylmethyl, 1H-indol-3-ylmethyl, 2,2-dioxo-2,3-dihydro-1H-2$\lambda^6$-benzo[c]thiophen-5-ylmethyl, 4,4,4-trifluorobutyl, cyclopropylmethyl, (4-hydroxy)cyclohexylmethyl, 4-oxo-cyclohexylmethyl,

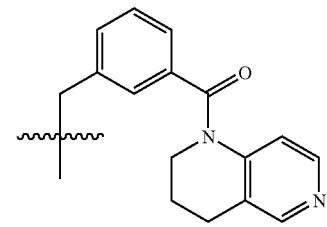

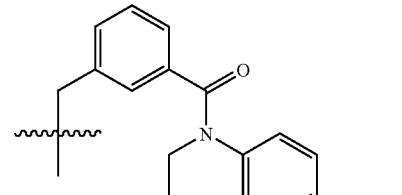

Me or

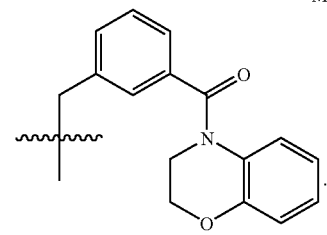

7. A compound according to claim 1, wherein the compound is of Formula (I), or its stereoisomers, tautomers, pharmaceutically acceptable salts thereof, wherein:

A is aminomethylcyclohexyl;

the group

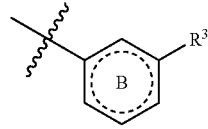

is selected from:

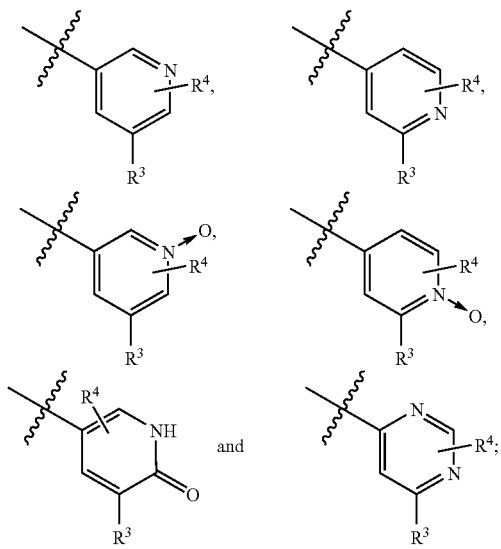

R³ is phenyl, 4-methoxycarbonylaminophenyl, 2-aminopyrid-4yl, or 4-hydroxy-2-oxo-1,2-dihydro-quinolin-6-yl;
R⁴ is H; and
R¹¹ is benzyl.

8. A compound according to claim 1, wherein the compound is selected from:
trans-4-Aminomethyl-cyclohexanecarboxylic acid[2-phenyl-1-(5-phenyl-pyridin-3-yl)-ethyl]-amide;
trans-4-Aminomethyl-cyclohexanecarboxylic acid[1-(1-oxy-5-phenyl-pyridin-3-yl)-2-phenyl-ethyl]-amide;
[trans-4-(5-{1-[(4-Aminomethyl-cyclohexanecarbonyl)-amino]-2-phenyl-ethyl}-pyridin-3-yl)-phenyl]-carbamic acid methyl ester;
trans-4-Aminomethyl-cyclohexanecarboxylic acid[2-phenyl-1-(2-phenyl-pyridin-4-yl)-ethyl]amide;
trans-4-Aminomethyl-cyclohexanecarboxylic acid[1-(1-oxy-2-phenyl-pyridin-4-yl)-2-phenyl-ethyl]-amide;
[4-(4-{1-[(trans-4-aminomethyl-cyclohexanecarbonyl)-amino]-2-phenyl-ethyl}-pyridin-2-yl)-phenyl]-carbamic acid methyl ester;
trans-4-Aminomethyl-cyclohexanecarboxylic acid {1-[5-(4-hydroxy-2-oxo-1,2-dihydro-quinolin-6-yl)-pyridin-3-yl]-2-phenyl-ethyl}-amide;
[4-(5-{1-[(trans-4-Aminomethyl-cyclohexanecarbonyl)-amino]-2-phenyl-ethyl}-2-oxo-1,2-dihydro-pyridin-3-yl)-phenyl]-carbamic acid methyl ester;
trans-4-aminomethyl-cyclohexanecarboxylic acid[2-phenyl-1-(6-phenyl-pyrimidin-4-yl)-ethyl]amide;
[4-(6-{1-[(trans-4-aminomethyl-cyclohexanecarbonyl)-amino]-2-phenyl-ethyl}-pyrimidin-4-yl)-phenyl]-carbamic acid methyl ester;
[4-(6-{1-[(trans-4-Aminomethyl-cyclohexanecarbonyl)-amino]-2-phenyl-ethyl}-pyrimidin-4-yl)-phenyl]-carbamic acid methyl ester;
trans-4-Aminomethyl-cyclohexanecarboxylic acid {1-[6-(4-hydroxy-2-oxo-1,2-dihydro-quinolin-6-yl)-pyrimidin-4-yl]-2-phenyl-ethyl}-amide;
trans-4-Aminomethyl-cyclohexanecarboxylic acid[1-(2'-amino-[2,4']bipyridinyl-4-yl)-2-phenyl-ethyl]-amide;
or a stereoisomer, tautomer, pharmaceutically acceptable salt thereof.

9. A pharmaceutical composition, comprising: a pharmaceutically acceptable carrier and a compound of claim 1 or a pharmaceutically acceptable salt thereof.

10. A method of treating a thromboembolic disorder, wherein the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis comprising administering to a patient in need thereof a therapeutically effective amount of a compound of claim 1 or a pharmaceutically acceptable salt thereof.

\* \* \* \* \*